United States Patent
Buckley et al.

(10) Patent No.: US 11,285,218 B2
(45) Date of Patent: Mar. 29, 2022

(54) DEGRADATION OF BROMODOMAIN-CONTAINING PROTEIN 9 (BRD9) BY CONJUGATION OF BRD9 INHIBITORS WITH E3 LIGASE LIGAND AND METHODS OF USE

(71) Applicant: Dana-Farber Cancer Institute, Inc., Boston, MA (US)

(72) Inventors: Dennis Buckley, Boston, MA (US); James Bradner, Weston, MA (US); David Ian Remillard, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 16/312,586

(22) PCT Filed: Jun. 23, 2017

(86) PCT No.: PCT/US2017/039004
§ 371 (c)(1),
(2) Date: Dec. 21, 2018

(87) PCT Pub. No.: WO2017/223452
PCT Pub. Date: Dec. 28, 2017

(65) Prior Publication Data
US 2019/0247509 A1    Aug. 15, 2019

Related U.S. Application Data

(60) Provisional application No. 62/438,758, filed on Dec. 23, 2016, provisional application No. 62/353,793, filed on Jun. 23, 2016.

(51) Int. Cl.
| | | |
|---|---|---|
| C07D 471/04 | (2006.01) | |
| A61K 47/55 | (2017.01) | |
| C07D 495/04 | (2006.01) | |
| A61K 47/54 | (2017.01) | |

(52) U.S. Cl.
CPC ............ *A61K 47/55* (2017.08); *A61K 47/545* (2017.08); *C07D 471/04* (2013.01); *C07D 495/04* (2013.01)

(58) Field of Classification Search
CPC .................................................. C07D 471/04
See application file for complete search history.

(56) References Cited

U.S. PATENT DOCUMENTS

2015/0291562 A1    10/2015   Crew et al.

FOREIGN PATENT DOCUMENTS

| WO | WO 2011/008260 A2 | 1/2011 | |
|---|---|---|---|
| WO | WO 2013/106643 A2 | 7/2013 | |
| WO | WO 2014/078257 A1 | 5/2014 | |
| WO | WO 2015/058160 A1 | 4/2015 | |
| WO | WO-2017180417 A1 * | 10/2017 | ........... C07D 471/04 |

OTHER PUBLICATIONS

Winter "Phthalimide conjugation as a strategy for in vivo target protein degradation" Science 348 (6241), 1376-1381 Published online May 21, 2015.*
Martin "Structure-Based Design of an in Vivo Active Selective BRD9 Inhibitor" J. Med. Chem. 2016, 59, 4462-4475, Published: Feb. 25, 2016.*
Adams, P. D. et al., "*PHENIX*: a comprehensive Python-based system for macromolecular structure solution," Acta Cryst., D66: 213-221 (2010).
Douglass, E. F. et al., "A Comprehensive Mathematical Model for Three-Body Binding Equilibria," J. Am. Chem. Soc., 135:6092-6099 (2013).
Emsley, P. & Cowtan, K., "*Coot*: model-building tools for molecular graphics," Acta Cryst., D60:2126-2132 (2004).
Fischer, E. S. et al., "Structure of the DDB1-CRBN E3 ubiquitin ligase in complex with thalidomide," Nature, 512:49-53 (2014).
Kabsch, W., "Integration, scaling, space-group assignment and post-refinement," Acta Cryst. D66:133-144 (2010).
McAlister, G. C. et al., "MultiNotch MS3 Enables Accurate, Sensitive, and Multiplexed Detection of Differential Expression across Cancer Cell Line Proteomes," Anal. Chem., 86:7150-7158 (2014).
McCoy, A. J. et al., "*Phaser* crystallographic software," J. Appl. Cryst., 40:658-674 (2007).

(Continued)

*Primary Examiner* — David K O'Dell
(74) *Attorney, Agent, or Firm* — Burns & Levinson, LLP; Daniel W. Clarke; Shawn P. Foley

(57) ABSTRACT

The present application provides bifunctional compounds of Formula (I):

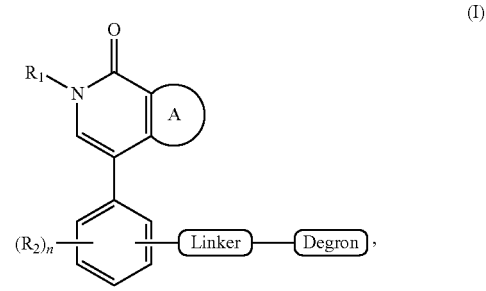

or
Targeting Ligand
or an enantiomer, diastereomer, or stereoisomer thereof, or pharmaceutically acceptable salt, hydrate, solvate, or prodrug thereof, which act as protein degradation inducing moieties for bromodomain-containing protein 9 (BRD9). The present application also provides methods for the targeted degradation of BRD9 through the use of the bifunctional compounds that link a ubiquitin ligase-binding moiety to a ligand that is capable of binding to BRD9 which can be utilized in the treatment of disorders modulated by BRD9.

4 Claims, 19 Drawing Sheets

(56) References Cited

OTHER PUBLICATIONS

Remillard, D. et al., "Degradation of the BAF Complex Factor BRD9 by Heterobifunctional Ligands," Angew. Chem. Int. Ed., 56:5738-5743 (2017).
Smart, O. S. et al., "Exploiting structure similarity in refinement: automated NCS and target-structure restraints in BUSTER," Acta Cryst. D68:368-380 (2012).
Tanaka, M. et al., "Design and characterization of bivalent BET inhibitors," Nature Chemical Biology, 12:1089-1096 and Online Methods (2016).
Theodoulou, N. H. et al., "Discovery of I-BRD9, a Selective Cell Active Chemical Probe for Bromodomain Containing Protein 9 Inhibition," J. Med. Chem., 59:1425-1439 (2015).
Weekes, M. P. et al., "Quantitative Temporal Viromics: An Approach to Investigate Host-Pathogen Interaction," Cell, 157:1460-1472 (2014).
Lai, A. et al., "Modular PROTAC Design for the Degradation of Oncogenic BCR-ABL", Angew. Chem. Int. Ed., 2016, vol. 55, No. 2, pp. 807-810.
Raina, K. et al., "PROTAC-induced BET Protein Degradation as a Therapy for Castration-resistant Prostate Cancer", Proc. Natl. Acad. Sci. U.S.A., 2016, vol. 113, No. 26, pp. 7124-7129.
Zengerle, M. et al., "Selective Small Molecule Induced Degradation of the BET Bromodomain Protein BRD4", ACS Chem. Biol., 2015, vol. 10, No. 8, pp. 1770-1777.
Bondeson Daniel P., et al., "Lessons in PROTAC Design From Selective Degradation with a Promiscuous Warhead", Cell Chem. Biol., 2018, vol. 25, No. 1, pp. 78-87.
Liu Xingui, et al., "Assays and Technologies for Developing Proteolysis Targeting Chimera Degraders", Future Med. Chem., 2020, vol. 12, No. 12, pp. 1155-1179.
Manda Sudhakar, et al., "Design, Synthesis, and Biological Evaluation of Proteolysis Targeting Chimeras (PROTACs) for the Dual Degradation of IGF-1R and Src", Molecules, 2020, vol. 25, pp. 1-18.
Su Shang, et al., "Potent and Preferential Degradation of CDK6 via Proteolysis Targeting Chimera Degraders", J. Med. Chem., 2019, vol. 62, pp. 7575-7582.
Huang, Hai-Tsang, et al., "A Chemoproteomic Approach to Query the Degradable Kinome Using a Multi-Kinase Degrader", Cell Chem. Biol., 2018, vol. 25, No. 1, pp. 88-99.
Nowak, Radoslaw P., et al., "Plasticity in Binding Confers Selectivity in Ligand Induced Protein Degradation", Nat. Chem. Biol., 2018, vol. 14, No. 7, pp. 706-714.
Pettersson, Mariell, et al., "Proteolysis Targeting Chimeras (PROTACs)—Past, Present and Future", Drug Discovery Today: Technologies, 2019, vol. 31, pp. 15-27.
Meslamani, Jamel, et al., "Structural Features and Inhibitors of Bromodomains", Drug Discov. Today Technol. 2016 vol. 19, pp. 3-15.

\* cited by examiner

DEGRADATION OF BROMODOMAIN-CONTAINING PROTEIN 9 (BRD9) BY CONJUGATION OF BRD9 INHIBITORS WITH E3 LIGASE LIGAND AND METHODS OF USE

RELATED APPLICATIONS

This application is a U.S. National Phase application, filed under 35 U.S.C. § 371, of International Application No. PCT/US2017/039004, filed on Jun. 23, 2017, which claims priority to and the benefit of U.S. Appl. No. 62/353,793, filed on Jun. 23, 2016 and U.S. Appl. No. 62/438,758, filed on Dec. 23, 2016, the entire contents of each of which are incorporated herein by reference.

BACKGROUND

Ubiquitin-Proteasome Pathway (UPP) is a critical pathway that regulates proteins and degrades misfolded or abnormal proteins. UPP is central to multiple cellular processes, and if defective or imbalanced, leads to pathogenesis of a variety of diseases. The covalent attachment of ubiquitin to specific protein substrates is achieved through the action of E3 ubiquitin ligases. These ligases comprise over 500 different proteins and are categorized into multiple classes defined by the structural element of their E3 functional activity. For example, cereblon (CRBN) interacts with damaged DNA binding protein 1 and forms an E3 ubiquitin ligase complex with Cullin 4 in which the proteins recognized by CRBN are ubiquitinated and degraded by proteasomes. Various immunomodulatory drugs (IMiDs), e.g., thalidomide and lenalidomide, binds to CRBN and modulates CRBN's role in the ubiquitination and degradation of protein factors involved in maintaining regular cellular function.

Bifunctional compounds composed of a target protein-binding moiety and an E3 ubiquitin ligase-binding moiety have been shown to induce proteasome-mediated degradation of selected proteins. These drug-like molecules offer the possibility of temporal control over protein expression, and could be useful as biochemical reagents for the treatment of diseases.

BRD9 is part of the SWI/SNF or BAF nucleosome-remodeling complex. The SWLSNF or BAF nucleosome-remodeling complex is a highly conserved multi-subunit complex, which uses the energy of ATP hydrolysis to remodel chromatin and mobilize nucleosomes. Studies have suggested that SWI/SNF activates transcription by remodeling nucleosomes, thereby permitting increased access of transcription factors for their binding sites. SWI/SNF has also been shown to be required for transcriptional repression of some genes, suggesting that SWLSNF controls transcription in diverse ways. Several subunits of SWLSNF possess intrinsic tumour-suppressor activity or are required for the activity of other tumour-suppressor genes, supporting a role of this complex in cancer development. For example, conditional inactivation of the Snf5 gene results in a highly penetrant cancer phenotype in mice. Moreover, various studies have determined that genes encoding subunits of the SWI/SNF or BAF complex are mutated in cancer about 20% of the time.

Inhibition of SWLSNF remodeling complex and BRD9 has been shown to affect cancer development and cell viability. Small molecule inhibitors of BRD9 have been identified, however, most of the known inhibitors possess poor potency. Alternative strategies to inhibit SWI/SNF remodeling complex and bromodomain proteins, such as BRD9, are needed. At present, suitable compounds with alternative mechanisms of action targeting BRD9 are not available. The present application addresses the need.

SUMMARY

The present application relates to novel bifunctional compounds, which function to recruit targeted proteins to E3 ubiquitin ligase for degradation, and methods of preparation and uses thereof. The bifunctional compound is of Formula X:

(X)

wherein:
the Targeting Ligand is capable of binding to a targeted protein, such as a bromodomain-containing protein (e.g., BRD9);
the Linker is a group that covalently binds to the Targeting Ligand and the Degron; and
the Degron is capable of binding to a ubiquitin ligase, such as an E3 ubiquitin ligase (e.g., cereblon).

The present application also relates to targeted degradation of proteins through the use of bifunctional compounds, including bifunctional compounds that link an E3 ubiquitin ligase-binding moiety to a ligand that binds the targeted proteins.

The present application also relates to a bifunctional compound of Formula I:

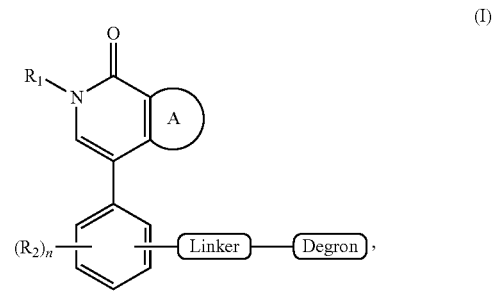

(I)

or
Targeting Ligand
or an enantiomer, diastereomer, stereoisomer, or pharmaceutically acceptable salt thereof, wherein:
$R_1$, $R_2$, A, and n are each as defined herein;
the Linker is a group that covalently binds to

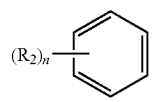

in Formula (I) and the Degron;
the Degron is capable of binding to a ubiquitin ligase, such as an E3 ubiquitin ligase (i.e., cereblon); and
the Targeting Ligand is capable of binding to a targeted protein, such as BRD9.

The present application further relates to a Degron of Formula D1 or Formula D2:

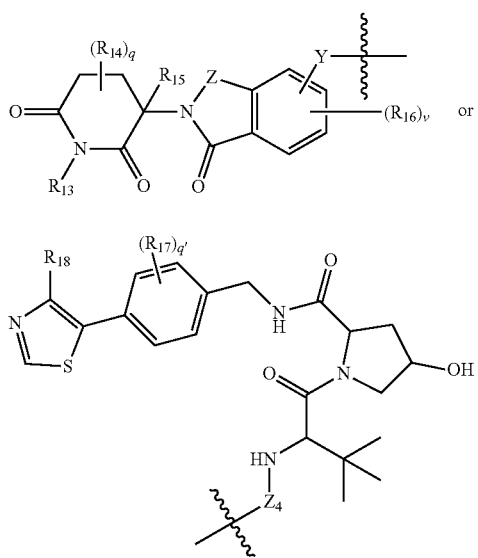

(D1)

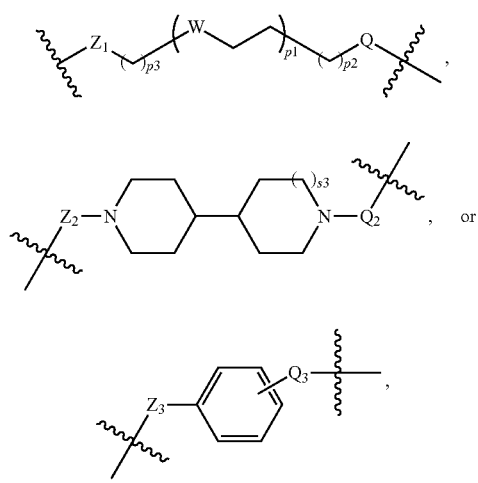

(D2)

or an enantiomer, diastereomer, or stereoisomer thereof, wherein Y, Z, $Z_4$, $R_{13}$, $R_{14}$, $R_{15}$, $R_{16}$, $R_{17}$, $R_{18}$, v, q, and q' are each as defined herein.

The present application further includes a Linker of Formula L1, L2, or L3:

(L1)

(L2)

(L3)

or an enantiomer, diastereomer, or stereoisomer thereof, wherein p1, p2, p3, s3, W, Q, $Q_2$, $Q_3$, $Z_1$, $Z_2$, and $Z_3$ are each as defined herein, the Linker is covalently bonded to a Degron via the

next to Q, $Q_2$, or $Q_3$, and covalently bonded to a Targeting Ligand via the

next to $Z_1$, $Z_2$, or $Z_3$.

The present application also relates to a pharmaceutical composition comprising a therapeutically effective amount of a bifunctional compound of the application, or an enantiomer, diastereomer, or stereoisomer thereof, or pharmaceutically acceptable salt, hydrate, solvate, or prodrug thereof, and a pharmaceutically acceptable carrier.

Another aspect of the present application relates to a method of inhibiting a bromodomain protein (e.g., BRD9). The method comprises administering to a subject in need thereof an effective amount of a bifunctional compound of the application, or an enantiomer, diastereomer, or stereoisomer thereof, or pharmaceutically acceptable salt, hydrate, solvate, or prodrug thereof, or a pharmaceutical composition of the application.

Another aspect of the present application relates to a method of modulating (e.g., decreasing) the amount of a bromodomain protein (e.g., BRD9). The method comprises administering to a subject in need thereof a therapeutically effective amount of a bifunctional compound of the application, or an enantiomer, diastereomer, or stereoisomer thereof, or pharmaceutically acceptable salt, hydrate, solvate, or prodrug thereof, or a pharmaceutical composition of the application.

Another aspect of the present application relates to a method of inhibiting BRD9. The method comprises administering to a subject in need thereof an effective amount of a bifunctional compound of the application, or an enantiomer, diastereomer, or stereoisomer thereof, or pharmaceutically acceptable salt, hydrate, solvate, or prodrug thereof, or a pharmaceutical composition of the application.

Another aspect of the present application relates to a method of modulating BRD9. The method comprises administering to a subject in need thereof a therapeutically effective amount of a bifunctional compound of the application, or an enantiomer, diastereomer, or stereoisomer thereof, or pharmaceutically acceptable salt, hydrate, solvate, or prodrug thereof, or a pharmaceutical composition of the application.

Another aspect of the present application relates to a method of treating or preventing a disease (e.g., a disease in which BRD9 plays a role). The method comprises administering to a subject in need thereof an effective amount of a bifunctional compound of the application, or an enantiomer, diastereomer, or stereoisomer thereof, or pharmaceutically acceptable salt, hydrate, solvate, or prodrug thereof, or a pharmaceutical composition of the application. In one aspect, the disease is BRD9 mediated disorder. In one aspect, the disease is a proliferative disease (e.g., a proliferative disease in which BRD9 plays a role).

Another aspect of the present application relates to a method of treating or preventing cancer in a subject, wherein the cancer cell comprises an activated BRD9 or wherein the subject is identified as being in need of BRD9 inhibition for the treatment or prevention of cancer. The method comprises administering to the subject an effective amount of a bifunctional compound of the application, or an enantiomer, diastereomer, or stereoisomer thereof, or pharmaceutically acceptable salt, hydrate, solvate, or prodrug thereof, or a pharmaceutical composition of the application.

Another aspect of the present application relates to a kit comprising a bifunctional compound capable of inhibiting BRD9 activity, selected from a bifunctional compound of the application, or an enantiomer, diastereomer, or stereoisomer thereof, or pharmaceutically acceptable salt, hydrate, solvate, or prodrug thereof.

Another aspect of the present application relates to a kit comprising a bifunctional compound capable of modulating (e.g., decreasing) the amount of BRD9, selected from a bifunctional compound of the application, or an enantiomer, diastereomer, or stereoisomer thereof, or pharmaceutically acceptable salt, hydrate, solvate, or prodrug thereof.

Another aspect of the present application relates to a bifunctional compound of the application, or an enantiomer, diastereomer, or stereoisomer thereof, or pharmaceutically acceptable salt, hydrate, solvate, or prodrug thereof, or a pharmaceutical composition of the application, for use in the manufacture of a medicament for inhibiting a bromodomain protein (e.g., BRD9) or for modulating (e.g., decreasing) the amount of a bromodomain protein (e.g., BRD9).

Another aspect of the present application relates to a bifunctional compound of the application, or an enantiomer, diastereomer, or stereoisomer thereof, or pharmaceutically acceptable salt, hydrate, solvate, or prodrug thereof, or a pharmaceutical composition of the application, for use in the manufacture of a medicament for inhibiting BRD9 or for modulating (e.g., decreasing) the amount of BRD9.

Another aspect of the present application relates to a bifunctional compound of the application, or an enantiomer, diastereomer, or stereoisomer thereof, or pharmaceutically acceptable salt, hydrate, solvate, or prodrug thereof, or a pharmaceutical composition of the application, for use in the manufacture of a medicament for treating or preventing a disease (e.g., a disease in which BRD9 plays a role). In one aspect, the disease is a BRD9 mediated disorder. In one aspect, the disease is a proliferative disease (e.g., a proliferative disease in which BRD9 plays a role).

Another aspect of the present application relates to a bifunctional compound of the application, or an enantiomer, diastereomer, or stereoisomer thereof, or pharmaceutically acceptable salt, hydrate, solvate, or prodrug thereof, or a pharmaceutical composition of the application, for use in the manufacture of a medicament for treating or preventing cancer in a subject, wherein the cancer cell comprises an activated BRD9 or wherein the subject is identified as being in need of BRD9 inhibition for the treatment or prevention of cancer.

Another aspect of the present application relates to a bifunctional compound of the application, or an enantiomer, diastereomer, or stereoisomer thereof, or pharmaceutically acceptable salt, hydrate, solvate, or prodrug thereof, or a pharmaceutical composition of the application, for use in inhibiting a bromodomain protein (e.g., BRD9) or modulating (e.g., decreasing) the amount of a bromodomain protein (e.g., BRD9).

Another aspect of the present application relates to a bifunctional compound of the application, or an enantiomer, diastereomer, or stereoisomer thereof, or pharmaceutically acceptable salt, hydrate, solvate, or prodrug thereof, or a pharmaceutical composition of the application, for use in inhibiting BRD9 or modulating (e.g., decreasing) the amount of BRD9.

Another aspect of the present application relates to a bifunctional compound of the application, or an enantiomer, diastereomer, or stereoisomer thereof, or pharmaceutically acceptable salt, hydrate, solvate, or prodrug thereof, or a pharmaceutical composition of the application, for use in treating or preventing a disease (e.g., a disease in which BRD9 plays a role). In one aspect, the disease is BRD9 mediated disorder. In one aspect, the disease is a proliferative disease (e.g., a proliferative disease in which BRD9 plays a role).

Another aspect of the present application relates to a bifunctional compound of the application, or an enantiomer, diastereomer, or stereoisomer thereof, or pharmaceutically acceptable salt, hydrate, solvate, or prodrug thereof, or a pharmaceutical composition of the application, for use in treating or preventing cancer in a subject, wherein the cancer cell comprises an activated BRD9 or wherein the subject is identified as being in need of BRD9 inhibition for the treatment or prevention of cancer.

The present application provides inhibitors of BRD9 that are therapeutic agents in the treatment or prevention of diseases such as cancer and metastasis.

The present application further provides compounds and compositions with an improved efficacy and/or safety profile relative to known BRD9 inhibitors. The present application also provides agents with novel mechanisms of action toward BRD9 proteins in the treatment of various types of diseases including cancer and metastasis.

The compounds and methods of the present application address unmet needs in the treatment of diseases or disorders in which pathogenic or oncogenic endogenous proteins (e.g., BRD9) play a role, such as cancer.

The details of the disclosure are set forth in the accompanying description below. Although methods and materials similar or equivalent to those described herein can be used in the practice or testing of the present application, illustrative methods and materials are now described. In the case of conflict, the present specification, including definitions, will control. In addition, the materials, methods, and examples are illustrative only and are not intended to be limiting. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

The contents of all references (including literature references, issued patents, published patent applications, and co-pending patent applications) cited throughout this application are hereby expressly incorporated herein in their entireties by reference. The references cited herein are not admitted to be prior art to the application.

DETAILED DESCRIPTION

Figure 1A:
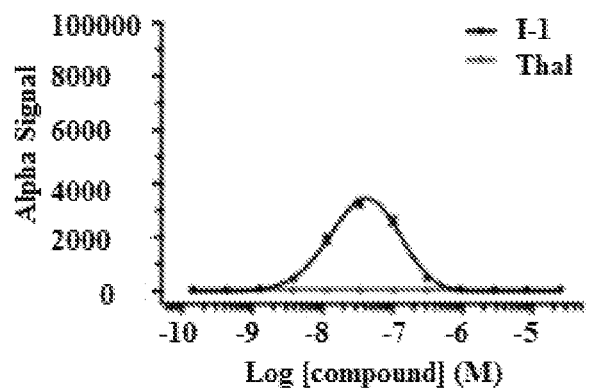
FIG. 1A is a graph measuring the formation of the BRD9:CRBN-DDBI protein complex induced by compound I-1 and unmodified thalidomide as detected by luminescence. The luminescence signal was measured as the concentration of compound I-1 and thalidomide was decreased. Compound I-1 was able to significantly induce formation of the complex relative to unmodified thalidomide. The x-axis is compound concentration measured in log units and the y-axis is the alpha signal measured in intensity.
Figure 1B:
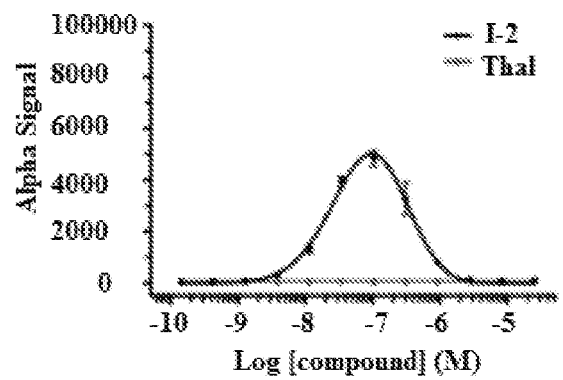
FIG. 1B is a graph measuring the formation of the BRD9:CRBN-DDBI protein complex induced by compound I-2 and unmodified thalidomide as detected by luminescence. The luminescence signal was measured as the concentration of compound I-2 and thalidomide was decreased. Compound I-2 was able to significantly induce formation of the complex relative to unmodified thalidomide. The x-axis is compound concentration measured in log units and the y-axis is the alpha signal measured in intensity.
Figure 1C:
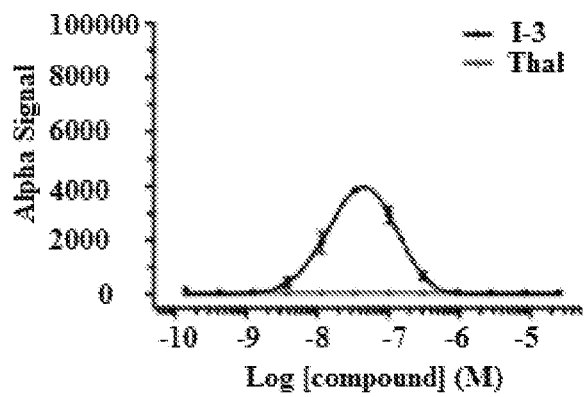
FIG. 1C is a graph measuring the formation of the BRD9:CRBN-DDBI protein complex induced by compound I-3 and unmodified thalidomide as detected by luminescence. The luminescence signal was measured as the concentration of compound I-3 and thalidomide was decreased. Compound I-3 was able to significantly induce formation of the complex relative to unmodified thalidomide. The x-axis is compound concentration measured in log units and the y-axis is the alpha signal measured in intensity.
Figure 2A:
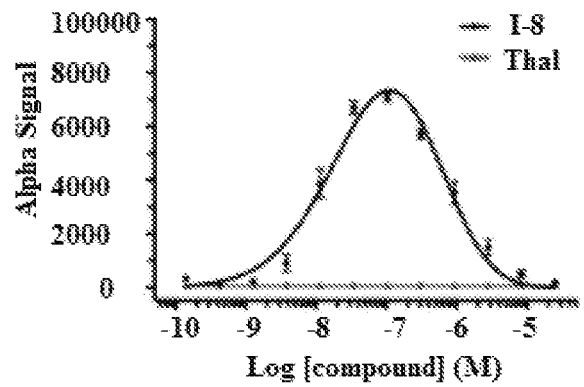
FIG. 2A is a graph measuring the formation of the BRD9:CRBN-DDBI protein complex induced by compound I-8 and unmodified thalidomide as detected by luminescence. The luminescence signal was measured as the concentration of compound I-8 and thalidomide was decreased. Compound I-8 was able to significantly induce formation of the complex relative to unmodified thalidomide. The x-axis is compound concentration measured in log units and the y-axis is the alpha signal measured in intensity.
Figure 2B:
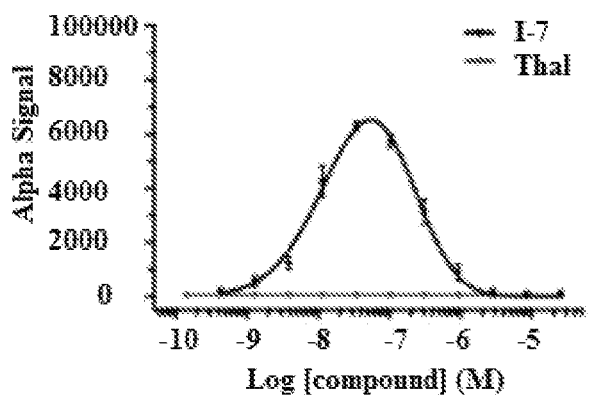
FIG. 2B is a graph measuring the formation of the BRD9:CRBN-DDBI protein complex induced by compound I-7 and unmodified thalidomide as detected by luminescence. The luminescence signal was measured as the concentration of compound I-7 and thalidomide was decreased. Compound I-7 was able to significantly induce formation of the complex relative to unmodified thalidomide. The x-axis is compound concentration measured in log units and the y-axis is the alpha signal measured in intensity.
Figure 2C:
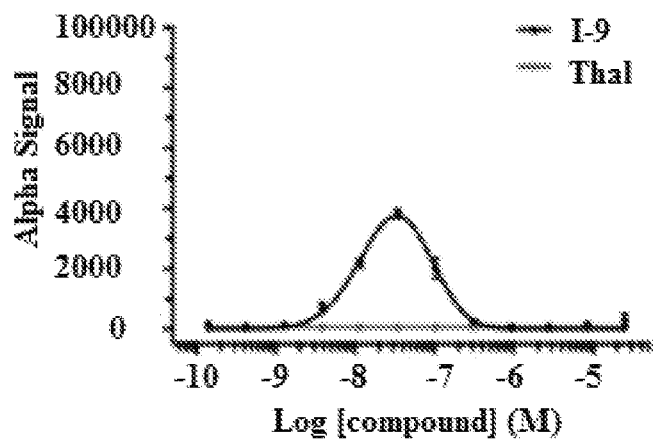
FIG. 2C is a graph measuring the formation of the BRD9:CRBN-DDBI protein complex induced by compound I-9 and unmodified thalidomide as detected by luminescence. The luminescence signal was measured as the concentration of compound I-9 and thalidomide was decreased. Compound I-9 was able to significantly induce formation of the complex relative to unmodified thalidomide. The x-axis is compound concentration measured in log units and the y-axis is the alpha signal measured in intensity.
Figure 3A:
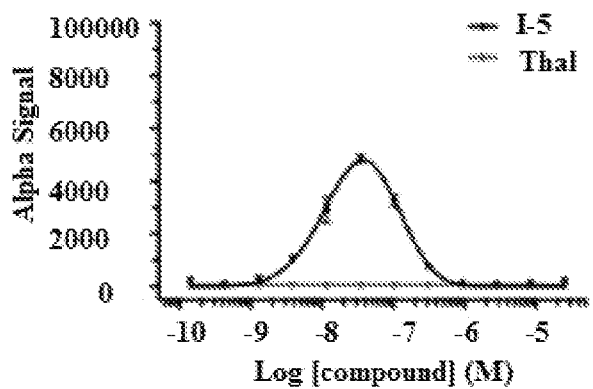
FIG. 3A is a graph measuring the formation of the BRD9:CRBN-DDBI protein complex induced by compound I-5 and unmodified thalidomide as detected by luminescence. The luminescence signal was measured as the concentration of compound I-5 and thalidomide was decreased. Compound I-5 was able to significantly induce formation of the complex relative to unmodified thalidomide. The x-axis is compound concentration measured in log units and the y-axis is the alpha signal measured in intensity.
Figure 3B:
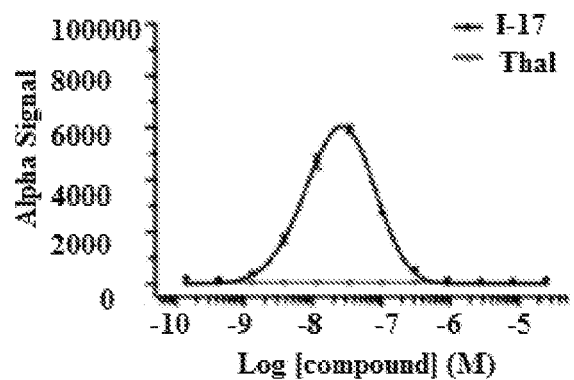
FIG. 3B is a graph measuring the formation of the BRD9:CRBN-DDBI protein complex induced by compound I-17 and unmodified thalidomide as detected by luminescence. The luminescence signal was measured as the concentration of compound I-17 and thalidomide was decreased. Compound I-17 was able to significantly induce formation of the complex relative to unmodified thalidomide. The x-axis is compound concentration measured in log units and the y-axis is the alpha signal measured in intensity.
Figure 3C:
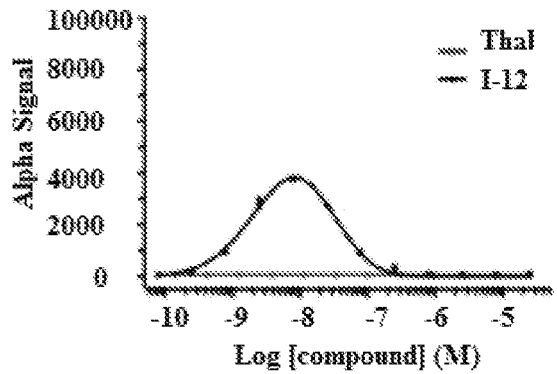
FIG. 3C is a graph measuring the formation of the BRD9:CRBN-DDBI protein complex induced by compound I-12 and unmodified thalidomide as detected by luminescence. The luminescence signal was measured as the concentration of compound I-12 and thalidomide was decreased. Compound I-12 was able to significantly induce formation of the complex relative to unmodified thalidomide. The x-axis is compound concentration measured in log units and the y-axis is the alpha signal measured in intensity.
Figure 4A:
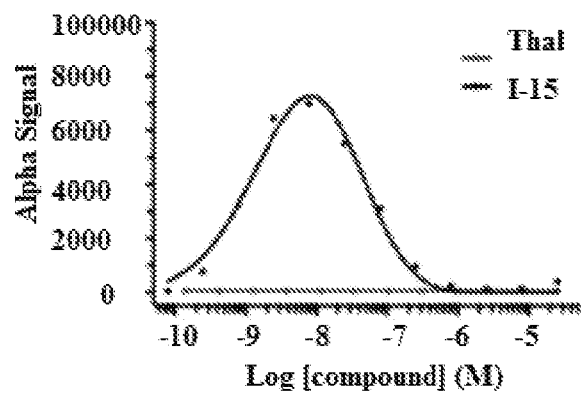
FIG. 4A is a graph measuring the formation of the BRD9:CRBN-DDBI protein complex induced by compound I-15 and unmodified thalidomide as detected by luminescence. The luminescence signal was measured as the concentration of compound I-15 and thalidomide was decreased. Compound I-15 was able to significantly induce formation of the complex relative to unmodified thalidomide. The x-axis is compound concentration measured in log units and the y-axis is the alpha signal measured in intensity.
Figure 4B:
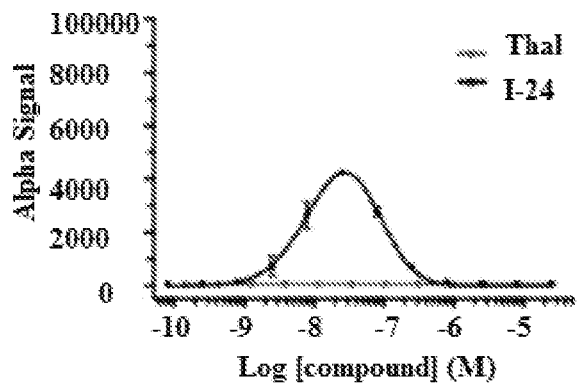
FIG. 4B is a graph measuring the formation of the BRD9:CRBN-DDBI protein complex induced by compound I-24 and unmodified thalidomide as detected by luminescence. The luminescence signal was measured as the concentration of compound I-24 and thalidomide was decreased. Compound I-24 was able to significantly induce formation of the complex relative to unmodified thalidomide. The x-axis is compound concentration measured in log units and the y-axis is the alpha signal measured in intensity.
Figure 4C:
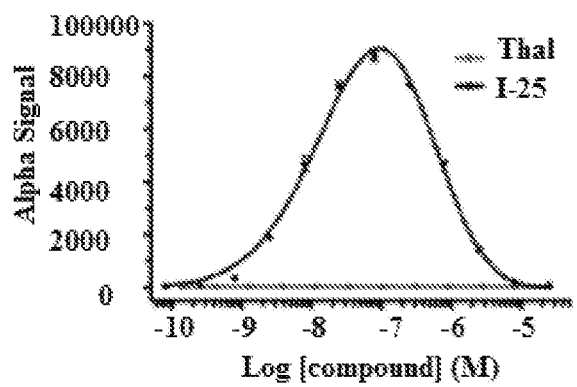
FIG. 4C is a graph measuring the formation of the BRD9:CRBN-DDBI protein complex induced by compound I-25 and unmodified thalidomide as detected by luminescence. The luminescence signal was measured as the concentration of compound I-25 and thalidomide was decreased. Compound I-25 was able to significantly induce formation of the complex relative to unmodified thalidomide. The x-axis is compound concentration measured in log units and the y-axis is the alpha signal measured in intensity.
Figure 5A:
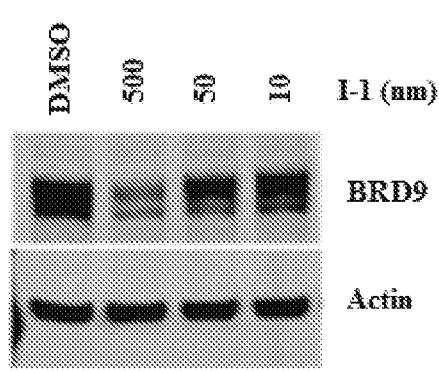
FIG. 5A is a Western Blot image of the effect of 500, 50, and 10 nM of I-1 on BRD9 degradation where actin was used as a control.
Figure 5B:
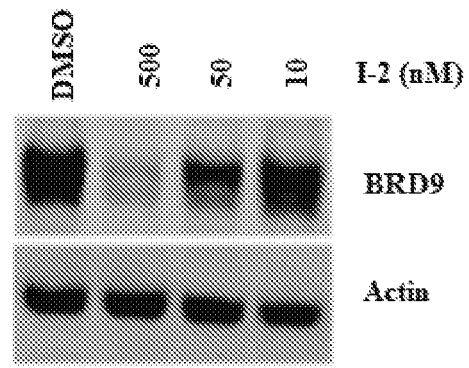
FIG. 5B is a Western Blot image of the effect of 500, 50, and 10 nM of I-2 on BRD9 degradation where actin was used as a control.
Figure 5C:
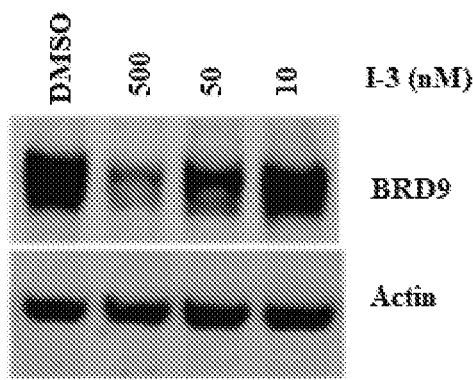
FIG. 5C is a Western Blot image of the effect of 500, 50, and 10 nM of I-3 on BRD9 degradation where actin was used as a control.
Figure 5D:
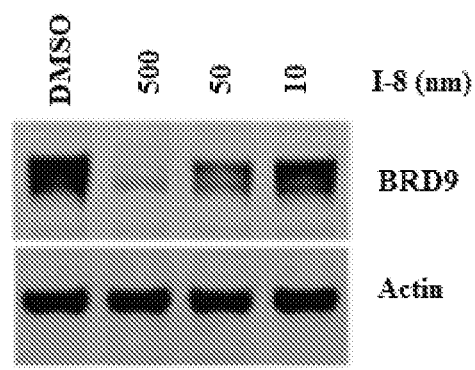
FIG. 5D is a Western Blot image of the effect of 500, 50, and 10 nM of I-8 on BRD9 degradation where actin was used as a control.
Figure 5E:
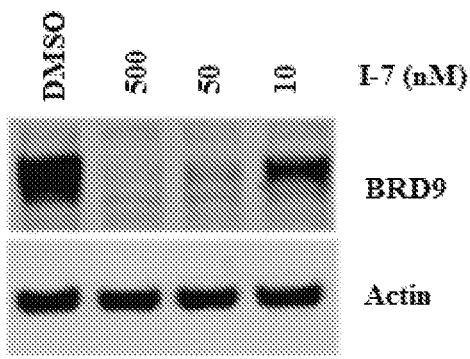
FIG. 5E is a Western Blot image of the effect of 500, 50, and 10 nM of I-7 on BRD9 degradation where actin was used as a control.
Figure 5F:
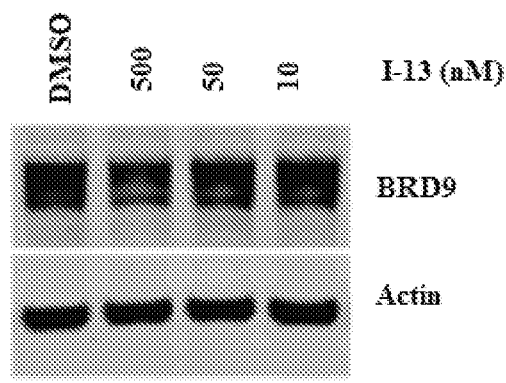
FIG. 5F is a Western Blot image of the effect of 500, 50, and 10 nM of I-13 on BRD9 degradation where actin was used as a control.
Figure 6A:
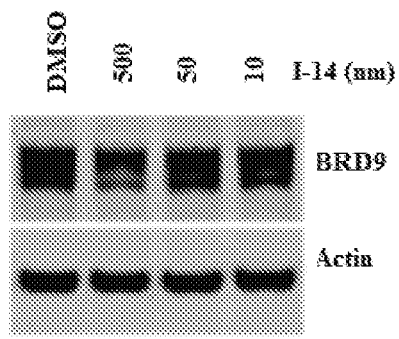
FIG. 6A is a Western Blot image of the effect of 500, 50, and 10 nM of I-14 on BRD9 degradation where actin was used as a control.
Figure 6B:
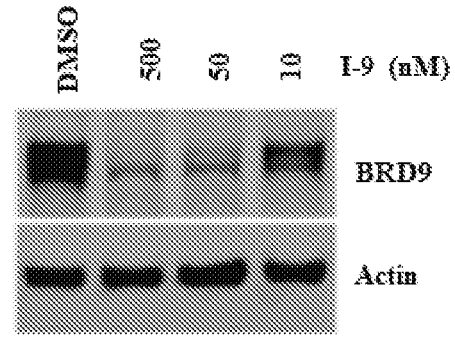
FIG. 6B is a Western Blot image of the effect of 500, 50, and 10 nM of I-9 on BRD9 degradation where actin was used as a control.
Figure 6C:
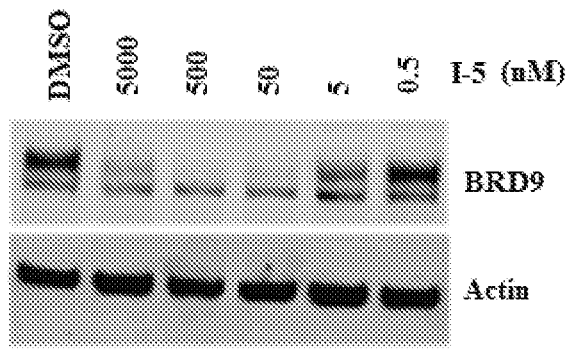
FIG. 6C is a Western Blot image of the effect of 500, 50, and 10 nM of I-5 on BRD9 degradation.
Figure 6D:
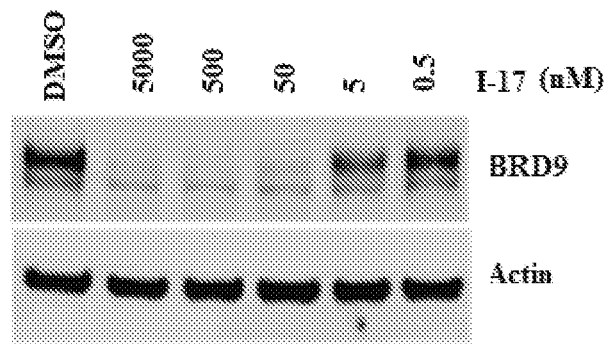
FIG. 6D is a Western Blot image of the effect of 500, 50, and 10 nM of I-17 on BRD9 degradation where actin was used as a control.
Figure 7A:
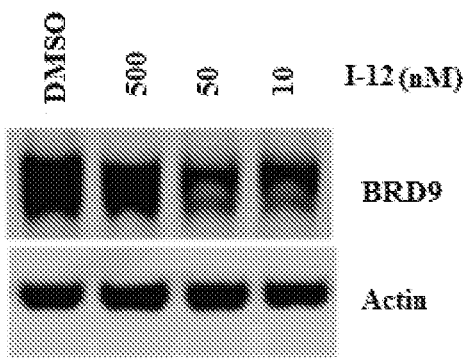
FIG. 7A is a Western Blot image of the effect of 500, 50, and 10 nM of I-12 on BRD9 degradation where actin was used as a control.
Figure 7B:
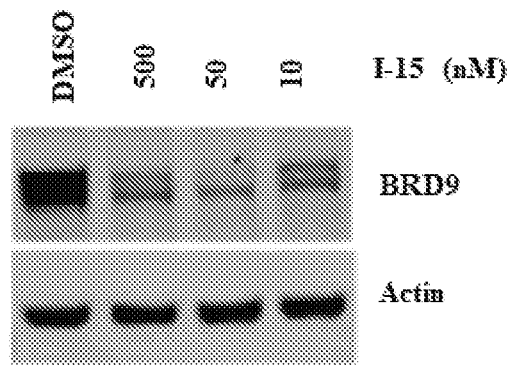
FIG. 7B is a Western Blot image of the effect of 500, 50, and 10 nM of I-15 on BRD9 degradation where actin was used as a control.
Figure 7C:
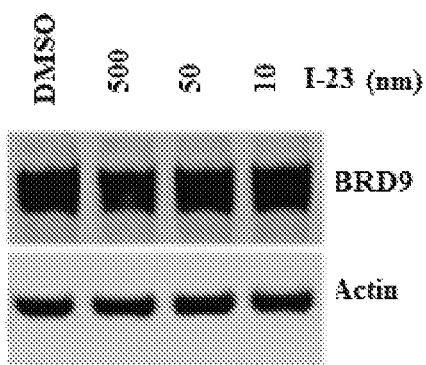
FIG. 7C is a Western Blot image of the effect of 500, 50, and 10 nM of I-23 on BRD9 degradation where actin was used as a control.
Figure 7D:
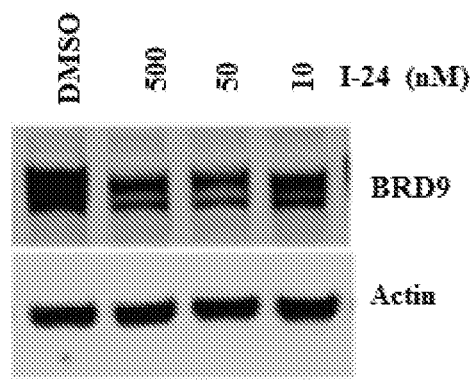
FIG. 7D is a Western Blot image of the effect of 500, 50, and 10 nM of I-24 on BRD9 degradation where actin was used as a control.
Figure 7E:
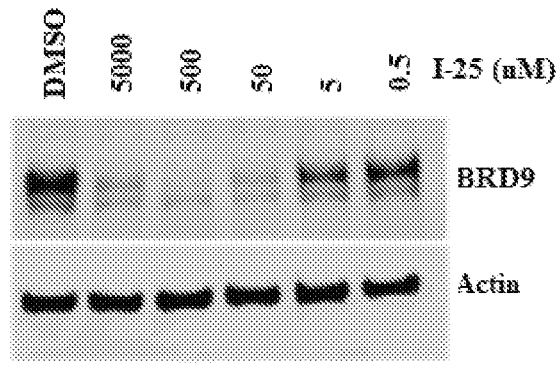
FIG. 7E is a Western Blot image of the effect of 500, 50, and 10 nM of I-25 on BRD9 degradation where actin was used as a control.

The present application relates to novel bifunctional compounds, which function to recruit targeted proteins to E3 ubiquitin ligase for degradation, and methods of preparation and uses thereof. The bifunctional compound is of Formula X:

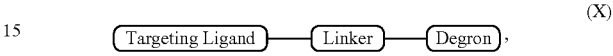

wherein:
the Targeting Ligand is capable of binding to a targeted protein, such as a bromodomain-containing protein (e.g., BRD9);
the Linker is a group that covalently binds to the Targeting Ligand and the Degron; and
the Degron is capable of binding to a ubiquitin ligase, such as an E3 ubiquitin ligase (e.g., cereblon).

The present application also relates to targeted degradation of proteins through the use of bifunctional compounds, including bifunctional compounds that link an E3 ubiquitin ligase-binding moiety to a ligand that binds the targeted proteins.

The present application also relates to a bifunctional compound of Formula I:

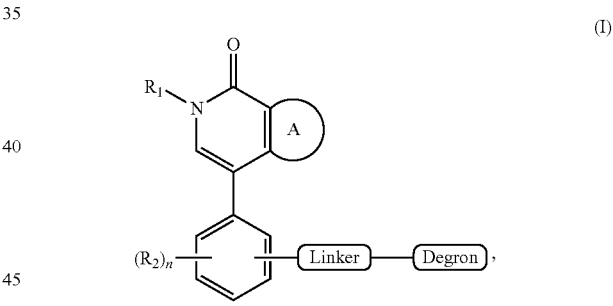

or
Targeting Ligand
or an enantiomer, diastereomer, stereoisomer, or pharmaceutically acceptable salt thereof, wherein:
$R_1$, $R_2$, A, and n are each as defined herein;
the Linker is a group that covalently binds to

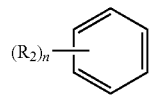

in Formula (I) and the Degron:
the Degron is capable of binding to a ubiquitin ligase, such as an E3 ubiquitin ligase (i.e., cereblon); and
the Targeting Ligand is capable of binding to a targeted protein, such as BRD9.

The present application further relates to a Degron of Formula D1:

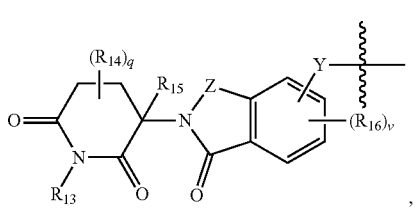

(D1)

or an enantiomer, diastereomer, or stereoisomer thereof, wherein Y, Z, $R_{13}$, $R_{14}$, $R_{15}$, $R_{16}$, q, and v are each as defined herein.

The present application further relates to a Degron of Formula D2:

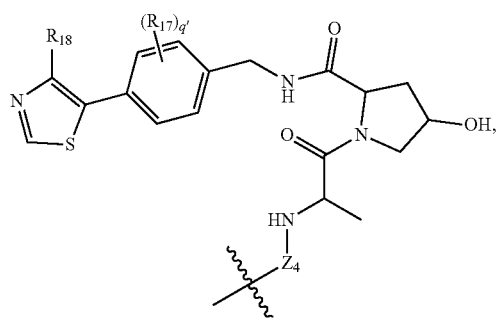

(D2)

or an enantiomer, diastereomer, or stereoisomer thereof, wherein $Z_4$, $R_{17}$, $R_{18}$, and q' are each as defined herein.

The present application further relates to a Linker of Formula L1:

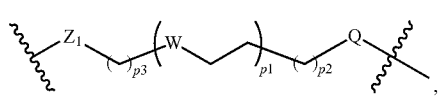

(L1)

or an enantiomer, diastereomer, or stereoisomer thereof, wherein p1, p2, p3, W, Q, and $Z_1$ are each as defined herein, the Linker is covalently bonded to a Degron via the

next to Q, and covalently bonded to a Targeting Ligand via the

next to $Z_1$.

The present application further relates to a Linker of Formula L2:

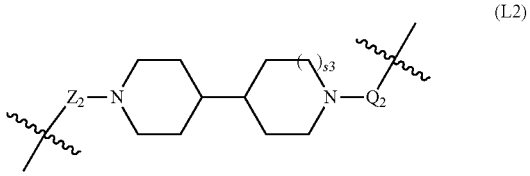

(L2)

or an enantiomer, diastereomer, or stereoisomer thereof, wherein s3, $Q_2$, and $Z_2$ are each as defined herein, the Linker is covalently bonded to a Degron via the

next to $Q_2$, and covalently bonded to the Targeting Ligand via the

next to $Z_2$.

The present application further relates to a Linker of Formula L3:

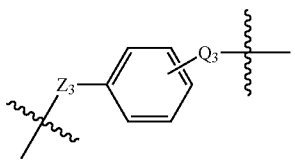

(L3)

or an enantiomer, diastereomer, or stereoisomer thereof, wherein $Q_3$ and $Z_3$ are each as defined herein, the Linker is covalently bonded to a Degron via the

next to $Q_3$, and covalently bonded to a Targeting Ligand via the

next to $Z_3$.

Targeting Ligand

Targeting Ligand (TL) (or target protein moiety or target protein ligand or ligand) is a small molecule which is capable of binding to a target protein of interest, such BRD9.

In one embodiment, a Targeting Ligand is a compound of Formula TL-I:

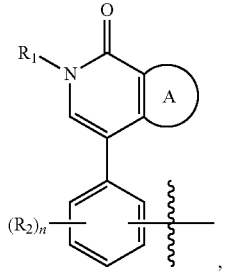

(TL-I)

or an enantiomer, diastereomer, stereoisomer, or pharmaceutically acceptable salt thereof, wherein:

A is phenyl or 5- or 6-membered heteroaryl containing 1 or 2 heteroatoms selected from N and S, wherein the phenyl or heteroaryl is optionally substituted with 1 to 3 $R_3$;

$R_1$ is H, $(C_1-C_4)$ alkyl, or $(C_1-C_4)$ haloalkyl;

each $R_2$ is independently $(C_1-C_4)$ alkyl, $(C_1-C_4)$ haloalkyl, $(C_1-C_4)$ alkoxy, $(C_1-C_4)$ haloalkoxy, halogen, OH, or $NH_2$;

each $R_3$ is independently $(C_1-C_4)$ alkyl, $(C_1-C_4)$ haloalkyl, $(C_1-C_4)$ alkoxy, $(C_1-C_4)$ haloalkoxy, halogen, OH, $NH_2$, or

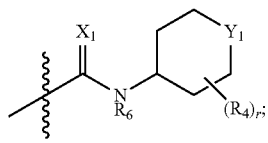

$X_1$ is $NR_5$ or O;

$Y_1$ is $S(O)_a$ or $NR_5$;

each $R_4$ is independently $(C_1-C_4)$ alkyl, $(C_1-C_4)$ haloalkyl, halogen, or —C(O)$(C_1-C_3)$alkyl;

each $R_5$ is independently H or $(C_1-C_4)$ alkyl;

$R_6$ is H or $(C_1-C_4)$ alkyl;

a is 0, 1, or 2; and n and r are each independently 0, 1, 2, or 3;

wherein the Targeting Ligand is bonded to the Linker via the

next to

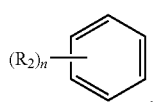

In some embodiments, A is

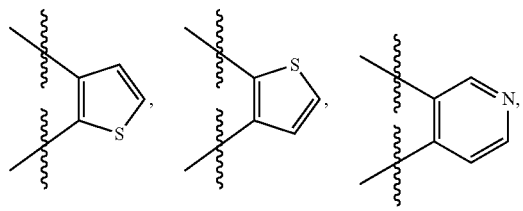

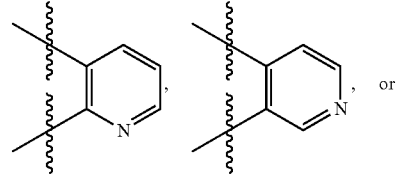

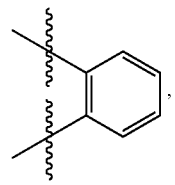

wherein each A is optionally substituted with 1 to 3 $R_3$. In other embodiments, A is

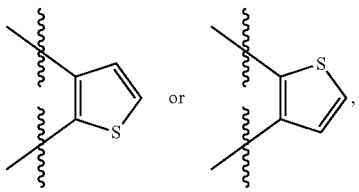

wherein each A is optionally substituted with 1 to 3 $R_3$. In other embodiments, A is

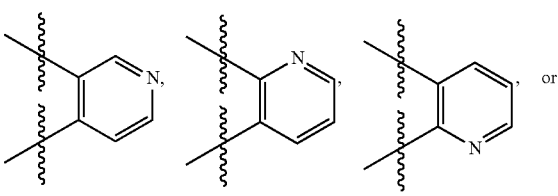

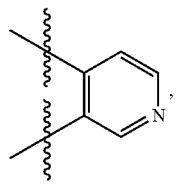

wherein each A is optionally substituted with 1 to 3 $R_3$. In other embodiments, A is

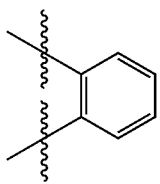 [SMILES: *c1ccccc1*]

optionally substituted with 1 to 3 $R_3$. In other embodiments, A is

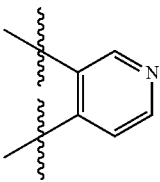 [SMILES: *c1ccncc1*]

optionally substituted with 1 to 3 $R_3$. In other embodiments. A is

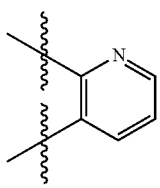 [SMILES: *c1cccnc1*]

optionally substituted with 1 to 3 $R_3$. In other embodiments, A is

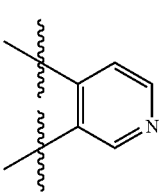 [SMILES: *c1ccncc1*]

optionally substituted with 1 to 3 $R_3$. In other embodiments, A is

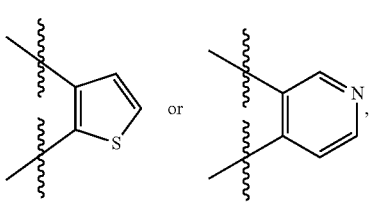

wherein each A is optionally substituted with 1 to 3 $R_3$. In other embodiments. A is

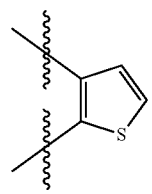 [SMILES: *c1ccsc1*]

optionally substituted with 1 to 3 $R_3$. In other embodiments, A is

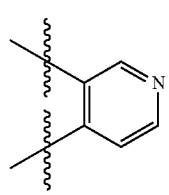 [SMILES: *c1ccncc1*]

optionally substituted with 1 to 3 $R_3$. In other embodiments, A is

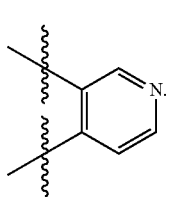 [SMILES: *c1ccncc1*]

In some embodiments, $R_1$ is H, $(C_1\text{-}C_3)$ alkyl, or $(C_1\text{-}C_3)$ haloalkyl. In other embodiments, $R_1$ is H or $(C_1\text{-}C_4)$ alkyl. In other embodiments, $R_1$ is H, methyl, ethyl, n-propyl, or i-propyl. In other embodiments, $R_1$ is H, methyl or ethyl. In other embodiments, $R_1$ is H. In other embodiments, $R_1$ is $(C_1\text{-}C_4)$ alkyl. In other embodiments, $R_1$ is methyl, ethyl, n-propyl, or i-propyl. In other embodiments, $R_1$ is methyl or ethyl. In other embodiments, $R_1$ is $(C_1\text{-}C_4)$ alkyl or $(C_1\text{-}C_4)$ haloalkyl.

In some embodiments, at least one $R_2$ is $(C_1\text{-}C_3)$ alkyl, $(C_1\text{-}C_3)$ haloalkyl, $(C_1\text{-}C_3)$ alkoxy, $(C_1\text{-}C_3)$ haloalkoxy, halogen, OH, or $NH_2$. In other embodiments, at least one $R_2$ is $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, or halogen. In other embodiments, at least one $R_2$ is halogen, OH, or $NH_2$. In other embodiments, at least one $R_2$ is $(C_1\text{-}C_4)$ alkyl, $(C_1\text{-}C_4)$ haloalkyl, $(C_1\text{-}C_4)$ alkoxy, or $(C_1\text{-}C_4)$ haloalkoxy. In other embodiments, at least one $R_2$ is $(C_1\text{-}C_4)$ alkyl, $(C_1\text{-}C_4)$ alkoxy, or halogen. In other embodiments, at least one $R_2$ is $(C_1\text{-}C_4)$ alkoxy or halogen. In other embodiments, at least one $R_2$ is $(C_1\text{-}C_4)$ alkoxy. In other embodiments, at least one $R_2$ is $(C_1\text{-}C_3)$ alkoxy. In other embodiments, at least one $R_2$ is methoxy, ethoxy, n-propoxy, or i-propoxy. In other embodiments, at least one $R_2$ is methoxy or ethoxy. In other embodiments, at least one $R_2$ is methoxy.

In some embodiments, at least one $R_3$ is $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, halogen, OH, $NH_2$, or

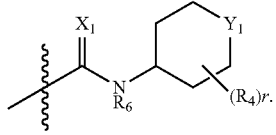

In other embodiments, at least one $R_3$ is $(C_1\text{-}C_4)$ alkyl, $(C_1\text{-}C_4)$ haloalkyl, $(C_1\text{-}C_4)$ alkoxy, $(C_1\text{-}C_4)$ haloalkoxy, halogen, OH, or $NH_2$. In some embodiments, at least one $R_3$ is

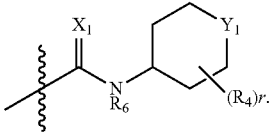

In other embodiments, at least one $R_3$ is $(C_1\text{-}C_4)$ alkyl, $(C_1\text{-}C_4)$ haloalkyl, $(C_1\text{-}C_4)$ alkoxy, or $(C_1\text{-}C_4)$ haloalkoxy. In other embodiments, at least one $R_3$ is $(C_1\text{-}C_4)$ alkyl, halogen. OH, or $NH_2$. In other embodiments, at least one $R_3$ is $(C_1\text{-}C_4)$ alkyl, $(C_1\text{-}C_4)$ alkoxy, halogen, OH, or $NH_2$. In other embodiments, at least one $R_3$ is $(C_1\text{-}C_3)$ alkyl, $(C_1\text{-}C_3)$ haloalkyl, $(C_1\text{-}C_3)$ alkoxy, $(C_1\text{-}C_3)$ haloalkoxy, halogen, OH, or $NH_2$.

In some embodiments, $X_1$ is $NR_5$. In other embodiments, $X_1$ is NH. In other embodiments. $X_1$ is O.

In some embodiments, $Y_1$ is $S(O)_a$. In other embodiments, $Y_1$ is $S(O)_2$. In other embodiments, $Y_1$ is $S(O)$. In other embodiments, $Y_1$ is S. In other embodiments, $Y_1$ is $NR_5$.

In some embodiments, at least one $R_4$ is $(C_1\text{-}C_3)$ alkyl, $(C_1\text{-}C_3)$ haloalkyl, halogen, or $—C(O)(C_1\text{-}C_3)$alkyl. In other embodiments, at least one $R_4$ is $(C_1\text{-}C_3)$ alkyl, $(C_1\text{-}C_3)$ haloalkyl, or halogen. In other embodiments, at least one R is $(C_1\text{-}C_3)$ alkyl, $(C_1\text{-}C_3)$ haloalkyl, or $—C(O)(C_1\text{-}C_3)$alkyl. In other embodiments, at least one $R_4$ is $(C_1\text{-}C_3)$ alkyl, halogen, or $—C(O)(C_1\text{-}C_3)$alkyl. In other embodiments, at least one $R_4$ is $(C_1\text{-}C_3)$ alkyl or $—C(O)(C_1\text{-}C_3)$alkyl. In other embodiments, at least one $R_1$ is $(C_1\text{-}C_3)$ alkyl or halogen.

In some embodiments, $R_5$ is H or $(C_1\text{-}C_3)$ alkyl. In other embodiments, $R_5$ is H. In other embodiments, $R_5$ is $(C_1\text{-}C_4)$ alkyl. In other embodiments, $R_5$ is $(C_1\text{-}C_3)$ alkyl. In other embodiments, $R_5$ is H, methyl, ethyl, n-propyl, or i-propyl. In other embodiments, $R_5$ is H, methyl, or ethyl. In other embodiments, $R_5$ is methyl, ethyl, n-propyl, or i-propyl. In other embodiments, $R_5$ is methyl or ethyl.

In some embodiments, $R_6$ is H or $(C_1\text{-}C_3)$ alkyl. In other embodiments, $R_6$ is H. In other embodiments, $R_6$ is $(C_1\text{-}C_4)$ alkyl. In other embodiments, $R_6$ is $(C_1\text{-}C_3)$ alkyl. In other embodiments, $R_6$ is H, methyl, ethyl, n-propyl, or i-propyl. In other embodiments, $R_6$ is H, methyl, or ethyl. In other embodiments, $R_6$ is methyl, ethyl, n-propyl, or i-propyl. In other embodiments, $R_6$ is methyl or ethyl.

In some embodiments, a is 0. In other embodiments, a is 1. In other embodiments, a is 2. In other embodiments, a is 0 or 1. In other embodiments, a is 1 or 2.

In some embodiments, n is 0. In other embodiments, n is 1. In other embodiments, n is 2. In other embodiments, n is 3. In other embodiments, n is 0 or 1. In other embodiments, n is 1 or 2. In other embodiments, n is 0, 1 or 2. In other embodiments, n is 1, 2 or 3.

In some embodiments, r is 0. In other embodiments, r is 1. In other embodiments, r is 2. In other embodiments, r is 3. In other embodiments, r is 0 or 1. In other embodiments, r is 1 or 2. In other embodiments, r is 0, 1 or 2. In other embodiments, r is 1, 2 or 3.

Any of the groups described herein for any of A, $X_1$, $Y_1$, $R_1$, $R_2$, $R_3$, $R_4$, $R_5$, $R_6$, a, n, and r can be combined with any of the groups described herein for one or more of the remainder of A, $X_1$, $Y_1$, $R_1$, $R_2$, $R_3$, $R_4$, $R_5$, $R_6$, a, n, and r, and may further be combined with any of the groups described herein for the Linker.

For a Targeting Ligand of Formula TL-I:

(1) In one embodiment, A is

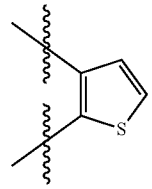 [SMILES: *c1ccsc1*]

and $R_3$ is

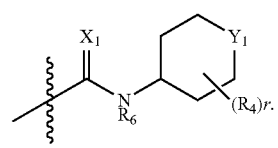

(2) In one embodiment, A is

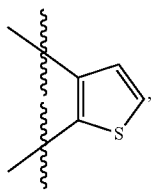 [SMILES: *c1ccsc1*]

$R_3$ is

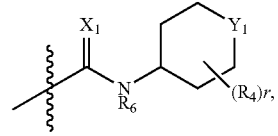

and $X_1$ is $NR_5$.

(3) In one embodiment, A is

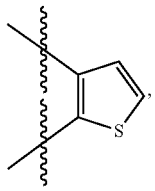 [SMILES: *c1ccsc1*]

$R_3$, is

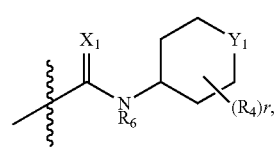

and $X_1$ is NH.

(4) In one embodiment, A is
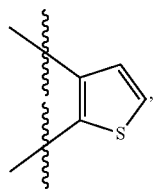 [SMILES: *c1ccsc1*]
$R_3$ is
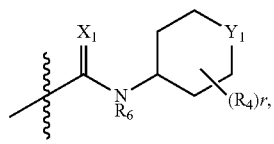
and $X_1$ is O.
(5) In one embodiment, A is
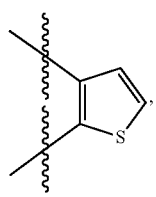 [SMILES: *c1ccsc1*]
$R_3$ is
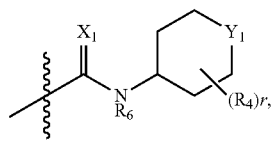
and $Y_1$ is S.
(6) In one embodiment, A is
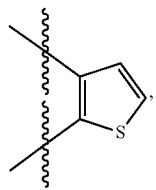 [SMILES: *c1ccsc1*]
$R_3$ is
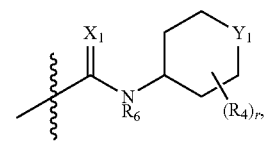
and $Y_1$ is S(O).
(7) In one embodiment, A is
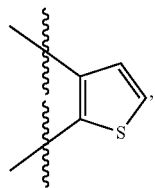 [SMILES: *c1ccsc1*]
$R_3$ is
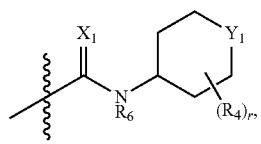
and $Y_1$ is $S(O)_2$.
(8) In one embodiment, A is
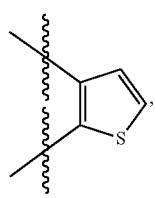 [SMILES: *c1ccsc1*]
$R_3$ is
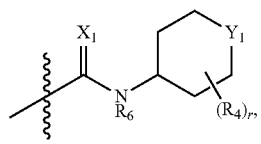
$X_1$ is $NR_5$, and $Y_1$ is S.
(9) In one embodiment, A is
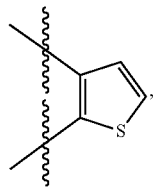 [SMILES: *c1ccsc1*]
$R_3$ is
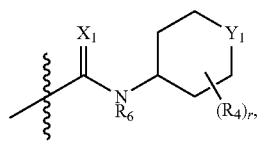
$X_1$ is $NR_5$, and $Y_1$ is S(O).

(10) In one embodiment, A is
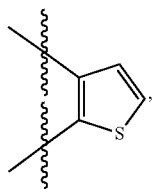 [SMILES: *c1ccsc1*]
$R_3$ is
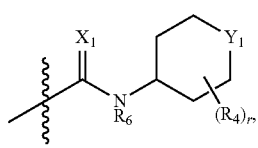
$X_1$ is $NR_5$, and $Y_1$ is $S(O)_2$.
(11) In one embodiment, A is
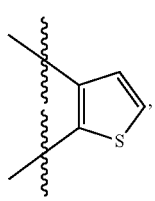 [SMILES: *c1ccsc1*]
$R_3$ is
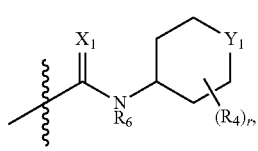
$X_1$ is NH, and $Y_1$ is S.
(12) In one embodiment, A is
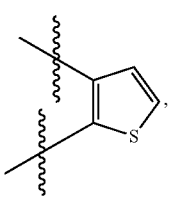 [SMILES: *c1ccsc1*]
$R_3$ is
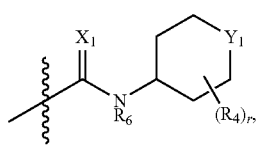
$X_1$ is NH, and $Y_1$ is S(O).
(13) In one embodiment, A is
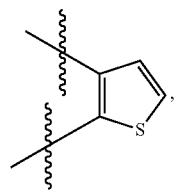 [SMILES: *c1ccsc1*]
$R_3$ is
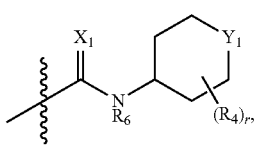
$X_1$ is NH, and $Y_1$ is S(O).
(14) In one embodiment, A is
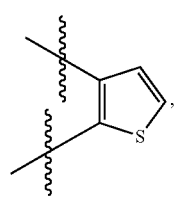 [SMILES: *c1ccsc1*]
$R_3$ is
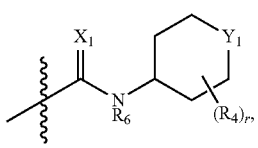
$X_1$ is NH, and $Y_1$ is S(O).
(15) In one embodiment, A is
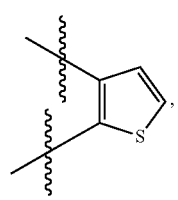 [SMILES: *c1ccsc1*]
$R_3$ is
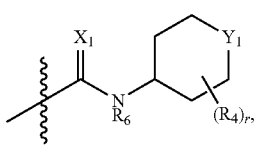
$X_1$ is NH, and $Y_1$ is S(O).

(16) In one embodiment, A is

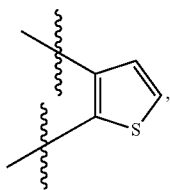 [SMILES: *c1ccsc1*]

$R_3$ is

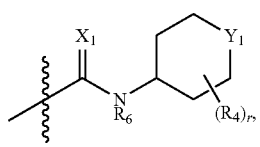

$X_1$ is O, and $Y_1$ is $S(O)_2$.

(17) In one embodiment, A, $R_3$, $X_1$, and $Y_1$ are each as defined, where applicable, in any one of (1)-(16), and $R_1$ is H.
(18) In one embodiment, A, $R_3$, $X_1$, and $Y_1$ are each as defined, where applicable, in any one of (1)-(16), and $R_1$ is $(C_1-C_4)$ alkyl.
(19) In one embodiment, A, $R_3$, $X_1$, and $Y_1$ are each as defined, where applicable, in any one of (1)-(16), and $R_1$ is methyl.
(20) In one embodiment, A, $R_3$, $X_1$, and $Y_1$ are each as defined, where applicable, in any one of (1)-(16), and $R_1$ is ethyl.
(21) In one embodiment, A, $R_3$, $X_1$, and $Y_1$ are each as defined, where applicable, in any one of (1)-(16), and $R_2$ is $(C_1-C_4)$ alkoxy.
(22) In one embodiment, A, $R_3$, $X_1$, and $Y_1$ are each as defined, where applicable, in any one of (1)-(16), and $R_2$ is $(C_1-C_4)$ methoxy.
(23) In one embodiment, A, $R_3$, $X_1$, and $Y_1$ are each as defined, where applicable, in any one of (1)-(16), $R_1$ is H, and $R_2$ is $(C_1-C_4)$ alkoxy.
(24) In one embodiment, A, $R_3$, $X_1$, and $Y_1$ are each as defined, where applicable, in any one of (1)-(16), $R_1$ is H, and $R_2$ is $(C_1-C_4)$ methoxy.
(25) In one embodiment, A, $R_3$, $X_1$, and $Y_1$ are each as defined, where applicable, in any one of (1)-(16), $R_1$ is $(C_1-C_4)$ alkyl, and $R_2$ is $(C_1-C_4)$ alkoxy.
(26) In one embodiment, A, $R_3$, $X_1$, and $Y_1$ are each as defined, where applicable, in any one of (1)-(16), $R_1$ is $(C_1-C_4)$ alkyl, and $R_2$ is methoxy.
(27) In one embodiment, A, $R_3$, $X_1$, and $Y_1$ are each as defined, where applicable, in any one of (1)-(16), $R_1$ is methyl, and $R_2$ is $(C_1-C_4)$ alkoxy.
(28) In one embodiment, A, $R_3$, $X_1$, and $Y_1$ are each as defined, where applicable, in any one of (1)-(16). $R_1$ is methyl, and $R_2$ is methoxy.
(29) In one embodiment, A, $R_3$, $X_1$, and $Y_1$ are each as defined, where applicable, in any one of (1)-(16), $R_1$ is ethyl, and $R_2$ is $(C_1-C_4)$ alkoxy.
(30) In one embodiment, A, $R_1$, $X_1$, and $Y_1$ are each as defined, where applicable, in any one of (1)-(16), $R_1$ is ethyl, and $R_2$ is methoxy.
(31) In one embodiment, A, $R_1$, $R_3$, $X_1$, and $Y_1$ are each as defined in any one of (17)-(20), and n is 1.
(32) In one embodiment, A, $R_1$, $R_3$, $X_1$, and $Y_1$ are each as defined in any one of (17)-(20), and n is 2.
(33) In one embodiment, A, $R_2$, $R_3$, $X_1$, and $Y_1$ are each as defined in (21) or (22), and n is 1.
(34) In one embodiment, A, $R_2$, $R_3$, $X_1$, and $Y_1$ are each as defined in (21) or (22), and n is 2.
(35) In one embodiment, A, $R_1$, $R_2$, R %, $X_1$, and $Y_1$ are each as defined in any one of (23)-(30), and n is 1.
(36) In one embodiment, A, $R_1$, $R_2$, $R_3$, $X_1$, and $Y_1$ are each as defined in any one of (23)-(30), and n is 2.
(37) In one embodiment, A, $R_1$, $R_2$, $R_3$, $X_1$, $Y_1$, and n are each as defined, where applicable, in any one of (31)-(36), and r is 0.
(38) In one embodiment, A, $R_1$, $R_2$, $R_3$. $X_1$, $Y_1$, n, and r are each as defined, where applicable, in any one of (31)-(37), and $R_6$ is H.
(39) In one embodiment, A, $R_1$, $R_2$, $R_3$, $X_1$, $Y_1$, n, and r are each as defined, where applicable, in any one of (31)-(37), and $R_6$ is methyl.
(40) In one embodiment, A is

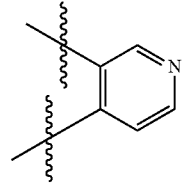 [SMILES: *c1ccncc1*]

and R is $(C_1-C_4)$ alkyl.

(41) In one embodiment, A is

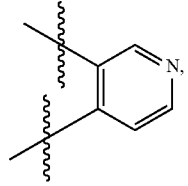 [SMILES: *c1ccncc1*]

$R_1$ is $(C_1-C_4)$ alkyl, and $R_2$ is $(C_1-C_4)$ alkoxy.

(42) In one embodiment, A is

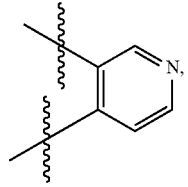 [SMILES: *c1ccncc1*]

$R_1$ is $(C_1-C_4)$ alkyl, and $R_2$ is methoxy.

(43) In one embodiment, A is

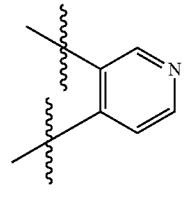 [SMILES: *c1ccncc1*]

$R_1$ is methyl.

(44) In one embodiment, A is

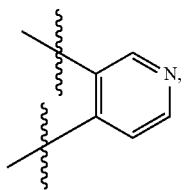 [SMILES: *c1ccncc1*]

$R_1$ is methyl, and $R_2$ is $(C_1-C_4)$ alkoxy.

(45) In one embodiment, A is

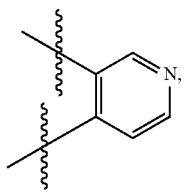 [SMILES: *c1ccncc1*]

$R_1$ is methyl, and $R_2$ is methoxy.

(46) In one embodiment, A is

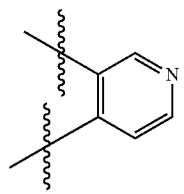 [SMILES: *c1ccncc1*]

and $R_1$ is ethyl.

(47) In one embodiment, A is

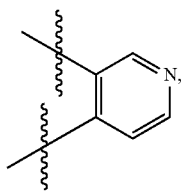 [SMILES: *c1ccncc1*]

$R_1$ is ethyl, and $R_2$ is $(C_1-C_4)$ alkoxy.

(48) In one embodiment, A is

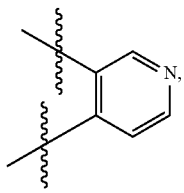 [SMILES: *c1ccncc1*]

$R_1$ is ethyl, and $R_2$ is methoxy.

(49) In one embodiment, A is

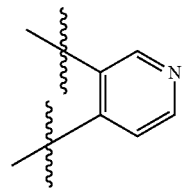 [SMILES: *c1ccncc1*]

$R_1$ is H.

(50) In one embodiment, A is

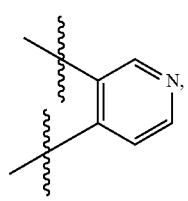 [SMILES: *c1ccncc1*]

$R_1$ is H, and $R_2$ is $(C_1-C_4)$ alkoxy.

(51) In one embodiment, A is

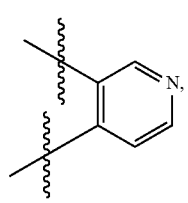 [SMILES: *c1ccncc1*]

$R_1$ is H, and $R_2$ is methoxy.

(52) In one embodiment, A, $R_1$, and $R_3$ are each as defined, where applicable, in any one of (40)-(51), and n is 1.

(53) In one embodiment, A, $R_1$, and $R_3$ are each as defined, where applicable, in any one of (40)-(51), and n is 2.

(54) In one embodiment, $R_1$ is $(C_1-C_4)$ alkyl and $R_2$ is $(C_1-C_4)$ alkoxy.

(55) In one embodiment, $R_1$ is $(C_1-C_3)$ alkyl and $R_2$ is $(C_1-C_3)$ alkoxy.

(56) In one embodiment, $R_1$ is $(C_1-C_4)$ alkyl and $R_2$ is methoxy.

(57) In one embodiment, $R_1$ is methyl and $R_2$ is $(C_1-C_4)$ alkoxy.

(58) In one embodiment, $R_1$ is ethyl and $R_2$ is $(C_1-C_4)$ alkoxy.

(59) In one embodiment, $R_1$ is methyl and $R_2$ is methoxy.

(60) In one embodiment, $R_1$ is ethyl and $R_2$ is methoxy.

(61) In one embodiment, $R_1$ is $(C_1-C_4)$ alkyl, $R_2$ is $(C_1-C_4)$ alkoxy, and n is 1.

(62) In one embodiment, $R_1$ is $(C_1-C_3)$ alkyl, $R_2$ is $(C_1-C_3)$ alkoxy, and n is 1.

(63) In one embodiment, $R_1$ is $(C_1-C_4)$ alkyl, $R_2$ is methoxy, and n is 1.

(64) In one embodiment, $R_1$ is methyl, $R_2$ is $(C_1-C_4)$ alkoxy, and n is 1.

(65) In one embodiment, $R_1$ is ethyl, $R_2$ is $(C_1-C_4)$ alkoxy, and n is 1.

(66) In one embodiment, $R_1$ is methyl, $R_2$ is methoxy, and n is 1.

(67) In one embodiment, $R_1$ is ethyl, $R_2$ is methoxy, and n is 1.
(68) In one embodiment, $R_1$ is $(C_1-C_4)$ alkyl, $R_2$ is $(C_1-C_4)$ alkoxy, and n is 2.
(69) In one embodiment, $R_1$ is $(C_1-C_3)$ alkyl, $R_2$ is $(C_1-C_3)$ alkoxy, and n is 2.
(70) In one embodiment, $R_1$ is $(C_1-C_4)$ alkyl, $R_2$ is methoxy, and n is 2.
(71) In one embodiment, $R_1$ is methyl, $R_2$ is $(C_1-C_4)$ alkoxy, and n is 2.
(72) In one embodiment, $R_1$ is ethyl, $R_2$ is $(C_1-C_4)$ alkoxy, and n is 2.
(73) In one embodiment, $R_1$ is methyl, $R_2$ is methoxy, and n is 2.
(74) In one embodiment, $R_1$ is ethyl, $R_2$ is methoxy, and n is 2.

In one embodiment, the compound of Formula TL-I is of Formula TL-Ia or TL-Ib:

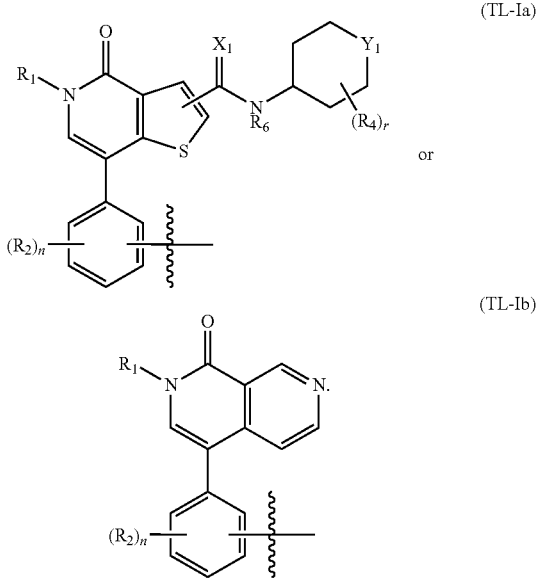

wherein $X_1$, $Y_1$, $R_1$, $R_2$, $R_3$, $R_4$, $R_5$, $R_6$, a, n, and r are each as defined above in Formula TL-I.

For a Targeting Ligand of Formula TL-Ia or TL-Ib:
(1) In one embodiment, $R_1$ is $(C_1-C_4)$ alkyl and $R_2$ is $(C_1-C_4)$ alkoxy.
(2) In one embodiment, $R_1$ is $(C_1-C_3)$ alkyl and $R_2$ is $(C_1-C_3)$ alkoxy.
(3) In one embodiment, $R_1$ is $(C_1-C_4)$ alkyl and $R_2$ is methoxy.
(4) In one embodiment, $R_1$ is methyl and $R_2$ is $(C_1-C_4)$ alkoxy.
(5) In one embodiment, $R_1$ is ethyl and $R_2$ is $(C_1-C_4)$ alkoxy.
(6) In one embodiment, $R_1$ is methyl and $R_2$ is methoxy.
(7) In one embodiment, $R_1$ is ethyl and $R_2$ is methoxy.
(8) In one embodiment, $R_1$ is $(C_1-C_4)$ alkyl, $R_2$ is $(C_1-C_4)$ alkoxy, and n is 1.
(9) In one embodiment, $R_1$ is $(C_1-C_3)$ alkyl, $R_2$ is $(C_1-C_3)$ alkoxy, and n is 1.
(10) In one embodiment, $R_1$ is $(C_1-C_4)$ alkyl, $R_2$ is methoxy, and n is 1.
(11) In one embodiment, $R_1$ is methyl, $R_2$ is $(C_1-C_4)$ alkoxy, and n is 1.
(12) In one embodiment, $R_1$ is ethyl, $R_2$ is $(C_1-C_4)$ alkoxy, and n is 1.
(13) In one embodiment, $R_1$ is methyl, $R_2$ is methoxy, and n is 1.
(14) In one embodiment, $R_1$ is ethyl, $R_2$ is methoxy, and n is 1.
(15) In one embodiment, $R_1$ is $(C_1-C_4)$ alkyl, $R_2$ is $(C_1-C_4)$ alkoxy, and n is 2.
(16) In one embodiment, $R_1$ is $(C_1-C_3)$ alkyl, $R_2$ is $(C_1-C_3)$ alkoxy, and n is 2.
(17) In one embodiment, $R_1$ is $(C_1-C_4)$ alkyl, $R_2$ is methoxy, and n is 2.
(18) In one embodiment, $R_1$ is methyl, $R_2$ is $(C_1-C_4)$ alkoxy, and n is 2.
(19) In one embodiment, $R_1$ is ethyl, $R_2$ is $(C_1-C_4)$ alkoxy, and n is 2.
(20) In one embodiment, $R_1$ is methyl, $R_2$ is methoxy, and n is 2.
(21) In one embodiment, $R_1$ is ethyl, $R_2$ is methoxy, and n is 2.
(22) In one embodiment, $R_1$, $R_2$, and n are each as defined, where applicable, in any one of (1)-(21), and $X_1$ is $NR_5$.
(23) In one embodiment, $R_1$, $R_2$, and n are each as defined, where applicable, in any one of (1)-(21), and $X_1$ is NH.
(24) In one embodiment, $R_1$, $R_2$, and n are each as defined, where applicable, in any one of (1)-(21), $X_1$ is O.
(25) In one embodiment, $R_1$, $R_2$, and n are each as defined, where applicable, in any one of (1)-(21), and $Y_1$ is S.
(26) In one embodiment, $R_1$, $R_2$, and n are each as defined, where applicable, in any one of (1)-(21), and $Y_1$ is S(O).
(27) In one embodiment, $R_1$, $R_2$, and n are each as defined, where applicable, in any one of (1)-(21), and $Y_1$ is $S(O)_2$.
(28) In one embodiment, $R_1$, $R_2$, and n are each as defined, where applicable, in any one of (1)-(21), $X_1$ is $NR_5$, and $Y_1$ is S.
(29) In one embodiment, $R_1$, $R_2$, and n are each as defined, where applicable, in any one of (1)-(21), $X_1$ is $NR_5$, and $Y_1$ is S(O).
(30) In one embodiment, $R_1$, $R_2$, and n are each as defined, where applicable, in any one of (1)-(21), $X_1$ is $NR_5$, and $Y_1$ is $S(O)_2$.
(31) In one embodiment, $R_1$, $R_2$, and n are each as defined, where applicable, in any one of (1)-(21), $X_1$ is NH, and $Y_1$ is S.
(32) In one embodiment, $R_1$, $R_2$, and n are each as defined, where applicable, in any one of (1)-(21). $X_1$ is NH, and $Y_1$ is S(O).
(33) In one embodiment, $R_1$, $R_2$, and n are each as defined, where applicable, in any one of (1)-(21), $X_1$ is NH, and $Y_1$ is $S(O)_2$.
(34) In one embodiment, $R_1$, $R_2$, and n are each as defined, where applicable, in any one of (1)-(21), $X_1$ is O, and $Y_1$ is S.
(35) In one embodiment, $R_1$, $R_2$, and n are each as defined, where applicable, in any one of (1)-(21), $X_1$ is O, and $Y_1$ is S(O).
(36) In one embodiment, $R_1$, $R_2$, and n are each as defined, where applicable, in any one of (1)-(21), $X_1$ is O, and $Y_1$ is $S(O)_2$.
(37) In one embodiment, $X_1$ is $NR_5$ and $Y_1$ is $S(O)_2$.
(38) In one embodiment, $X_1$ is NH and $Y_1$ is $S(O)_2$.

(39) In one embodiment, $X_1$ is O and $Y_1$ is $S(O)_2$.
(40) In one embodiment, $X_1$ and $Y_1$ are each as defined in any one of (37)-(39), and r is 0.
(41) In one embodiment, $X_1$ and $Y_1$ are each as defined in any one of (37)-(39), and r is 1.
(42) In one embodiment, $X_1$ and $Y_1$ are each as defined in any one of (37)-(39), and r is 2.
(43) In one embodiment, $X_1$, $Y_1$, and r are each as defined, where applicable, in any one of (37)-(42), and $R_1$ is $(C_1-C_4)$ alkyl.
(44) In one embodiment, $X_1$, $Y_1$, and r are each as defined, where applicable, in any one of (37)-(42), and $R_1$ is methyl.
(45) In one embodiment, $X_1$, $Y_1$, and r are each as defined, where applicable, in any one of (37)-(42), and $R_1$ is ethyl.
(46) In one embodiment, $X_1$, $Y_1$, and r are each as defined, where applicable, in any one of (37)-(42), and $R_2$ is $(C_1-C_4)$ alkoxy.
(47) In one embodiment, $X_1$, $Y_1$, and r are each as defined, where applicable, in any one of (37)-(42), and $R_2$ is $(C_1-C_4)$ ethoxy.
(48) In one embodiment, $X_1$, $Y_1$, $R_1$, $R_2$, and r are each as defined, where applicable, in any one of (37)-(47), and n is 1.
(49) In one embodiment, $X_1$, $Y_1$, $R_1$, $R_2$, and r are each as defined, where applicable, in any one of (37)-(47), and n is 2.

$X_1$, $Y_1$, $R_1$, $R_2$, $R_4$, $R_5$, $R_6$, a, n, and r can each be selected from any of the groups and combined as described above in Formula TL-I.

In another embodiment, the compound of Formula TL-I is of Formula TL-Ic:

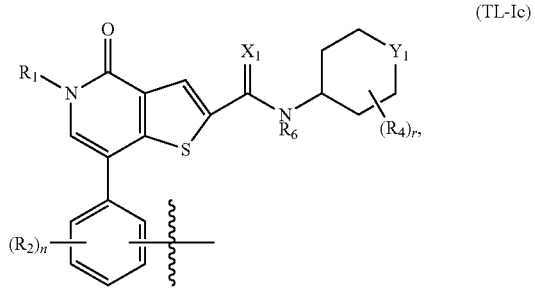

(TL-Ic)

wherein $X_1$, $Y_1$, $R_1$, $R_2$, $R_3$, $R_4$, $R_5$, $R_6$, a, n, and r are each as defined above in Formula TL-I.

For a Targeting Ligand of Formula TL-Ic:
(1) In one embodiment, $R_1$ is $(C_1-C_4)$ alkyl and $R_2$ is $(C_1-C_4)$ alkoxy.
(2) In one embodiment, $R_1$ is $(C_1-C_3)$ alkyl and $R_2$ is $(C_1-C_3)$ alkoxy.
(3) In one embodiment, $R_1$ is $(C_1-C_4)$ alkyl and $R_2$ is methoxy.
(4) In one embodiment, $R_1$ is methyl and $R_2$ is $(C_1-C_4)$ alkoxy.
(5) In one embodiment, $R_1$ is ethyl and $R_2$ is $(C_1-C_4)$ alkoxy.
(6) In one embodiment, $R_1$ is methyl and $R_2$ is methoxy.
(7) In one embodiment, $R_1$ is ethyl and $R_2$ is methoxy.
(8) In one embodiment, $R_1$ is $(C_1-C_4)$ alkyl, $R_2$ is $(C_1-C_4)$ alkoxy, and n is 1.
(9) In one embodiment, $R_1$ is $(C_1-C_3)$ alkyl, $R_2$ is $(C_1-C_3)$ alkoxy, and n is 1.
(10) In one embodiment, $R_1$ is $(C_1-C_4)$ alkyl, $R_2$ is methoxy, and n is 1.
(11) In one embodiment, $R_1$ is methyl, $R_2$ is $(C_1-C_4)$ alkoxy, and n is 1.
(12) In one embodiment, $R_1$ is ethyl, $R_2$ is $(C_1-C_4)$ alkoxy, and n is 1.
(13) In one embodiment, $R_1$ is methyl, $R_2$ is methoxy, and n is 1.
(14) In one embodiment, $R_1$ is ethyl, $R_2$ is methoxy, and n is 1.
(15) In one embodiment, $R_1$ is $(C_1-C_4)$ alkyl, $R_2$ is $(C_1-C_4)$ alkoxy, and n is 2.
(16) In one embodiment, $R_1$ is $(C_1-C_3)$ alkyl, $R_2$ is $(C_1-C_3)$ alkoxy, and n is 2.
(17) In one embodiment, $R_1$ is $(C_1-C_4)$ alkyl, $R_2$ is methoxy, and n is 2.
(18) In one embodiment, $R_1$ is methyl, $R_2$ is $(C_1-C_4)$ alkoxy, and n is 2.
(19) In one embodiment, $R_1$ is ethyl, $R_2$ is $(C_1-C_4)$ alkoxy, and n is 2.
(20) In one embodiment, $R_1$ is methyl, $R_2$ is methoxy, and n is 2.
(21) In one embodiment, $R_1$ is ethyl, $R_2$ is methoxy, and n is 2.
(22) In one embodiment, $R_1$, $R_2$, and n are each as defined, where applicable, in any one of (1)-(21), and $X_1$ is $NR_5$.
(23) In one embodiment, $R_1$, $R_2$, and n are each as defined, where applicable, in any one of (1)-(21), and $X_1$ is NH.
(24) In one embodiment, $R_1$, $R_2$, and n are each as defined, where applicable, in any one of (1)-(21), $X_1$ is O.
(25) In one embodiment, $R_1$, $R_2$, and n are each as defined, where applicable, in any one of (1)-(21), and $Y_1$ is S.
(26) In one embodiment, $R_1$, $R_2$, and n are each as defined, where applicable, in any one of (1)-(21), and $Y_1$ is S(O).
(27) In one embodiment, $R_1$, $R_2$, and n are each as defined, where applicable, in any one of (1)-(21), and $Y_1$ is $S(O)_2$.
(28) In one embodiment, $R_1$, $R_2$, and n are each as defined, where applicable, in any one of (1)-(21), $X_1$ is $NR_5$, and $Y_1$ is S.
(29) In one embodiment, $R_1$, $R_2$, and n are each as defined, where applicable, in any one of (1)-(21), $X_1$ is $NR_5$, and $Y_1$ is S(O).
(30) In one embodiment, $R_1$, $R_2$, and n are each as defined, where applicable, in any one of (1)-(21), $X_1$ is $NR_5$, and $Y_1$ is $S(O)_2$.
(31) In one embodiment, $R_1$, $R_2$, and n are each as defined, where applicable, in any one of (1)-(21), $X_1$ is NH, and $Y_1$ is S.
(32) In one embodiment, $R_1$, $R_2$, and n are each as defined, where applicable, in any one of (1)-(21), $X_1$ is NH, and $Y_1$ is S(O).
(33) In one embodiment, $R_1$, $R_2$, and n are each as defined, where applicable, in any one of (1)-(21), $X_1$ is NH, and $Y_1$ is $S(O)_2$.
(34) In one embodiment, $R_1$, $R_2$, and n are each as defined, where applicable, in any one of (1)-(21), $X_1$ is O, and Y is S.
(35) In one embodiment, $R_1$, $R_2$, and n are each as defined, where applicable, in any one of (1)-(21), $X_1$ is O, and $Y_1$ is S(O).

(36) In one embodiment, $R_1$, $R_2$, and n are each as defined, where applicable, in any one of (1)-(21), $X_1$ is O, and $Y_1$ is $S(O)_2$.
(37) In one embodiment, $X_1$ is $NR_5$ and $Y_1$ is $S(O)_2$.
(38) In one embodiment, $X_1$ is NH and $Y_1$ is $S(O)_2$.
(39) In one embodiment, $X_1$ is O and $Y_1$ is $S(O)_2$.
(40) In one embodiment, $X_1$ and $Y_1$ are each as defined in any one of (37)-(39), and r is 0.
(41) In one embodiment, $X_1$ and $Y_1$ are each as defined in any one of (37)-(39), and r is 1.
(42) In one embodiment, $X_1$ and $Y_1$ are each as defined in any one of (37)-(39), and r is 2.
(43) In one embodiment, $X_1$, $Y_1$, and r are each as defined, where applicable, in any one of (37)-(42), and $R_1$ is $(C_1-C_4)$ alkyl.
(44) In one embodiment, $X_1$, $Y_1$, and r are each as defined, where applicable, in any one of (37)-(42), and $R_1$ is methyl.
(45) In one embodiment, $X_1$, $Y_1$, and r are each as defined, where applicable, in any one of (37)-(42), and $R_1$ is ethyl.
(46) In one embodiment, $X_1$, $Y_1$, and r are each as defined, where applicable, in any one of (37)-(42), and $R_2$ is $(C_1-C_4)$ alkoxy.
(47) In one embodiment, $X_1$, $Y_1$, and r are each as defined, where applicable, in any one of (37)-(42), and $R_2$ is $(C_1-C_4)$ ethoxy.
(48) In one embodiment, $X_1$, $Y_1$, $R_1$, $R_2$, and r are each as defined, where applicable, in any one of (37)-(47), and n is 1.
(49) In one embodiment, $X_1$, $Y_1$, $R_1$, $R_2$, and r are each as defined, where applicable, in any one of (37)-(47), and n is 2.

$X_1$, $Y_1$, $R_1$, $R_2$, $R_4$, $R_5$, $R_6$, a, n, and r can each be selected from any of the groups and combined as described above in Formula TL-I.

Some embodiments of present application relate to the Targeting Ligand (TL) having the one of structures in Table A:

TABLE A

Structures of Targeting Ligands

| Cmpd No. | Structure |
|---|---|
| TL-1 | |
| TL-2 | |
| TL-3 | 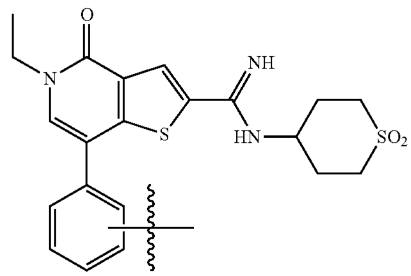 |
| TL-4 | 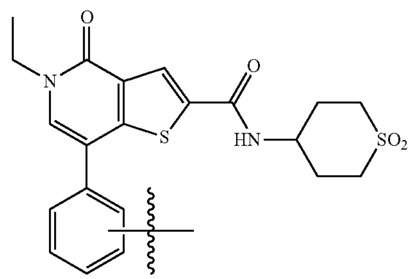 |
| TL-5 | 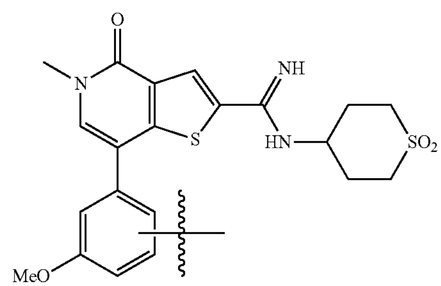 |
| TL-6 | 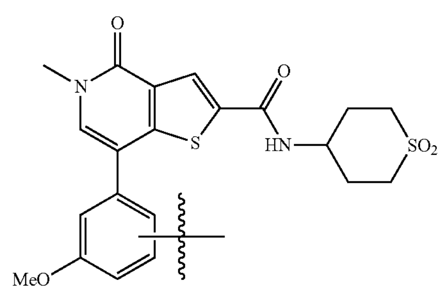 |

Degron

The Degron serves to link a targeted protein, through a Linker and a Targeting Ligand, to a ubiquitin ligase for proteosomal degradation. In one embodiment, the Degron is capable of binding to a ubiquitin ligase, such as an E3 ubiquitin ligase. In one embodiment, the Degron is capable of binding to cereblon.

In one embodiment, the Degron is of Formula D1:

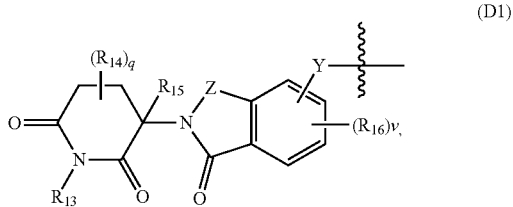

or an enantiomer, diastereomer, or stereoisomer thereof, wherein:

Y is a bond, $(CH_2)_{1-6}$ $(CH_2)_{0-6}$—O, $(CH_2)_{0-6}$—C(O)NR$_{11}$, $(CH_2)_{0-6}$—NR$_{11}$C(O), $(CH_2)_{0-6}$—NH, or $(CH_2)_{0-6}$—NR$_{12}$;

Z is C(O) or C(R$_{13}$)$_2$;

R$_{11}$ is H or $C_1$-$C_6$ alkyl;

R$_{12}$ is $C_1$-$C_6$ alkyl or C(O)—$C_1$-$C_6$ alkyl:

each R$_{13}$ is independently H or $C_1$-$C_3$ alkyl;

each R$_{14}$ is independently $C_1$-$C_3$ alkyl;

R$_{15}$ is H, deuterium, $C_1$-$C_3$ alkyl, F, or Cl;

each R$_{16}$ is independently halogen, OH, $C_1$-$C_6$ alkyl, or $C_1$-$C_6$ alkoxy;

q is 0, 1, or 2; and v is 0, 1, 2, or 3, wherein the Degron is covalently bonded to the Linker via

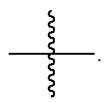

In one embodiment, Z is C(O).

In one embodiment, Z is C(O) or CH$_2$.

In one embodiment, Z is C(R$_{13}$)$_2$; and each R$_{13}$ is H. In one embodiment, Z is C(R$_{13}$)$_2$; and one of R$_{13}$ is H, and the other is $C_1$-$C_3$ alkyl selected from methyl, ethyl, and propyl. In one embodiment, Z is C(R$_{13}$)$_2$; and each R$_{13}$ is independently selected from methyl, ethyl, and propyl.

In one embodiment, Y is a bond.

In one embodiment, Y is a bond, O, or NH.

In one embodiment, Y is $(CH_2)_1$, $(CH_2)_2$, $(CH_2)_3$, $(CH_2)_4$, $(CH_2)_5$, or $(CH_2)_6$. In one embodiment, Y is $(CH_2)_1$, $(CH_2)_2$, or $(CH_2)_3$. In one embodiment, Y is $(CH_2)_1$ or $(CH_2)_2$.

In one embodiment, Y is O, CH$_2$—O, $(CH_2)_2$—O, $(CH_2)_3$—O, $(CH_2)_4$—O, $(CH_2)_5$—O, or $(CH_2)_6$—O. In one embodiment, Y is O. CH$_2$—O, $(CH_2)_2$—O, or $(CH_2)_3$—O. In one embodiment, Y is O or CH$_2$—O. In one embodiment, Y is O.

In one embodiment, Y is C(O)NR$_{11}$, CH$_2$—C(O)NR$_1$, $(CH_2)_2$—C(O)NR$_{11}$, $(CH_2)_3$—C(O)NR$_{11}$, $(CH_2)_4$—C(O)NR$_{11}$, $(CH_2)_5$—C(O)NR$_{11}$, or $(CH_2)_6$—C(O)NR$_{11}$. In one embodiment, Y is C(O)NR$_{11}$, CH$_2$—C(O)NR$_{11}$, $(CH_2)_2$—C(O)NR$_1$, or $(CH_2)_3$—C(O)NR$_{11}$. In one embodiment, Y is C(O)NR$_{11}$ or CH$_2$—C(O)NR$_{11}$. In one embodiment, Y is C(O)NR$_{11}$.

In one embodiment, Y is NR$_{11}$C(O), CH$_2$—NR$_{11}$C(O), $(CH_2)_2$—NR$_{11}$C(O). $(CH_2)_3$—NR$_{11}$C(O), $(CH_2)_4$—NR$_{11}$C(O), $(CH_2)_5$—NR$_{11}$C(O), or $(CH_2)_6$—NR$_{11}$C(O). In one embodiment, Y is NR$_{11}$C(O), CH$_2$—NR$_{11}$C(O), $(CH_2)_2$—NR$_{11}$C(O), or $(CH_2)_3$—NR$_{11}$C(O). In one embodiment, Y is NR$_{11}$C(O) or CH$_2$—NR$_{11}$C(O). In one embodiment, Y is NR$_{11}$C(O).

In one embodiment, R$_{11}$ is H. In one embodiment, R$_{11}$ is selected from methyl, ethyl, propyl, butyl, i-butyl, t-butyl, pentyl, i-pentyl, and hexyl. In one embodiment, R$_{11}$ is $C_1$-$C_3$ alkyl selected from methyl, ethyl, and propyl.

In one embodiment, Y is NH, CH$_2$—NH, $(CH_2)_2$—NH. $(CH_2)_3$—NH, $(CH_2)_4$—NH, $(CH_2)_5$—NH, or $(CH_2)_6$—NH. In one embodiment, Y is NH, CH$_2$—NH, $(CH_2)_2$—NH, or $(CH_2)_3$—NH. In one embodiment, Y is NH or CH$_2$—NH. In one embodiment, Y is NH.

In one embodiment, Y is NR$_{12}$, CH$_2$—NR$_{12}$, $(CH_2)_2$—NR$_{12}$, $(CH_2)_3$—NR$_{12}$, $(CH_2)_4$—NR$_{12}$, $(CH_2)_5$—NR$_{12}$, or $(CH_2)_6$—NR$_2$. In one embodiment, Y is NR$_{12}$. CH$_2$—NR$_{12}$, $(CH_2)_2$—NR$_{12}$, or $(CH_2)_3$—NR$_{12}$. In one embodiment, Y is NR$_{12}$ or CH$_2$—NR$_{12}$. In one embodiment, Y is NR$_{12}$.

In one embodiment, R$_{12}$ is selected from methyl, ethyl, propyl, butyl, i-butyl, t-butyl, pentyl, i-pentyl, and hexyl. In one embodiment, R$_{12}$ is $C_1$-$C_3$ alkyl selected from methyl, ethyl, and propyl.

In one embodiment, R$_{12}$ is selected from C(O)-methyl, C(O)-ethyl, C(O)-propyl, C(O)-butyl, C(O)-i-butyl, C(O)-t-butyl, C(O)-pentyl, C(O)-i-pentyl, and C(O)-hexyl. In one embodiment, R$_{12}$ is C(O)—$C_1$-$C_3$ alkyl selected from C(O)-methyl, C(O)-ethyl, and C(O)-propyl.

In one embodiment, R$_{13}$ is H.

In one embodiment, R$_{13}$ is $C_1$-$C_3$ alkyl selected from methyl, ethyl, and propyl. In one embodiment, R$_{13}$ is methyl.

In one embodiment, q is 0.

In one embodiment, q is 1.

In one embodiment, q is 2.

In one embodiment, each R$_{14}$ is independently $C_1$-$C_3$ alkyl selected from methyl, ethyl, and propyl.

In one embodiment, v is 0.

In one embodiment, v is 1.

In one embodiment, v is 2.

In one embodiment, v is 3.

In one embodiment, each R$_{16}$ is independently selected from halogen (e.g., F, Cl, Br, and I), OH, $C_1$-$C_6$ alkyl (e.g., methyl, ethyl, propyl, butyl, i-butyl, t-butyl, pentyl, i-pentyl, and hexyl), and $C_1$-$C_6$ alkoxy (e.g., methoxy, ethoxy, propoxy, butoxy, i-butoxy, t-butoxy, and pentoxy). In a further embodiment, each R$_{16}$ is independently selected from F, Cl, OH, methyl, ethyl, propyl, butyl, i-butyl, t-butyl, methoxy, and ethoxy.

In one embodiment, R$_{15}$ is H, deuterium, or $C_1$-$C_3$ alkyl. In another embodiment, R$_{15}$ is H or $C_1$-$C_3$ alkyl. In a further embodiment, R$_{15}$ is in the (S) or (R) configuration. In a further embodiment, R$_1$ is in the (S) configuration. In one embodiment, the compound comprises a racemic mixture of (S)—R$_{15}$ and (R)—R$_{15}$.

In one embodiment, R$_{15}$ is H.

In one embodiment, R$_{15}$ is deuterium.

In one embodiment, R$_{15}$ is $C_1$-$C_3$ alkyl selected from methyl, ethyl, and propyl. In one embodiment, R$_{15}$ is methyl.

In one embodiment, R$_{15}$ is F or $C_1$. In a further embodiment, R$_{15}$ is in the (S) or (R) configuration. In a further embodiment, R$_{15}$ is in the (R) configuration. In one embodiment, the compound comprises a racemic mixture of (S)—R$_{15}$ and (R)—R$_{15}$. In one embodiment, R$_{15}$ is F.

Any of the groups described herein for any of Y, Z, R$_{11}$, R$_{12}$, R$_{13}$, R$_{14}$, R$_{15}$, R$_{16}$, q and v can be combined with any of the groups described herein for one or more of the remainder of Y, Z, R$_{11}$, R$_{12}$, R$_{13}$, R$_{14}$, R$_{15}$, R$_{16}$, q and v, and may further be combined with any of the groups described herein for the Linker.

For a Degron of Formula D1:

(1) In one embodiment, Z is C(O) and Y is a bond.

(2) In one embodiment, Z is C(O) and Y is NH.

(3) In one embodiment, Z is C(O) and Y is $(CH_2)_{0-6}$—O. In a further embodiment, Y is O.
(4) In one embodiment, Z is C(O); Y is a bond; and q and v are each 0.
(5) In one embodiment, Z is C(O); Y is NH; and q and v are each 0.
(6) In one embodiment, Z is C(O); Y is $(CH_2)_{0-6}$—O; and q and v are each 0. In a further embodiment, Y is O.
(7) In one embodiment, Z is C(O); Y is a bond; and $R_{13}$ is H.
(8) In one embodiment, Z is C(O); Y is a bond; and $R_{15}$ is H.
(9) In one embodiment, Z is C(O); Y is NH; and $R_{13}$ is H.
(10) In one embodiment, Z is C(O); Y is NH; and $R_{15}$ is H.
(11) In one embodiment, Z is C(O); Y is a bond; $R_{13}$ is H; and $R_{15}$ is H.
(12) In one embodiment, Z is C(O); Y is NH; $R_{13}$ is H; and $R_{15}$ is H.
(13) In one embodiment, Z is C(O); Y is $(CH_2)_{0-6}$—O; and $R_{13}$ is H. In a further embodiment, Y is O.
(14) In one embodiment, Z is C(O); Y is $(CH_2)_{0-6}$—O; and $R_{15}$ is H. In a further embodiment, Y is O.
(15) In one embodiment, Z is C(O); Y is $(CH_2)_{0-6}$—O; $R_{13}$ is H; and $R_{15}$ is H. In a further embodiment, Y is O.
(16) In one embodiment, q and v are each 0; and Y, Z, $R_{13}$, $R_{15}$, and $R_{16}$ are each as defined in any of (1)-(3) and (7)-(15).
(17) In one embodiment, Z is $CH_2$ and Y is a bond.
(18) In one embodiment, Z is $CH_2$ and Y is NH.
(19) In one embodiment, Z is $CH_2$ and Y is $(CH_2)_{0-6}$—O. In a further embodiment, Y is O.
(20) In one embodiment, Z is $CH_2$; Y is a bond; and q and v are each 0.
(21) In one embodiment, Z is $CH_2$; Y is NH; and q and v are each 0.
(22) In one embodiment, Z is $CH_2$; Y is $(CH_2)_{0-6}$—O; and q and v are each 0. In a further embodiment, Y is O.
(23) In one embodiment, Z is $CH_2$; Y is a bond; and $R_{13}$ is H.
(24) In one embodiment, Z is $CH_2$; Y is a bond; and $R_{15}$ is H.
(25) In one embodiment, Z is $CH_2$; Y is NH; and $R_{13}$ is H.
(26) In one embodiment, Z is $CH_2$; Y is NH; and $R_{15}$ is H.
(27) In one embodiment, Z is $CH_2$; Y is a bond; $R_{13}$ is H; and $R_{15}$ is H.
(28) In one embodiment, Z is $CH_2$; Y is NH; $R_{13}$ is H; and $R_{15}$ is H.
(29) In one embodiment, Z is $CH_2$; Y is $(CH_2)_{0-6}$—O; and $R_{13}$ is H. In a further embodiment, Y is O.
(30) In one embodiment, Z is $CH_2$; Y is $(CH_2)_{0-6}$—O; and $R_{15}$ is H. In a further embodiment, Y is O.
(31) In one embodiment, Z is $CH_2$; Y is $(CH_2)_{0-6}$—O; $R_{13}$ is H; and $R_{15}$ is H. In a further embodiment, Y is O.
(32) In one embodiment, q and v are each 0; and Y, Z, $R_{13}$, $R_{15}$, and $R_{16}$ are each as defined in any of (17)-(19) and (23)-(31).

In one embodiment, the Degron is of Formula D1a, D1b, D1c, D1d, D1e, D1f, D1g, D1h, D1i, D1j, D1k, or D1l:

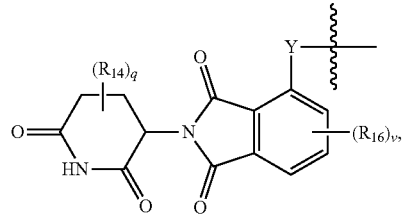

(D1a)

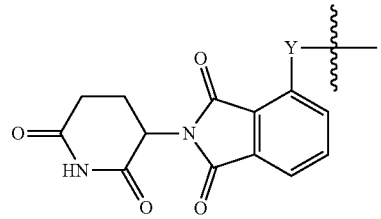

(D1b),

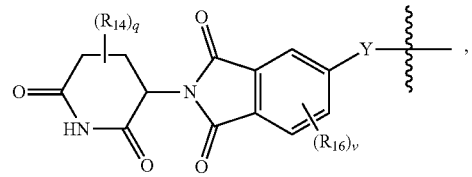

(D1c),

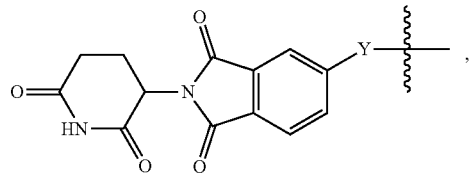

(D1d),

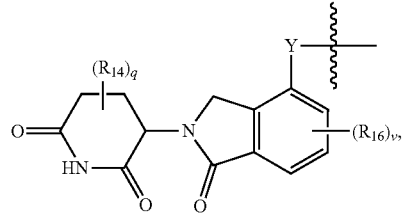

(D1e)

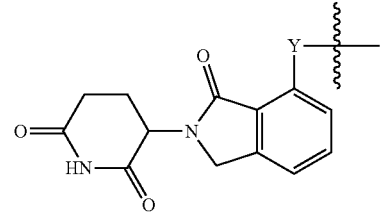

(D1f),

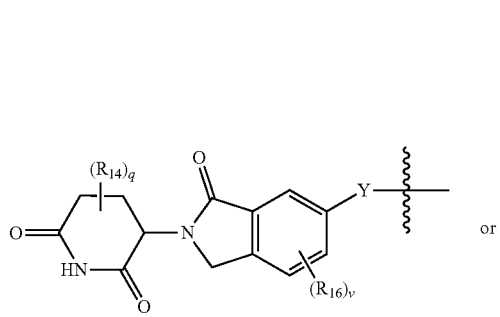

(D1g) or

-continued

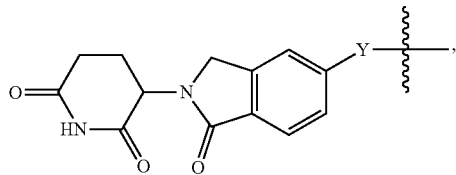
(D1h)

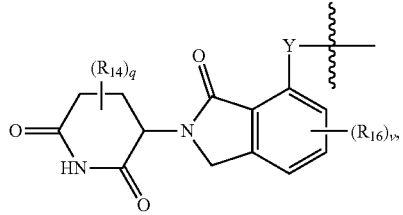
(D1i)

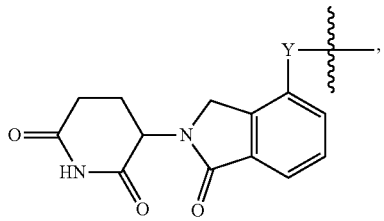
(D1j)

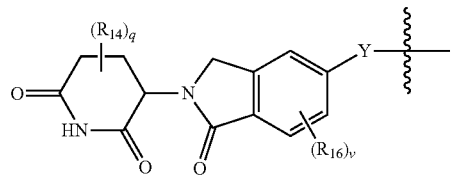
(D1k) or

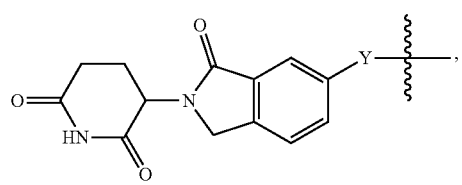
(D1l)

or an enantiomer, diastereomer, or stereoisomer thereof, wherein Y, $R_{14}$, $R_{16}$, q, and v are each as defined above in Formula D1, and can be selected from any moieties or combinations thereof described above.

In one embodiment, Y is a bond, O, or NH. In one embodiment, Y is a bond. In one embodiment, Y is O. In one embodiment, Y is NH.

In one embodiment, the Degron is of Formula D2:

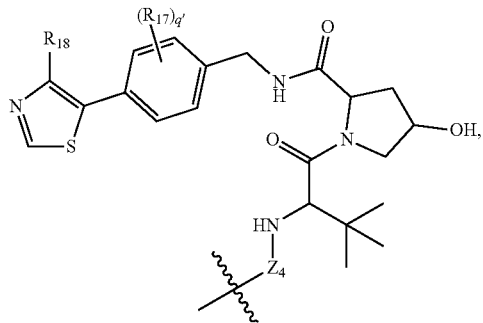
(D2)

or an enantiomer, diastereomer, or stereoisomer thereof, wherein:
$Z_4$ is absent or C(O);
each $R_{17}$ is independently $C_1$-$C_3$ alkyl;
q' is 0, 1, 2, 3 or 4; and
$R_{18}$ is H or $C_1$-$C_3$ alkyl,
wherein the Degron is covalently bonded to another moiety (e.g., a compound, or a Linker) via

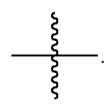

In one embodiment, $Z_4$ is absent.
In one embodiment, $Z_4$ is C(O).
In one embodiment, q' is 0.
In one embodiment, q' is 1.
In one embodiment, q' is 2.
In one embodiment, q' is 3.
In one embodiment, each $R_{17}$ is independently $C_1$-$C_3$ alkyl selected from methyl, ethyl, and propyl.
In one embodiment, $R_{15}$ is methyl, ethyl, or propyl. In one embodiment, $R_{15}$ is methyl.
In one embodiment, the Degron is of Formula D2a:

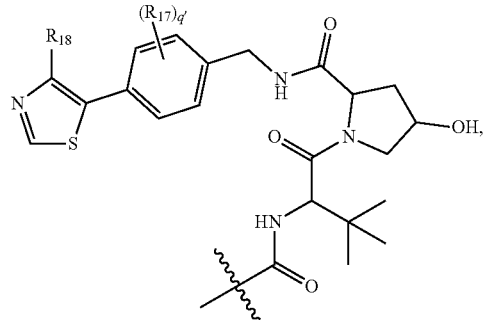
(D2a)

or an enantiomer, diastereomer, or stereoisomer thereof, wherein:
each $R_{17}$ is independently $C_1$-$C_3$ alkyl;
q' is 0, 1, 2, 3 or 4; and
$R_{18}$ is H or $C_1$-$C_3$ alkyl,
wherein the Degron is covalently bonded to another moiety (e.g., a compound, or a Linker) via

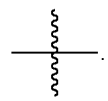

In one embodiment, q' is 0.
In one embodiment, q' is 1.
In one embodiment, q' is 2.
In one embodiment, q' is 3.
In one embodiment, each $R_{17}$ is independently $C_1$-$C_3$ alkyl selected from methyl, ethyl, and propyl.
In one embodiment, $R_{15}$ is methyl, ethyl, or propyl. In one embodiment, $R_{15}$ is methyl.

In one embodiment, the Degron is of Formula D2b:

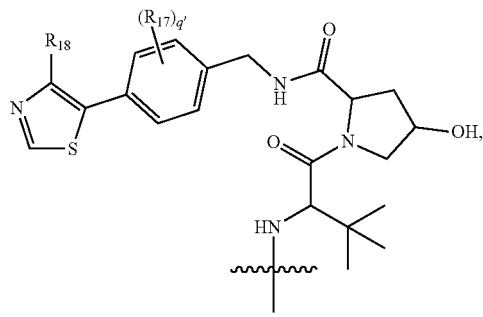
(D2b)

or an enantiomer, diastereomer, or stereoisomer thereof, wherein:

each $R_{17}$ is independently $C_1$-$C_3$ alkyl, q' is 0, 1, 2, 3 or 4; and $R_{15}$ is H or $C_1$-$C_3$ alkyl, wherein the Degron is covalently bonded to another moiety (e.g., a compound, or a Linker) via

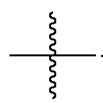

In one embodiment, q' is 0.

In one embodiment, q' is 1.

In one embodiment, q' is 2.

In one embodiment, q' is 3.

In one embodiment, each $R_{17}$ is independently $C_1$-$C_3$ alkyl selected from methyl, ethyl, and propyl.

In one embodiment, $R_{15}$ is methyl, ethyl, or propyl. In one embodiment, $R_{15}$ is methyl.

In one embodiment, the Degron is of Formula D2c or D2d:

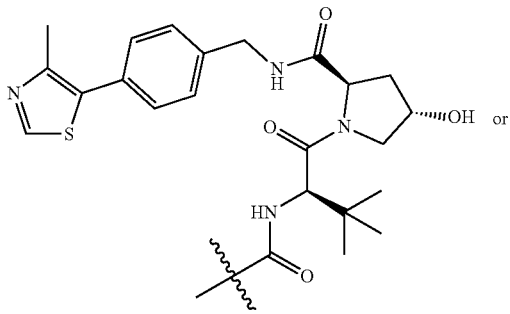
(D2c)

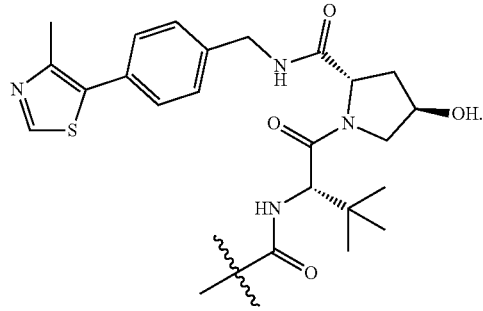
(D2d)

In one embodiment the Degron is of Formula D2e or D2f

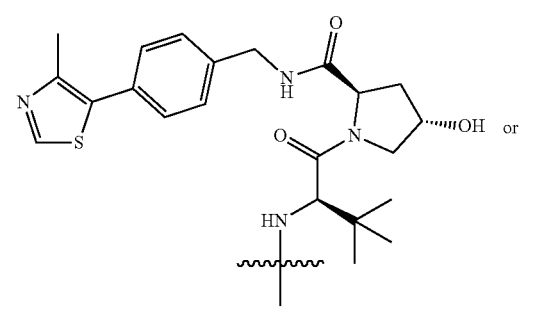
(D2e)

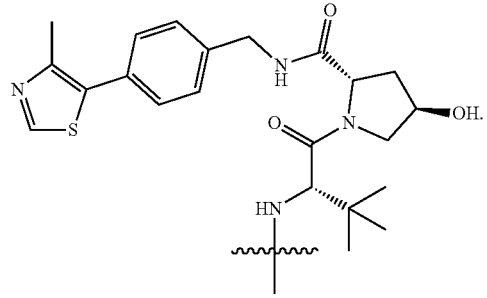
(D2f)

Linker

The Linker is a bond, a carbon chain, carbocyclic ring, or heterocyclic ring that serves to link a Targeting Ligand with a Degron. In one embodiment, the carbon chain optionally comprises one, two, three, or more heteroatoms selected from N, O, and S. In one embodiment, the carbon chain comprises only saturated chain carbon atoms. In one embodiment, the carbon chain optionally comprises two or more unsaturated chain carbon atoms (e.g., C=C or C≡C). In one embodiment, one or more chain carbon atoms in the carbon chain are optionally substituted with one or more substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl)$_2$, CN, $C_3$-$C_8$ cycloalkyl, heterocyclyl, phenyl, and heteroaryl).

In one embodiment, the Linker comprises at least 5 chain atoms (e.g., C, O, N, and S).

In one embodiment, the Linker comprises less than 25 chain atoms (e.g., C, O, N, and S). In one embodiment, the Linker comprises less than 20 chain atoms (e.g., C, O, N, and S). In one embodiment, the Linker comprises 4, 5, 6, 7, 8, 9, 10, 11, 12, 13, 14, 15, 16, 17, 18, 19, 20, 21, 22, 23, or 24 chain atoms (e.g., C, O, N, and S). In one embodiment, the Linker comprises 5, 6, 7, 8, 9, 10, 11, 12, 13, 14, 15, 16, 17, 18, 19, 20, 21, 22, 23, or 24 chain atoms (e.g., C, O, N, and S). In one embodiment, the Linker comprises 5, 7, 9, 11, 13, 15, 17, or 19 chain atoms (e.g., C, O, N, and S). In one embodiment, the Linker comprises 5, 7, 9, or 11 chain atoms (e.g., C, O, N, and S). In one embodiment, the Linker comprises 11, 13, 15, 17, or 19 chain atoms (e.g., C, O, N, and S). In one embodiment, the Linker comprises 11, 13, 15, 17, 19, 21, or 23 chain atoms (e.g., C, O, N, and S). In one embodiment, the Linker comprises 6, 8, 10, 12, 14, 16, 18, 20, 22, or 24 chain atoms (e.g., C, O, N, and S). In one embodiment, the Linker comprises 6, 8, 10, 12, 14, 16, 18, or 20 chain atoms (e.g., C, O, N, and S). In one embodiment, the Linker comprises 6, 8, 10, or 12 chain atoms (e.g., C, O, N, and S). In one embodiment, the Linker comprises 12, 14, 16, 18, or 20 chain atoms (e.g., C, O, N, and S).

In one embodiment, the Linker comprises from 11 to 19 chain atoms (e.g., C. O. N, and S).

In one embodiment, the Linker is a carbon chain optionally substituted with non-bulky substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl)$_2$, and CN). In one embodiment, the non-bulky substitution is located on the chain carbon atom proximal to the Degron (i.e., the carbon atom is separated from the carbon atom to which the Degron is bonded by at least 3, 4, or 5 chain atoms in the Linker). In one embodiment, the non-bulky substitution is located on the chain carbon atom proximal to the Targeting Ligand (i.e., the carbon atom is separated from the carbon atom to which the Degron is bonded by at least 3, 4, or 5 chain atoms in the Linker).

In one embodiment the Linker is of Formula L1:

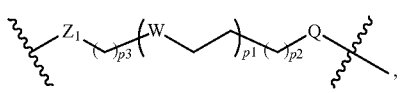
(L1)

or an enantiomer, diastereomer, or stereoisomer thereof, wherein p1 is an integer selected from 0 to 12:
p2 is an integer selected from 0 to 12;
p3 is an integer selected from 1 to 6;
each W is independently absent, $CH_2$, O, S, or $NR_{19}$;
$Z_1$ is absent, C(O), $CH_2$, O, $(CH_2)NR_{19}$, $O(CH_2)_jC(O)NR_{19}$, $C(O)NR_{19}$, $(CH_2)_jC(O)NR_{19}$, $NR_{19}C(O)$, $(CH_2)_jNR_{19}C(O)$, $(CH_2)_kNR_{19}(CH_2)_jC(O)NR_{19}$, $NR_{19}(CH_2)_jC(O)NR_{19}$, or

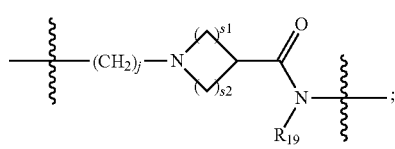

each $R_{19}$ is independently H or $C_1$-$C_3$ alkyl;
s1 and s2 are each independently 1, 2, or 3;
j is 1, 2, or 3;
k is 1, 2, or 3; and
Q is absent, $NHC(O)CH_2$, or $O(CH_2)_{1-2}$;

wherein the Linker is covalently bonded to a Degron via the

next to Q, and covalently bonded to a Targeting Ligand via the

next to $Z_1$.

In one embodiment, the total number of chain atoms in the Linker is less than 30. In a further embodiment, the total number of chain atoms in the Linker is less than 20.

For a Linker of Formula L1:
(1) In one embodiment, p1 is an integer selected from 0 to 10.
(2) In one embodiment, p1 is an integer selected from 1 to 10.
(3) In one embodiment, p1 is selected from 1, 2, 3, 4, 5, and 6.
(4) In one embodiment, p1 is 0, 1, 3, or 5.
(5) In one embodiment, p1 is 0, 1, 2, or 3.
(6) In one embodiment, p1 is 0.
(7) In one embodiment, p1 is 1.
(8) In one embodiment, p1 is 2.
(9) In one embodiment, p1 is 3.
(10) In one embodiment, p1 is 4.
(11) In one embodiment, p is 5.
(12) In one embodiment, p2 is an integer selected from 0 to 10.
(13) In one embodiment, p2 is selected from 0, 1, 2, 3, 4, 5, and 6.
(14) In one embodiment, p2 is 0, 1, 2, or 3.
(15) In one embodiment, p2 is 0.
(16) In one embodiment, p2 is 1.
(17) In one embodiment, p2 is 2.
(18) In one embodiment, p2 is 3.
(19) In one embodiment, p3 is an integer selected from 1 to 5.
(20) In one embodiment, p3 is 2, 3, 4, or 5.
(21) In one embodiment, p3 is 0, 1, 2, or 3.
(22) In one embodiment, p3 is 0.
(23) In one embodiment, p3 is 1.
(24) In one embodiment, p3 is 2.
(25) In one embodiment, p3 is 3.
(26) In one embodiment, p3 is 4.
(27) In one embodiment, at least one W is $CH_2$.
(28) In one embodiment, at least one W is O.
(29) In one embodiment, at least one W is S.
(30) In one embodiment, at least one W is NH.
(31) In one embodiment, at least one W is $NR_{19}$; and each $R_{19}$ is independently $C_1$-$C_3$ alkyl selected from methyl, ethyl, and propyl.
(32) In one embodiment, each W is O.
(33) In one embodiment, each W is $CH_2$.
(34) In one embodiment, j is 1, 2, or 3.
(35) In one embodiment, j is 1.
(36) In one embodiment, j is 2.
(37) In one embodiment, j is 3.
(38) In one embodiment, j is 2 or 3.

(39) In one embodiment, j is 1 or 2.
(40) In one embodiment, k is 1, 2, or 3.
(41) In one embodiment, k is 1.
(42) In one embodiment, k is 2.
(43) In one embodiment, k is 3.
(44) In one embodiment, k is 2 or 3.
(45) In one embodiment, k is 1 or 2.
(46) In one embodiment, Q is absent.
(47) In one embodiment, Q is $NHC(O)CH_2$.
(48) In one embodiment, Q is $O(CH_2)_{1-2}$.
(49) In one embodiment, Q is $OCH_2$.
(50) In one embodiment, Q is $OCH_2CH_2$.
(51) In one embodiment, $Z_1$ is absent.
(52) In one embodiment, $Z_1$ is $O(CH_2)_jC(O)NR_{19}$; and $R_{19}$ is $C_1$-$C_3$ alkyl selected from methyl, ethyl, and propyl.
(53) In one embodiment, $Z_1$ is $O(CH_2)_jC(O)NR_{19}$; and $R_{19}$ is H.
(54) In one embodiment, $Z_1$ is $O(CH_2)_jC(O)NR_{19}$; $R_{19}$ is $C_1$-$C_3$ alkyl selected from methyl, ethyl, and propyl; and j is 1.
(55) In one embodiment, $Z_1$ is $O(CH_2)_jC(O)NR_{19}$; $R_{19}$ is H; and j is 1.
(56) In one embodiment, $Z_1$ is $O(CH_2)_jC(O)NR_{19}$; $R_{19}$ is $C_1$-$C_3$ alkyl selected from methyl, ethyl, and propyl; and j is 2.
(57) In one embodiment, $Z_1$ is $O(CH_2)C(O)NR_{19}$; $R_{19}$ is H; and j is 2.
(58) In one embodiment, $Z_1$ is $O(CH_2)_jC(O)NR_{19}$; $R_{19}$ is $C_1$-$C_3$ alkyl selected from methyl, ethyl, and propyl; and j is 3.
(59) In one embodiment, $Z_1$ is $O(CH_2)_jC(O)NR_{11}$; and $R_{19}$ is H; and j is 3.
(60) In one embodiment, $Z_1$ is $C(O)NR_{19}$; and $R_{19}$ is H.
(61) In one embodiment, $Z_1$ is $C(O)NR_{19}$; and $R_{19}$ is $C_1$-$C_3$ alkyl selected from methyl, ethyl, and propyl.
(62) In one embodiment, $Z_1$ is $(CH_2)C(O)NR_{19}$; and $R_{19}$ is H.
(63) In one embodiment, $Z_1$ is $(CH_2)C(O)NR_{19}$; and $R_{19}$ is $C_1$-$C_3$ alkyl selected from methyl, ethyl, and propyl.
(64) In one embodiment, $Z_1$ is $(CH_2)_jC(O)NR_{19}$; $R_{19}$ is H; and j is 1.
(65) In one embodiment, $Z_1$ is $(CH_2)_jC(O)NR_{19}$; $R_{19}$ is $C_1$-$C_3$ alkyl selected from methyl, ethyl, and propyl; and j is 1
(66) In one embodiment, $Z_1$ is $(CH_2)C(O)NR_{19}$; $R_{19}$ is H; and j is 2.
(67) In one embodiment, $Z_1$ is $(CH_2)_jC(O)NR_{19}$; Rig is $C_1$-$C_3$ alkyl selected from methyl, ethyl, and propyl; and j is 2.
(68) In one embodiment, $Z_1$ is $(CH_2)_jC(O)NR_{19}$; $R_{19}$ is H; and j is 3.
(69) In one embodiment, $Z_1$ is $(CH_2)_jC(O)NR_{19}$; $R_{19}$ is $C_1$-$C_3$ alkyl selected from methyl, ethyl, and propyl; and j is 3.
(70) In one embodiment, $Z_1$ is $NR_{19}C(O)$; and $R_{19}$ is H.
(71) In one embodiment, $Z_1$ is $NR_{19}C(O)$; and $R_{19}$ is $C_1$-$C_3$ alkyl selected from methyl, ethyl, and propyl.
(72) In one embodiment, $Z_1$ is $(CH_2)_jNR_{19}C(O)$; and $R_{19}$ is H.
(73) In one embodiment, $Z_1$ is $(CH_2)_jNR_{19}C(O)$; and $R_{19}$ is $C_1$-$C_3$ alkyl selected from methyl, ethyl, and propyl.
(74) In one embodiment, $Z_1$ is $(CH_2)_jNR_{19}C(O)$; $R_{19}$ is H; and j is 1.
(75) In one embodiment, $Z_1$ is $(CH_2)_jNR_{19}C(O)$; $R_{19}$ is $C_1$-$C_3$ alkyl selected from methyl, ethyl, and propyl; and j is 1
(76) In one embodiment, $Z_1$ is $(CH_2)_jNR_{19}C(O)$; Rig is H; and j is 2.
(77) In one embodiment, $Z_1$ is $(CH_2)_jNR_{19}C(O)$; $R_{19}$ is $C_1$-$C_3$ alkyl selected from methyl, ethyl, and propyl; and j is 2.
(78) In one embodiment, $Z_1$ is $(CH_2)_jNR_{19}C(O)$; $R_{19}$ is H; and j is 3.
(79) In one embodiment, $Z_1$ is $(CH_2)NR_{19}C(O)$; $R_{19}$ is $C_1$-$C_3$ alkyl selected from methyl, ethyl, and propyl; and j is 3.
(80) In one embodiment, $Z_1$ is $(CH_2)_kNR_{19}(CH_2)_jC(O)NR_{19}$; and each $R_{19}$ is independently H or $C_1$-$C_3$ alkyl selected from methyl, ethyl, and propyl.
(81) In one embodiment, $Z_1$ is $(CH_2)_kNR_{19}(CH_2)_jC(O)NR_{19}$; and one of $R_{11}$ is H and one of $R_{19}$ is $C_1$-$C_3$ alkyl selected from methyl, ethyl, and propyl. In one embodiment, $Z_1$ is $(CH_2)_kNR_{19}(CH_2)_jC(O)NH$.
(82) In one embodiment, $Z_1$ is $(CH_2)_jNR_{19}(CH_2)C(O)NR_{19}$; each $R_{19}$ is independently H or $C_1$-$C_3$ alkyl selected from methyl, ethyl, and propyl; and j is 1.
(83) In one embodiment, $Z_1$ is $(CH_2)_kNR_{19}(CH_2)_jC(O)NR_{19}$; each $R_{19}$ is independently H or $C_1$-$C_3$ alkyl selected from methyl, ethyl, and propyl; and k is 1.
(84) In one embodiment, $Z_1$ is $(CH_2)_kNR_{19}(CH_2)_jC(O)NR_{19}$; each $R_{19}$ is independently H or $C_1$-$C_3$ alkyl selected from methyl, ethyl, and propyl; j is 1; and k is 1.
(85) In one embodiment, $Z_1$ is $(CH_2)_kNR_{19}(CH_2)_jC(O)NR_{19}$ one of $R_{19}$ is H and one of Rig is $C_1$-$C_3$ alkyl selected from methyl, ethyl, and propyl; and j is 1. In one embodiment, $Z_1$ is $(CH_2)_kNR_{19}(CH_2)C(O)NH$.
(86) In one embodiment, $Z_1$ is $(CH_2)_kNR_{19}(CH_2)_jC(O)NR_{19}$; one of $R_{19}$ is H and one of $R_{19}$ is $C_1$-$C_3$ alkyl selected from methyl, ethyl, and propyl; and k is 1. In one embodiment, $Z_1$ is $(CH_2)NR_{19}(CH_2)_jC(O)NH$.
(87) In one embodiment, $Z_1$ is $(CH_2)_kNR_{19}(CH_2)_jC(O)NR_{19}$; one of $R_{19}$ is H and one of $R_{19}$ is $C_1$-$C_3$ alkyl selected from methyl, ethyl, and propyl; j is 1; and k is 1. In one embodiment, $Z_1$ is $(CH_2)NR_{19}(CH_2)C(O)NH$. In one embodiment, $Z_1$ is $(CH_2)N(CH_3)(CH_2)C(O)NH$.
(88) In one embodiment, $Z_1$ is $(CH_2)_kNR_{19}(CH_2)_jC(O)NR_{19}$; each $R_{19}$ is independently H or $C_1$-$C_3$ alkyl selected from methyl, ethyl, and propyl; and j is 2.
(89) In one embodiment, $Z_1$ is $(CH_2)_kNR_{19}(CH_2)_jC(O)NR_9$; each $R_{19}$ is independently H or $C_1$-$C_3$ alkyl selected from methyl, ethyl, and propyl; and k is 2.
(90) In one embodiment, $Z_1$ is $(CH_2)_kNR_{19}(CH_2)_jC(O)NR_{19}$; one of $R_{19}$ is H and one of $R_{19}$ is $C_1$-$C_3$ alkyl selected from methyl, ethyl, and propyl; and j is 2. In one embodiment, $Z_1$ is $(CH_2)_kNR_{19}(CH_2)_2C(O)NH$.
(91) In one embodiment, $Z_1$ is $(CH_2)_kNR_{19}(CH_2)_jC(O)NR_{19}$; one of $R_{19}$ is H and one of $R_{19}$ is $C_1$-$C_3$ alkyl selected from methyl, ethyl, and propyl; and k is 2. In one embodiment, $Z_1$ is $(CH_2)_2NR_{19}(CH_2)C(O)NH$.
(92) In one embodiment, $Z_1$ is $(CH_2)_kNR_{19}(CH_2)_jC(O)NR_{19}$; each $R_{19}$ is independently H or $C_1$-$C_3$ alkyl selected from methyl, ethyl, and propyl; and j is 3.
(93) In one embodiment, $Z_1$ is $(CH_2)_kNR_{19}(CH_2)_jC(O)NR_{19}$; each $R_{19}$ is independently H or $C_1$-$C_3$ alkyl selected from methyl, ethyl, and propyl; and k is 3.
(94) In one embodiment, $Z_1$ is $(CH_2)_kNR_{19}(CH_2)_jC(O)NR_{19}$; one of $R_{19}$ is H and one of $R_{19}$ is $C_1$-$C_3$ alkyl selected from methyl, ethyl, and propyl; and j is 3. In one embodiment, $Z_1$ is $(CH_2)_kNR_{19}(CH_2)_3C(O)NH$.
(95) In one embodiment, $Z_1$ is $(CH_2)_kNR_{19}(CH_2)_jC(O)NR_{19}$; one of $R_{19}$ is H and one of $R_{19}$ is $C_1$-$C_3$ alkyl selected from methyl, ethyl, and propyl; and k is 3. In one embodiment, $Z_1$ is $(CH_2)_3NR_{19}(CH_2)C(O)NH$.

(96) In one embodiment, $Z_1$ is $NR_{19}(CH_2)C(O)NR_{19}$; and each $R_{19}$ is independently H or $C_1$-$C_3$ alkyl selected from methyl, ethyl, and propyl.
(97) In one embodiment, $Z_1$ is $NR_{19}(CH_2)C(O)NR_{19}$; and each $R_{19}$ is H.
(98) In one embodiment, $Z_1$ is $NR_{19}(CH_2)C(O)NR_{19}$; one of $R_{19}$ is H and one of $R_{19}$ is $C_1$-$C_3$ alkyl selected from methyl, ethyl, and propyl; and j is 1.
(99) In one embodiment, $Z_1$ is $NR_{19}(CH_2)C(O)NR_{19}$; $R_{19}$ is H; and j is 1.
(100) In one embodiment, $Z_1$ is $NR_{19}(CH_2)_jC(O)NR_{19}$; one of $R_{19}$ is H and one of $R_{19}$ is $C_1$-$C_3$ alkyl selected from methyl, ethyl, and propyl; and j is 2.
(101) In one embodiment, $Z_1$ is $NR_9(CH_2)C(O)NR_{19}$; $R_{19}$ is H; and j is 2.
(102) In one embodiment, $Z_1$ is $NR_{19}(CH_2)C(O)NR_{19}$; one of $R_{19}$ is H and one of $R_{19}$ is $C_1$-$C_3$ alkyl selected from methyl, ethyl, and propyl; and j is 3.
(103) In one embodiment, $Z_1$ is $NR_{19}(CH_2)_jC(O)NR_9$; and $R_{19}$ is H; and j is 3.
(104) In one embodiment, $Z_1$ is

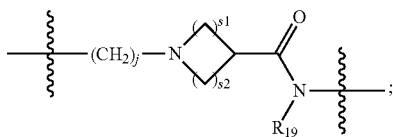

and $R_{19}$ is H.
(105) In one embodiment, $Z_1$ and $R_{19}$ are as defined in (104), and s1 is 1.
(106) In one embodiment, $Z_1$ and $R_{19}$ are defined in (104), s1 is 1; and s2 is 1.
(107) In one embodiment, $Z_1$ is as defined in (104), s1 is 1; and s2 is 2.
(108) In one embodiment, $Z_1$ and $R_1$ are as defined in (104), s1 is 1; and s2 is 3.
(109) In one embodiment, $Z_1$ and $R_{19}$ are as defined in (104), and s1 is 2.
(110) In one embodiment, $Z_1$ and $R_{19}$ are as defined in (104), s1 is 2; and s2 is 1.
(111) In one embodiment, $Z_1$ and $R_{19}$ are as defined in (104), s1 is 2; and s2 is 2.
(112) In one embodiment, $Z_1$ and $R_{19}$ are as defined in (104), s1 is 2; and s2 is 3.
(113) In one embodiment, $Z_1$ and $R_{19}$ are as defined in (104), and s1 is 3.
(114) In one embodiment, $Z_1$ and $R_{19}$ are as defined in (104), s1 is 3; and s2 is 1.
(115) In one embodiment, $Z_1$ and $R_{19}$ are as defined in (104), s1 is 3; and s2 is 2.
(116) In one embodiment, $Z_1$ and $R_{19}$ are as defined in (104), s1 is 3; and s2 is 3.
(117) In one embodiment, $Z_1$ and $R_{19}$ are as defined in (104), s1 is 1; s2 is 1; and j is 1.
(118) In one embodiment, $Z_1$ and $R_{19}$ are as defined in (104), s1 is 1; s2 is 1; and j is 2.
(119) In one embodiment, $Z_1$ and $R_{19}$ are as defined in (104), s1 is 1; s2 is 1; and j is 3.
(120) In one embodiment, $Z_1$ is

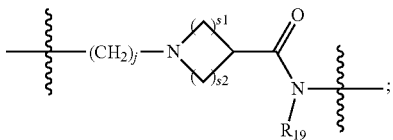

and $R_{19}$ is $C_1$-$C_3$ alkyl selected from methyl, ethyl, and propyl.
(121) In one embodiment, $Z_1$ and $R_{19}$ are as defined in (120), and s1 is 1.
(122) In one embodiment, $Z_1$ and $R_{19}$ are as defined in (120), s1 is 1; and s2 is 1.
(123) In one embodiment, $Z_1$ and $R_{19}$ are as defined in (120), s1 is 1; and s2 is 2.
(124) In one embodiment, $Z_1$ and $R_{19}$ are as defined in (120), s1 is 1; and s2 is 3.
(125) In one embodiment, $Z_1$ and $R_{19}$ are as defined in (120), and s1 is 2.
(126) In one embodiment, $Z_1$ and $R_{19}$ are as defined in (120), s1 is 2; and s2 is 1.
(127) In one embodiment, $Z_1$ and $R_{19}$ are as defined in (120), s1 is 2; and s2 is 2.
(128) In one embodiment, $Z_1$ and $R_{19}$ are as defined in (120), s1 is 2; and s2 is 3.
(129) In one embodiment, $Z_1$ and $R_{19}$ are as defined in (120), and s1 is 3.
(130) In one embodiment, $Z_1$ and $R_{19}$ are as defined in (120), s1 is 3; and s2 is 1.
(131) In one embodiment, $Z_1$ and $R_{19}$ are as defined in (120), s1 is 3; and s2 is 2.
(132) In one embodiment, $Z_1$ and $R_{19}$ are as defined in (120), s1 is 3; and s2 is 3.
(133) In one embodiment, $Z_1$ and $R_{19}$ are as defined in (120), s1 is 1; s2 is 1; and j is 1.
(134) In one embodiment, $Z_1$ and $R_{19}$ are as defined in (120), s1 is 1; s2 is 1; and j is 2.
(135) In one embodiment, $Z_1$ and $R_{19}$ are as defined in (120), s1 is 1; s2 is 1; and j is 3.
(136) In one embodiment, $Z_1$ is part of the Targeting Ligand that is bonded to the Linker, namely, $Z_1$ is formed from reacting a functional group of the Targeting Ligand with the Linker.
(137) In one embodiment, p1 is 1 and $Z_1$ is $(CH_2)_jC(O)NH$.
(138) In one embodiment, p1 is 1 and $Z_1$ is $(CH_2)C(O)NH$.
(139) In one embodiment, p1 is 1 and $Z_1$ is $(CH_2)_2C(O)NH$.
(140) In one embodiment, p1 is 1 and $Z_1$ is $(CH_2)_3C(O)NH$.
(141) In one embodiment, p1 is 1, $Z_1$ is $(CH_2)C(O)NH$, and p3 is 1.
(142) In one embodiment, p1 is 1, $Z_1$ is $(CH_2)C(O)NH$, and p3 is 1.
(143) In one embodiment, p1 is 1. $Z_1$ is $(CH_2)_2C(O)NH$, and p3 is 1.
(144) In one embodiment, p1 is 1, $Z_1$ is $(CH_2)C(O)NH$, p3 is 1, and p2 is 0.
(145) In one embodiment, p1 is 1, $Z_1$ is $(CH_2)C(O)NH$, p3 is 1, and p2 is 0.
(146) In one embodiment, p1 is 1, $Z_1$ is $(CH_2)_2C(O)NH$, p3 is 1, and p2 is 0.
(147) In one embodiment, p1 is 1, $Z_1$ is $(CH_2)_jC(O)NH$, p3 is 1, p2 is 0, and each W is O.
(148) In one embodiment, p1 is 1, $Z_1$ is $(CH_2)C(O)NH$, p3 is 1, p2 is 0, and each W is O.
(149) In one embodiment, p1 is 1, $Z_1$ is $(CH_2)_2C(O)NH$, p3 is 1, p2 is 0, and each W is O.

(150) In one embodiment, p1 is 1. $Z_1$ is $(CH_2)C(O)NH$, p3 is 1, p2 is 0, and each W is $CH_2$.
(151) In one embodiment, p1 is 1, $Z_1$ is $(CH_2)C(O)NH$, p3 is 1, p2 is 0, and each W is $CH_2$.
(152) In one embodiment, p1 is 1, $Z_1$ is $(CH_2)_2C(O)NH$, p3 is 1, p2 is 0, and each W is $CH_2$.
(153) In one embodiment, p1 is 2 and $Z_1$ is $(CH_2)C(O)NH$.
(154) In one embodiment, p1 is 2 and $Z_1$ is $(CH_2)_2C(O)NH$.
(155) In one embodiment, p1 is 2 and $Z_1$ is $(CH_2)_3C(O)NH$.
(156) In one embodiment, p1 is 2, $Z_1$ is $(CH_2)_jC(O)NH$, and p3 is 2.
(157) In one embodiment, p1 is 2. $Z_1$ is $(CH_2)C(O)NH$, and p3 is 2.
(158) In one embodiment, p1 is 2, $Z_1$ is $(CH_2)_2C(O)NH$, and p3 is 2.
(159) In one embodiment, p1 is 2, $Z_1$ is $(CH_2)C(O)NH$, p3 is 2, and p2 is 0.
(160) In one embodiment, p1 is 2, $Z_1$ is $(CH_2)C(O)NH$, p3 is 2, and p2 is 0.
(161) In one embodiment, p1 is 2, $Z_1$ is $(CH_2)_2C(O)NH$, p3 is 2, and p2 is 0.
(162) In one embodiment, p1 is 2, $Z_1$ is $(CH_2)_jC(O)NH$, p3 is 2, p2 is 0, and each W is O.
(163) In one embodiment, p1 is 2. $Z_1$ is $(CH_2)C(O)NH$, p3 is 2, p2 is 0, and each W is O.
(164) In one embodiment, p1 is 2, $Z_1$ is $(CH_2)_2C(O)NH$, p3 is 2, p2 is 0, and each W is O.
(165) In one embodiment, p1 is 2, $Z_1$ is $(CH_2)C(O)NH$, p3 is 2, p2 is 0, and each W is $CH_2$.
(166) In one embodiment, p1 is 2, $Z_1$ is $(CH_2)C(O)NH$, p3 is 2, p2 is 0, and each W is $CH_2$.
(167) In one embodiment, p1 is 2, $Z_1$ is $(CH_2)_2C(O)NH$, p3 is 2, p2 is 0, and each W is $CH_2$.
(168) In one embodiment, p1 is 3 and $Z_1$ is $(CH_2)C(O)NH$.
(169) In one embodiment, p1 is 3 and $Z_1$ is $(CH_2)_2C(O)NH$.
(170) In one embodiment, p1 is 3 and $Z_1$ is $(CH_2)_3C(O)NH$.
(171) In one embodiment, p1 is 3, $Z_1$ is $(CH_2)C(O)NH$, and p3 is 3.
(172) In one embodiment, p1 is 3, $Z_1$ is $(CH_2)C(O)NH$, and p3 is 3.
(173) In one embodiment, p1 is 3, $Z_1$ is $(CH_2)_2C(O)NH$, and p3 is 3.
(174) In one embodiment, p1 is 3, $Z_1$ is $(CH_2)_jC(O)NH$, p3 is 3, and p2 is 1.
(175) In one embodiment, p1 is 3, $Z_1$ is $(CH_2)C(O)NH$, p3 is 3, and p2 is 1.
(176) In one embodiment, p1 is 3, $Z_1$ is $(CH_2)_2C(O)NH$, p3 is 3, and p2 is 1.
(177) In one embodiment, p1 is 3. $Z_1$ is $(CH_2)C(O)NH$, p3 is 3, p2 is 1, and each W is O.
(178) In one embodiment, p1 is 3, $Z_1$ is $(CH_2)C(O)NH$, p3 is 3, p2 is 1, and each W is O.
(179) In one embodiment, p1 is 3, $Z_1$ is $(CH_2)_2C(O)NH$, p3 is 3, p2 is 1, and each W is O.
(180) In one embodiment, p1 is 3, $Z_1$ is $(CH_2)C(O)NH$, p3 is 3, p2 is 1, and each W is $CH_2$.
(181) In one embodiment, p1 is 3, $Z_1$ is $(CH_2)C(O)NH$, p3 is 3, p2 is 1, and each W is $CH_2$.
(182) In one embodiment, p1 is 3, $Z_1$ is $(CH_2)_2C(O)NH$, p3 is 3, p2 is 1, and each W is $CH_2$.
(183) In one embodiment, p1 is 2, $Z_1$ is $(CH_2)C(O)NH$, and p3 is 1.
(184) In one embodiment, p1 is 2. $Z_1$ is $(CH_2)C(O)NH$, and p3 is 1.
(185) In one embodiment, p1 is 2, $Z_1$ is $(CH_2)_2C(O)NH$, and p3 is 1.
(186) In one embodiment, p1 is 2, $Z_1$ is $(CH_2)_jC(O)NH$, p3 is 1, and p2 is 1.
(187) In one embodiment, p1 is 2, $Z_1$ is $(CH_2)C(O)NH$, p3 is 1, and p2 is 1.
(188) In one embodiment, p1 is 2, $Z_1$ is $(CH_2)_2C(O)NH$, p3 is 1, and p2 is 1.
(189) In one embodiment, p1 is 2, $Z_1$ is $(CH_2)_jC(O)NH$, p3 is 1, p2 is 1, and each W is O.
(190) In one embodiment, p1 is 2, $Z_1$ is $(CH_2)C(O)NH$, p3 is 1, p2 is 1, and each W is O.
(191) In one embodiment, p1 is 2. $Z_1$ is $(CH_2)_2C(O)NH$, p3 is 1, p2 is 1, and each W is O.
(192) In one embodiment, p1 is 2, $Z_1$ is $(CH_2)C(O)NH$, p3 is 1, p2 is 1, and each W is $CH_2$.
(193) In one embodiment, p1 is 2, $Z_1$ is $(CH_2)C(O)NH$, p3 is 1, p2 is 1, and each W is $CH_2$.
(194) In one embodiment, p1 is 2, $Z_1$ is $(CH_2)_2C(O)NH$, p3 is 1, p2 is 1, and each W is $CH_2$.
(195) In one embodiment, p1 is 1, $Z_1$ is $(CH_2)C(O)NH$, and p3 is 2.
(196) In one embodiment, p1 is 1, $Z_1$ is $(CH_2)C(O)NH$, and p3 is 2.
(197) In one embodiment, p1 is 1. $Z_1$ is $(CH_2)_2C(O)NH$, and p3 is 2.
(198) In one embodiment, p1 is 1, $Z_1$ is $(CH_2)C(O)NH$, p3 is 2, and p2 is 0.
(199) In one embodiment, p1 is 1, $Z_1$ is $(CH_2)C(O)NH$, p3 is 2, and p2 is 0.
(200) In one embodiment, p1 is 1, $Z_1$ is $(CH_2)_2C(O)NH$, p3 is 2, and p2 is 0.
(201) In one embodiment, p1 is 1, $Z_1$ is $(CH_2)_jC(O)NH$, p3 is 2, p2 is 0, and each W is O.
(202) In one embodiment, p1 is 1, $Z_1$ is $(CH_2)C(O)NH$, p3 is 2, p2 is 0, and each W is O.
(203) In one embodiment, p1 is 1, $Z_1$ is $(CH_2)_2C(O)NH$, p3 is 2, p2 is 0, and each W is O.
(204) In one embodiment, p1 is 1. $Z_1$ is $(CH_2)C(O)NH$, p3 is 2, p2 is 0, and each W is $CH_2$.
(205) In one embodiment, p1 is 1, $Z_1$ is $(CH_2)C(O)NH$, p3 is 2, p2 is 0, and each W is $CH_2$.
(206) In one embodiment, p1 is 1, $Z_1$ is $(CH_2)_2C(O)NH$, p3 is 2, p2 is 0, and each W is $CH_2$.
(207) In one embodiment, p1 is 1, $Z_1$ is $(CH_2)C(O)NH$, and p3 is 3.
(208) In one embodiment, p1 is 1, $Z_1$ is $(CH_2)C(O)NH$, and p3 is 3.
(209) In one embodiment, p1 is 1, $Z_1$ is $(CH_2)_2C(O)NH$, and p3 is 3.
(210) In one embodiment, p1 is 1, $Z_1$ is $(CH_2)C(O)NH$, p3 is 3, and p2 is 0.
(211) In one embodiment, p1 is 1. $Z_1$ is $(CH_2)C(O)NH$, p3 is 3, and p2 is 0.
(212) In one embodiment, p1 is 1, $Z_1$ is $(CH_2)_2C(O)NH$, p3 is 3, and p2 is 0.
(213) In one embodiment, p1 is 1, $Z_1$ is $(CH_2)C(O)NH$, p3 is 3, p2 is 0, and each W is O.
(214) In one embodiment, p1 is 1, $Z_1$ is $(CH_2)C(O)NH$, p3 is 3, p2 is 0, and each W is O.
(215) In one embodiment, p1 is 1, $Z_1$ is $(CH_2)_2C(O)NH$, p3 is 3, p2 is 0, and each W is O.
(216) In one embodiment, p1 is 1, $Z_1$ is $(CH_2)_jC(O)NH$, p3 is 3, p2 is 0, and each W is $CH_2$.
(217) In one embodiment, p1 is 1, $Z_1$ is $(CH_2)C(O)NH$, p3 is 3, p2 is 0, and each W is $CH_2$.
(218) In one embodiment, p1 is 1. $Z_1$ is $(CH_2)_2C(O)NH$, p3 is 3, p2 is 0, and each W is $CH_2$.
(219) In one embodiment, p1 is 4 and $Z_1$ is $(CH_2)C(O)NH$.

(220) In one embodiment, p1 is 4 and $Z_1$ is $(CH_2)_2C(O)NH$.
(221) In one embodiment, p1 is 4 and $Z_1$ is $(CH_2)_3C(O)NH$.
(222) In one embodiment, p1 is 4, $Z_1$ is $(CH_2)C(O)NH$, and p3 is 2.
(223) In one embodiment, p1 is 4, $Z_1$ is $(CH_2)C(O)NH$, and p3 is 2.
(224) In one embodiment, p1 is 4, $Z_1$ is $(CH_2)_2C(O)NH$, and p3 is 2.
(225) In one embodiment, p1 is 4. $Z_1$ is $(CH_2)C(O)NH$, p3 is 2, and p2 is 0.
(226) In one embodiment, p1 is 4, $Z_1$ is $(CH_2)C(O)NH$, p3 is 2, and p2 is 0.
(227) In one embodiment, p1 is 4, $Z_1$ is $(CH_2)_2C(O)NH$, p3 is 2, and p2 is 0.
(228) In one embodiment, p1 is 4, $Z_1$ is $(CH_2)_jC(O)NH$, p3 is 2, p2 is 0, and each W is O.
(229) In one embodiment, p1 is 4, $Z_1$ is $(CH_2)C(O)NH$, p3 is 2, p2 is 0, and each W is O.
(230) In one embodiment, p1 is 4, $Z_1$ is $(CH_2)_2C(O)NH$, p3 is 2, p2 is 0, and each W is O.
(231) In one embodiment, p1 is 4. $Z_1$ is $(CH_2)_jC(O)NH$, p3 is 2, p2 is 0, and each W is $CH_2$.
(232) In one embodiment, p1 is 4, $Z_1$ is $(CH_2)C(O)NH$, p3 is 2, p2 is 0, and each W is $CH_2$.
(233) In one embodiment, p1 is 4, $Z_1$ is $(CH_2)_2C(O)NH$, p3 is 2, p2 is 0, and each W is $CH_2$.
(234) In one embodiment, p1 is 3, $Z_1$ is $(CH_2)C(O)NH$, and p3 is 2.
(235) In one embodiment, p1 is 3, $Z_1$ is $(CH_2)C(O)NH$, and p3 is 2.
(236) In one embodiment, p1 is 3, $Z_1$ is $(CH_2)_2C(O)NH$, and p3 is 2.
(237) In one embodiment, p1 is 3, $Z_1$ is $(CH_2)_jC(O)NH$, p3 is 2, and p2 is 0.
(238) In one embodiment, p1 is 3. $Z_1$ is $(CH_2)C(O)NH$, p3 is 2, and p2 is 0.
(239) In one embodiment, p1 is 3, $Z_1$ is $(CH_2)_2C(O)NH$, p3 is 2, and p2 is 0.
(240) In one embodiment, p1 is 3, $Z_1$ is $(CH_2)C(O)NH$, p3 is 2, p2 is 0, and each W is O.
(241) In one embodiment, p1 is 3, $Z_1$ is $(CH_2)C(O)NH$, p3 is 2, p2 is 0, and each W is O.
(242) In one embodiment, p1 is 3, $Z_1$ is $(CH_2)_2C(O)NH$, p3 is 2, p2 is 0, and each W is O.
(243) In one embodiment, p1 is 3, $Z_1$ is $(CH_2)C(O)NH$, p3 is 2, p2 is 0, and each W is $CH_2$.
(244) In one embodiment, p1 is 3, $Z_1$ is $(CH_2)C(O)NH$, p3 is 2, p2 is 0, and each W is $CH_2$.
(245) In one embodiment, p1 is 3. $Z_1$ is $(CH_2)_2C(O)NH$, p3 is 2, p2 is 0, and each W is $CH_2$.
(246) In one embodiment, p1 is 1, $Z_1$ is $(CH_2)_jC(O)NH$, and p3 is 2.
(247) In one embodiment, p1 is 1, $Z_1$ is $(CH_2)C(O)NH$, and p3 is 2.
(248) In one embodiment, p1 is 1, $Z_1$ is $(CH_2)_2C(O)NH$, and p3 is 2.
(249) In one embodiment, p1 is 1, $Z_1$ is $(CH_2)_jC(O)NH$, p3 is 2, and p2 is 1.
(250) In one embodiment, p1 is 1, $Z_1$ is $(CH_2)C(O)NH$, p3 is 2, and p2 is 1.
(251) In one embodiment, p1 is 1, $Z_1$ is $(CH_2)_2C(O)NH$, p3 is 2, and p2 is 1.
(252) In one embodiment, p1 is 1. $Z_1$ is $(CH_2)C(O)NH$, p3 is 2, p2 is 1, and each W is O.
(253) In one embodiment, p1 is 1, $Z_1$ is $(CH_2)C(O)NH$, p3 is 2, p2 is 1, and each W is O.
(254) In one embodiment, p1 is 1, $Z_1$ is $(CH_2)_2C(O)NH$, p3 is 2, p2 is 1, and each W is O.
(255) In one embodiment, p1 is 1, $Z_1$ is $(CH_2)C(O)NH$, p3 is 2, p2 is 1, and each W is $CH_2$.
(256) In one embodiment, p1 is 1, $Z_1$ is $(CH_2)C(O)NH$, p3 is 2, p2 is 1, and each W is $CH_2$.
(257) In one embodiment, p1 is 1, $Z_1$ is $(CH_2)_2C(O)NH$, p3 is 2, p2 is 1, and each W is $CH_2$.
(258) In one embodiment, p1 is 3, $Z_1$ is $O(CH_2)C(O)NH$, p3 is 2, p2 is 0, and each W is O.
(259) In one embodiment, p1 is 3, $Z_1$ is $O(CH_2)C(O)NH$, p3 is 2, p2 is 0, and each W is $CH_2$.
(260) In one embodiment, p1 is 2, $Z_1$ is $O(CH_2)C(O)NH$, p3 is 2, p2 is 0, and each W is O.
(261) In one embodiment, p1 is 2, $Z_1$ is $O(CH_2)C(O)NH$, p3 is 2, p2 is 0, and each W is $CH_2$.
(262) In one embodiment, p1 is 1, $Z_1$ is $O(CH_2)C(O)NH$, p3 is 3, p2 is 0, and each W is O.
(263) In one embodiment, p1 is 1, $Z_1$ is $O(CH_2)C(O)NH$, p3 is 3, p2 is 0, and each W is $CH_2$.
(264) In one embodiment, p1 is 2, $Z_1$ is $(CH_2)N(CH_3)CH_2C(O)NH$, p3 is 2, p2 is 0, and each W is $CH_2$.
(265) In one embodiment, p1 is 2, $Z_1$ is $(CH_2)N(CH_3)CH_2C(O)NH$, p3 is 2, p2 is 0, and each W is O.
(266) In one embodiment, p1 is 2, $Z_1$ is $C(O)NH$, p3 is 2, p2 is 0, and each W is $CH_2$.
(267) In one embodiment, p1 is 2, $Z_1$ is $C(O)NH$, p3 is 2, p2 is 0, and each W is O.
(268) In one embodiment, p1, $Z_1$, p3, p2, and W are each as defined, where applicable, in any one of (1)-(267), and Q is absent.
(269) In one embodiment, p1, $Z_1$, p3, p2, and W are each as defined, where applicable, in any one of (1)-(267), and Q is $NHC(O)CH_2$.
(270) In one embodiment, p1, $Z_1$, p3, p2, and W are each as defined, where applicable, in any one of (1)-(267), and Q is $O(CH_2)_{1-2}$.
(271) In one embodiment, p1, $Z_1$, p3, p2, and W are each as defined, where applicable, in any one of (1)-(267), and Q is $O(CH_2)$.
(272) In one embodiment, p1, $Z_1$, p3, p2, and W are each as defined, where applicable, in any one of (1)-(267), and Q is $O(CH_2CH_2)$.

In one embodiment, the Linker-Targeting Ligand (TL) has the structure selected from Table L:

TABLE L

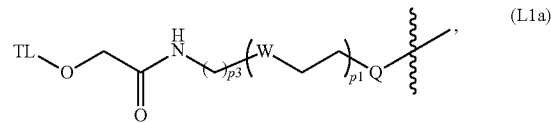
(L1a)

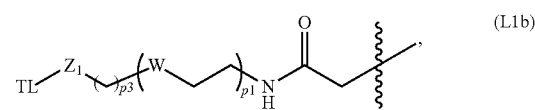
(L1b)

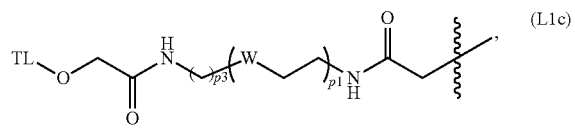
(L1c)

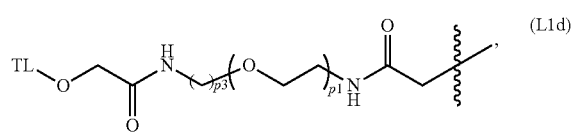
(L1d)

TABLE L-continued

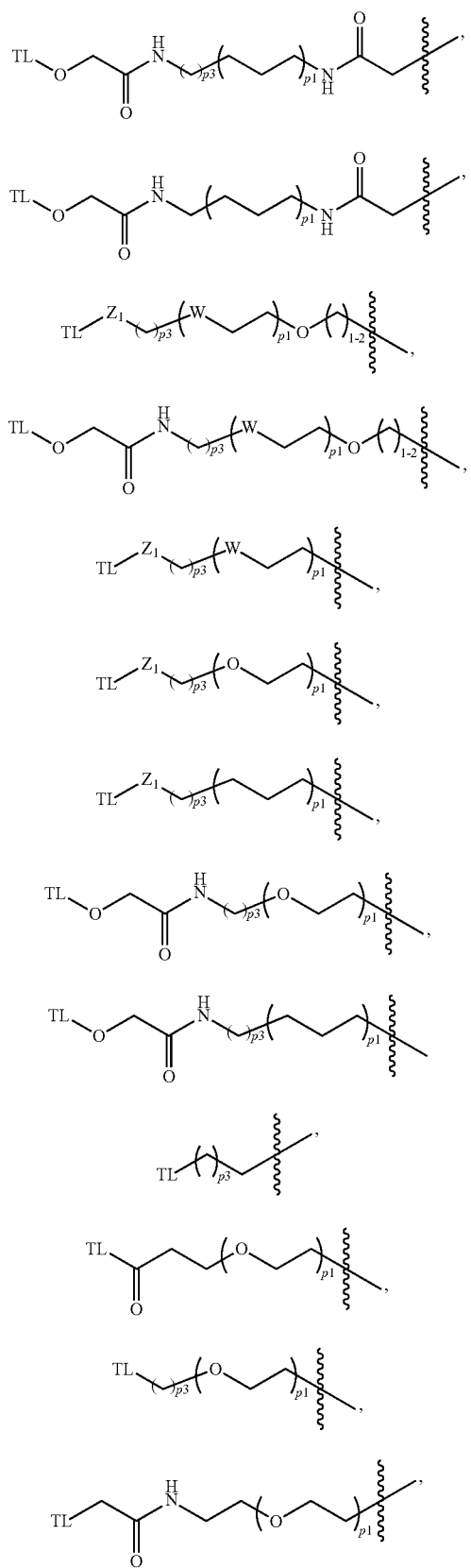
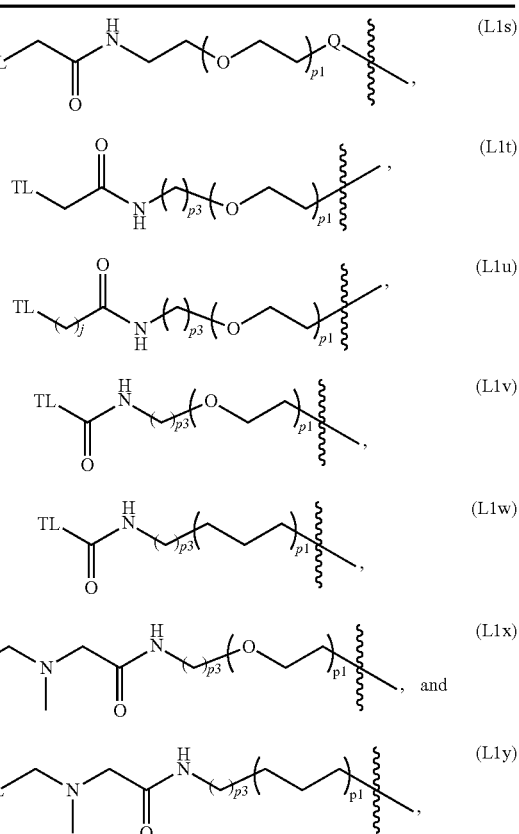

wherein $Z_1$, W, Q, TL, p1, p3, and j are each as described above.

In one embodiment, the present application provides the Degron-Linker (DL), wherein the Degron is of Formula D1, and the Linker is selected from L1a-L1k and L1m-L1y. In one embodiment, the present application provides the Degron-Linker (DL), wherein the Degron is of Formula D1, and the Linker is selected from L1a-L1k and L1m-L1u. In one embodiment, the present application provides the Degron-Linker (DL), wherein the Degron is of Formula D1, and the Linker is selected from L1a-L1k, L1m, and L1n. In one embodiment, the Degron is of Formula D1, and the Linker is selected from L1a-L1k and L1m-L1u. In one embodiment, the Degron is of Formula D1, and the Linker is selected from L1a-L1k, L1m, and L1n. In one embodiment, the Degron is of Formula D1, and the Linker is L1a, L1b, or L1c. In one embodiment, the Degron is of Formula D1, and the Linker is L1d, L1e, or L1f. In one embodiment, the Degron is of Formula D1, and the Linker is L1g or L1h. In one embodiment, the Degron is of Formula D1, and the Linker is L1i, L1j, or L1k. In one embodiment, the Degron is of Formula D1, and the Linker is L1m or L1n. In one embodiment, the Degron is of Formula D1, and the Linker is L1o-L1u. In one embodiment, the Degron is of Formula D1, and the Linker is L1o or L1p. In one embodiment, the Degron is of Formula D1, and the Linker is L1p or L1q. In one embodiment, the Degron is of Formula D1, and the Linker is L1r or L1s. In one embodiment, the Degron is of Formula D1, and the Linker is L1t or L1u. In one embodiment, the Degron is of Formula D1, and the Linker is L1v-L1y.

In one embodiment, the present application provides the Degron-Linker (DL), wherein the Degron is of Formula D1a, D1b, D1c, D1d, D1e, D1f, D1g, D1h, D1i, D1j, D1k, or D1l, and the Linker is selected from L1a-L1k and L1m-L1y. In one embodiment, the present application provides the Degron-Linker (DL), wherein the Degron is of Formula D1a. D1b, D1c, D1d, D1e, D1f, D1g, D1h, D1i, D1j, D1k, or D1l, and the Linker is selected from L1a-L1k and L1m-L1u. In one embodiment, the present application provides the Degron-Linker (DL), wherein the Degron is of Formula D1a, D1b, D1c, D1d, D1e, D1f, D1g, D1h, D1i, D1j, D1k, or D1l, and the Linker is selected from L1a-L1k, L1m, and L1n. In one embodiment, the Degron is of Formula D1a, D1b, D1c, D1d, D1e, D1f, D1g, D1h, D1i, D1j, D1k, or D1l, and the Linker is selected from L1a-L1k and L1m-L1u. In one embodiment, the Degron is of Formula D1a, D1b, D1c, D1d, D1e, D1f, D1g, D1h, D1i, D1j, D1k, or D1l, and the Linker is selected from L1a-L1k, L1m, and L1n. In one embodiment, the Degron is of Formula D1a, D1b, D1c, D1d, D1e, D1f, D1g, D1h, D1i, D1j, D1k, or D1l, and the Linker is L1a, L1b, or L1c. In one embodiment, the Degron is of Formula D1a, D1b, D1c, D1d, D1e, D1f, D1g, D1h, D1i, D1j, D1k, or D1l, and the Linker is L1d, L1e, or L1f. In one embodiment, the Degron is of Formula D1a, D1b, D1c, D1d, D1e, D1f, D1g, D1h, D1i, D1j, D1k, or D1l, and the Linker is L1g or L1h. In one embodiment, the Degron is of Formula D1a, D1b, D1c, D1d, D1e, D1f, D1g, D1h, D1i, D1j, D1k, or D1l, and the Linker is L1i, L1j, or L1k. In one embodiment, the Degron is of Formula D1a, D1b, D1c, D1d, D1e, D1f, D1g, D1h, D1i, D1j, D1k, or D1l, and the Linker is L1m or L1n. In one embodiment, the Degron is of Formula D1a, D1b, D1c, D1d, D1e, D1f, D1g, D1h, D1i, D1j, D1k, or D1l, and the Linker is L1o-L1u. In one embodiment, the Degron is of Formula D1a, D1b, D1c, D1d, D1e, D1f, D1g, D1h, D1i, D1j, D1k, or D1l, and the Linker is L1o or L1p. In one embodiment, the Degron is of Formula D1a, D1b, D1c, D1d, D1e, D1f, D1g, D1h, D1i, D1j, D1k, or D1l, and the Linker is L1p or L1q. In one embodiment, the Degron is of Formula D1a, D1b, D1c, D1d, D1e, D1f, D1g, D1h, D1i, D1j, D1k, or D1l, and the Linker is L1r or L1s. In one embodiment, the Degron is of Formula D1a, D1b, D1c, D1d, D1e, D1f, D1g, D1h, D1i, D1j, D1k, or D1l, and the Linker is L1t or L1u. In one embodiment, the Degron is of Formula D1a, D1b, D1c, D1d, D1e, D1f, D1g, D1h, D1i, D1j, D1k, or D1l, and the Linker is L1v-L1y.

In one embodiment, the present application provides the Degron-Linker (DL), wherein the Degron is of Formula D2, and the Linker is selected from L1a-L1k and L1m-L1y. In one embodiment, the present application provides the Degron-Linker (DL), wherein the Degron is of Formula D2, and the Linker is selected from L1a-L1k and L1m-L1u. In one embodiment, the present application provides the Degron-Linker (DL), wherein the Degron is of Formula D2, and the Linker is selected from L1a-L1k, L1m, and L1n. In one embodiment, the Degron is of Formula D2, and the Linker is selected from L1a-L1k and L1m-L1u. In one embodiment, the Degron is of Formula D2, and the Linker is selected from L1a-L1k, L1m, and L1n. In one embodiment, the Degron is of Formula D2, and the Linker is L1a, L1b, or L1c. In one embodiment, the Degron is of Formula D2, and the Linker is L1d, L1e, or L1f. In one embodiment, the Degron is of Formula D2, and the Linker is L1g or L1h. In one embodiment, the Degron is of Formula D2, and the Linker is L1i, L1j, or L1k. In one embodiment, the Degron is of Formula D2, and the Linker is L1m or L1n. In one embodiment, the Degron is of Formula D2, and the Linker is L1o-L1u. In one embodiment, the Degron is of Formula D2, and the Linker is L1o or L1p. In one embodiment, the Degron is of Formula D2, and the Linker is L1p or L1q. In one embodiment, the Degron is of Formula D2, and the Linker is L1r or L1s. In one embodiment, the Degron is of Formula D2, and the Linker is L1t or L1u. In one embodiment, the Degron is of Formula D2, and the Linker is L1v-L1y.

In one embodiment, the present application provides the Degron-Linker (DL), wherein the Degron is of Formula D2a or D2b, and the Linker is selected from L1a-L1k and L1m-L1y. In one embodiment, the present application provides the Degron-Linker (DL), wherein the Degron is of Formula D2a or D2b, and the Linker is selected from L1a-L1k and L1m-L1u. In one embodiment, the present application provides the Degron-Linker (DL), wherein the Degron is of Formula D2a or D2b, and the Linker is selected from L1a-L1k, L1m, and L1n. In one embodiment, the Degron is of Formula D2a or D2b, and the Linker is selected from L1a-L1k and L1m-L1u. In one embodiment, the Degron is of Formula D2a or D2b, and the Linker is selected from L1a-L1k, L1m, and L1n. In one embodiment, the Degron is of Formula D2a or D2b, and the Linker is L1a, L1b, or L1c. In one embodiment, the Degron is of Formula D2a or D2b, and the Linker is L1d, L1e, or L1f. In one embodiment, the Degron is of Formula D2a or D2b, and the Linker is L1g or L1h. In one embodiment, the Degron is of Formula D2a or D2b, and the Linker is L1, L1j, or Lk. In one embodiment, the Degron is of Formula D2a or D2b, and the Linker is L1m or L1n. In one embodiment, the Degron is of Formula D2a or D2b, and the Linker is L1o-L1u. In one embodiment, the Degron is of Formula D2a or D2b, and the Linker is L1o or L1p. In one embodiment, the Degron is of Formula D2a or D2b, and the Linker is L1p or L1q. In one embodiment, the Degron is of Formula D2a or D2b, and the Linker is L1r or L1s. In one embodiment, the Degron is of Formula D2a or D2b, and the Linker is L1t or L1u. In one embodiment, the Degron is of Formula D2a or D2b, and the Linker is L1v-L1y.

In one embodiment, the present application provides the Degron-Linker (DL), wherein the Degron is of Formula D2c or D2d, and the Linker is selected from L a-L k and L1m-L1y. In one embodiment, the present application provides the Degron-Linker (DL), wherein the Degron is of Formula D2c or D2d, and the Linker is selected from L1a-L1k and L1m-L1u. In one embodiment, the present application provides the Degron-Linker (DL), wherein the Degron is of Formula D2c or D2d, and the Linker is selected from L1a-L1k, L1m, and L1n. In one embodiment, the Degron is of Formula D2c or D2d, and the Linker is selected from L1a-L1k and L1m-L1u. In one embodiment, the Degron is of Formula D2c or D2d, and the Linker is selected from L1a-L1k, L1m, and L1n. In one embodiment, the Degron is of Formula D2c or D2d, and the Linker is L1a, L1b, or L1c. In one embodiment, the Degron is of Formula D2c or D2d, and the Linker is L1d, L1e, or L1f. In one embodiment, the Degron is of Formula D2c or D2d, and the Linker is L1g or L1h. In one embodiment, the Degron is of Formula D2c or D2d, and the Linker is L1i, L1j, or L1k. In one embodiment, the Degron is of Formula D2c or D2d, and the Linker is L1m or L1n. In one embodiment, the Degron is of Formula D2c or D2d, and the Linker is L1o-L1u. In one embodiment, the Degron is of Formula D2c or D2d, and the Linker is L1o or Lip. In one embodiment, the Degron is of Formula D2c or D2d, and the Linker is L1p or L1q. In one embodiment, the Degron is of Formula D2c or D2d, and the Linker is L1r or L1s. In one embodiment, the Degron is of Formula D2c or D2d, and the Linker is L1t or L1u. In one embodiment, the Degron is of Formula D2c or D2d, and the Linker is L1v-L1y.

In one embodiment, the present application provides the Degron-Linker (DL), wherein the Degron is of Formula D2e or D2f, and the Linker is selected from L1a-L1k and L1m-L1y. In one embodiment, the present application provides the Degron-Linker (DL), wherein the Degron is of Formula D2e or D2f, and the Linker is selected from L1a-L1k and L1m-L1u. In one embodiment, the present application provides the Degron-Linker (DL), wherein the Degron is of Formula D2e or D2f, and the Linker is selected from L a-L1k, L1m, and L1n. In one embodiment, the Degron is of Formula D2e or D2f, and the Linker is selected from L1a-L1k and L1m-L1u. In one embodiment, the Degron is of Formula D2e or D2f, and the Linker is selected from L1a-L1k, L1m, and L1n. In one embodiment, the Degron is of Formula D2e or D2f, and the Linker is L1a, L1b, or L1c. In one embodiment, the Degron is of Formula D2e or D2f, and the Linker is L1d, L1e, or L1f. In one embodiment, the Degron is of Formula D2e or D2f, and the Linker is L1g or L1h. In one embodiment, the Degron is of Formula D2e or D2f, and the Linker is L1i, L1j, or L1k. In one embodiment, the Degron is of Formula D2e or D2f, and the Linker is L1m or L1n. In one embodiment, the Degron is of Formula D2e or D2f, and the Linker is L1o-L1u. In one embodiment, the Degron is of Formula D2e or D2f, and the Linker is L1o or L1p. In one embodiment, the Degron is of Formula D2e or D2f, and the Linker is L1p or L1q. In one embodiment, the Degron is of Formula D2e or D2f, and the Linker is L r or L1s. In one embodiment, the Degron is of Formula D2e or D2f, and the Linker is L1t or L1u. In one embodiment, the Degron is of Formula D2e or D2f, and the Linker is L1v-L1y.

In one embodiment, the Linker is of Formula L2:

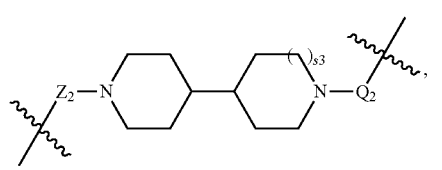

(L2)

or an enantiomer, diastereomer, or stereoisomer thereof, wherein s3 is 0 or 1:

$Z_2$ is absent, C(O), $CH_2$, $O(CH_2)_{j1}C(O)$, or $NR_{20}(CH_2)_{j1}C(O)$;

$R_{20}$ is H or $C_1$-$C_3$ alkyl;

$j_1$ is 1, 2, or 3; and $Q_2$ is absent, $NHC(O)CH_2$, or $C(O)(CH_2)_{1-4}$:

wherein the Linker is covalently bonded to a Degron via the

next to $Q_2$, and covalently bonded to a Targeting Ligand via the

next to $Z_2$.

For a Linker of Formula L2:

In one embodiment, s3 is 0.
In one embodiment, s3 is 1.
In one embodiment, $Z_2$ is absent.
In one embodiment, $Z_2$ is $CH_2$.
In one embodiment, $Z_2$ is C(O).
In one embodiment, $Z_2$ is $O(CH_2)_{j1}C(O)$. In one embodiment, $Z_2$ is $O(CH_2)C(O)$.
In one embodiment, Z is $NR_2(CH_2)_{j1}C(O)$.
In one embodiment, $Z_2$ is $NR_{20}(CH_2)_{j1}C(O)$; and $R_{20}$ is $C_1$-$C_3$ alkyl selected from methyl, ethyl, and propyl.
In one embodiment, $Z_2$ is $NR_{20}(CH_2)_{j1}C(O)$; and $R_{20}$ is H.
In one embodiment, $Z_2$ is $NR_{20}(CH_2)_{j1}C(O)$; $R_{20}$ is $C_1$-$C_3$ alkyl selected from methyl, ethyl, and propyl; and $j_1$ is 1.
In one embodiment, $Z_2$ is $NR_{20}(CH_2)_{j1}C(O)$; $R_{20}$ is $C_1$-$C_3$ alkyl selected from methyl, ethyl, and propyl; and $j_1$ is 2.
In one embodiment, $Z_2$ is $NR_{20}(CH_2)_{j1}C(O)$; $R_{20}$ is $C_1$-$C_3$ alkyl selected from methyl, ethyl, and propyl; and $j_1$ is 3.
In one embodiment, $Z_2$ is $NR_{20}(CH_2)_{j1}C(O)$; $R_{20}$ is H; and $j_1$ is 1.
In one embodiment, $Z_2$ is $NR_{20}(CH_2)_{j1}C(O)$; $R_{20}$ is H; and $j_1$ is 2.
In one embodiment, $Z_2$ is $NR_{20}(CH_2)_{j1}C(O)$; $R_{20}$ is H; and $j_1$ is 3.
In one embodiment, $Q_2$ is absent.
In one embodiment, $Q_2$ is $C(O)(CH_2)_{1-4}$.
In one embodiment, $Q_2$ is $NHC(O)CH_2$.
In one embodiment, s3 is 0 and $Q_2$ is absent.
In one embodiment, s3 is 0 and $Q_2$ is $C(O)(CH_2)_{1-4}$.
In one embodiment, s3 is 0 and $Q_2$ is $NHC(O)CH_2$.
In one embodiment, s3 is 1 and $Q_2$ is absent.
In one embodiment, s3 is 1 and $Q_2$ is $C(O)(CH_2)_4$.
In one embodiment, s3 is 1 and $Q_2$ is $NHC(O)CH_2$.
In one embodiment, $Q_2$ is absent and Z is absent.
In one embodiment, $Q_2$ is absent and Z is $CH_2$.
In one embodiment, $Q_2$ is absent and Z is C(O).
In one embodiment, $Q_2$ is absent and Z is $O(CH_2)_{j1}C(O)$.
In one embodiment, $Q_2$ is absent and Z is $NR_{20}(CH_2)_{j1}C(O)$.
In one embodiment, $Q_2$ is $C(O)(CH_2)_{1-4}$ and Z is absent.
In one embodiment, $Q_2$ is $C(O)CH_2)_{1-4}$ and Z is $CH_2$.
In one embodiment, $Q_2$ is $C(O)CH_2)_{1-4}$ and Z is C(O).
In one embodiment, $Q_2$ is $C(O)(CH_2)_{1-4}$ and Z is $O(CH_2)_{j1}C(O)$.
In one embodiment, $Q_2$ is $C(O)(CH_2)_{1-4}$ and Z is $NR_{20}(CH_2)_{j1}C(O)$.
In one embodiment, $Q_2$ is $NHC(O)CH_2$ and Z is absent.
In one embodiment, $Q_2$ is $NHC(O)CH_2$ and Z is $CH_2$.
In one embodiment, $Q_2$ is $NHC(O)CH_2$ and Z is C(O).
In one embodiment, $Q_2$ is $NHC(O)CH_2$ and Z is $O(CH_2)_{j1}C(O)$.
In one embodiment, $Q_2$ is $NHC(O)CH_2$ and Z is $NR_{20}(CH_2)_{j1}C(O)$.
In one embodiment, s3 is 0 and $Z_2$ is absent.
In one embodiment, s3 is 1 and $Z_2$ is absent.
In one embodiment, s3 is 0 and $Z_2$ is $CH_2$.
In one embodiment, s3 is 1 and $Z_2$ is $CH_2$.
In one embodiment, s3 is 0 and $Z_2$ is C(O).
In one embodiment, s3 is 1 and $Z_2$ is C(O).
In one embodiment, s3 is 0 and $Z_2$ is $NR_{20}(CH_2)_{j1}C(O)$.
In one embodiment, s3 is 1 and $Z_2$ is $NR_{20}(CH_2)_{j1}C(O)$.
In one embodiment, s3 is 0; $Z_2$ is $NR_{20}(CH_2)_{j1}C(O)$; and $R_{20}$ is H.
In one embodiment, s3 is 1; $Z_2$ is $NR_{20}(CH_2)_{j1}C(O)$; and $R_{20}$ is H.

In one embodiment, s3 is 0; $Z_2$ is $NR_{20}(CH_2)_{j1}C(O)$; and $R_{20}$ is $C_1$-$C_3$ alkyl selected from methyl, ethyl, and propyl.

In one embodiment, s3 is 1; $Z_2$ is $NR_{20}(CH_2)_{j1}C(O)$; and $R_{20}$ is $C_1$-$C_3$ alkyl selected from methyl, ethyl, and propyl.

In one embodiment, the Linker-Targeting Ligand (TL) has the structure selected from Table M:

TABLE M

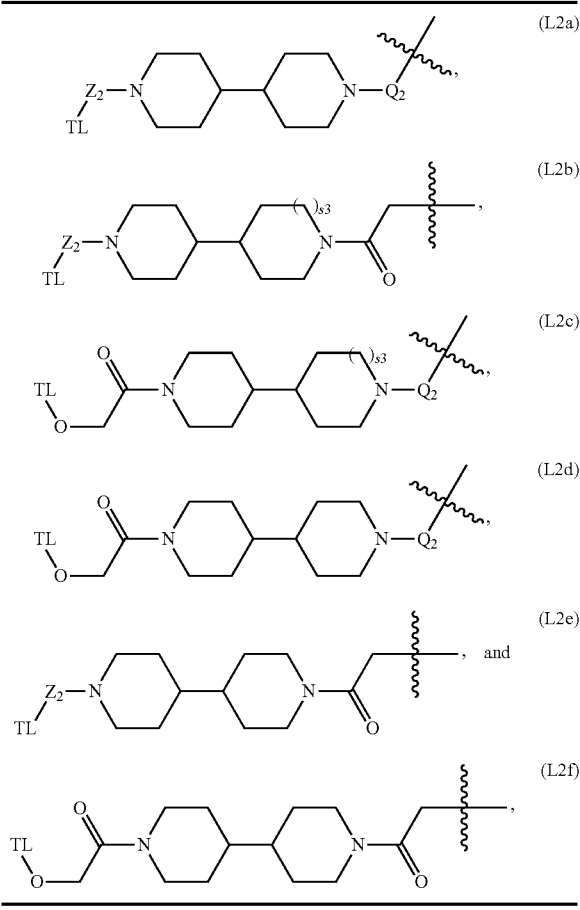

wherein $Z_2$, W, $Q_2$, TL, and s3 are each as described above.

Any one of the Degrons described herein can be covalently bound to any one of the Linkers described herein. Any one of the Targeting Ligands described herein can be covalently bound to any one of the Linkers described herein.

In one embodiment, the present application provides the Degron-Linker (DL), wherein the Degron is of Formula D1, and the Linker is selected from L2a-L2f. In one embodiment, the present application provides the Degron-Linker (DL), wherein the Degron is of Formula D1, and the Linker is selected from L2a. In one embodiment, the present application provides the Degron-Linker (DL), wherein the Degron is of Formula D1, and the Linker is selected from L2b or L2c. In one embodiment, the present application provides the Degron-Linker (DL), wherein the Degron is of Formula D1, and the Linker is selected from L2d or L2e. In one embodiment, the present application provides the Degron-Linker (DL), wherein the Degron is of Formula D1, and the Linker is selected from L2f. In one embodiment, the present application provides the Degron-Linker (DL), wherein the Degron is of Formula D1, and the Linker is selected from L2b-L2d. In one embodiment, the present application provides the Degron-Linker (DL), wherein the Degron is of Formula D1, and the Linker is selected from L2d or L2f.

In one embodiment, the present application provides the Degron-Linker (DL), wherein the Degron is of Formula D1a, D1b, D1c, D1d, D1e, D1f, D1g, D1h, D1i, D1j, D1k, or D1l, and the Linker is selected from L2a-L2f. In one embodiment, the present application provides the Degron-Linker (DL), wherein the Degron is of Formula D1a, D1b, D1c, D1d, D1e, D1f, D1g, D1h, D1i, D1j, D1k, or D1l, and the Linker is selected from L2a. In one embodiment, the present application provides the Degron-Linker (DL), wherein the Degron is of Formula D1a, D1b, D1c, D1d, D1e, D1f, D1g, D1h, D1i, D1j, D1k, or D1l, and the Linker is selected from L2b or L2c. In one embodiment, the present application provides the Degron-Linker (DL), wherein the Degron is of Formula D1a, D1b, D1c, D1d, D1e, D1f, D1g, D1h, D1i, D1j, D1k, or D1l, and the Linker is selected from L2d or L2e. In one embodiment, the present application provides the Degron-Linker (DL), wherein the Degron is of Formula D1a, D1b, D1c, D1d, D1e, D1f, D1g, D1h, D1i, D1j, D1k, or D1l, and the Linker is selected from L2f. In one embodiment, the present application provides the Degron-Linker (DL), wherein the Degron is of Formula D1a, D1b, D1c, D1d, D1e, D1f, D1g, D1h, D1i, D1j, D1k, or D1l, and the Linker is selected from L2b-L2d. In one embodiment, the present application provides the Degron-Linker (DL), wherein the Degron is of Formula D1a, D1b, D1c, D1d, D1e, D1f, D1g, D1h, D1i, D1j, D1k, or D1l, and the Linker is selected from L2d or L2f.

In one embodiment, the present application provides the Degron-Linker (DL), wherein the Degron is of Formula D2, and the Linker is selected from L2a-L2f. In one embodiment, the present application provides the Degron-Linker (DL), wherein the Degron is of Formula D2, and the Linker is selected from L2a. In one embodiment, the present application provides the Degron-Linker (DL), wherein the Degron is of Formula D2, and the Linker is selected from L2b or L2c. In one embodiment, the present application provides the Degron-Linker (DL), wherein the Degron is of Formula D2, and the Linker is selected from L2d or L2e. In one embodiment, the present application provides the Degron-Linker (DL), wherein the Degron is of Formula D2, and the Linker is selected from L2f. In one embodiment, the present application provides the Degron-Linker (DL), wherein the Degron is of Formula D2, and the Linker is selected from L2b-L2d. In one embodiment, the present application provides the Degron-Linker (DL), wherein the Degron is of Formula D2, and the Linker is selected from L2d or L2f.

In one embodiment, the present application provides the Degron-Linker (DL), wherein the Degron is of Formula D2a or D2b, and the Linker is selected from L2a-L2f. In one embodiment, the present application provides the Degron-Linker (DL), wherein the Degron is of Formula D2a or D2b, and the Linker is selected from L2a. In one embodiment, the present application provides the Degron-Linker (DL), wherein the Degron is of Formula D2a or D2b, and the Linker is selected from L2b or L2c. In one embodiment, the present application provides the Degron-Linker (DL), wherein the Degron is of Formula D2a or D2b, and the Linker is selected from L2d or L2e. In one embodiment, the present application provides the Degron-Linker (DL), wherein the Degron is of Formula D2a or D2b, and the Linker is selected from L2f. In one embodiment, the present application provides the Degron-Linker (DL), wherein the Degron is of Formula D2a or D2b, and the Linker is selected from L2b-L2d. In one embodiment, the present application provides the Degron-Linker (DL), wherein the Degron is of Formula D2a or D2b, and the Linker is selected from L2d or L2f.

In one embodiment, the present application provides the Degron-Linker (DL), wherein the Degron is of Formula D2c or D2d, and the Linker is selected from L2a-L2f. In one embodiment, the present application provides the Degron-Linker (DL), wherein the Degron is of Formula D2c or D2d, and the Linker is selected from L2a. In one embodiment, the present application provides the Degron-Linker (DL), wherein the Degron is of Formula D2c or D2d, and the Linker is selected from L2b or L2c. In one embodiment, the present application provides the Degron-Linker (DL), wherein the Degron is of Formula D2c or D2d, and the Linker is selected from L2d or L2e. In one embodiment, the present application provides the Degron-Linker (DL), wherein the Degron is of Formula D2c or D2d, and the Linker is selected from L2f. In one embodiment, the present application provides the Degron-Linker (DL), wherein the Degron is of Formula D2c or D2d, and the Linker is selected from L2b-L2d. In one embodiment, the present application provides the Degron-Linker (DL), wherein the Degron is of Formula D2c or D2d, and the Linker is selected from L2d or L2f.

In one embodiment, the present application provides the Degron-Linker (DL), wherein the Degron is of Formula D2e or D2f, and the Linker is selected from L2a-L2f. In one embodiment, the present application provides the Degron-Linker (DL), wherein the Degron is of Formula D2e or D2f, and the Linker is selected from L2a. In one embodiment, the present application provides the Degron-Linker (DL), wherein the Degron is of Formula D2e or D2f, and the Linker is selected from L2b or L2c. In one embodiment, the present application provides the Degron-Linker (DL), wherein the Degron is of Formula D2e or D2f, and the Linker is selected from L2d or L2e. In one embodiment, the present application provides the Degron-Linker (DL), wherein the Degron is of Formula D2e or D2f, and the Linker is selected from L2f. In one embodiment, the present application provides the Degron-Linker (DL), wherein the Degron is of Formula D2e or D2f, and the Linker is selected from L2b-L2d. In one embodiment, the present application provides the Degron-Linker (DL), wherein the Degron is of Formula D2e or D2f, and the Linker is selected from L2d or L2f.

In one embodiment, the Linker is of Formula L3:

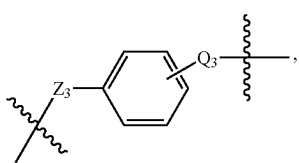

(L3)

or an enantiomer, diastereomer, or stereoisomer thereof, wherein $Z_3$ is absent, C(O), $CH_2$, $NR_{21}(CH_2)_{j2}$, $O(CH_2)_{j2}C(O)$, $O(CH_2)_{j2}C(O)NR_{21}$, $C(O)NR_{21}$, or $(CH_2)_{j2}C(O)NR_{21}$, each $R_{21}$ is independently H or $C_1$-$C_3$ alkyl;

j2 is 1, 2, or 3; and $Q_3$ is absent, $(CH_2)_{1-3}$, $(CH_2)_{1-3}NH$, or $NHC(O)CH_2$, wherein the Linker is covalently bonded to the Degron via the

next to $Q_3$, and covalently bonded to the Targeting Ligand via the

next to $Z_3$.

In one embodiment, $Z_3$ is absent.
In one embodiment, $Z_3$ is C(O).
In one embodiment, $Z_3$ is $CH_2$.
In one embodiment, $Z_3$ is $NR_{21}(CH_2)_{j2}$.
In one embodiment, $Z_3$ is $NR_{21}(CH_2)_{j2}$; and $R_{21}$ is H.
In one embodiment, $Z_3$ is $NR_{21}(CH_2)_{j2}$; and $R_{21}$ is $C_1$-$C_3$ alkyl selected from methyl, ethyl, and propyl.
In one embodiment, $Z_3$ is $NR_{21}(CH_2)_{j2}$; and j2 is 1.
In one embodiment, $Z_3$ is $NR_{21}(CH_2)_{j2}$; $R_{21}$ is H; and j2 is 1.
In one embodiment, $Z_3$ is $NR_{21}(CH_2)_{j2}$; $R_{21}$ is $C_1$-$C_3$ alkyl selected from methyl, ethyl, and propyl; and j2 is 1.
In one embodiment, $Z_3$ is $NR_{21}(CH_2)_{j2}$; and j2 is 2.
In one embodiment, $Z_3$ is $NR_{21}(CH_2)_{j2}$; $R_{21}$ is H; and j2 is 2.
In one embodiment, $Z_3$ is $NR_{21}(CH_2)_{j2}$; $R_{21}$ is $C_1$-$C_3$ alkyl selected from methyl, ethyl, and propyl; and j2 is 2.
In one embodiment, $Z_3$ is $NR_{21}(CH_2)_{j2}$; and j2 is 3.
In one embodiment, $Z_3$ is $NR_{21}(CH_2)_{j2}$; $R_{21}$ is H; and j2 is 3.
In one embodiment, $Z_3$ is $NR_{21}(CH_2)_{j2}$; $R_{21}$ is $C_1$-$C_3$ alkyl selected from methyl, ethyl, and propyl; and j2 is 3.
In one embodiment, $Z_3$ is $O(CH_2)_{j2}C(O)$.
In one embodiment, $Z_3$ is $O(CH_2)_{j2}C(O)$; and j2 is 1.
In one embodiment, $Z_3$ is $O(CH_2)_{j2}C(O)$; and j2 is 2.
In one embodiment, $Z_3$ is $O(CH_2)_{j2}C(O)$; and j2 is 3.
In one embodiment, $Z_3$ is $O(CH_2)_{j2}C(O)NR_{21}$.
In one embodiment, $Z_3$ is $O(CH_2)_{j2}C(O)NR_{21}$; and $R_{21}$ is H.
In one embodiment, $Z_3$ is $O(CH_2)_2C(O)NR_{21}$; and $R_{21}$ is $C_1$-$C_3$ alkyl selected from methyl, ethyl, and propyl.
In one embodiment, $Z_3$ is $O(CH_2)_{j2}C(O)NR_{21}$; and j2 is 1.
In one embodiment, $Z_3$ is $O(CH_2)_{j2}C(O)NR_{21}$; $R_{21}$ is H; and j2 is 1.
In one embodiment, $Z_3$ is $O(CH_2)_{j2}C(O)NR_{21}$; $R_{21}$ is $C_1$-$C_3$ alkyl selected from methyl, ethyl, and propyl; and j2 is 1.
In one embodiment, $Z_3$ is $O(CH_2)_{j2}C(O)NR_{21}$; and j2 is 2.
In one embodiment, $Z_3$ is $O(CH_2)_2C(O)NR_{21}$; $R_{21}$ is H; and j2 is 2.
In one embodiment, $Z_3$ is $O(CH_2)_2C(O)NR_{21}$; $R_{21}$ is $C_1$-$C_3$ alkyl selected from methyl, ethyl, and propyl; and j2 is 2.
In one embodiment, $Z_3$ is $O(CH_2)_2C(O)NR_{21}$; and j2 is 3.
In one embodiment, $Z_3$ is $O(CH_2)_2C(O)NR_{21}$; $R_{21}$ is H; and j2 is 3.
In one embodiment, $Z_3$ is $O(CH_2)_{j2}C(O)NR_{21}$; $R_{21}$ is $C_1$-$C_3$ alkyl selected from methyl, ethyl, and propyl; and j2 is 3.
In one embodiment, $Z_3$ is $C(O)NR_{21}$.

In one embodiment, $Z_3$ is $C(O)NR_{21}$; and $R_2$ is H.
In one embodiment, $Z_3$ is $C(O)NR_{21}$; and $R_{21}$ is $C_1$-$C_3$ alkyl selected from methyl, ethyl, and propyl.
In one embodiment, $Z_3$ is $(CH_2)_{j2}C(O)NR_{21}$.
In one embodiment, $Z_3$ is $(CH_2)_{j2}C(O)NR_{21}$; and $R_{21}$ is H.
In one embodiment, $Z_3$ is $(CH_2)_{j2}C(O)NR_{21}$; and $R_{21}$ is $C_1$-$C_3$ alkyl selected from methyl, ethyl, and propyl.
In one embodiment, $Z_3$ is $(CH_2)_{j2}C(O)NR_{21}$; and j2 is 1.
In one embodiment, $Z_3$ is $(CH_2)_{j2}C(O)NR_{21}$; $R_{21}$ is H; and j2 is 1.
In one embodiment, $Z_3$ is $(CH_2)_{j2}C(O)NR_{21}$; $R_{21}$ is $C_1$-$C_3$ alkyl selected from methyl, ethyl, and propyl; and j2 is 1.
In one embodiment, $Z_3$ is $(CH_2)_{j2}C(O)NR_{21}$; and j2 is 2.
In one embodiment, $Z_3$ is $(CH_2)_{j2}C(O)NR_{21}$; $R_{21}$ is H; and j2 is 2.
In one embodiment, $Z_3$ is $(CH_2)_{j2}C(O)NR_{21}$; $R_{21}$ is $C_1$-$C_3$ alkyl selected from methyl, ethyl, and propyl; and j2 is 2.
In one embodiment, $Z_3$ is $(CH_2)_{j2}C(O)NR_{21}$; and j2 is 3.
In one embodiment, $Z_3$ is $(CH_2)_{j2}C(O)NR_{21}$; $R_{21}$ is H; and j2 is 3.
In one embodiment, $Z_3$ is $(CH_2)_{j2}C(O)NR_{21}$; $R_{21}$ is $C_1$-$C_3$ alkyl selected from methyl, ethyl, and propyl; and j2 is 3.
In one embodiment, $Z_3$ is absent and $Q_3$ is absent.
In one embodiment, $Z_3$ is $C(O)$ and $Q_3$ is absent.
In one embodiment, $Z_3$ is $CH_2$ and $Q_3$ is absent.
In one embodiment, $Z_3$ is $NR_{21}(CH_2)_{j2}$ and $Q_3$ is absent.
In one embodiment, $Z_3$ is $O(CH_2)_2C(O)NR_{21}$ and $Q_3$ is absent.
In one embodiment, $Z_3$ is $O(CH_2)_{j2}C(O)$ and $Q_3$ is absent.
In one embodiment, $Z_3$ is $C(O)NR_{21}$ and $Q_3$ is absent.
In one embodiment, $Z_3$ is $(CH_2)_{j2}C(O)NR_{21}$ and $Q_3$ is absent.
In one embodiment, $Z_3$ is absent and $Q_3$ is $(CH_2)_{1-3}$.
In one embodiment, $Z_3$ is $C(O)$ and $Q_3$ is $(CH_2)_{1-3}$.
In one embodiment, $Z_3$ is $CH_2$ and $Q_3$ is $(CH_2)_{1-3}$.
In one embodiment, $Z_3$ is $NR_{21}(CH_2)_{j2}$ and Qs is $(CH_2)_3$.
In one embodiment, $Z_3$ is $O(CH_2)_{j2}C(O)NR_{21}$ and $Q_3$ is $(CH_2)_{1-3}$.
In one embodiment, $Z_3$ is $O(CH_2)_{j2}C(O)$ and $Q_3$ is $(CH_2)_{1-3}$.
In one embodiment, $Z_3$ is $C(O)NR_2$ and $Q_3$ is $(CH_2)_{1-3}$.
In one embodiment, $Z_3$ is $(CH_2)_{j2}C(O)NR_{21}$ and $Q_3$ is $(CH_2)_{1-3}$.
In one embodiment, $Z_3$ is absent and $Q_3$ is $(CH_2)_{1-3}NH$.
In one embodiment, $Z_3$ is $C(O)$ and $Q_3$ is $(CH_2)_{1-3}NH$.
In one embodiment, $Z_3$ is $CH_2$ and $Q_3$ is $(CH_2)_{1-3}NH$.
In one embodiment, $Z_3$ is $NR_{21}(CH_2)_{j2}$ and $Q_3$ is $(CH_2)_{1-3}NH$.
In one embodiment, $Z_3$ is $O(CH_2)_2C(O)NR_{21}$ and $Q_3$ is $(CH_2)_{1-3}NH$.
In one embodiment, $Z_3$ is $O(CH_2)_2C(O)$ and $Q_3$ is $(CH_2)_{1-3}NH$.
In one embodiment, $Z_3$ is $C(O)NR_{21}$ and $Q_3$ is $(CH_2)_{1-3}NH$.
In one embodiment, $Z_3$ is $(CH_2)_{j2}C(O)NR_{21}$ and $Q_3$ is $(CH_2)_{1-3}NH$.
In one embodiment, $Z_3$ is absent and $Q_3$ is $NHC(O)CH_2$.
In one embodiment, $Z_3$ is $C(O)$ and $Q_3$ is $NHC(O)CH_2$.
In one embodiment, $Z_3$ is $CH_2$ and $Q_3$ is a $NHC(O)CH_2$.
In one embodiment, $Z_3$ is $NR_{21}(CH_2)_{j2}$ and $Q_3$ is $NHC(O)CH_2$.
In one embodiment, $Z_3$ is $O(CH_2)_{j2}C(O)NR_{21}$ and $Q_3$ is $NHC(O)CH_2$.
In one embodiment, $Z_3$ is $O(CH_2)_{j2}C(O)$ and $Q_3$ is $NHC(O)CH_2$.
In one embodiment, $Z_3$ is $C(O)NR_{21}$ and $Q_3$ is a $NHC(O)CH_2$.
In one embodiment, $Z_3$ is $(CH_2)_{j2}C(O)NR_{21}$ and $Q_3$ is $NHC(O)CH_2$.

In one embodiment, the Linker-Targeting Ligand (TL) has the structure selected from Table N:

TABLE N

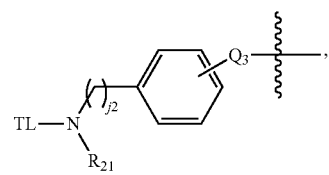
(L3a)

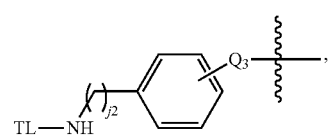
(L3b)

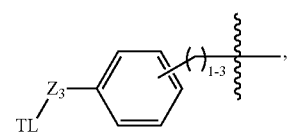
(L3c)

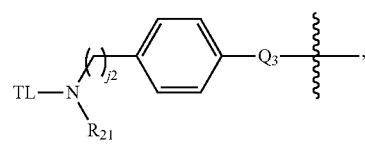
(L3d)

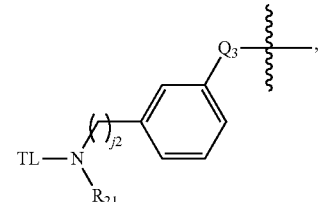
(L3e)

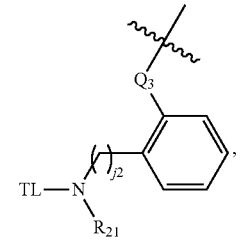
(L3f)

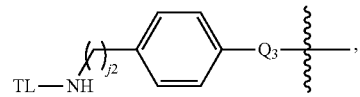
(L3g)

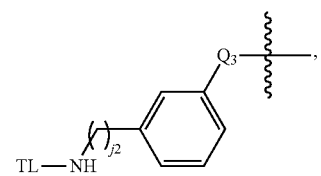
(L3h)

TABLE N-continued

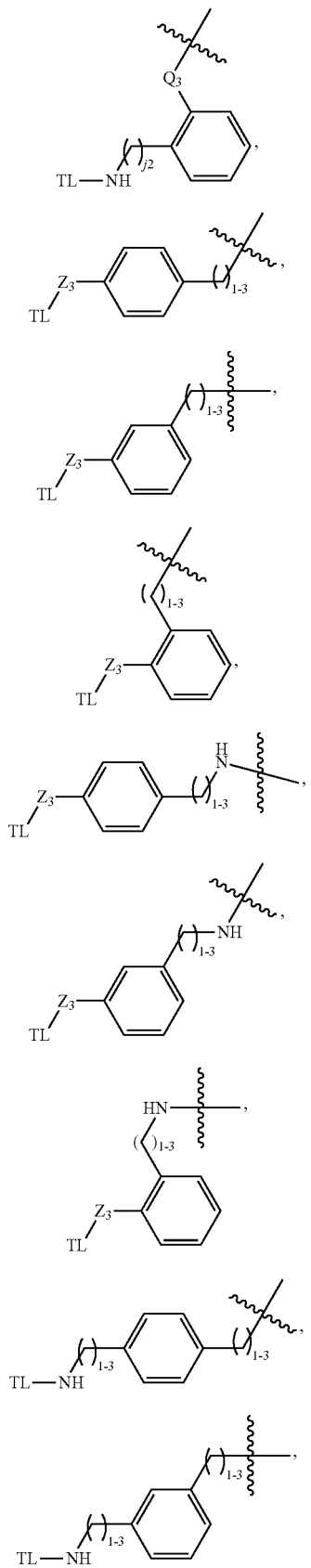

(L3i)
(L3j)
(L3k)
(L3m)
(L3n)
(L3o)
(L3p)
(L3q)
(L3r)

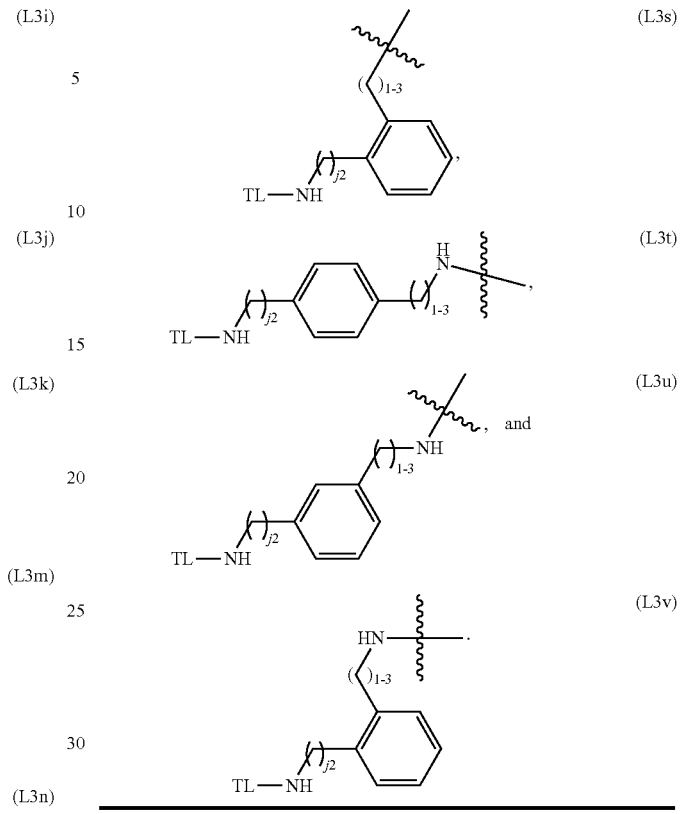

(L3s)
(L3t)
(L3u)
(L3v)

In one embodiment, the present application provides the Degron-Linker (DL), wherein the Degron is of Formula D1, and the Linker is selected from L3a-L3v. In one embodiment, the present application provides the Degron-Linker (DL), wherein the Degron is of Formula D1, and the Linker is selected from L3a-L3k. In one embodiment, the present application provides the Degron-Linker (DL), wherein the Degron is of Formula D1, and the Linker is selected from L3m-L3v. In one embodiment, the present application provides the Degron-Linker (DL), wherein the Degron is of Formula D1, and the Linker is selected from L3a-L3e. In one embodiment, the present application provides the Degron-Linker (DL), wherein the Degron is of Formula D1, and the Linker is selected from L3f-L3j. In one embodiment, the present application provides the Degron-Linker (DL), wherein the Degron is of Formula D1, and the Linker is selected from L3k-L3p. In one embodiment, the present application provides the Degron-Linker (DL), wherein the Degron is of Formula D1, and the Linker is selected from L3q-L3v.

In one embodiment, the present application provides the Degron-Linker (DL), wherein the Degron is of Formula D1a, D1b, D1c, D1d, D1e, D1f, D1g, D1h, D1i, D1j, D1k, or D1l, and the Linker is selected from L3a-L3v. In one embodiment, the present application provides the Degron-Linker (DL), wherein the Degron is of Formula D a, D b, D1c, D1d, D1e, D1f, D1g, D1h, D1i, D1j, D1k, or D1l, and the Linker is selected from L3a-L3k. In one embodiment, the present application provides the Degron-Linker (DL), wherein the Degron is of Formula D1a, D1b, D1c, D1d, D1e, D1f, D1g, D1h, D1i, D1j, D1k, or D1l, and the Linker is selected from L3m-L3v. In one embodiment, the present application provides the Degron-Linker (DL), wherein the Degron is of Formula D1a, D1b, D1c, D1d, D1e, D1f, D1g, D1h, D1i, D1j, D1k, or D1l, and the Linker is selected from L3a-L3e. In one embodiment, the present application provides the Degron-Linker (DL), wherein the Degron is of Formula D1a, D1b, D1c, D1d, D1e, D1f, D1g, D1h, D1i, D1j, D1k, or D1l, and the Linker is selected from L3f-L3j. In one embodiment, the present application provides the Degron-Linker (DL), wherein the Degron is of Formula D1a, D1b, D1c, D1d, D1e, D1f, D1g, D1h, D1i, D1j, D1k, or D1l, and the Linker is selected from L3k-L3p. In one embodiment, the present application provides the Degron-Linker (DL), wherein the Degron is of Formula D1a, D1b, D1c, D1d, D1e, D1f, D1g, D1h, D1i, D1j, D1k, or D1l, and the Linker is selected from L3q-L3v.

In one embodiment, the present application provides the Degron-Linker (DL), wherein the Degron is of Formula D2, and the Linker is selected from L3a-L3v. In one embodiment, the present application provides the Degron-Linker (DL), wherein the Degron is of Formula D2, and the Linker is selected from L3a-L3k. In one embodiment, the present application provides the Degron-Linker (DL), wherein the Degron is of Formula D2, and the Linker is selected from L3m-L3v. In one embodiment, the present application provides the Degron-Linker (DL), wherein the Degron is of Formula D2, and the Linker is selected from L3a-L3e. In one embodiment, the present application provides the Degron-Linker (DL), wherein the Degron is of Formula D2, and the Linker is selected from L3f-L3j. In one embodiment, the present application provides the Degron-Linker (DL), wherein the Degron is of Formula D2, and the Linker is selected from L3k-L3p. In one embodiment, the present application provides the Degron-Linker (DL), wherein the Degron is of Formula D2, and the Linker is selected from L3q-L3v.

In one embodiment, the present application provides the Degron-Linker (DL), wherein the Degron is of Formula D2a or D2b, and the Linker is selected from L3a-L3v. In one embodiment, the present application provides the Degron-Linker (DL), wherein the Degron is of Formula D2a or D2b, and the Linker is selected from L3a-L3k. In one embodiment, the present application provides the Degron-Linker (DL), wherein the Degron is of Formula D2a or D2b, and the Linker is selected from L3m-L3v. In one embodiment, the present application provides the Degron-Linker (DL), wherein the Degron is of Formula D2a or D2b, and the Linker is selected from L3a-L3e. In one embodiment, the present application provides the Degron-Linker (DL), wherein the Degron is of Formula D2a or D2b, and the Linker is selected from L3f-L3j. In one embodiment, the present application provides the Degron-Linker (DL), wherein the Degron is of Formula D2a or D2b, and the Linker is selected from L3k-L3p. In one embodiment, the present application provides the Degron-Linker (DL), wherein the Degron is of Formula D2a or D2b, and the Linker is selected from L3q-L3v.

In one embodiment, the present application provides the Degron-Linker (DL), wherein the Degron is of Formula D2c or D2d, and the Linker is selected from L3a-L3v. In one embodiment, the present application provides the Degron-Linker (DL), wherein the Degron is of Formula D2c or D2d, and the Linker is selected from L3a-L3k. In one embodiment, the present application provides the Degron-Linker (DL), wherein the Degron is of Formula D2c or D2d, and the Linker is selected from L3m-L3v. In one embodiment, the present application provides the Degron-Linker (DL), wherein the Degron is of Formula D2c or D2d, and the Linker is selected from L3a-L3e. In one embodiment, the present application provides the Degron-Linker (DL), wherein the Degron is of Formula D2c or D2d, and the Linker is selected from L3f-L3j. In one embodiment, the present application provides the Degron-Linker (DL), wherein the Degron is of Formula D2c or D2d, and the Linker is selected from L3k-L3p. In one embodiment, the present application provides the Degron-Linker (DL), wherein the Degron is of Formula D2c or D2d, and the Linker is selected from L3q-L3v.

In one embodiment, the present application provides the Degron-Linker (DL), wherein the Degron is of Formula D2e or D2f, and the Linker is selected from L3a-L3v. In one embodiment, the present application provides the Degron-Linker (DL), wherein the Degron is of Formula D2e or D2f, and the Linker is selected from L3a-L3k. In one embodiment, the present application provides the Degron-Linker (DL), wherein the Degron is of Formula D2e or D2f, and the Linker is selected from L3m-L3v. In one embodiment, the present application provides the Degron-Linker (DL), wherein the Degron is of Formula D2e or D2f, and the Linker is selected from L3a-L3e. In one embodiment, the present application provides the Degron-Linker (DL), wherein the Degron is of Formula D2e or D2f, and the Linker is selected from L3f-L3j. In one embodiment, the present application provides the Degron-Linker (DL), wherein the Degron is of Formula D2e or D2f, and the Linker is selected from L3k-L3p. In one embodiment, the present application provides the Degron-Linker (DL), wherein the Degron is of Formula D2e or D2f, and the Linker is selected from L3q-L3v.

In one embodiment, the Linker is designed and optimized based on SAR (structure-activity relationship) and X-ray crystallography of the Targeting Ligand with regard to the location of attachment for the Linker.

In one embodiment, the optimal Linker length and composition vary by the Targeting Ligand and can be estimated based upon X-ray structure of the Targeting Ligand bound to its target. Linker length and composition can be also modified to modulate metabolic stability and pharmacokinetic (PK) and pharmacodynamics (PD) parameters.

Some embodiments of present application relate to the Degron-Linkers (DL) having one of the following structures in Table B: Table B: Structures of Degron-Linkers TABLE B
Structures of Degron-Linkers
| Cmpd No. | Structure |
|---|---|
| DL-1 | 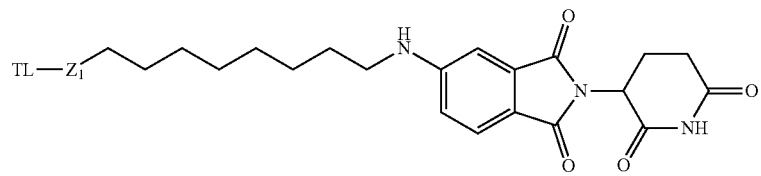 |
| DL-2 | 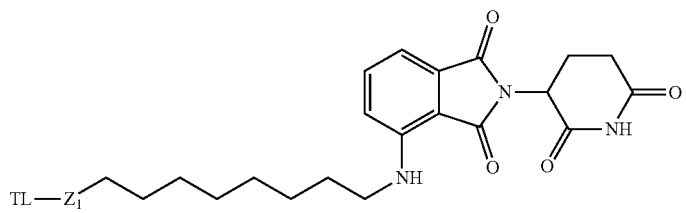 |
| DL-3 | 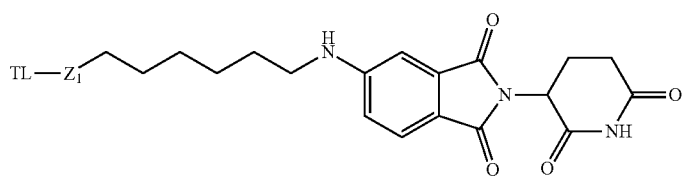 |
| DL-4 | 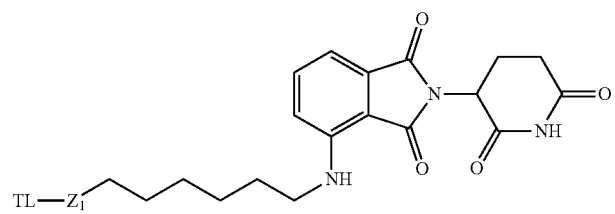 |
| DL-5 | 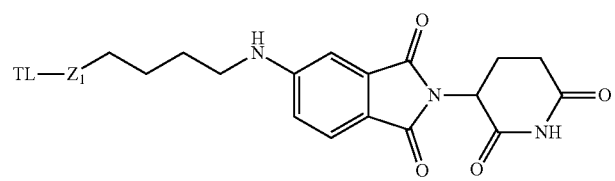 |
| DL-6 | 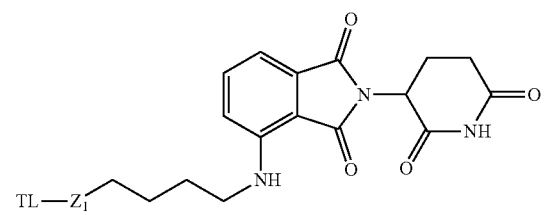 |
| DL-7 | 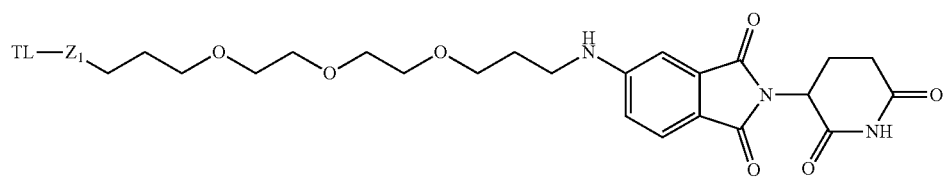 |

TABLE B-continued
Structures of Degron-Linkers
| Cmpd No. | Structure |
|---|---|
| DL-8 | 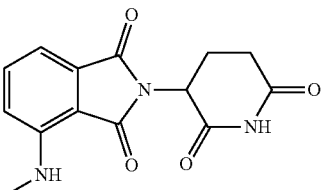 |
| DL-9 | 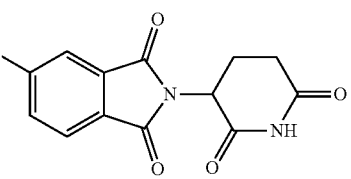 |
| DL-10 | 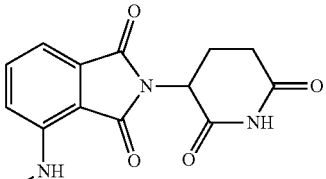 |
| DL-11 | 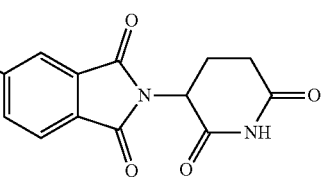 |
| DL-12 | 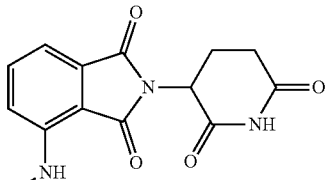 |
| DL-13 | 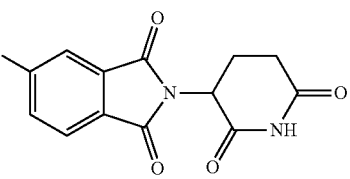 |
| DL-14 | 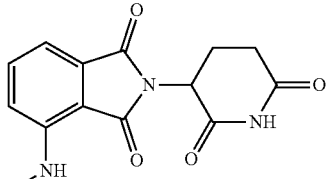 |

TABLE B-continued
Structures of Degron-Linkers
| Cmpd No. | Structure |
|---|---|
| DL-15 | 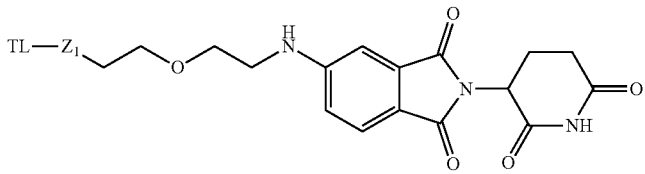 |
| DL-16 | 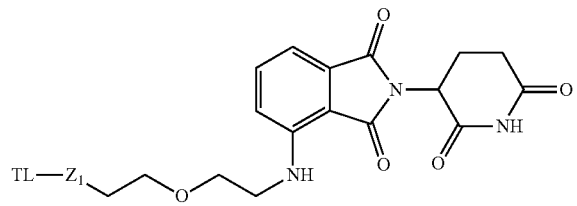 |
| DL-17 | 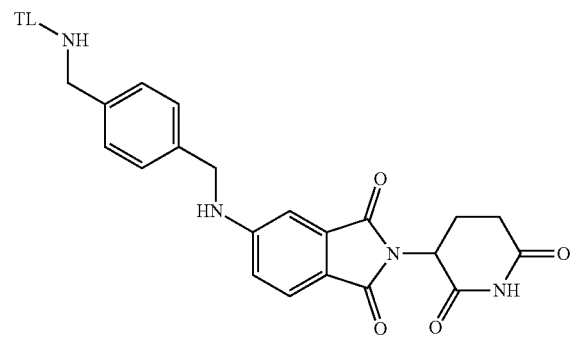 |
| DL-18 | 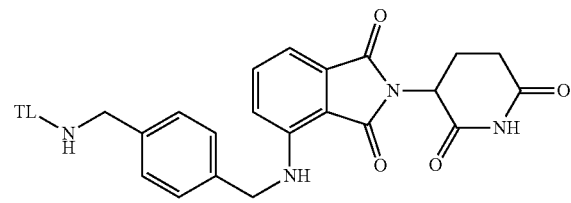 |
| DL-19 | 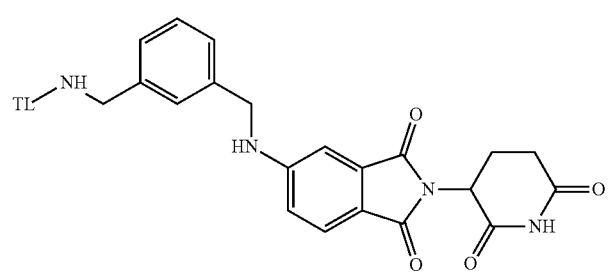 |
| DL-20 | 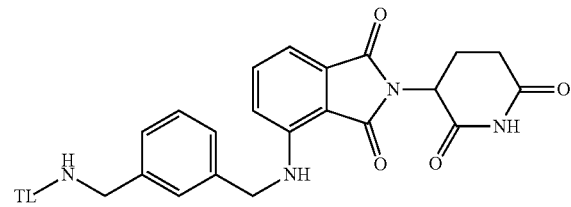 |

TABLE B-continued
Structures of Degron-Linkers
| Cmpd No. | Structure |
|---|---|
| DL-21 | 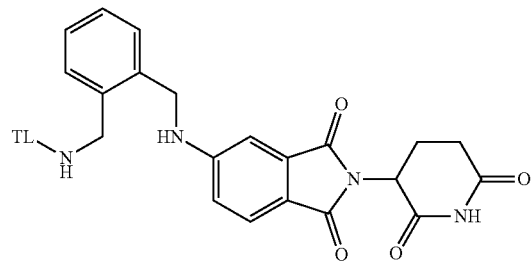 |
| DL-22 | 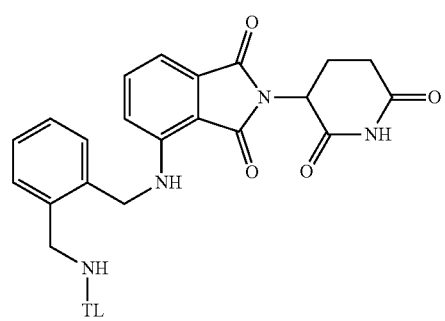 |
| DL-23 | 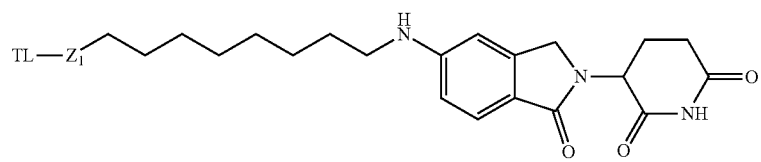 |
| DL-24 | 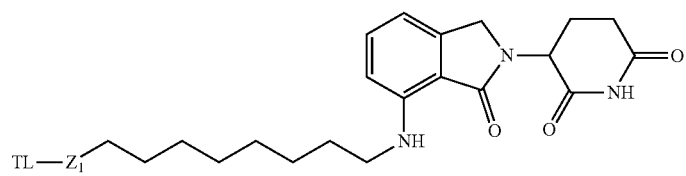 |
| DL-25 | 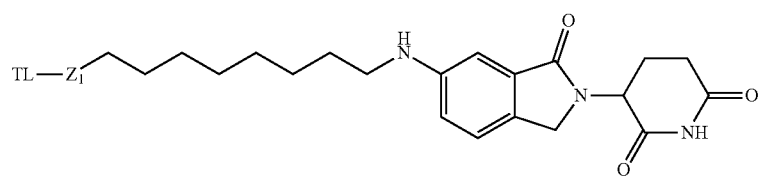 |
| DL-26 | 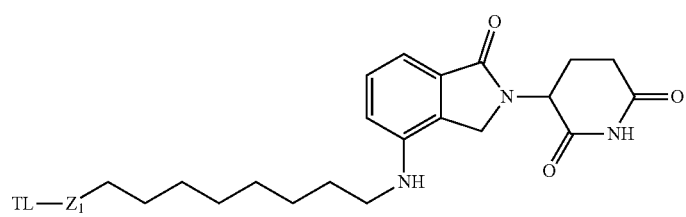 |

Some embodiments of present application relate to the bifunctional compounds having one of the following structures in Table C:
TABLE C
Structures of Bifunctional Degraders
| Cmpd No. | Structure |
|---|---|
| I-1 | 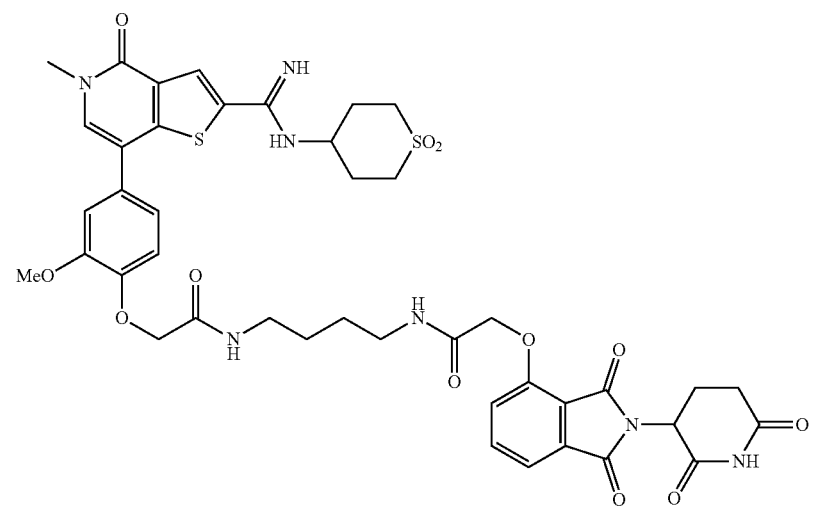 [SMILES: COc1cc(-c2cn(C)c(=O)c3cc(C(=N)NC4CCS(=O)(=O)CC4)sc23)ccc1OCC(=O)NCCCCNC(=O)COc1cccc2c1C(=O)N(C1CCC(=O)NC1=O)C2=O] |
| I-2 | 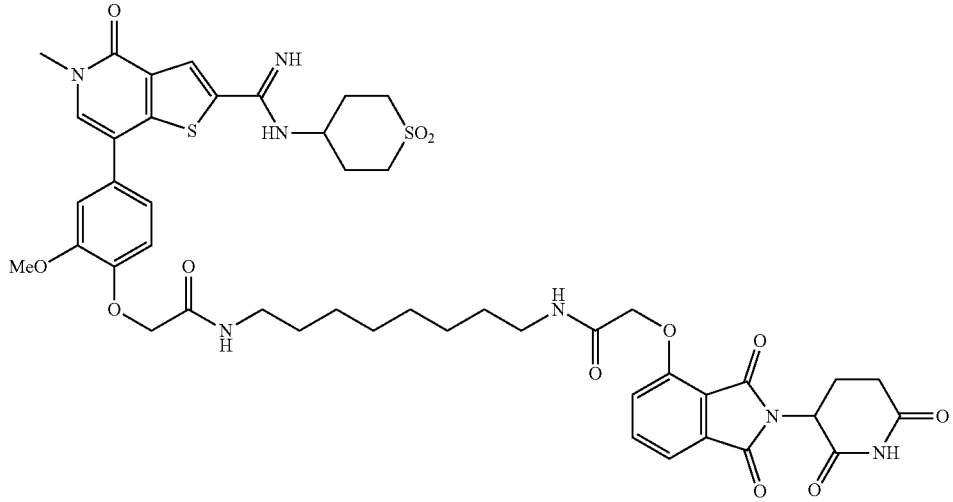 [SMILES: COc1cc(-c2cn(C)c(=O)c3cc(C(=N)NC4CCS(=O)(=O)CC4)sc23)ccc1OCC(=O)NCCCCCCCCNC(=O)COc1cccc2c1C(=O)N(C1CCC(=O)NC1=O)C2=O] |
| I-3 | 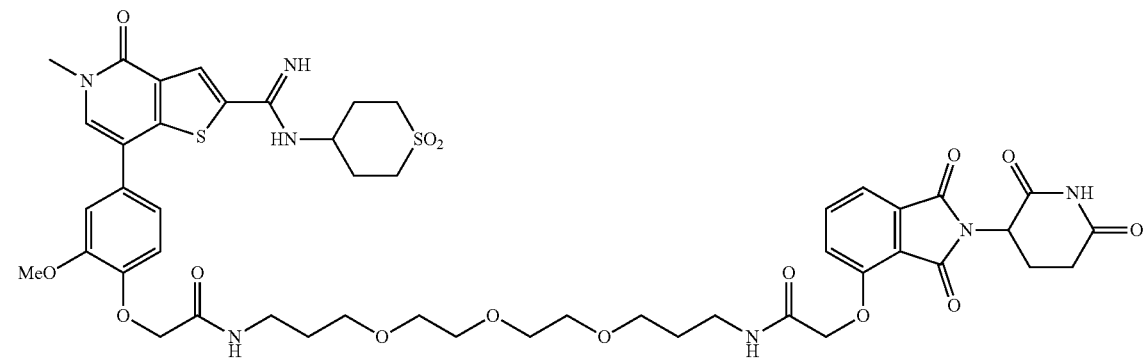 [SMILES: COc1cc(-c2cn(C)c(=O)c3cc(C(=N)NC4CCS(=O)(=O)CC4)sc23)ccc1OCC(=O)NCCCOCCOCCOCCCNC(=O)COc1cccc2c1C(=O)N(C1CCC(=O)NC1=O)C2=O] |

TABLE C-continued

Structures of Bifunctional Degraders

| Cmpd No. | Structure |
|---|---|
| I-4 | 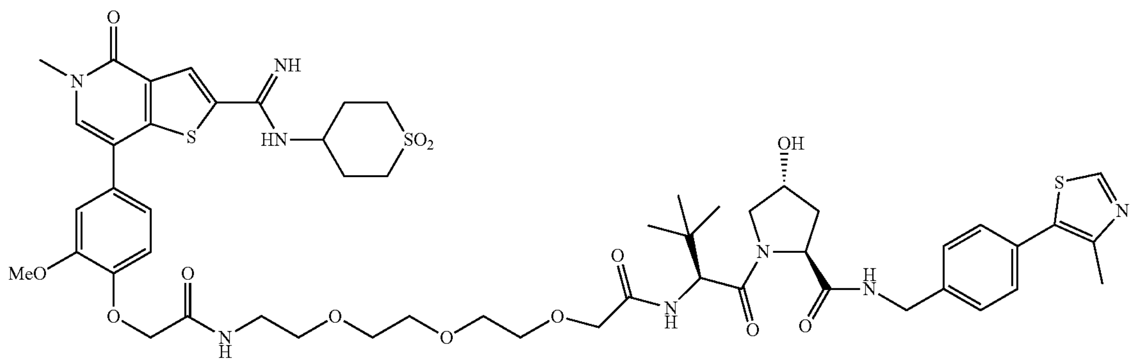 [SMILES: COc1cc(-c2cn(C)c(=O)c3cc(C(=N)NC4CCS(=O)(=O)CC4)sc23)ccc1OCC(=O)NCCOCCOCCOCC(=O)N[C@H](C(=O)N1C[C@H](O)C[C@H]1C(=O)NCc1ccc(-c2scnc2C)cc1)C(C)(C)C] |
| I-5 | 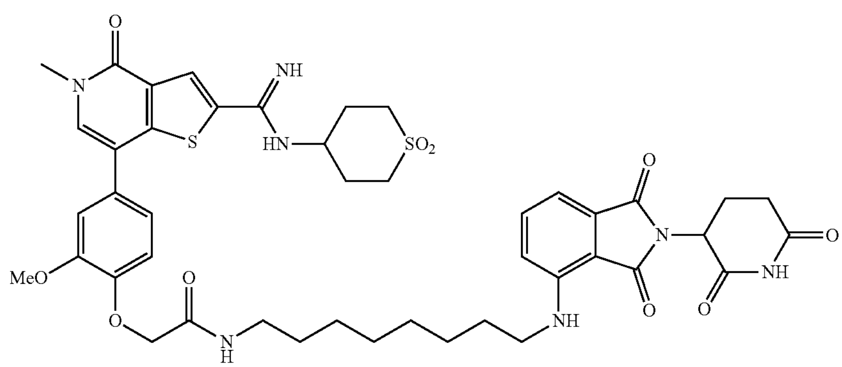 [SMILES: COc1cc(-c2cn(C)c(=O)c3cc(C(=N)NC4CCS(=O)(=O)CC4)sc23)ccc1OCC(=O)NCCCCCCCCNc1cccc2c1C(=O)N(C1CCC(=O)NC1=O)C2=O] |
| I-6 | 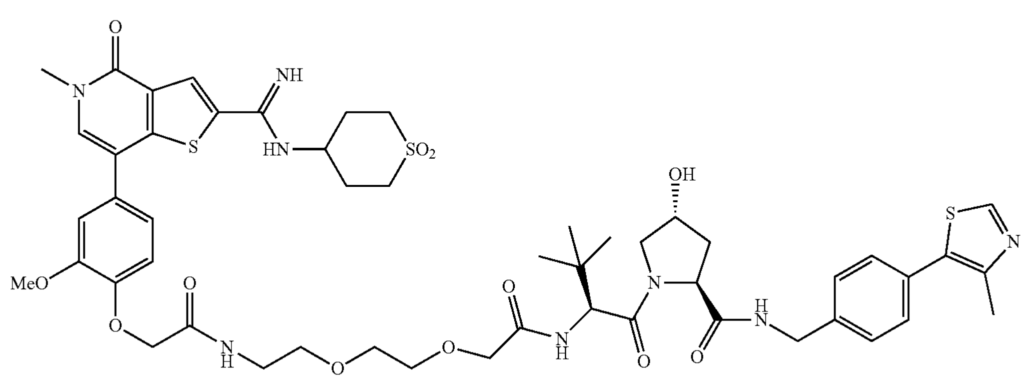 [SMILES: COc1cc(-c2cn(C)c(=O)c3cc(C(=N)NC4CCS(=O)(=O)CC4)sc23)ccc1OCC(=O)NCCOCCOCC(=O)N[C@H](C(=O)N1C[C@H](O)C[C@H]1C(=O)NCc1ccc(-c2scnc2C)cc1)C(C)(C)C] |

TABLE C-continued

Structures of Bifunctional Degraders

| Cmpd No. | Structure |
| --- | --- |
| I-7 | 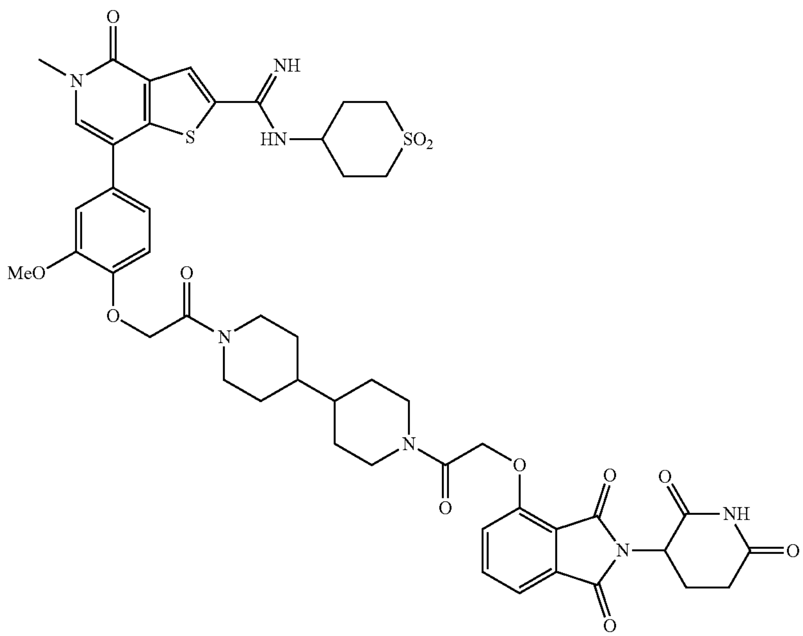 [SMILES: COc1cc(-c2cn(C)c(=O)c3cc(C(=N)NC4CCS(=O)(=O)CC4)sc23)ccc1OCC(=O)N1CCC(C2CCN(C(=O)COc3cccc4c3C(=O)N(C3CCC(=O)NC3=O)C4=O)CC2)CC1] |
| I-8 | 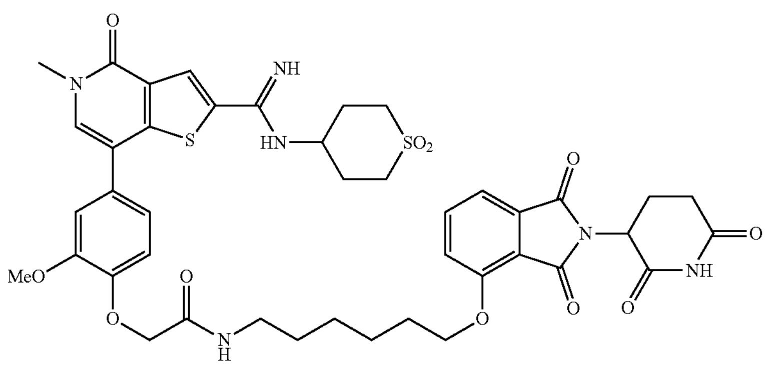 [SMILES: COc1cc(-c2cn(C)c(=O)c3cc(C(=N)NC4CCS(=O)(=O)CC4)sc23)ccc1OCC(=O)NCCCCCCOc1cccc2c1C(=O)N(C1CCC(=O)NC1=O)C2=O] |
| I-9 | 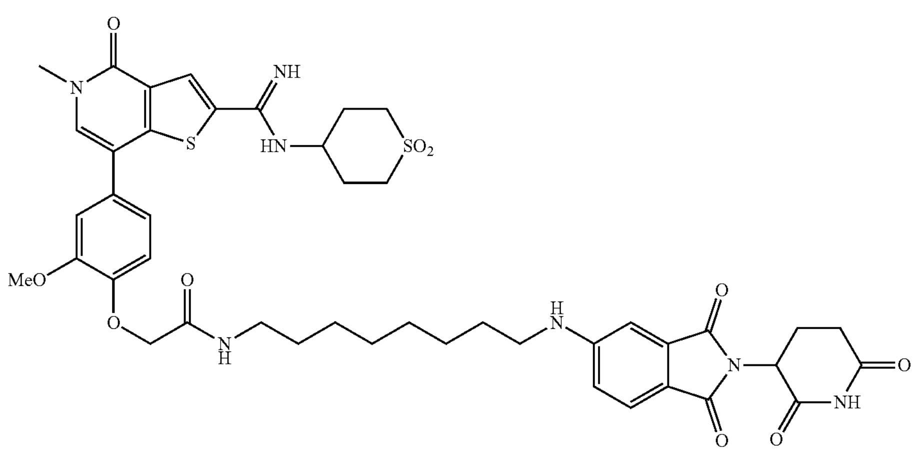 [SMILES: COc1cc(-c2cn(C)c(=O)c3cc(C(=N)NC4CCS(=O)(=O)CC4)sc23)ccc1OCC(=O)NCCCCCCCCNc1ccc2c(c1)C(=O)N(C1CCC(=O)NC1=O)C2=O] |

TABLE C-continued

Structures of Bifunctional Degraders

| Cmpd No. | Structure |
|---|---|
| I-10 | 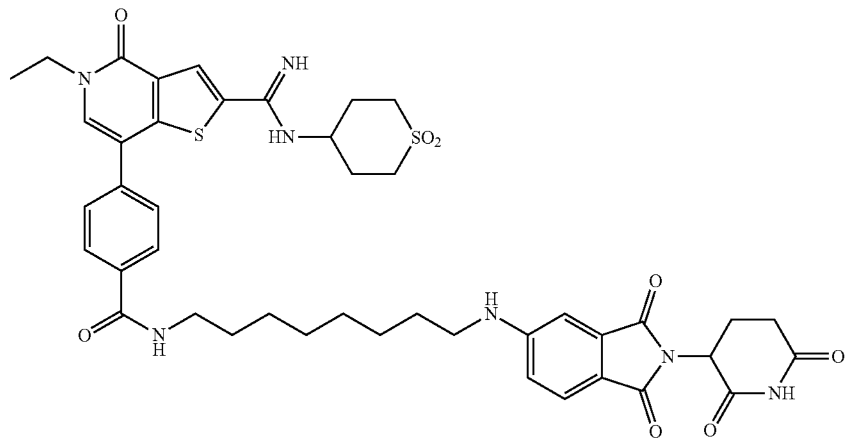 [SMILES: CCn1cc(-c2ccc(C(=O)NCCCCCCCCNc3ccc4c(c3)C(=O)N(C3CCC(=O)NC3=O)C4=O)cc2)c2sc(C(=N)NC3CCS(=O)(=O)CC3)cc2c1=O] |
| I-11 | 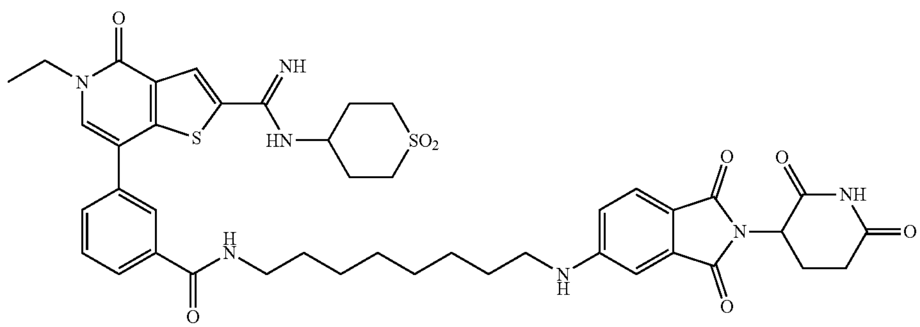 [SMILES: CCn1cc(-c2cccc(C(=O)NCCCCCCCCNc3ccc4c(c3)C(=O)N(C3CCC(=O)NC3=O)C4=O)c2)c2sc(C(=N)NC3CCS(=O)(=O)CC3)cc2c1=O] |
| I-12 | 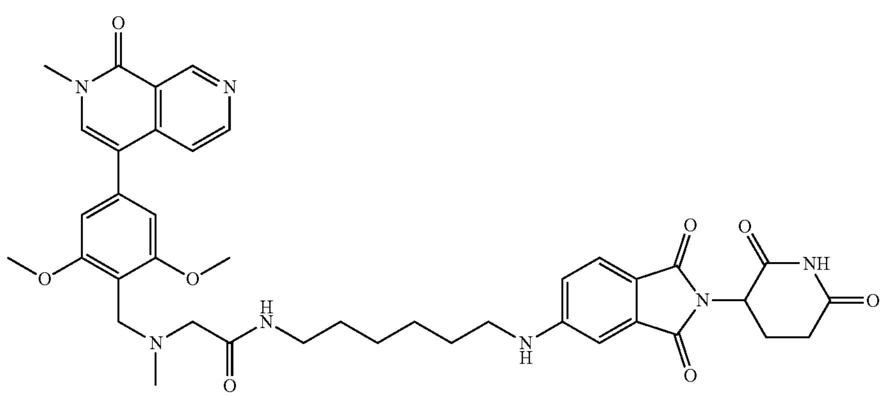 [SMILES: COc1cc(-c2cn(C)c(=O)c3cnccc23)cc(OC)c1CN(C)CC(=O)NCCCCCCNc1ccc2c(c1)C(=O)N(C1CCC(=O)NC1=O)C2=O] |
| I-13 | 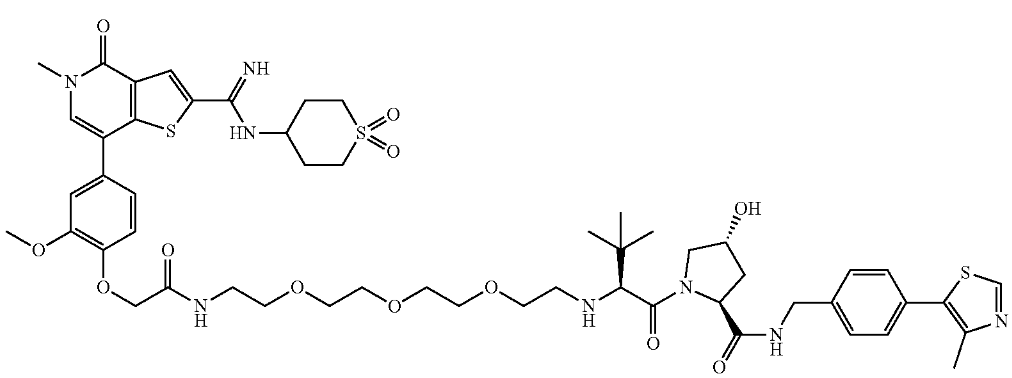 [SMILES: COc1cc(-c2cn(C)c(=O)c3cc(C(=N)NC4CCS(=O)(=O)CC4)sc23)ccc1OCC(=O)NCCOCCOCCOCCN[C@H](C(=O)N1C[C@H](O)C[C@H]1C(=O)NCc1ccc(-c2scnc2C)cc1)C(C)(C)C] |

TABLE C-continued

Structures of Bifunctional Degraders

| Cmpd No. | Structure |
| --- | --- |
| I-14 | 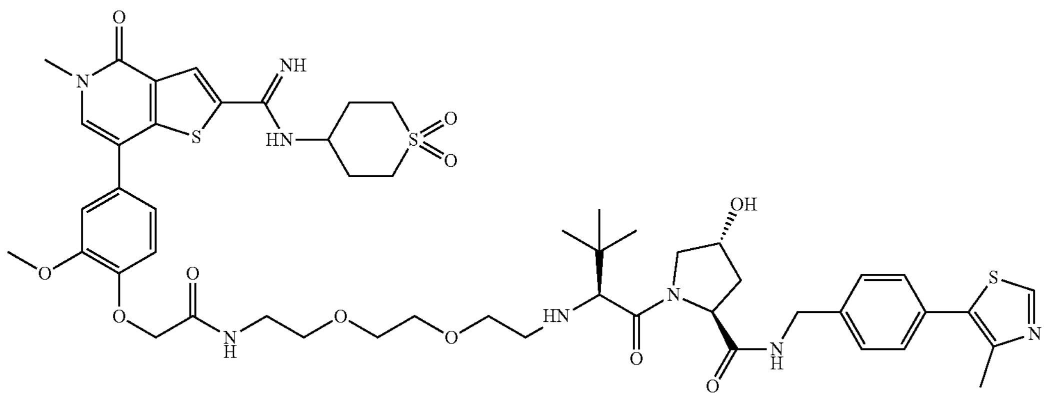 [SMILES: COc1cc(-c2cn(C)c(=O)c3cc(C(=N)NC4CCS(=O)(=O)CC4)sc23)ccc1OCC(=O)NCCOCCOCCN[C@H](C(=O)N1C[C@H](O)C[C@H]1C(=O)NCc1ccc(-c2scnc2C)cc1)C(C)(C)C] |
| I-15 | 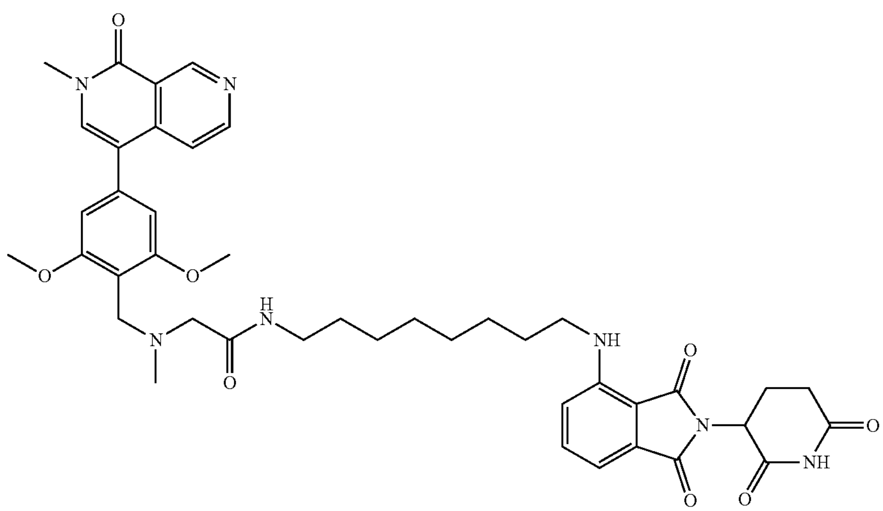 |
| I-16 | 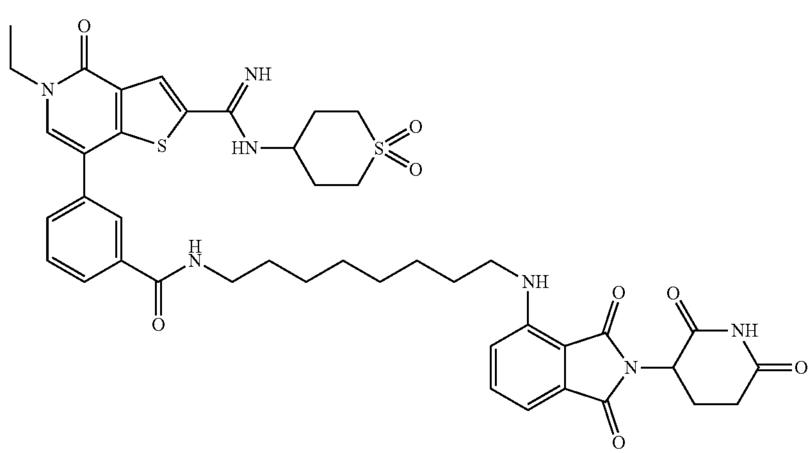 [SMILES: CCn1cc(-c2cccc(C(=O)NCCCCCCCCNc3cccc4c3C(=O)N(C3CCC(=O)NC3=O)C4=O)c2)c2sc(C(=N)NC3CCS(=O)(=O)CC3)cc2c1=O] |

TABLE C-continued

Structures of Bifunctional Degraders

| Cmpd No. | Structure |
|---|---|
| I-17 | 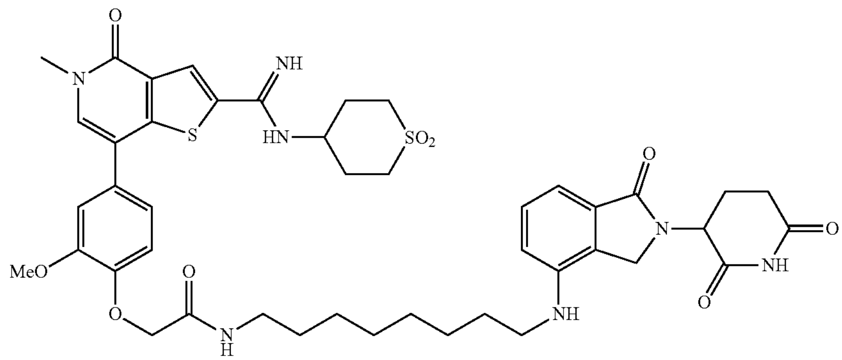 [SMILES: COc1cc(-c2cn(C)c(=O)c3cc(C(=N)NC4CCS(=O)(=O)CC4)sc23)ccc1OCC(=O)NCCCCCCCCNc1cccc2c1CN(C1CCC(=O)NC1=O)C2=O] |
| I-18 | 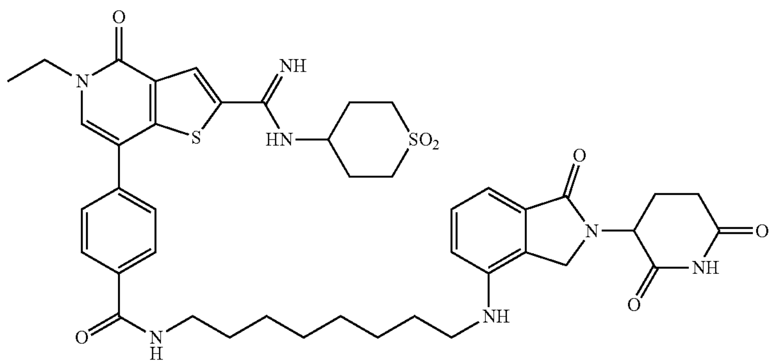 [SMILES: CCn1cc(-c2ccc(C(=O)NCCCCCCCCNc3cccc4c3CN(C3CCC(=O)NC3=O)C4=O)cc2)c2sc(C(=N)NC3CCS(=O)(=O)CC3)cc2c1=O] |
| I-19 | 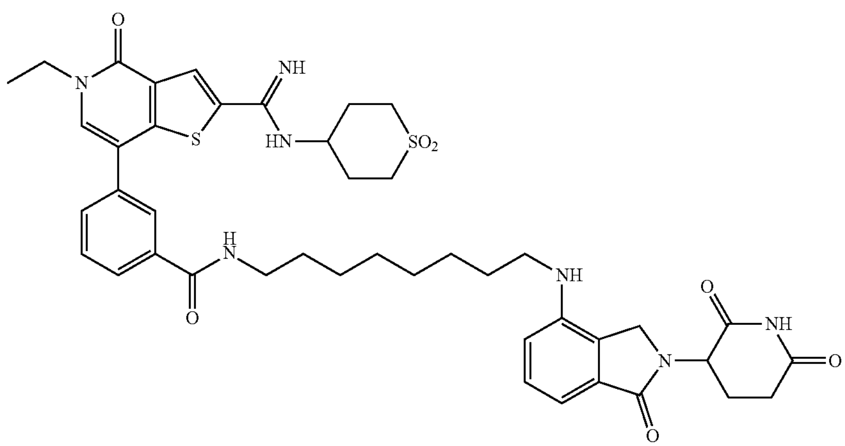 [SMILES: CCn1cc(-c2cccc(C(=O)NCCCCCCCCNc3cccc4c3CN(C3CCC(=O)NC3=O)C4=O)c2)c2sc(C(=N)NC3CCS(=O)(=O)CC3)cc2c1=O] |
| I-20 | 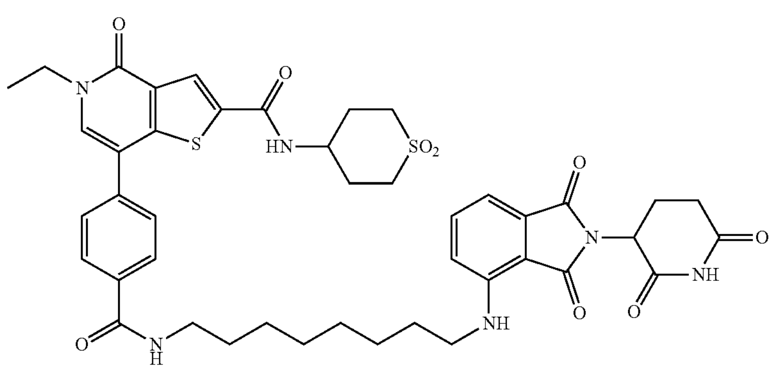 [SMILES: CCn1cc(-c2ccc(C(=O)NCCCCCCCCNc3cccc4c3C(=O)N(C3CCC(=O)NC3=O)C4=O)cc2)c2sc(C(=O)NC3CCS(=O)(=O)CC3)cc2c1=O] |

TABLE C-continued

Structures of Bifunctional Degraders

| Cmpd No. | Structure |
|---|---|
| I-21 | 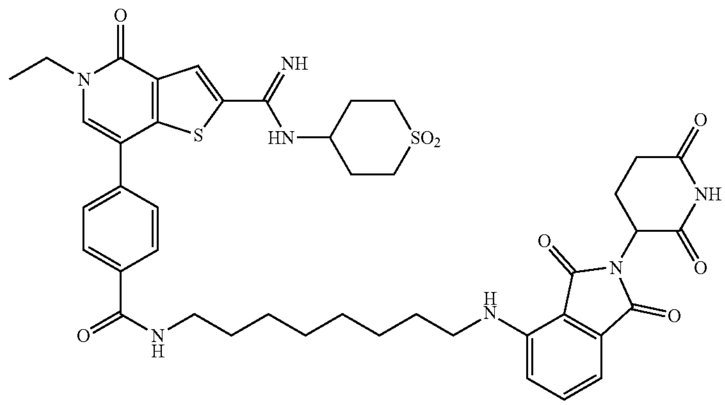 [SMILES: CCn1cc(-c2ccc(C(=O)NCCCCCCCCNc3cccc4c3C(=O)N(C3CCC(=O)NC3=O)C4=O)cc2)c2sc(C(=N)NC3CCS(=O)(=O)CC3)cc2c1=O] |
| I-22 | 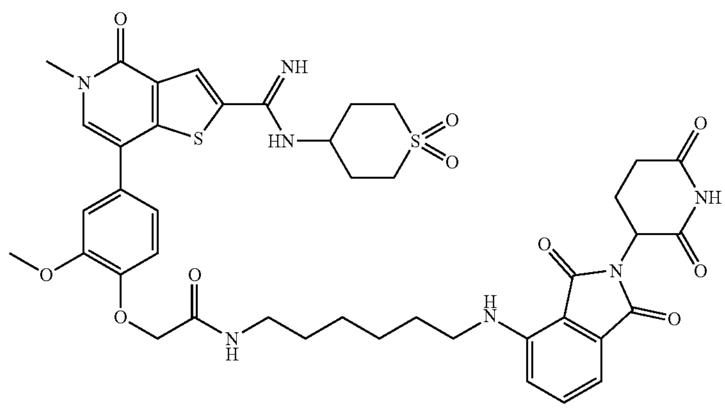 [SMILES: COc1cc(-c2cn(C)c(=O)c3cc(C(=N)NC4CCS(=O)(=O)CC4)sc23)ccc1OCC(=O)NCCCCCCNc1cccc2c1C(=O)N(C1CCC(=O)NC1=O)C2=O] |
| I-23 | 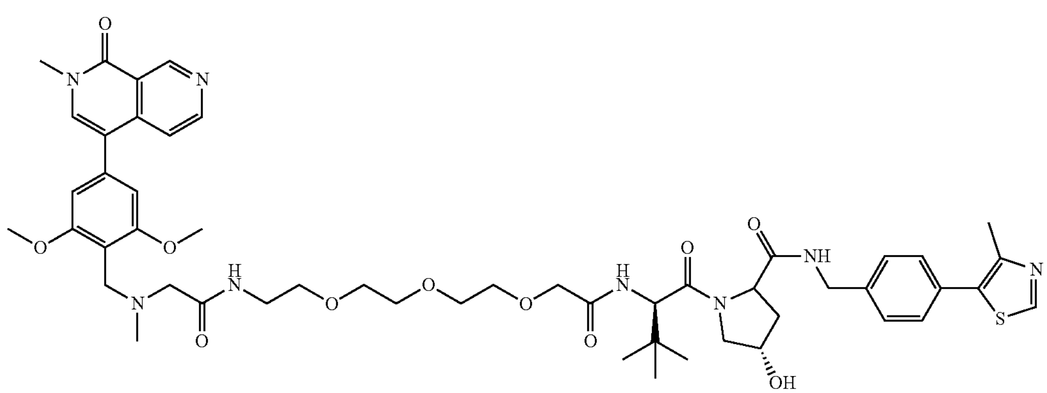 [SMILES: COc1cc(-c2cn(C)c(=O)c3cnccc23)cc(OC)c1CN(C)CC(=O)NCCOCCOCCOCC(=O)N[C@@H](C(=O)N1C[C@@H](O)CC1C(=O)NCc1ccc(-c2scnc2C)cc1)C(C)(C)C] |

TABLE C-continued

Structures of Bifunctional Degraders

| Cmpd No. | Structure |
|---|---|
| I-24 | 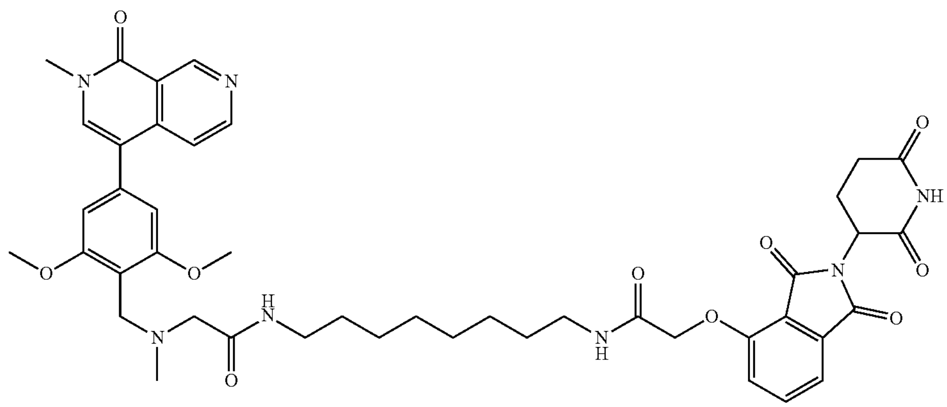 [SMILES: COc1cc(-c2cn(C)c(=O)c3cnccc23)cc(OC)c1CN(C)CC(=O)NCCCCCCCCNC(=O)COc1cccc2c1C(=O)N(C1CCC(=O)NC1=O)C2=O] |
| I-25 | 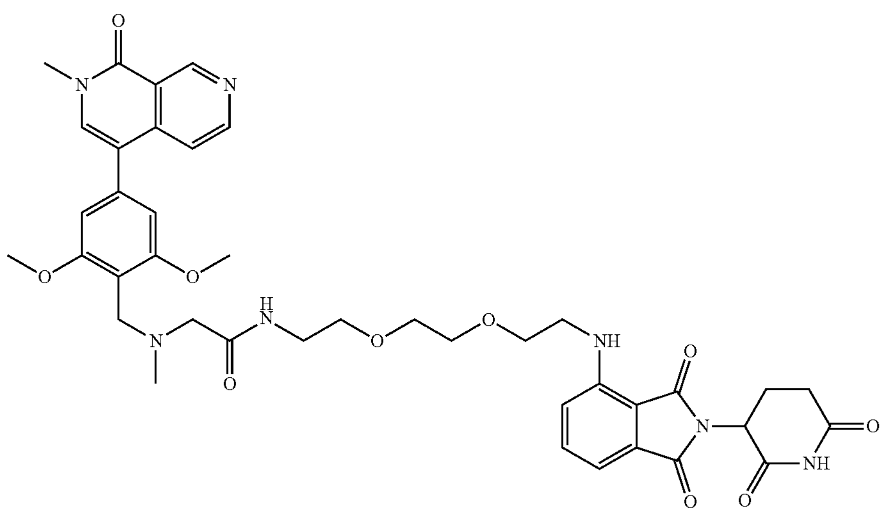 [SMILES: COc1cc(-c2cn(C)c(=O)c3cnccc23)cc(OC)c1CN(C)CC(=O)NCCOCCOCCNc1cccc2c1C(=O)N(C1CCC(=O)NC1=O)C2=O] |
| I-26 | 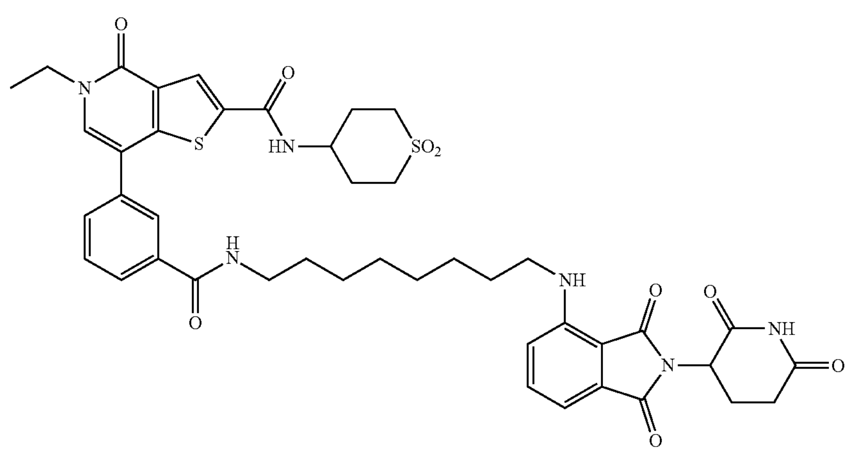 [SMILES: CCn1cc(-c2cccc(C(=O)NCCCCCCCCNc3cccc4c3C(=O)N(C3CCC(=O)NC3=O)C4=O)c2)c2sc(C(=O)NC3CCS(=O)(=O)CC3)cc2c1=O] |

Some of the foregoing compounds can comprise one or more asymmetric centers, and thus can exist in various isomeric forms, such as stereoisomers and/or diastereomers. Accordingly, compounds of the application may be in the form of an individual enantiomer, diastereomer or geometric isomer, or may be in the form of a mixture of stereoisomers. In one embodiment, the compounds of the application are enantiopure compounds. In another embodiment, mixtures of stereoisomers or diastereomers are provided.

Furthermore, certain compounds, as described herein, may have one or more double bonds that can exist as either the Z or E isomer, unless otherwise indicated. The application additionally encompasses the compounds as individual Z/E isomers substantially free of other E/Z isomers and alternatively, as mixtures of various isomers.

In one embodiment, the present application provides compounds that target proteins, such as BRD9 for degradation, which have numerous advantages, such as protein activity, over inhibitors of protein function and can a) overcome resistance in certain cases; b) prolong the kinetics of drug effect by destroying the protein, thus requiring resynthesis of the protein even after the compound has been metabolized; c) target all functions of a protein at once rather than a specific catalytic activity or binding event; d) expand the number of drug targets by including all proteins that a ligand can be developed for, rather than proteins whose activity can be affected by a small molecule inhibitor, antagonist or agonist; and e) have increased potency compared to inhibitors due to the possibility of the small molecule acting catalytically.

Some embodiments of the present application relate to degradation or loss of 30% to 100% of the target protein. Some embodiments relate to the loss of 50-100% of the target protein. Other embodiments relate to the loss of 75-95% of the targeted protein.

A bifunctional compound of the present application (e.g., a bifunctional compound of any of the formulae described herein, or selected from any bifunctional compounds described herein) is capable of modulating (e.g., decreasing) the amount of a targeted protein (e.g., BRD9). A bifunctional compound of the present application (e.g., a bifunctional compound of any of the formulae described herein, or selected from any bifunctional compounds described herein) is also capable of degrading a targeted protein (e.g., BRD9) through the UPP pathway. Accordingly, a bifunctional compound of the present application (e.g., a bifunctional compound of any of the formulae described herein, or selected from any bifunctional compounds described herein) is capable of treating or preventing a disease or disorder in which BRD9 plays a role. A bifunctional compound of the present application (e.g., a bifunctional compound of any of the formulae described herein, or selected from any so bifunctional compounds described herein) is also capable of treating or preventing a disease or disorder in which BRD9 plays a role or in which BRD9 is deregulated (e.g., overexpressed).

Modulation of BRD9 through UPP-mediated degradation by a bifunctional compound of the application, such as those described herein, provides a novel approach to the treatment, prevention, or amelioration of diseases or disorders in which BRD9 plays a role including, but not limited to, cancer and metastasis, inflammation, arthritis, systemic lupus erthematosus, skin-related disorders, pulmonary disorders, cardiovascular disease, ischemia, neurodegenerative disorders, liver disease, gastrointestinal disorders, viral and bacterial infections, central nervous system disorders, Alzheimer's disease, Parkinson's disease, Huntington's disease, amyotrophic lateral sclerosis, spinal cord injury, and peripheral neuropathy. Further, modulation of BRD9 through UPP-mediated degradation by a bifunctional compound of the application, such as those described herein, also provides a new paradigm for treating, preventing, or ameliorating diseases or disorders in which BRD9 is deregulated.

In one embodiment, a bifunctional compound of any of the formulae described herein, or selected from any bifunctional compounds described herein of the present application is more efficacious in treating a disease or condition or is more capable of treating a disease or condition resistant to the Targeting Ligand than when the Targeting Ligand is administered alone or not bonded to a Linker and a Degron.

In a further embodiment, the disease of condition is cancer. In one embodiment, a bifunctional compound of any of the formulae described herein, or selected from any bifunctional compounds described herein of the present application is capable of modulating or decreasing the amount of BRD9, and thus is useful in treating a disease or condition in which BRD9 plays a role. In a further embodiment, the disease or condition is cancer.

In one embodiment, the bifunctional compound of the present application that is more efficacious in treating a disease or condition or is more capable of treating a disease or condition resistant to the Targeting Ligand than when the Targeting Ligand is administered alone or not bonded to a Linker and a Degron is more potent in inhibiting the growth of cells or decreasing the viability of cells than the Targeting Ligand when the Targeting Ligand is administered alone or not bonded to a Linker and a Degron. In a further embodiment, the cells are cancer cells. In one embodiment, the bifunctional compound inhibits the growth of cells or decreases the viability of cells at an $IC_{50}$ that is lower than the $IC_{50}$ of the Targeting Ligand when the Targeting Ligand is administered alone or not bonded to a Linker and a Degron for inhibiting the growth or decreasing the viability of the cells. In a further embodiment, the cells are cancer cells. In one embodiment, the $IC_{50}$ of the bifunctional compound is at most 90%, 80%, 70%, 60%, 50%, 40%, 30%6, 20%, 10%, 8%, 5%6, 4%, 3%, 2%, 1%, 0.8%, 0.5%, 0.4%, 0.3%, 0.2%, or 0.1° of the $IC_{50}$ of the Targeting Ligand. In one embodiment, the $IC_{50}$ of the bifunctional compound is at most 50%, 40%, 30%, 20%, 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 30%, 20%, 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 10%, 8%6, 5%, 4%, 3%, 2%, 1%6, 0.8%, 0.5%, 0.4%, 0.3%, 0.2%, or 0.1% of the $IC_{50}$ of the Targeting Ligand. In one embodiment, the $IC_{50}$ of the bifunctional compound is at most 5%, 4%, 3%, 2%, 1%, 0.8%, 0.5%, 0.4%, 0.3%, 0.26, or 0.1% of the $IC_{50}$ of the Targeting Ligand. In one embodiment, the $IC_{50}$ of the bifunctional compound is at most 2%, 1%, 0.8%, 0.5%, 0.4%, 0.3° %, 0.2%, or 0.1% of the $IC_{50}$ of the Targeting Ligand. In one embodiment, the $IC_{50}$ of the bifunctional compound is at most 1%, 0.8%, 0.5%, 0.4%, 0.3%, 0.2%, or 0.1% of the $IC_{50}$ of the Targeting Ligand. In one embodiment, the bifunctional compound inhibits the growth of cells or decreases the viability of cells at an $E_{max}$ that is lower than the $E_{max}$ of the Targeting Ligand when the Targeting Ligand is administered alone or not bonded to a Linker and a Degron for inhibiting the growth or decreasing the viability of the cells. In a further embodiment, the cells are cancer cells. In one embodiment, the $E_{max}$ of the bifunctional compound is at most 90%, 80%, 70%, 60%, 50%, 40%, 30%, 20%, 10%, 8%, 5%, 4%, 3%, 2%, or 1% of the $E_{max}$ of the Targeting Ligand. In one embodiment, the $E_{max}$ of the bifunctional compound is at most 50%, 40%, 30%, 20%, 10%, 8%, 5%, 4%, 3%, 2%, or 1% of the $E_{max}$ of the Targeting Ligand. In one embodiment, the $E_{max}$ of the bifunctional compound is at most 90%, 80%, 70%, 60%, 50%, 40%, 30%, 20%, or 10% of the $E_{max}$ of the Targeting Ligand.

In some embodiments, the inhibition of BRD9 activity is measured by $IC_{50}$.

In some embodiments, the inhibition of BRD9 activity is measured by $EC_{50}$.

Potency of the inhibitor can be determined by $EC_{50}$ value. A compound with a lower $EC_{50}$ value, as determined under substantially similar conditions, is a more potent inhibitor relative to a compound with a higher $EC_{50}$ value. In some embodiments, the substantially similar conditions comprise determining a BRD9-dependent cell proliferation in vitro or in vivo in cells expressing BRD9.

Potency of the inhibitor can also be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining a BRD9-dependent cell proliferation, in vitro or in vivo in cells expressing BRD9.

In one embodiment, the bifunctional compounds of the present application are useful as anticancer agents, and thus may be useful in the treatment of cancer, by effecting tumor cell death or inhibiting the growth of tumor cells. In certain exemplary embodiments, the disclosed anticancer agents are useful in the treatment of cancers and other proliferative disorders, including, but not limited to breast cancer, cervical cancer, colon and rectal cancer, leukemia, lung cancer, non-small cell lung cancer, melanoma, multiple myeloma, non-Hodgkin's lymphoma, ovarian cancer, pancreatic cancer, prostate cancer, gastric cancer, leukemias, including but not limited to myeloid, lymphocytic, myelocytic and lymphoblastic leukemias, malignant melanomas, and T-cell lymphoma.

A "selective BRD9 inhibitor." can be identified, for example, by comparing the ability of a compound to inhibit BRD9 protein activity to its ability to inhibit other bromodomain proteins. For example, a substance may be assayed for its ability to inhibit BRD9 protein activity, as well as BRD1, BRD4, and/or BRD7, and/or other bromodomains. In some embodiments, the selectivity can be identified by measuring the $EC_{50}$ or $IC_{50}$ of the compounds.

Definitions

Listed below are definitions of various terms used in this application. These definitions apply to the terms as they are used throughout this specification and claims, unless otherwise limited in specific instances, either individually or as part of a larger group.

The term "alkyl," as used herein, refers to saturated, straight or branched-chain hydrocarbon radicals containing, in certain embodiments, between one and six carbon atoms. For example $C_1$-$C_3$ alkyl includes methyl, ethyl, n-propyl, and isopropyl. Examples of $C_1$-$C_6$ alkyl radicals include, but are not limited to, methyl, ethyl, propyl, isopropyl, n-butyl, tert-butyl, neopentyl, and n-hexyl radicals.

The term "alkoxy" refers to an —O-alkyl radical. For example $C_1$-$C_3$ alkoxy includes methoxy, ethoxy, n-propoxy, and isopropoxy. Examples of $C_1$-$C_6$ alkyl radicals include, but are not limited to, methoxy, ethoxy, propoxy, isopropoxy, n-butoxy, tert-butoxy, neopentoxy, and n-hexoxy radicals.

The terms "hal," "halo," and "halogen," as used herein, refer to an atom selected from fluorine, chlorine, bromine and iodine.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound. Examples of $C_3$-$C_8$ cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1]heptyl, and bicyclo [2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue attached to a heteroaryl ring. Examples include, but are not limited to, pyridinylmethyl, pyrimidinylmethyl and the like.

The term "heterocyclyl," or "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, and (iv) the nitrogen heteroatom may optionally be quaternized. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl), e.g., —NH($C_1$-$C_6$ alkyl), where $C_1$-$C_{12}$ alkyl is as previously defined.

The term "dialkylamino" refers to a group having the structure —N($C_1$-$C_{12}$ alkyl)$_2$, e.g., —NH($C_1$-$C_6$ alkyl), where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the application, any of the aryls, substituted aryls, heteroaryls and substituted heteroaryls described herein, can be any aromatic group. Aromatic groups can be substituted or unsubstituted.

The terms "hal," "halo," and "halogen," as used herein, refer to an atom selected from fluorine, chlorine, bromine and iodine.

As described herein, compounds of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I, —OH, protected hydroxy, —NO$_2$, —CN, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)— heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH— heterocycloalkyl, —NHC(O)—C$_2$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)— heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$—heterocycloalkyl, NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, NHC(O)NH-heterocycloalkyl, —NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH— C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_2$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

It is understood that the aryls, heteroaryls, alkyls, and the like can be substituted.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma: Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors. Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors: Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast: Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "BRD9" herein refers to bromodomain-containing protein 9.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

As used herein, "preventing" or "prevent" describes reducing or eliminating the onset of the symptoms or complications of the disease, condition or disorder.

The term "targeted protein(s)" is used interchangeably with "target protein(s)", unless the context clearly dictates otherwise. In one embodiment, a "targeted protein" is BRD9.

The terms "disease(s)", "disorder(s)", and "condition(s)" are used interchangeably, unless the context clearly dictates otherwise.

The term "therapeutically effective amount" of a bifunctional compound or pharmaceutical composition of the application, as used herein, means a sufficient amount of the bifunctional compound or pharmaceutical composition so as to decrease the symptoms of a disorder in a subject. As is well understood in the medical arts a therapeutically effective amount of a bifunctional compound or pharmaceutical composition of this application will be at a reasonable benefit/risk ratio applicable to any medical treatment. It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed: the specific composition employed: the age, body weight, general health, sex and diet of the patient: the time of administration, route of administration, and rate of excretion of the specific compound employed; the duration of the treatment; drugs used in combination or coincidental with the specific compound employed; and like factors well known in the medical arts.

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977). The salts can be prepared in situ during the final isolation and purification of the compounds of the application, or separately by reacting the free base or acid function with a suitable acid or base.

Examples of pharmaceutically acceptable salts include, but are not limited to, nontoxic acid addition salts: salts formed with inorganic acids such as hydrochloric acid, hydrobromic acid, phosphoric acid, sulfuric acid and perchloric acid, or with organic acids such as acetic acid, maleic acid, tartaric acid, citric acid, succinic acid or malonic acid. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the bifunctional compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein, refers to those prodrugs of the bifunctional compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application. "Prodrug", as used herein, means a compound which is convertible in vivo by metabolic means (e.g., by hydrolysis) to afford any compound delineated by the formulae of the instant application. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). "Design and Application of Prodrugs. Textbook of Drug Design and Development, Chapter 5, 113-191 (1991); Bundgaard, et al., *Journal of Drug Deliver Reviews*, 8:1-38 (1992); Bundgaard, *J. of Pharmaceutical Sciences*, 77:285 et seq. (1988); Higuchi and Stella (eds.) *Prodrugs as Novel Drug Delivery Systems*, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This application also encompasses pharmaceutical compositions containing, and methods of treating disorders through administering, pharmaceutically acceptable prodrugs of bifunctional compounds of the application. For example, compounds of the application having free amino, amido, hydroxy or carboxylic groups can be converted into prodrugs.

Prodrugs include compounds wherein an amino acid residue, or a polypeptide chain of two, three, or four amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, omithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in *Advanced Drug Delivery Reviews*, 1996, 19, 1 15. Carbamate prodrugs of hydroxy and amino groups are also included, as are carbonate prodrugs, sulfonate esters and sulfate esters of hydroxy groups, Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in. *J. Med. Chem*. 1996, 39, 10. Free amines can also be derivatized as amides, sulfonamides or phosphonamides. All of these prodrug moieties may incorporate groups including but not limited to ether, amine and carboxylic acid functionalities.

The application also provides for a pharmaceutical composition comprising a therapeutically effective amount of a bifunctional compound of the application, or an enantiomer, diastereomer, stereoisomer, or pharmaceutically acceptable salt thereof, and a pharmaceutically acceptable carrier.

In another aspect, the application provides a kit comprising a bifunctional compound capable of inhibiting BRD9 activity selected from one or more compounds disclosed herein, or a pharmaceutically acceptable salt, hydrate, solvate, prodrug, stereoisomer, or tautomer thereof, optionally in combination with a second agent and instructions for use in treating cancer.

In another aspect, the application provides a method of synthesizing a bifunctional compound disclosed herein.

The synthesis of the bifunctional compounds of the application can be found herein and in the Examples below.

Other embodiments are a method of making a bifunctional compound of any of the formulae herein using any one, or combination of, reactions delineated herein. The method can include the use of one or more intermediates or chemical reagents delineated herein.

Another aspect is an isotopically labeled bifunctional compound of any of the formulae delineated herein. Such compounds have one or more isotope atoms which may or may not be radioactive, including but not limited to $^3$H, $^2$H, $^{14}$C, $^{13}$C, $^{18}$F, $^{35}$S, $^{32}$P, $^{125}$I, and $^{131}$I introduced into the bifunctional compound. Such compounds are useful for drug metabolism studies and diagnostics, as well as therapeutic applications.

A bifunctional compound of the application can be prepared as a pharmaceutically acceptable acid addition salt by reacting the free base form of the compound with a pharmaceutically acceptable inorganic or organic acid. Alternatively, a pharmaceutically acceptable base addition salt of a bifunctional compound of the application can be prepared by reacting the free acid form of the bifunctional compound with a pharmaceutically acceptable inorganic or organic base.

Alternatively, the salt forms of the bifunctional compounds of the application can be prepared using salts of the starting materials or intermediates.

The free acid or free base forms of the bifunctional compounds of the application can be prepared from the corresponding base addition salt or acid addition salt from, respectively. For example, a bifunctional compound of the application in an acid addition salt form can be converted to the corresponding free base by treating with a suitable base, including but not limited to ammonium hydroxide solution, sodium hydroxide. A bifunctional compound of the application in a base addition salt form can be converted to the corresponding free acid by treating with a suitable acid, including but not limited to hydrochloric acid.

Prodrugs of the bifunctional compounds of the application can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized bifunctional compound of the application with a suitable carbamylating agent, including but not limited to 1,1-acyloxyalkylcarbanochloridate, paranitrophenyl carbonate.

Protected derivatives of the bifunctional compounds of the application can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present application can be conveniently prepared or formed during the process of the application, as solvates or hydrates. Hydrates of bifunctional compounds of the present application can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic, including but not limited to hydrochloric, sulfuric, nitric acids, aluminum trichloride or organic, including but not limited to camphorsulfonic acid, p-toluenesulfonic acid, acetic acid, ytterbium triflate. Acids are useful in either catalytic or stoichiometric amounts to facilitate chemical reactions. Bases are any basic chemical, which can be inorganic, including but not limited to sodium bicarbonate, potassium hydroxide or organic, including but not limited to triethylamine, pyridine. Bases are useful in either catalytic or stoichiometric amounts to facilitate chemical reactions.

Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein, such as therapeutic or prophylactic administration, to a subject.

When any variable occurs more than one time in any constituent or formula for a compound, its definition at each occurrence is independent of its definition at every other occurrence. Thus, for example, if a group is shown to be substituted with one or more $R^{14}$ moieties, then $R^{14}$ at each occurrence is selected independently from the definition of $R^{14}$. Also, combinations of substituents and/or variables are permissible, but only if such combinations result in stable compounds within a designated atom's normal valency.

In addition, some of the compounds of this application have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present application.

Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981).

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385: errata 511: Cahn et al., *Angew. Chem.* 1966, 78, 413; Cahn and Ingold, *J. Chem. Soc.* 1951 (London), 612; Calm et al., *Experientia* 1956, 12, 81: Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertible by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. The compounds of this application may also be represented in multiple tautomeric forms, in such instances, the application expressly includes all tautomeric forms of the compounds described herein (e.g., alkylation of a ring system may result in alkylation at multiple sites, the application expressly includes all such reaction products).

In the present application, the structural formula of the bifunctional compound represents a certain isomer for convenience in some cases, but the present application includes all isomers, such as geometrical isomers, optical isomers based on an asymmetrical carbon, stereoisomers, tautomers, and the like. In the present specification, the structural formula of the compound represents a certain isomer for convenience in some cases, but the present application includes all isomers, such as geometrical isomers, optical isomers based on an asymmetrical carbon, stereoisomers, tautomers, and the like.

Additionally, the compounds of the present application, for example, the salts of the bifunctional compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The synthesized bifunctional compounds can be separated from a reaction mixture and further purified by a method such as column chromatography, high pressure liquid chromatography, or recrystallization. As can be appreciated by the skilled artisan, further methods of synthesizing the bifunctional compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this application may be modified by appending various functionalities via any synthetic means delineated herein to enhance selective biological properties. Such modifications are known in the art and include those which increase biological penetration into a given biological system, including but not limited to blood, lymphatic system, central nervous system, increase oral availability, increase solubility to allow administration by injection, alter metabolism and alter rate of excretion.

The compounds of the application are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Method of Synthesizing the Compounds

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; and Greene, T. W., Wuts, P. G. M., *Protective Groups in Organic Synthesis*, $3^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application. The processes generally provide the desired final compound at or near the end of the overall process, although it may be desirable in certain instances to further convert the compound to a pharmaceutically acceptable salt, ester or prodrug thereof. Suitable synthetic routes are depicted in the schemes below.

Those skilled in the art will recognize if a stereocenter exists in the compounds disclosed herein. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds of the present application can be prepared in a number of ways well known to those skilled in the art of organic synthesis. By way of example, compounds of the present application can be synthesized using the methods described below, together with synthetic methods known in the art of synthetic organic chemistry, or variations thereon as appreciated by those skilled in the art. Preferred methods include but are not limited to those methods described below.

Compounds of the present application can be synthesized by following the steps outlined in General Scheme 1 and 2 which comprise different sequences of assembling intermediates. Starting materials are either commercially available or made by known procedures in the reported literature or as illustrated.

General Scheme 1 Synthesis of Thalidomide-based Degronimids

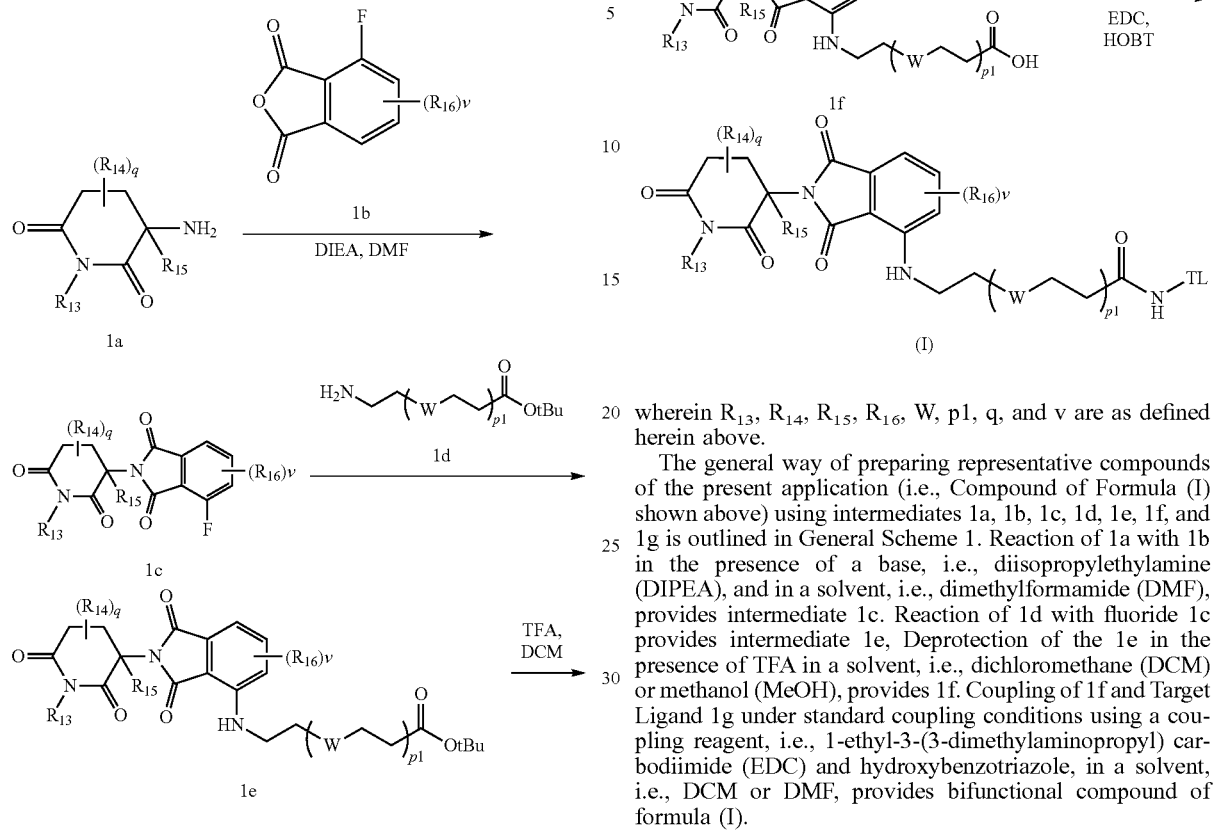

wherein $R_{13}$, $R_{14}$, $R_{15}$, $R_{16}$, W, p1, q, and v are as defined herein above.

The general way of preparing representative compounds of the present application (i.e., Compound of Formula (I) shown above) using intermediates 1a, 1b, 1c, 1d, 1e, 1f, and 1g is outlined in General Scheme 1. Reaction of 1a with 1b in the presence of a base, i.e., diisopropylethylamine (DIPEA), and in a solvent, i.e., dimethylformamide (DMF), provides intermediate 1c. Reaction of 1d with fluoride 1c provides intermediate 1e, Deprotection of the 1e in the presence of TFA in a solvent, i.e., dichloromethane (DCM) or methanol (MeOH), provides 1f. Coupling of 1f and Target Ligand 1g under standard coupling conditions using a coupling reagent, i.e., 1-ethyl-3-(3-dimethylaminopropyl) carbodiimide (EDC) and hydroxybenzotriazole, in a solvent, i.e., DCM or DMF, provides bifunctional compound of formula (I).

General Scheme 1 Synthesis of Thalidomide-based Degronimids

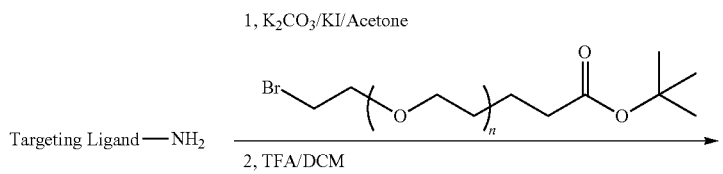

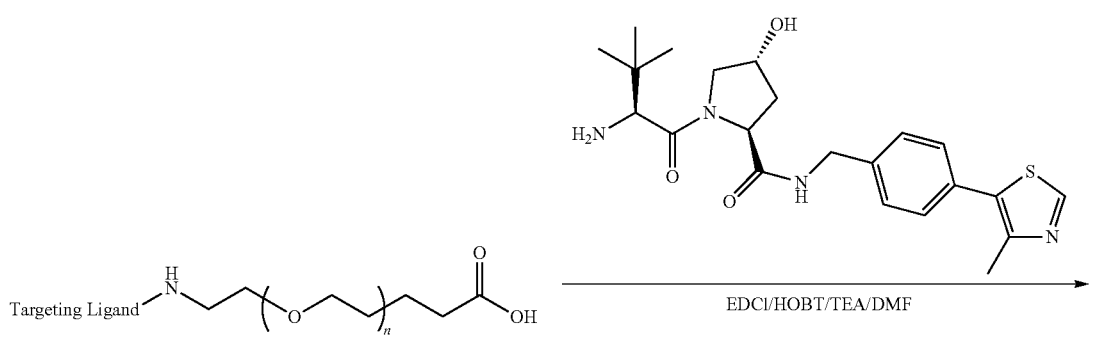

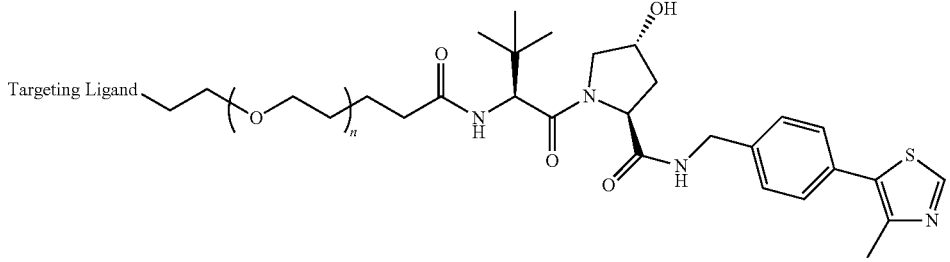

Biological Assays
Cell Viability Assay

Wild-type or cereblon null cells are treated with various concentrations of a bifunctional compound of the invention and allowed to grow. Cells are then assayed to determine cell viability by measuring the amount of ATP present, which is an indicator of cell metabolic activity. Results are graphed as relative luminescent values.

Methods of the Application

In another aspect, the application provides a method of modulating a bromodomain protein, comprising contacting the bromodomain protein with a bifunctional compound disclosed herein, or an enantiomer, diastereomer, or stereoisomer thereof, or pharmaceutically acceptable salt, hydrate, solvate, or prodrug thereof, or with a pharmaceutical composition disclosed herein. In some embodiments, the bromodomain protein is BRD9.

In another aspect, the application provides a method of inhibiting a bromodomain protein, comprising contacting the protein with a bifunctional compound disclosed herein, or an enantiomer, diastereomer, or stereoisomer thereof, or pharmaceutically acceptable salt, hydrate, solvate, or prodrug thereof, or with a pharmaceutical composition disclosed herein. In some embodiments, the bromodomain protein is BRD9.

In still another aspect, the application provides a method of inhibiting bromodomain-containing protein 9 (BRD9), the method comprising administering to a subject in need thereof an effective amount of a bifunctional compound disclosed herein, or an enantiomer, diastereomer, or stereoisomer thereof, or pharmaceutically acceptable salt, hydrate, solvate, or prodrug thereof.

In still another aspect, the application provides a method of inhibiting bromodomain-containing protein 9 (BRD9), the method comprising administering to a subject in need thereof an effective amount of a pharmaceutical composition comprising a bifunctional compound disclosed herein, or an enantiomer, diastereomer, or stereoisomer thereof, or pharmaceutically acceptable salt, hydrate, solvate, or prodrug thereof and a pharmaceutically acceptable carrier.

Another aspect of the application provides a method of treating or preventing a disease, the method comprising administering to a subject in need thereof an effective amount of a bifunctional compound disclosed herein, or an enantiomer, diastereomer, or stereoisomer thereof, or pharmaceutically acceptable salt, hydrate, solvate, or prodrug thereof. In some embodiments, the disease is mediated by a bromodomain protein. In further embodiments, the bromodomain protein is BRD9.

Another aspect of the application provides a method of treating or preventing a disease, the method comprising administering to a subject in need thereof an effective amount of a pharmaceutical composition comprising a bifunctional compound disclosed herein, or an enantiomer, diastereomer, or stereoisomer thereof, or pharmaceutically acceptable salt, hydrate, solvate, or prodrug thereof and a pharmaceutically acceptable carrier. In some embodiments, the disease is mediated by a bromodomain protein. In further embodiments, the bromodomain protein is BRD9.

In some embodiments, the disease is mediated by BRD9. In other embodiments, BRD9 plays a role in the initiation or development of the disease.

In certain embodiments, the disease or disorder is cancer or a proliferation disease.

In further embodiments, the disease or disorder is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In further embodiments, the disease or disorder is sarcoma. In further embodiments, the disease or disorder is sarcoma of the bones, muscles, tendons, cartilage, nerves, fat, or blood vessels. In further embodiments, the disease or disorder is soft tissue sarcoma, bone sarcoma, or osteosarcoma. In further embodiments, the disease or disorder is angiosarcoma, fibrosarcoma, liposarcoma, leiomyosarcoma, Karposi's sarcoma, osteosarcoma, gastrointestinal stromal tumor, Synovial sarcoma, Pleomorphic sarcoma, chondrosarcoma, Ewing's sarcoma, reticulum cell sarcoma, meningiosarcoma, botryoid sarcoma, rhabdomyosarcoma, or embryonal rhabdomyosarcoma.

In further embodiments, the disease or disorder is multiple myeloma.

In other embodiments, the disease or disorder is inflammation, arthritis, rheumatoid arthritis, spondyiarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy, or B-Cell Lymphoma.

In further embodiments, the disease or disorder is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, dermatitis, pain, pulmonary disorders, lung inflammation, adult respiratory distress syndrome, pulmonary sarcoisosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia or lymphoma.

Another aspect of the application provides a method of treating a bromodomain protein mediated disorder, the method comprising administering to a subject in need thereof an effective amount of a bifunctional compound disclosed herein, or an enantiomer, diastereomer, or stereoisomer thereof, or pharmaceutically acceptable salt, hydrate, solvate, or prodrug thereof. In some embodiments, the bifunctional compound is an inhibitor of BRD9. In other embodiments, the subject is administered an additional therapeutic agent. In other embodiments, the bifunctional compound and the additional therapeutic agent are administered simultaneously or sequentially.

Another aspect of the application provides a method of treating a bromodomain protein mediated disorder, the method comprising administering to a subject in need thereof an effective amount of a pharmaceutical composition comprising a bifunctional compound disclosed herein, or an enantiomer, diastereomer, or stereoisomer thereof, or pharmaceutically acceptable salt, hydrate, solvate, or prodrug thereof and a pharmaceutically acceptable carrier. In some embodiments, the bifunctional compound is an inhibitor of BRD9. In other embodiments, the subject is administered an additional therapeutic agent. In other embodiments, the pharmaceutical composition comprising a bifunctional compound and the additional therapeutic agent are administered simultaneously or sequentially.

In other embodiments, the disease or disorder is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

Another aspect of the present application provides a method of treating or preventing a proliferative disease. The method comprises administering to a subject in need thereof an effective amount of a bifunctional compound of the application, or an enantiomer, diastereomer, or stereoisomer thereof, or pharmaceutically acceptable salt, hydrate, solvate, or prodrug thereof.

Another aspect of the present application is a method of treating or preventing a proliferative disease. The method comprises administering to a subject in need thereof an effective amount of a pharmaceutical composition comprising a bifunctional compound disclosed herein, or an enantiomer, diastereomer, or stereoisomer thereof, or pharmaceutically acceptable salt, hydrate, solvate, or prodrug thereof and a pharmaceutically acceptable carrier.

In another aspect, the application provides a method of treating or preventing cancer, wherein the cancer cell comprises activated BRD9, comprising administering to a subject in need thereof an effective amount of a bifunctional compound disclosed herein, or an enantiomer, diastereomer, or stereoisomer thereof, or pharmaceutically acceptable salt, hydrate, solvate, or prodrug thereof.

In another aspect, the application provides a method of treating or preventing cancer, wherein the cancer cell comprises activated BRD9, comprising administering to a subject in need thereof an effective amount of a pharmaceutical composition comprising a bifunctional compound disclosed herein, or an enantiomer, diastereomer, or stereoisomer thereof, or pharmaceutically acceptable salt, hydrate, solvate, or prodrug thereof and a pharmaceutically acceptable carrier.

In certain embodiments, the BRD9 activation is selected from mutation of BRD9, amplification of BRD9, expression of BRD9, and ligand mediated activation of BRD9.

Another aspect of the application provides a method of treating or preventing cancer in a subject, wherein the subject is identified as being in need of BRD9 inhibition for the treatment of cancer, comprising administering to the subject an effective amount of a bifunctional compound disclosed herein, or an enantiomer, diastereomer, or stereoisomer thereof, or pharmaceutically acceptable salt, hydrate, solvate, or prodrug thereof.

Another aspect of the application provides a method of treating or preventing cancer in a subject, wherein the subject is identified as being in need of BRD9 inhibition for the treatment of cancer, comprising administering to the subject an effective amount of a pharmaceutical composition comprising a bifunctional compound disclosed herein, or an enantiomer, diastereomer, or stereoisomer thereof, or pharmaceutically acceptable salt, hydrate, solvate, or prodrug thereof and a pharmaceutically acceptable carrier.

In certain embodiments, the application provides a method of treating any of the disorders described herein, wherein the subject is a human. In certain embodiments, the application provides a method of preventing any of the disorders described herein, wherein the subject is a human.

In another aspect, the application provides a bifunctional compound disclosed herein, or an enantiomer, diastereomer, or stereoisomer thereof, or pharmaceutically acceptable salt, hydrate, solvate, or prodrug thereof, for use in the manufacture of a medicament for treating or preventing a disease in which BRD9 plays a role.

In still another aspect, the application provides a bifunctional compound of the application, or an enantiomer, diastereomer, or stereoisomer thereof, or pharmaceutically acceptable salt, hydrate, solvate, or prodrug thereof for use in treating or preventing a disease in which BRD9 plays a role.

In another aspect, the application provides a pharmaceutical composition comprising a bifunctional compound disclosed herein, or an enantiomer, diastereomer, or stereoisomer thereof, or pharmaceutically acceptable salt, hydrate, solvate, or prodrug thereof and a pharmaceutically acceptable carrier, for use in the manufacture of a medicament for treating or preventing a disease in which BRD9 plays a role.

In still another aspect, the application provides a pharmaceutical composition comprising a bifunctional compound disclosed herein, or an enantiomer, diastereomer, or stereoisomer thereof, or pharmaceutically acceptable salt, hydrate, solvate, or prodrug thereof and a pharmaceutically acceptable carrier, for use in treating or preventing a disease in which BRD9 plays a role.

As inhibitors of BRD9, the bifunctional compounds and compositions of this application are particularly useful for treating or lessening the severity of a disease, condition, or disorder where a bromodomain protein is implicated in the disease, condition, or disorder. In one aspect, the present application provides a method for treating or lessening the severity of a disease, condition, or disorder where a bromodomain protein is implicated in the disease state. In another aspect, the present application provides a method for treating or lessening the severity of a bromodomain protein mediated disease, condition, or disorder where inhibition of enzymatic activity is implicated in the treatment of the disease. In another aspect, this application provides a method for treating or lessening the severity of a disease, condition, or disorder with bifunctional compounds that inhibit enzymatic activity by binding to the bromodomain protein. Another aspect provides a method for treating or lessening the severity of a bromodomain protein mediated disease, condition, or disorder by inhibiting enzymatic activity of the protein with a bromodomain protein inhibitor.

In some embodiments, said method is used to treat or prevent a condition selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this application provides bifunctional compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer. The term "cancer" includes, but is not limited to, the following cancers: breast; ovary; cervix; prostate: testis, genitourinary tract: esophagus; larynx, glioblastoma; neuroblastoma; stomach; skin, keratoacanthoma; lung, epidermoid carcinoma, large cell carcinoma, small cell carcinoma, lung adenocarcinoma: bone; colon; colorectal: adenoma; pancreas, adenocarcinoma; thyroid, follicular carcinoma, undifferentiated carcinoma, papillary carcinoma; seminoma; melanoma; sarcoma bladder carcinoma; liver carcinoma and biliary passages; kidney carcinoma: myeloid disorders; lymphoid disorders. Hodgkin's, hairy cells: buccal cavity and pharynx (oral), lip, tongue, mouth, pharynx; small intestine; colonrectum, large intestine, rectum, brain and central nervous system: chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma. Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma Wilms' tumor, bone tumors, and soft-tissue sarcomas, common solid tumors of adults such as head and neck cancers, such as oral, laryngeal, nasopharyngeal and esophageal, genitourinary cancers, such as prostate, bladder, renal, uterine, ovarian, testicular, lung cancer, such as small-cell and non-small cell, breast cancer, pancreatic cancer, melanoma and other skin cancers, stomach cancer, brain tumors, tumors related to Gorlin's syndrome, such as medulloblastoma or meningioma, and liver cancer. Additional exemplary forms of cancer which may be treated by the subject bifunctional compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the bifunctional compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the application, the present application provides for the use of one or more bifunctional compounds of the application in the manufacture of a medicament for the treatment of cancer, including without limitation the various types of cancer disclosed herein.

In some embodiments, the bifunctional compounds of this application are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the bifunctional compounds of this application are useful for treating hematopoietic disorders, in particular, acute-myelogenous leukemia (AML), chronic-myelogenous leukemia (CML), acute-promyelocytic leukemia, and acute lymphocytic leukemia (ALL).

This application further embraces the treatment or prevention of cell proliferative disorders such as hyperplasias, dysplasias and pre-cancerous lesions, Dysplasia is the earliest form of pre-cancerous lesion recognizable in a biopsy by a pathologist. The subject bifunctional compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

Another aspect of this application provides a method for the treatment or lessening the severity of a disease selected from a proliferative or hyperproliferative disease, or a neurodegenerative disease, comprising administering an effective amount of a bifunctional compound, or a pharmaceutically acceptable composition comprising a bifunctional compound, to a subject in need thereof.

As inhibitors of BRD9 protein, the compounds and compositions of this application are also useful in biological samples. One aspect of the application is inhibiting protein activity in a biological sample, which method comprises contacting said biological sample with a bifunctional compound of the application or a composition comprising said bifunctional compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of protein activity in a biological sample is useful for a variety of purposes that are known to one of skill in the art. Examples of such purposes include, but are not limited to, blood transfusion, organ-transplantation, and biological specimen storage.

Another aspect of this application is the study of BRD9 protein in biological and pathological phenomena; the study of intracellular signal transduction pathways mediated by such proteins; and the comparative evaluation of new protein inhibitors. Examples of such uses include, but are not limited to, biological assays such as enzyme assays and cell-based assays.

The activity of the compounds and compositions of the present application as BRD9 inhibitors may be assayed in vitro, in vivo, or in a cell line. In vitro assays include assays that determine inhibition of either the enzyme activity or ATPase activity of the activated protein. Alternate in vitro assays quantitate the ability of the inhibitor to bind to the bromodomain protein and may be measured either by radio labelling the inhibitor prior to binding, isolating the inhibitor/bromodomain complex and determining the amount of radio label bound, or by running a competition experiment where new inhibitors are incubated with the bromodomain bound to known radioligands, Detailed conditions for assaying a compound utilized in this application as an inhibitor of various bromodomain proteins are set forth in the Examples below.

In accordance with the foregoing, the present application further provides a method for preventing or treating any of the diseases or disorders described above in a subject in need of such treatment, which method comprises administering to said subject a therapeutically effective amount of a bifunctional compound of the application, or an enantiomer, diastereomer, or stereoisomer thereof, or pharmaceutically acceptable salt, hydrate, solvate, or prodrug thereof. For any of the above uses, the required dosage will vary depending on the mode of administration, the particular condition to be treated and the effect desired.

Pharmaceutical Compositions

In another aspect, the application provides a pharmaceutical composition comprising a therapeutically effective amount of a bifunctional compound of the present application or an enantiomer, diastereomer, or stereoisomer thereof, or pharmaceutically acceptable salt, hydrate, solvate, or prodrug thereof, and a pharmaceutically acceptable carrier.

Bifunctional compounds of the application can be administered as pharmaceutical compositions by any conventional route, in particular enterally, e.g., orally in the form of tablets or capsules, or parenterally in the form of injectable solutions or suspensions, or topically in the form of lotions, gels, ointments or creams, or in a nasal or suppository form. Pharmaceutical compositions comprising a compound of the present application in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, including but not limited to lactose, dextrose, sucrose, mannitol, sorbitol, cellulose and/or glycine; b) lubricants, including but not limited to silica, talcum, stearic acid, its magnesium or calcium salt and/or polyethyleneglycol; for tablets also c) binders, including but not limited to magnesium aluminum silicate, starch paste, gelatin, tragacanth, methylcellulose, sodium carboxymethylcellulose and or polyvinylpyrrolidone; if desired d) disintegrants, including but not limited to starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application to the skin and eyes are preferably aqueous solutions, ointments, creams or gels well-known in the art. Such may contain solubilizers, stabilizers, tonicity enhancing agents, buffers and preservatives.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxy propylene-block polymers, wool fat, sugars such as lactose, glucose and sucrose; starches such as corn starch and potato starch; cellulose and its derivatives such as sodium carboxymethyl cellulose, ethyl cellulose and cellulose acetate: powdered tragacanth; malt: gelatin: talc; excipients such as cocoa butter and suppository waxes, oils such as peanut oil, cottonseed oil; safflower oil; sesame oil; olive oil; corn oil and soybean oil: glycols such a propylene glycol or polyethylene glycol: esters such as ethyl oleate and ethyl laurate, agar: buffering agents such as magnesium hydroxide and aluminum hydroxide: alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this application can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous, or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, including but not limited to tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds and compositions of the application can be administered in therapeutically effective amounts in a combinational therapy with one or more therapeutic agents (pharmaceutical combinations) or modalities, including but not limited to an anti-proliferative, anti-cancer, immunomodulatory or anti-inflammatory agent. Where the compounds of the application are administered in conjunction with other therapies, dosages of the co-administered compounds will of course vary depending on the type of co-drug employed, on the specific drug employed, on the condition being treated and so forth. Compounds and compositions of the application can be administered in therapeutically effective amounts in a combinational therapy with one or more therapeutic agents (pharmaceutical combinations) or modalities, including but not limited to anti-proliferative, anti-cancer, immunomodulatory or anti-inflammatory agent, and/or non-drug therapies. For example, synergistic effects can occur with anti-proliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy includes the administration of the subject compounds in further combination with one or more other biologically active ingredients (such as, but not limited to, a second BRD9 inhibitor, a second and different antineoplastic agent, a bromodomain inhibitor (i.e., BRD1, BRD2, BRD4, BRD7, etc.) and non-drug therapies (such as, but not limited to, surgery or radiation treatment). For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

In another aspect of the application, the compounds may be administered in combination with one or more separate pharmaceutical agents, including but not limited to a chemotherapeutic agent, an immunotherapeutic agent, or an adjunctive therapeutic agent.

Combination Therapy

In one aspect, a treatment regimen is provided comprising the administration of a compound of the present invention or a pharmaceutically acceptable composition, salt, isotopic analog (such as a deuterated derivative), or prodrug thereof in combination or in alternation with at least one additional therapeutic agent. The combinations and/or alternations disclosed herein can be administered for beneficial, additive, or synergistic effect in the treatment of abnormal cellular proliferative disorders.

In one aspect of this embodiment, the second active compound is an immune modulator, including but not limited to a checkpoint inhibitor. Checkpoint inhibitors for use in the methods described herein include, but are not limited to PD-1 inhibitors, PD-L1 inhibitors, PD-L2 inhibitors, CTLA-4 inhibitors, LAG-3 inhibitors, TIM-3 inhibitors, and V-domain Ig suppressor of T-cell activation (VISTA) inhibitors, or combination thereof.

In one embodiment, the checkpoint inhibitor is a PD-1 inhibitor that blocks the interaction of PD-1 and PD-L1 by binding to the PD-1 receptor, and in turn inhibits immune suppression. In one embodiment, the checkpoint inhibitor is a PD-1 checkpoint inhibitor selected from nivolumab, pembrolizumab, pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.).

In one embodiment, the checkpoint inhibitor is a PD-L1 inhibitor that blocks the interaction of PD-1 and PD-L1 by binding to the PD-L1 receptor, and in turn inhibits immune suppression. PD-L1 inhibitors include, but are not limited to, avelumab, atezolizumab, durvalumab, KN035, and BMS-936559 (Bristol-Myers Squibb).

In one aspect of this embodiment, the checkpoint inhibitor is a CTLA-4 checkpoint inhibitor that binds to CTLA-4 and inhibits immune suppression. CTLA-4 inhibitors include, but are not limited to, ipilimumab, tremelimumab (AstraZeneca and MedImmune), AGEN1884 and AGEN2041 (Agenus).

In another embodiment, the checkpoint inhibitor is a LAG-3 checkpoint inhibitor. Examples of LAG-3 checkpoint inhibitors include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). In yet another aspect of this embodiment, the checkpoint inhibitor is a TIM-3 checkpoint inhibitor. A specific TIM-3 inhibitor includes, but is not limited to, TSR-022 (Tesaro).

In another embodiment, the compound for use in combination therapy is a LAG-3 targeting ligand. In another embodiment, the compound for use in combination therapy is a TIM-3 targeting ligand. In another embodiment, the compound for use in combination therapy is a aromatase inhibitor. In another embodiment, the compound for use in combination therapy is a progestin receptor targeting ligand. In another embodiment, the compound for use in combination therapy is a CYP3A4 targeting ligand. In another embodiment, the compound for use in combination therapy is a TORC1 or TORC2 targeting ligand.

In specific embodiments, the treatment regimen includes the administration of a compound of the present invention or a pharmaceutically acceptable composition, salt, isotopic analog, or prodrug thereof in combination or alternation with at least one additional kinase inhibitor. In one embodiment, the at least one additional kinase inhibitor is selected from a phosphoinositide 3-kinase (PI3K) inhibitor, a Bruton's tyrosine kinase (BTK) inhibitor, a cyclin-dependent kinase inhibitor, or a spleen tyrosine kinase (Syk) inhibitor, or a combination thereof.

In one embodiment, the additional active agent is the small molecule BET inhibitor. MK-8628 (CAS 202590-98-5) (6H-thieno(3,2-f)-(1,2,4)triazolo(4,3-a)-(1,4)diazepine-6-acetamide, 4-(4-chlorophenyl)-N-(4-hydroxyphenyl)2,3,9-trimethyl. (6S).

In one embodiment, a compound of the present invention or a pharmaceutically acceptable composition, salt, isotopic analog, or prodrug thereof is combined in a dosage form with the PIk3 inhibitor.

PI3k inhibitors that may be used in the present invention are well known. Examples of PI3 kinase inhibitors include but are not limited to Wortmannin, demethoxyviridin, perifosine, idelalisib, Pictilisib, Palomid 529, ZSTK474, PWT33597, CUDC-907, and AEZS-136, duvelisib, GS-9820. GDC-0032 (2-[4-[2-(2-Isopropyl-5-methyl-1,2,4-triazol-3-yl)-5,6-dihydroimidazo[1,2-d][1.4]benzoxazepin-9-yl]pyrazol-1-yl]-2-methylpropanamide). MLN-1117 ((2R)-1-Phenoxy-2-butanyl hydrogen (S)-methylphosphonate; or Methyl(oxo) {[(2R)-1-phenoxy-2-butanyl]oxy} phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-(2-(methyloxy)-5-[4-(4-pyridazinyl)-6-quinolinyl]-3-pyridinyl) benzenesulfonamide), TGX-221 ((±)-7-Methyl-2-(morpholin-4-yl)-9-(1-phenylaminoethyl)-pyrido[1,2-a]pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl) sulfamoyl)phenyl)-3-methoxy-4 methylbenzamide), BAY-80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione). CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d]pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecane-18-oate), PF-05212384 (N-[4-[[4-(Dimethylamino)-1-piperidinyl] carbonyl]phenyl]-N'-[4-(4,6-di-4-morpholinyl-1,3,5-triazin-2-yl)phenyl]urea), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile), XL-765 (N-(3-(N-(3-(3,5-dimethoxyphenylamino)quinoxalin-2-yl)sulfamoyl)phenyl)-3-methoxy-4-methylbenzamide), and GSK-1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4,5h]isochromen-10-yl] acetate (also known as sonolisib)).

BTK inhibitors for use in the present invention are well known. Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide]. LFM-A13 (alpha-cyano-beta-hvdroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl)phenyl) benzamide. CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g]quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino)pyrimidine-5-carboxamide hydrochloride), QL-47 (1-(1-acryloylindolin-6-yl)-9-(1-methyl-1H-pyrazol-4-yl)benzo[h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference. In one embodiment, a compound of the present invention or a pharmaceutically acceptable composition, salt, isotopic analog, or prodrug thereof is combined in a dosage form with the BTK inhibitor.

Syk inhibitors for use in the present invention are well known, and include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a] pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl] methyl dihydrogen phosphate), fostamatinib disodium salt (sodium (6-((5-fluoro-2-((3,4,5-trimethoxyphenyl)amino) pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R,2S)-2-Amino-cyclohexylamino]-4-(5,6-dimethyl-pyridin-2-ylamino)-pyridazine-3-carboxylic acid amide), imatinib (Gleevec; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino)pyrimidine-5-carboxamide), PRT-062607 (4-((3-(2H-1,2,3-triazol-2-yl)phenyl)amino)-2-(((1R,2S)-2-aminocyclohexyl) amino)pyrimidine-5-carboxamide hydrochloride), $R_{12}$ (3,3'-((5-fluoropyrimidine-2,4-diyl)bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4]oxazin-3(4H)-one), YM 193306 (see Singh et al., *J. Med Chem.* 2012, 55, 3614-3643), 7-azaindole, piceatannol, ER-27319 (see Singh et al.), PRT060318 (see Singh et al.), luteolin (see Singh et al.), apigenin (see Singh et al.), quercetin (see Singh et al.), fisetin (see Singh et al.), myricetin (see Singh et al.), morin (see Singh et al.). In one embodiment a compound of the present invention or a pharmaceutically acceptable composition, salt, isotopic analog, or prodrug thereof is combined in a dosage form with the Syk inhibitor.

In specific embodiments, the method of treatment provided includes the administration of a compound of the present invention or a pharmaceutically acceptable composition, salt, isotopic analog, or prodrug thereof in combination or alternation with at least one additional chemotherapeutic agent.

In one embodiment, the at least one additional chemotherapeutic agent combined or alternated with a compound of the present invention is a protein cell death-1 (PD-1) inhibitor. PD-1 inhibitors are known in the art, and include, for example, nivolumab (BMS), pembrolizumab (Merck), pidilizumab (CureTech/Teva), AMP-244 (Amplimmune/GSK), BMS-936559 (BMS), and MED14736 (Roche/Genentech). In one embodiment, a compound of the present invention or a pharmaceutically acceptable composition, salt, isotopic analog, or prodrug thereof is combined in a dosage form with the PD-1 inhibitor. In one embodiment the PD-1 inhibitor is pembrolizumab.

In one embodiment, the at least one additional chemotherapeutic agent combined or alternated with a compound of the present invention is a CTLA-4 inhibitor. CTLA-4 inhibitors are known in the art, and include, for example, ipilimumab (Yervoy) marketed by Bristol-Myers Squibb and tremelimumab marketed by Pfizer.

In one embodiment, the at least one additional chemotherapeutic agent combined or alternated with the compound of the present invention is a BET inhibitor. BET inhibitors are known in the art, and include, for example, JQ1, I-BET 151 (a.k.a. GSK1210151A), I-BET 762 (a.k.a. GSK525762), OTX-015 (a.k.a. MK-8268, IUPAC 6H-Thieno[3,2-f][1,2,4]triazolo[4,3-a][1,4]diazepine-6-acetamide, 4-(4-chlorophenyl)-N-(4-hydroxyphenyl)-2,3,9-trimethyl-), TEN-010, CPI-203, CPI-0610, RVX-208, and LY294002. In one embodiment the BET inhibitor used in combination or alternation with a compound of the present invention for treatment of a tumor or cancer is JQ1 ((S)-tert-butyl 2-(4-(4-chlorophenyl)-2,3,9-trimethyl-6H-thieno[3,2-f][1,2,4]triazolo[4,3-a][1,4]diazepin-6-yl)acetate). In an alternative embodiment the BET inhibitor used in combination or alternation with a compound of the present invention for treatment of a tumor or cancer is I-BET 151 (2H-Imidazo[4,5-c]quinolin-2-one, 7-(3,5-dimethyl-4-isoxazolyl)-1,3-dihydro-8-methoxy-1-[(1R)-1-(2-pyridinyl)ethyl]-).

In one embodiment, the at least one additional chemotherapeutic agent combined or alternated with the compound of the present invention is a MEK inhibitor. MEK inhibitors for use in the present invention are well known, and include, for example, tametinib/GSK1 120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC 1193-5369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA1 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK-162/ARRY438162 (5-[(4-Bromo-2-fluorophenyl)amino]-4-fluoro-N-(2-hydroxyethoxy)-1-methyl-1H-benzimidazole-6-carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2yl)methyl)benzamide), or AZD8330 (2-((2-fluoro-4-iodophenyl)amino)-N-(2 hydroxyethoxy)-1, and 5-dimethyl-6-oxo-1,6-dihydropyridine-3-carboxamide). In one embodiment, a compound of the present invention or a pharmaceutically acceptable composition, salt, isotopic analog, or prodrug thereof is combined in a dosage form with the MEK inhibitor.

In one embodiment, the at least one additional chemotherapeutic agent combined or alternated with the compound of the present invention is a Raf inhibitor. Raf inhibitors for use in the present invention are well known, and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), and Sorafenib N-Oxide (4-[4-[[[[4-Chloro-3(trifluoroMethyl)phenyl]aMino]carbonyl]aMino]phenoxy]-N-Methyl-2pyridinecarboxaMide 1-Oxide). In one embodiment, a compound of the present invention or a pharmaceutically acceptable composition, salt, isotopic analog, or prodrug thereof is combined in a dosage form with the Raf inhibitor.

In one embodiment, the at least one additional chemotherapeutic agent combined or alternated with the compound of the present invention is a B-cell lymphoma 2 (Bcl-2) protein inhibitor. BCL-2 inhibitors are known in the art, and include, for example, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy benzamide), ABT-737 (4-[4-1-[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]

thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), or G3139 (Oblimersen). In one embodiment, a compound of the present invention or a pharmaceutically acceptable composition, salt, isotopic analog, or prodrug thereof is combined in a dosage form with the at least one BCL-2 inhibitor. In one embodiment the at least one BCL-2 inhibitor is ABT-199 (Venetoclax).

In one embodiment, the treatment regimen includes the administration of a compound of the present invention or a pharmaceutically acceptable composition, salt, isotopic analog, or prodrug thereof in combination or alternation with at least one additional chemotherapeutic agent selected from, but are not limited to, Imatinib mesylate (Gleevac), Dasatinib (Sprycel), Nilotinib (Tasigna), Bosutinib (Bosulif), Trastuzumab (Herceptin), Pertuzumab (Perjeta™), Lapatinib (Tykerb), Gefitinib (Iressa), Erlotinib (Tarceva), Cetuximab (Erbitux), Panitumumab (Vectibix), Vandetanib (Caprelsa), Vemurafenib (Zelboraf), Vorinostat (Zolinza), Romidepsin (Istodax), Bexarotene (Tagretin), Alitretinoin (Panretin), Tretinoin (Vesanoid), Carfilizomib (Kyprolis™), Pralatrexate (Folotyn), Bevacizumab (Avastin), Ziv-aflibercept (Zaltrap), Sorafenib (Nexavar), Sunitinib (Sutent), Pazopanib (Votrient), Regorafenib (Stivarga), and Cabozantinib (Cometriq™).

In some embodiments, the pharmaceutical combination or composition described herein can be administered to the subject in combination or further combination with other chemotherapeutic agents for the treatment of a tumor or cancer. If convenient, the pharmaceutical combination or composition described herein can be administered at the same time as another chemotherapeutic agent, in order to simplify the treatment regimen. In some embodiments, the pharmaceutical combination or composition and the other chemotherapeutic can be provided in a single formulation. In one embodiment, the use of the pharmaceutical combination or composition described herein is combined in a therapeutic regime with other agents. Such agents may include, but are not limited to, tamoxifen, midazolam, letrozole, bortezomib, anastrozole, goserelin, an mTOR inhibitor, a PI3 kinase inhibitor as described above, a dual mTOR-PI3K inhibitor, a MEK inhibitor as described above, a RAS inhibitor, ALK inhibitor, an HSP inhibitor (for example, HSP70 and HSP 90 inhibitor, or a combination thereof), a BCL-2 inhibitor as described above, apopototic inducing compounds, an AKT inhibitor, including but not limited to, MK-2206 (1,2,4-Triazolo[3,4-f][1,6]naphthyridin-3(2H)-one, 8-[4-(1-aminocyclobutyl)phenyl]-9-phenyl-), GSK690693, Perifosine, (KRX-0401), GDC-0068, Triciribine, AZD5363, Honokiol, PF-04691502, and Miltefosine, a PD-1 inhibitor as described above including but not limited to, Nivolumab, CT-011, MK-3475, BMS936558, and AMP-514 or a FLT-3 inhibitor, including but not limited to, P406, Dovitinib, Quizartinib ($AC_{1220}$), Amuvatinib (MP-470), Tandutinib (MLN518), ENMD-2076, and KW-2449, or a combination thereof. Examples of mTOR inhibitors include but are not limited to rapamycin and its analogs, everolimus (Afinitor), temsirolimus, ridaforolimus, sirolimus, and deforolimus. Examples of RAS inhibitors include but are not limited to Reolysin and siG12D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol. In a particular embodiment, a compound described herein is administered in combination with letrozole and/or tamoxifen. Other chemotherapeutic agents that can be used in combination with the compounds described herein include, but are not limited to, chemotherapeutic agents that do not require cell cycle activity for their anti-neoplastic effect.

In one embodiment, the treatment regimen includes the administration of a compound of the present invention or a pharmaceutically acceptable composition, salt, isotopic analog, or prodrug thereof in combination or alternation with at least one additional therapy. The second therapy can be an immunotherapy. As discussed in more detail below, the combination agent can be conjugated to an antibody, radioactive agent, or other targeting agent that directs the active compound as described herein to the diseased or abnormally proliferating cell. In another embodiment, the pharmaceutical combination or composition is used in combination with another pharmaceutical or a biologic agent (for example an antibody) to increase the efficacy of treatment with a combined or a synergistic approach. In an embodiment, the pharmaceutical combination or composition can be used with T-cell vaccination, which typically involves immunization with inactivated autoreactive T cells to eliminate a cancer cell population as described herein. In another embodiment, the pharmaceutical combination or composition is used in combination with a bispecific T-cell Engager (BiTE), which is an antibody designed to simultaneously bind to specific antigens on endogenous T cells and cancer cells as described herein, linking the two types of cells.

In one embodiment, the additional therapy is a monoclonal antibody (MAb). Some MAbs stimulate an immune response that destroys cancer cells. Similar to the antibodies produced naturally by B cells, these MAbs "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

Another group of cancer therapeutic MAbs are the immunoconjugates. These MAbs, which are sometimes called immunotoxins or antibody-drug conjugates, consist of an antibody attached to a cell-killing substance, such as a plant or bacterial toxin, a chemotherapy drug, or a radioactive molecule. The antibody latches onto its specific antigen on the surface of a cancer cell, and the cell-killing substance is taken up by the cell. FDA-approved conjugated MAbs that work this way include ado-trastuzumab emtansine, which targets the HER-2 molecule to deliver the drug DM1, which inhibits cell proliferation, to HER-2 expressing metastatic breast cancer cells.

Immunotherapies with T cells engineered to recognize cancer cells via bispecific antibodies (bsAbs) or chimeric antigen receptors (CARs) are approaches with potential to ablate both dividing and non/slow-dividing subpopulations of cancer cells.

Bispecific antibodies, by simultaneously recognizing target antigen and an activating receptor on the surface of an immune effector cell, offer an opportunity to redirect immune effector cells to kill cancer cells. Another approach is the generation of chimeric antigen receptors by fusing extracellular antibodies to intracellular signaling domains. Chimeric antigen receptor-engineered T cells are able to specifically kill tumor cells in a MHC-independent way.

In certain aspects, the additional therapy is another therapeutic agent, for example, an anti-inflammatory agent, a chemotherapeutic agent, a radiotherapeutic agent, or an immunosuppressive agent.

Suitable chemotherapeutic agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: Vincristine (Oncovin) or liposomal vincristine (Marqibo), Daunorubicin (daunomycin or Cerubidine) or doxorubicin (Adriamycin), Cytarabine (cytosine arabinoside, ara-C, or Cytosar), L-asparaginase (Elspar) or PEG-L-asparaginase (pegaspargase or Oncaspar), Etoposide (VP-16), Teniposide (Vumon), 6-mercaptopurine (6-MP or Purinethol), Methotrexate, Cyclophosphamide (Cytoxan). Prednisone, Dexamethasone (Decadron), imatinib (Gleevec marketed by Novartis), dasatinib (Sprycel), nilotinib (Tasigna), bosutinib (Bosulif), and ponatinib (Iclusig™). Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Suitable immunosuppressive agents include, but are not limited to: calcineurin inhibitors, e.g., a cyclosporin or an ascomycin, e.g., Cyclosporin A (NEORAL), FK506 (tacrolimus), pimecrolimus, a mTOR inhibitor, e.g., rapamycin or a derivative thereof, e.g., Sirolimus (RAPAMUNE), Everolimus (Certican), temsirolimus, zotarolimus, biolimus-7, biolimus-9, a rapalog, e.g., ridaforolimus, azathioprine, campath 1H, a SIP receptor modulator, e.g., fingolimod or an analog thereof, an anti IL-8 antibody, mycophenolic acid or a salt thereof, e.g., sodium salt, or a prodrug thereof, e.g., Mycophenolate Mofetil (CELLCEPT), OKT3 (ORTHOCLONE OKT3), Prednisone, ATGAM, THYMOGLOBULIN, Brequinar Sodium, OKT4, T10B9.A-3A, 33B3.1, 15-deoxyspergualin, tresperimus, Leflunomide ARAVA, CTLAI-Ig, anti-CD25, anti-IL2R, Basiliximab (SIMULECT), Daclizumab (ZENAPAX), mizorbine, methotrexate, dexamethasone, ISAtx-247, SDZ ASM 981 (pimecrolimus, Elidel), CTLA41g (Abatacept), belatacept, LFA3lg, etanercept (sold as Enbrel by Immunex), adalimumab (Humira), infliximab (Remicade), an anti-LFA-1 antibody, natalizumab (Antegren), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In certain embodiments, a pharmaceutical combination or composition described herein is administered to the subject prior to treatment with another chemotherapeutic agent, during treatment with another chemotherapeutic agent, after administration of another chemotherapeutic agent, or a combination thereof.

In some embodiments, the selective pharmaceutical combination or composition can be administered to the subject such that the other chemotherapeutic agent can be administered either at higher doses (increased chemotherapeutic dose intensity) or more frequently (increased chemotherapeutic dose density), Dose-dense chemotherapy is a chemotherapy treatment plan in which drugs are given with less time between treatments than in a standard chemotherapy treatment plan. Chemotherapy dose intensity represents unit dose of chemotherapy administered per unit time, Dose intensity can be increased or decreased through altering dose administered, time interval of administration, or both.

In one embodiment of the invention, the pharmaceutical combination or composition described herein can be administered in a concerted regimen with another agent such as a non-DNA-damaging, targeted anti-neoplastic agent or a hematopoietic growth factor agent. It has recently been reported that the untimely administration of hematopoietic growth factors can have serious side effects. For example, the use of the EPO family of growth factors has been associated with arterial hypertension, cerebral convulsions, hypertensive encephalopathy, thromboembolism, iron deficiency, influenza like syndromes and venous thrombosis. The G-CSF family of growth factors has been associated with spleen enlargement and rupture, respiratory distress syndrome, allergic reactions and sickle cell complications. By combining the administration of the pharmaceutical combination or composition as described herein with the timely administration of hematopoietic growth factors, for example, at the time point wherein the affected cells are no longer under growth arrest, it is possible for the health care practitioner to decrease the amount of the growth factor to minimize the unwanted adverse effects while achieving the desired therapeutic benefit. As such, in one embodiment, the use of the pharmaceutical combination, composition, or methods described herein is combined with the use of hematopoietic growth factors including, but not limited to, granulocyte colony stimulating factor (G-CSF, for example, sold as Neupogen (filgrastin), Neulasta (peg-filgrastin), or lenograstin), granulocyte-macrophage colony stimulating factor (GM-CSF, for example sold as molgramostim and sargramostim (Leukine)), M-CSF (macrophage colony stimulating factor), thrombopoietin (megakaryocyte growth development factor (MGDF), for example sold as Romiplostim and Eltrombopag) interleukin (IL)-12, interleukin-3, interleukin-11 (adipogenesis inhibiting factor or oprelvekin), SCF (stem cell factor, steel factor, kit-ligand, or KL) and erythropoietin (EPO), and their derivatives (sold as for example epoetin-α as Darbopoetin, Epocept, Nanokine, Epofit, Epogin, Eprex and Procrit: epoetin-β sold as for example NeoRecormon, Recormon and Micera), epoetin-delta (sold as for example Dynepo), epoetin-omega (sold as for example Epomax), epoetin zeta (sold as for example Silapo and Reacrit) as well as for example Epocept, EPOTrust, Erypro Safe, Repoeitin, Vintor, Epofit, Erykine, Wepox, Espogen, Relipoeitin, Shanpoietin, Zyrop and EPIAO). In one embodiment, the pharmaceutical combination or composition is administered prior to administration of the hematopoietic growth factor. In one embodiment, the hematopoietic growth factor administration is timed so that the pharmaceutical combination or composition's effect on HSPCs has dissipated. In one embodiment, the growth factor is administered at least 20 hours after the administration of a pharmaceutical combination or composition described herein.

If desired, multiple doses of a pharmaceutical combination or composition described herein can be administered to the subject. Alternatively, the subject can be given a single dose of a pharmaceutical combination or composition described herein.

In one embodiment, the activity of an active compound for a purpose described herein can be augmented through conjugation to an agent that targets the diseased or abnormally proliferating cell or otherwise enhances activity, delivery, pharmacokinetics or other beneficial property.

A selected compound described herein can be administered in conjugation or combination with a Fv fragment. Fv fragments are the smallest fragment made from enzymatic cleavage of IgG and IgM class antibodies. Fv fragments have the antigen-binding site made of the VH and VC regions, but they lack the CHI and CL regions. The VH and VL chains are held together in Fv fragments by non-covalent interactions.

In one embodiment, a selected compound as described herein can be administered in combination with an antibody fragment selected from the group consisting of an ScFv, domain antibody, diabody, triabody, tetrabody, Bis-scFv, minibody, Fab2, or Fab3 antibody fragment. In one embodiment, the antibody fragment is a ScFv. Genetic engineering methods allow the production of single chain variable fragments (ScFv), which are Fv type fragments that include the VH and VL domains linked with a flexible peptide When the linker is at least 12 residues long, the ScFv fragments are primarily monomeric. Manipulation of the orientation of the V-domains and the linker length creates different forms of Fv molecules linkers that are 3-11 residues long yield scFv molecules that are unable to fold into a functional Fv domain. These molecules can associate with a second scFv molecule, to create a bivalent diabody. In one embodiment, the antibody fragment administered in combination with a selected compound described herein is a bivalent diabody. If the linker length is less than three residues, scFv molecules associate into triabodies or tetrabodies. In one embodiment, the antibody fragment is a triabody. In one embodiment, the antibody fragment is a tetrabody. Multivalent scFvs possess greater functional binding affinity to their target antigens than their monovalent counterparts by having binding to two more target antigens, which reduces the off-rate of the antibody fragment. In one embodiment, the antibody fragment is a minibody. Minibodies are scFv-CH3 fusion proteins that assemble into bivalent dimers. In one embodiment, the antibody fragment is a Bis-scFv fragment. Bis-scFv fragments are bispecific. Miniaturized ScFv fragments can be generated that have two different variable domains, allowing these Bis-scFv molecules to concurrently bind to two different epitopes.

In one embodiment, a selected compound described herein is administered in conjugation or combination with a bispecific dimer (Fab2) or trispecific dimer (Fab3). Genetic methods are also used to create bispecific Fab dimers (Fab2) and trispecific Fab trimers (Fab3). These antibody fragments are able to bind 2 (Fab2) or 3 (Fab3) different antigens at once.

In one embodiment, a selected compound described herein is administered in conjugation or combination with an rIgG antibody fragment, rIgG antibody fragments refers to reduced IgG (75,000 daltons) or half-IgG. It is the product of selectively reducing just the hinge-region disulfide bonds. Although several disulfide bonds occur in IgG, those in the hinge-region are most accessible and easiest to reduce, especially with mild reducing agents like 2-mercaptoethylamine (2-MEA). Half-IgG are frequently prepared for the purpose of targeting the exposing hinge-region sulfhydryl groups that can be targeted for conjugation, either antibody immobilization or enzyme labeling.

In other embodiments, a selected active compound described herein can be linked to a radioisotope to increase efficacy, using methods well known in the art. Any radioisotope that is useful against cancer cells can be incorporated into the conjugate, for example, but not limited to, $^{131}$I, $^{123}$I, $^{192}$Ir, $^{32}$P, $^{90}$Sr, $^{198}$Au, $^{226}$Ra, $^{90}$Y, $^{241}$Am, $^{252}$Cf, $^{60}$Co, or $^{137}$Cs.

Examples of early and recent antibody-drug conjugates, discussing drugs, linker chemistries and classes of targets for product development that may be used in the present invention can be found in the reviews by Casi, G, and Neri, D., *J. Control Release* 161(2):422-428, 2012, Chari, R. V., *Acc. Chem. Rev.*, 41(1):98-107, 2008, Sapra, P, and Shor, B., *Pharmacol. Ther.*, 138(3):452-69, 2013, Schliemann, C, and Neri, D., *Biochim. Biophys. Acta.*, 1776(2):175-92, 2007, Sun, Y., Yu, F., and Sun, B. W., Yao Xueue Bao, 44(9):943-52, 2009, Teicher. B. A., and Chari, R. V., *Clin. Cancer Res.*, 17(20):6389-97, 2011, Firer, M. A., and Gellerman, G. J., *J. Hematol. Oncol.*, 5:70, 2012, Vlachakis, D, and Kossida, S., *Comput. Math. Methods Med.*, 2013; 2013:282398, Epub 2013 Jun. 19, Lambert, J. M., *Br. J. Clin. Pharmacol.*, 76(2):248-62, 2013, Concalves, A., Tredan, O., Villanueva, C, and Dumontet, C., *Bull. Cancer,* 99(12): 1183-1191, 2012, Newland, A. M., *Pharmacotherapy,* 33(1):93-104, 2013. Lopus, M., *Cancer Lett.*, 307(2):113-118, 2011, Chu. Y. W, and Poison, A., *Future Oncol.*, 9(3):355-368, 2013, Bertholjotti, I., *Chimia,* 65(9): 746-748, 2011, Vincent, K. J., and Zurini, M., *Biotechnol. J.*, 7(12): 1444-1450, 2012, Haeuw, J. F., Caussanel, V., and Beck, A., *Med. Sci.*, 25(12):1046-1052, 2009 and Govindan, S. V., and Goldenberg, D. M., *Expert Opin. Biol. Ther.*, 12(7):873-890, 2012.

In one embodiment the pharmaceutical composition or combination as described herein can be used to treat any disorder described herein.

EXAMPLES

Analytical Methods, Materials, and Instrumentation

All reactions are monitored on a Waters Acquity UPLC/MS system (Waters PDA eλ Detector, QDa Detector, Sample manager—FL, Binary Solvent Manager) using Acquity UPLC® BEH C18 column (2.1×50 mm, 1.7 μm particle size): solvent gradient=90% A at 0 min, 1% A at 1.8 min; solvent A=0.1% formic acid in Water: solvent B=0.1% formic acid in Acetonitrile; flow rate: 0.6 mL/min. Reaction products are purified by flash column chromatography using CombiFlash®Rf with Teledyne Isco RediSep®Rf High Performance Gold or Silicycle SiliaSep™ High Performance columns (4 g, 12 g, 24 g, 40 g, or 80 g), Waters HPLC system using SunFire™ Prep C18 column (19×100 mm, 5 μm particle size): solvent gradient=80% A at 0 min, 5% A at 25 min: solvent A=0.035% TFA in Water: solvent B=0.035% TFA in MeOH; flow rate: 25 mL/min (Method A), and Waters Acquity UPLC/MS system (Waters PDA e?, Detector, QDa Detector, Sample manager—FL, Binary Solvent Manager) using Acquity UPLC® BEH $C_{118}$ column (2.1×50 mm, 1.7 μm particle size): solvent gradient=80% A at 0 min, 5% A at 2 min: solvent A=0.1% formic acid in Water; solventB=0.1% formic acid in Acetonitrile; flow rate: 0.6 mL/min (method B). The purity of all compounds is over 95% and is analyzed with Waters LC/MS system. $^1$H NMR is obtained using a 500 MHz Bruker Avance III. Chemical shifts are reported relative to dimethyl sulfoxide (δ=2.50) for $^1$H NMR, Data are reported as (br=broad, s=singlet, d=doublet, t=triplet, q=quartet, m=multiplet).

Abbreviations used in the following examples and elsewhere herein are:
- atm atmosphere
- br broad
- DCM dichloromethane
- DIEA N,N-diisopropylethylamine
- DMA N,N-dimethylacetamide
- DMF N,N-dimethylformamide
- DMSO dimethyl sulfoxide
- EDCI 1-ethyl-3-(3-dimethylaminopropyl) carbodiimide
- ESI electrospray ionization
- EtOAc ethyl acetate
- HCl hydrochloric acid
- h hour(s)
- HATU bis(dimethylamino)methylene]-1H-1,2,3-triazolo[4,5-b]pyridinium 3-oxide hexafluoro-phosphate
- HPLC high-performance liquid chromatography
- LCMS liquid chromatography-mass spectrometry
- m multiplet
- MeOH methanol
- MHz megahertz
- min minutes
- MS mass spectrometry
- NMR nuclear magnetic resonance
- $Pd_2(dba)_3$ tris(dibenzylideneacetone)dipalladium(O)
- ppm parts per million
- TBAF tetra-n-butylammonium fluoride
- THF tetrahydrofuran
- TLC thin layer chromatography
- Xphos 2-dicyclohexylphosphino-2',4',6'-triisopropylbiphenyl Example 1. Synthesis of CRBN Targeting Ligand and Linker Fragments 2-(2,6-Dioxopiperidin-3-yl)-4-hydroxyisoindoline-1,3-dione 3-Hydroxyphthalic anhydride (1.641 g, 10 mmol, 1 eq) and 3-aminopiperidine-2,6-dione hydrochloride (1.646 g, 10 mmol, 1 eq) were dissolved in pyridine (40 mL, 0.25 M) and heated to 110° C. After 14 hours, the mixture was cooled to room temperature and concentrated under reduced pressure. Purification by column chromatography (ISCO, 24 g silica column, 0-10% MeOH/DCM) afforded the desired product as a tan solid (2.424 g, 8.84 mmol, 88%).

$^1$H NMR (400 MHz, DMSO-$d_6$) δ 11.08 (s, 2H), 7.65 (dd, J=8.4, 7.2 Hz, 1H), 7.36-7.28 (m, 1H), 7.25 (dd, J=8.4, 0.6 Hz, 1H), 5.07 (dd, J=12.8, 5.4 Hz, 1H), 2.88 (ddd, J=17.3, 14.0, 5.4 Hz, 1H), 2.63-2.50 (m, 2H), 2.08-1.95 (m, 1H). LCMS: 275 (M+H)

tert-Butyl 2-((2-(2,6-dioxopiperidin-3-yl)-1,3-dioxoisoindolin-1-yl)oxy)acetate 2-(2,6-Dioxopiperidin-3-yl)-4-hydroxyisoindoline-1,3-dione (1.568 g, 5.71 mmol, 1 eq) was dissolved in DMF (57 mL, 0.1 M) at room temperature. Potassium carbonate (1.19 g, 8.58 mmol, 1.5 eq) and tert-butyl bromoacetate (0.843 mL, 5.71 mmol, 1 eq) were then added. After 2 hours, the mixture was diluted with EtOAc, washed once with water, and twice with brine. The organic layer was dried over sodium sulfate, filtered and concentrated under reduced pressure. Purification by column chromatography (ISCO, 24 g silica column, 0-100% EtOAc/hexanes, 21 minute gradient) afforded the desired product as a cream colored solid (2.06 g, 5.30 mmol, 93%).

$^1$H NMR (500 MHz, chloroform-d) δ 7.94 (s, 1H), 7.67 (dd, J=8.4, 7.3 Hz, 1H), 7.52 (d, J=6.8 Hz, 1H), 7.11 (d, J=8.3 Hz, 1H), 4.97 (dd, J=12.3, 5.3 Hz, 1H), 4.79 (s, 2H), 2.95-2.89 (m, 1H), 2.85-2.71 (m, 2H), 2.14 (dtd, J=10.2, 5.0, 2.7 Hz, 1H), 1.48 (s, 9H). LCMS: 389.33 (M+H).

2-((2-(2,6-Dioxopiperidin-3-yl)-1,3-dioxoisoindolin-4-yl)oxy)acetic acid

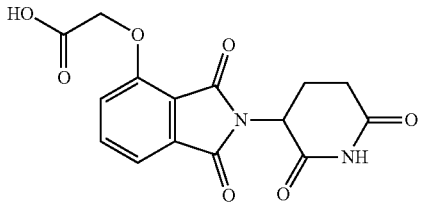 [SMILES: O=C(O)COc1cccc2c1C(=O)N(C1CCC(=O)NC1=O)C2=O]

tert-Butyl 2-((2-(2,6-dioxopiperidin-3-yl)-1,3-dioxoisoindolin-4-yl)oxy)acetate (2.06 g, 5.30 mmol, 1 eq) was dissolved in TFA (53 mL, 0.1M) at room temperature. After 4 hours, the solution was diluted with DCM and concentrated under reduced pressure. The resultant cream colored solid (1.484 g, 4.47 mmol, 84%) was deemed sufficiently pure and carried onto the next step without further purification.

$^1$H NMR (500) MHz, DMSO-$d_6$) 11.11 (s, 1H), 7.79 (dd, J=8.4, 7.4 Hz, 1H), 7.48 (d, J=7.2 Hz, 1H), 7.39 (d, J=8.6 Hz, 1H), 5.10 (dd, J=12.8, 5.4 Hz, 1H), 4.99 (s, 2H), 2.93-2.89 (m, 1H), 2.63-2.51 (m, 2H), 2.04 (ddd, J=10.5, 5.4, 3.1 Hz, 1H). LCMS: 333.25 (M+H).

tert-Butyl (8-(2-((2-(2,6-dioxopiperidin-3-yl)-1,3-dioxoisoindolin-4-yl)oxy)acetamido)octyl)carbamate

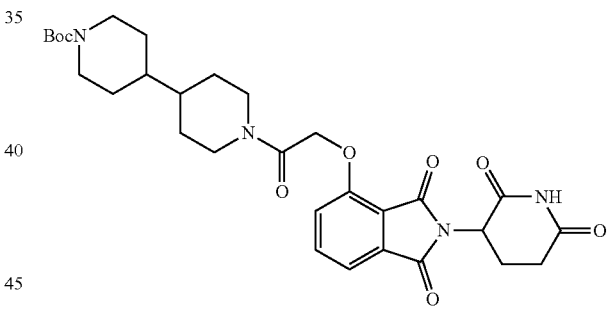

Boc-1,8-diaminooctane (2.10 g, 8.59 mmol, 1.1 eq) was dissolved in DMF (86 mL). In a separate flask, 2-((2-(2,6-dioxopiperidin-3-yl)-1,3-dioxoisoindolin-4-yl)oxy)acetic acid (2.60 g, 7.81 mmol, 1 eq) was dissolved in DMF (78 mL). The solution of Boc-1,8-diaminooctane in DMF was then added, followed by DIPEA (4.08 mL, 23.4 mmol, 3 eq) and HATU (2.97 g, 7.81 mmol, 1 eq). The mixture was stirred for 19 hours at room temperature and diluted with EtOAc (600 mL). The organic layer was washed sequentially with 200 mL of half saturated sodium chloride, 200 mL 10% citric acid (aq.), 200 mL of half saturated sodium chloride, 200 mL of saturated sodium bicarbonate (aq.), 200 mL water and twice with 200 mL brine. The organic layer was dried over sodium sulfate, filtered and concentrated under reduced pressure. Purification by column chromatography (ISCO, 40 g column, 0-5% MeOH/DCM, 35 minute gradient) afforded the desired product as a white solid (3.53 g, 6.32 mmol, 81%).

$^1$H NMR (500 MHz, chloroform-d) δ 8.49 (s, 1H), 7.74 (dd, J=8.3, 7.4 Hz, 1H), 7.55 (d, J=7.2 Hz, 1H), 7.39 (t, J=5.3 Hz, 1H), 7.19 (d, J=8.4 Hz, 1H), 4.97 (dd, J=12.4, 5.3 Hz, 1H), 4.63 (d, J=2.2 Hz, 2H), 4.59 (d, J=10.0 Hz, 1H), 3.36 (q, J=6.9 Hz, 2H), 3.12-3.03 (m, 2H), 2.95-2.72 (m, 3H), 2.16 (ddt, J=10.3, 5.2, 2.7 Hz, 1H), 1.59 (p, J=7.1 Hz, 2H), 1.37 (d, J=67.6 Hz, 19H). LCMS: 559.47 (M+H).

N-(8-Aminooctyl)-2-((2-(2,6-dioxopiperidin-3-yl)-1,3-dioxoisoindolin-4-yl)oxy)acetamide trifluoroacetate

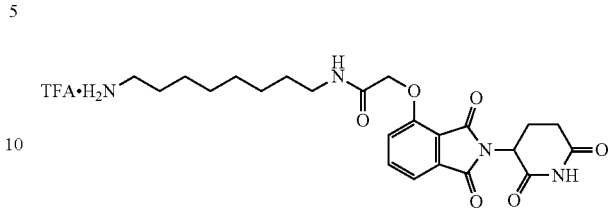

tert-Butyl (8-(2-((2-(2,6-dioxopiperidin-3-yl)-1,3-dioxoisoindolin-4-yl)oxy)acetamido)octyl)carbamate (3.53 g, 6.32 mmol, 1 eq) was dissolved in TFA (63 mL, 0.1 M) and heated to 50° C. After 1 hour, the mixture was cooled to room temperature, diluted with MeOH and concentrated under reduced pressure. The crude material was triturated with diethyl ether and dried under vacuum to afford a white solid (2.93 g, 5.12 mmol, 81%).

$^1$H NMR (500 MHz, methanol-$d_4$) δ 7.82 (dd, J=8.4, 7.4 Hz, 1H), 7.55 (d, J=7.2 Hz, 1H), 7.44 (d, J=8.4 Hz, 1H), 5.14 (dd, J=12.5, 5.5 Hz, 1H), 4.76 (s, 2H), 3.33 (dd, J=6.8, 1.8 Hz, 1H), 3.30 (s, 1H), 2.94-2.85 (m, 3H), 2.80-2.69 (m, 2H), 2.19-2.11 (m, 1H), 1.60 (dq, J=24.8, 7.0 Hz, 4H), 1.37 (s, 8H). LCMS 459.45 (M+H).

tert-Butyl 1'-(2-((2-(2,6-dioxopiperidin-3-yl)-1,3-dioxoisoindolin-4-yl)oxy)acetyl)-[4,4'-bipiperidine]-1-carboxylate 2-((2-(2,6-Dioxopiperidin-3-yl)-1,3-dioxoisoindolin-4-yl)oxy)acetic acid (166.1 mg, 0.50 mmol, 1 eq) and tert-butyl [4,4'-bipiperidine]-1-carboxylate (134.2 mg, 0.50 mmol, 1 eq) were dissolved in DMF (10 mL), DIPEA (261.3 microliters, 1.50 mmol, 3 eq) and HATU (190.1 mg, 0.50 mmol, 1 eq) were added and the mixture was stirred for 14 hours, upon which additional HATU (190.1 mg, 0.50 mmol, 1 eq) was added to ensure complete conversion. After an additional 8 hours, the mixture was diluted with EtOAc and washed with 10% citric acid (aq), saturated sodium bicarbonate, water and twice with brine. The organic layer was dried over sodium sulfate, filtered and concentrated under reduced pressure. Purification by column chromatography (ISCO, 12 g silica column, 0-10% MeOH/DCM, 25 minute gradient) gave the desired product as a light yellow oil (0.33 g, quant yield), which was carried forward to the next step.

$^1$H NMR (500 MHz, Chloroform-d) δ 7.68 (t, J=7.9 Hz, 1H), 7.51 (d, J=7.3 Hz, 1H), 7.31 (dd, J=34.7, 8.6 Hz, 1H), 5.03-4.81 (m, 3H), 4.57 (t, J=13.2 Hz, 1H), 4.19-3.92 (m, 3H), 3.02 (q, J=13.1 Hz, 1H), 2.78-2.72 (m, 1H), 2.66-2.49

(m, 3H), 2.10 (d, J=11.0 Hz, 1H), 1.82-1.51 (m, 5H), 1.45 (s, 9H), 1.39-1.05 (m, 7H). LCMS 583.44 (M+H).

4-(2-([4,4'-Bipiperidin]-1-yl)-2-oxoethoxy)-2-(2,6-dioxopiperidin-3-yl)isoindoline-1,3-dione trifluoroacetate

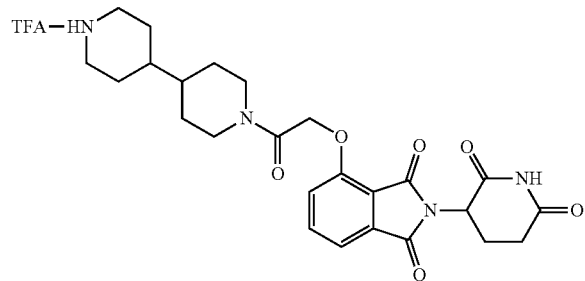

tert-Butyl 1'-(2-((2-(2,6-dioxopiperidin-3-yl)-1,3-dioxoisoindolin-4-yl)oxy)acetyl)-[4,4'-bipiperidine]-1-carboxylate (0.33 g, 0.566 mmol) was dissolved in TFA (5.7 mL) and heated to 50° C. After 35 minutes, the mixture was cooled to room temperature, diluted with MeOH/DCM and concentrated under reduced pressure. The crude material was triturated with diethyl ether and dried under vacuum to afford a cream colored solid (192.8 g, 0.478 mmol, 96% over 2 steps).

$^1$H NMR (500 MHz, Methanol-$d_4$) δ 7.76 (dd, J=8.5, 7.3 Hz, 1H), 7.50 (d, J=6.2 Hz, 1H), 7.37 (d, J=8.5 Hz, 1H), 5.17 (dd, J=14.5, 5.2 Hz, 1H), 5.11 (dt, J=12.6, 5.0 Hz, 1H), 5.03 (dd, J=14.4, 2.4 Hz, 1H), 4.50 (d, J=13.3 Hz, 1H), 4.07 (d, J=13.2 Hz, 1H), 3.39 (d, J=12.8 Hz, 2H), 3.10 (t, J=12.3 Hz, 1H), 2.94 (t, J=12.7 Hz, 2H), 2.89-2.82 (m, 1H), 2.79-2.61 (m, 3H), 2.14 (dq, J=10.6, 3.1 Hz, 1H), 2.00-1.88 (m, 2H), 1.78 (d, J=11.4 Hz, 2H), 1.53-1.27 (m, 5H), 1.09 (d, J=12.2 Hz, 1H). LCMS 483.35 (M+H).

tert-Butyl (8-((2-(2,6-dioxopiperidin-3-yl)-1,3-dioxoisoindolin-4-yl)amino)octyl)carbamate

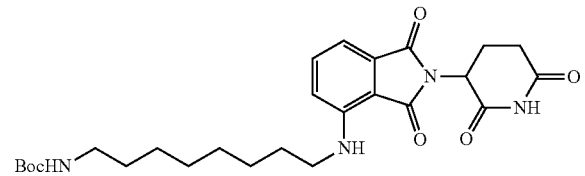 [SMILES: CC(C)(C)OC(=O)NCCCCCCCCNc1cccc2c1C(=O)N(C1CCC(=O)NC1=O)C2=O]

2-(2,6-Dioxopiperidin-3-yl)-4-fluoroisoindoline-1,3-dione (481.6 mg, 1.74 mmol, 1 eq) and tert-butyl (8-aminooctyl)carbamate (467.7 mg, 1.91 mmol, 1.1 eq) were dissolved in NMP (8.7 mL, 0.2M), DIPEA (606 uL, 3.48 mmol, 2 eq) was added and the mixture was heated to 90° C. After 15 hours, the mixture was diluted with EtOAc and washed with 10% citric acid (aq), saturated sodium bicarbonate, water and three times with brine. The organic layer was dried over sodium sulfate, filtered and concentrated under reduced pressure. Purification by column chromatography (ISCO, 12 g column, 0-5% MeOH/DCM, 25 minute gradient) afforded the desired product as a yellow oil (0.55 g, 1.099 mmol, 63%).

$^1$H NMR (500 MHz; Chloroform-d) δ 8.00 (s, 1H), 7.53-7.46 (m, 1H), 7.09 (d, J=7.1 Hz, 1H), 6.88 (d, J=8.5 Hz, 1H), 6.23 (s, 1H), 4.92 (dd, J=12.1, 5.2 Hz, 1H), 4.51 (s, 1H), 3.26 (q, J=6.6 Hz, 2H), 3.11 (d, J=5.9 Hz, 2H), 2.90 (d, J=15.8 Hz, 1H), 2.83-2.72 (m, 2H), 2.15-2.11 (m, 1H), 1.65 (q, J=7.1 Hz, 2H), 1.38 (d, J=59.1 Hz, 19H). LCMS 501.42 (M+H).

4-((8-Aminooctyl)amino)-2-(2,6-dioxopiperidin-3-yl)isoindoline-1,3-dione

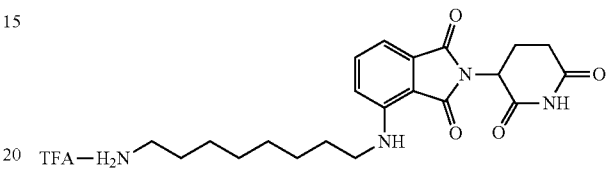

tert-Butyl (8-((2-(2,6-dioxopiperidin-3-yl)-1,3-dioxoisoindolin-4-yl)amino)octyl)carbamate (0.55 g, 1.099 mmol, 1 eq) was dissolved in TFA (11 mL) and heated to 50° C. After 40 minutes, the mixture was cooled to room temperature, diluted with MeOH/DCM and concentrated under reduced pressure. The crude material was triturated with diethyl ether and dried under vacuum to afford a cream colored solid (522.97 mg, 1.016 mmol, 93%).

$^1$H NMR (500 MHz, methanol-$d_4$) δ 7.59-7.51 (m, 1H), 7.04 (dd, J=7.9, 1.7 Hz, 2H), 5.06 (dd, J=12.4, 5.5 Hz, 1H), 3.34 (d, J=7.0 Hz, 2H), 2.95-2.81 (m, 3H), 2.79-2.66 (m, 2H), 2.15-2.08 (m, 1H), 1.67 (tt, J=12.2, 7.2 Hz, 4H), 1.43 (d, J=22.2 Hz, 8H). LCMS 401.39 (M+H).

tert-Butyl (8-((2-(2,6-dioxopiperidin-3-yl)-1,3-dioxoisoindolin-5-yl)amino)octyl)carbamate

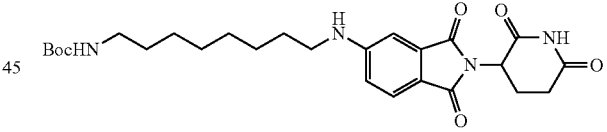

2-(2,6-Dioxopiperidin-3-yl)-5-fluoroisoindoline-1,3-dione (294 mg, 1.06 mmol, 1 eq) and tert-butyl (8-aminooctyl) carbamate (286 mg, 1.17 mmol, 1.1 eq) were dissolved in NMP (5.3 mL, 0.2M), DIPEA (369 uL, 2.12 mmol, 2 eq) was added and the mixture was heated to 90° C. After 19 hours, the mixture was diluted with EtOAc, washed with water, and washed three times with brine. The organic layer was dried over sodium sulfate, filtered and concentrated under reduced pressure. Purification by column chromatography (ISCO, 12 g column, 0-10% MeOH/DCM, 30 minute gradient) afforded the desired product as a brown solid (0.28 g, 0.668 mmol, 63%).

$^1$H NMR (500 MHz; Chloroform-d) δ 8.12 (s, 1H), 7.62 (d, J=8.3 Hz, 1H), 7.02 (s, 1H), 6.81 (d, J=7.2 Hz, 1H), 4.93 (dd, J=12.3, 5.3 Hz, 1H), 4.51 (s, 1H), 3.21 (t, J=7.2 Hz, 2H), 3.09 (d, J=6.4 Hz, 2H), 2.90 (dd, J=18.3, 15.3 Hz, 1H), 2.82-2.68 (m, 2H), 2.16-2.08 (m, 1H), 1.66 (p, J=7.2 Hz, 2H), 1.37 (d, J=62.3 Hz, 20H). LCMS 501.41 (M+H).

5-((8-Aminooctyl)amino)-2-(2,6-dioxopiperidin-3-yl)isoindoline-1,3-dione trifluoroacetate

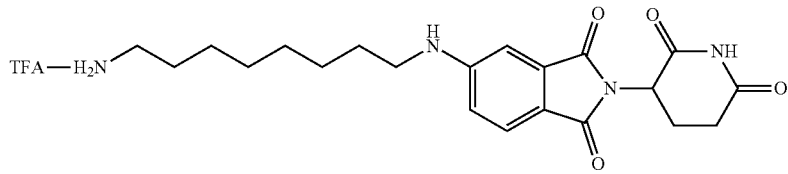

tert-Butyl (8-((2-(2,6-dioxopiperidin-3-yl)-1,3-dioxoisoindolin-5-yl)amino)octyl)carbamate (334.5 g, 0.668 mmol, 1 eq) was dissolved in TFA (6.7 mL) and heated to 50° C. After 1 hour, the mixture was cooled to room temperature, diluted with DCM and concentrated under reduced pressure. The crude material was triturated with diethyl ether and dried under vacuum to afford a dark yellow foam (253.1 mg, 0.492 mmol, 74%).

$^1$H NMR (500 MHz, methanol-$d_4$) δ 7.56 (d, J=8.4 Hz, 1H), 6.97 (d, J=2.1 Hz, 1H), 6.83 (dd, J=8.4, 2.2 Hz, 1H), 5.04 (dd, J=12.6, 5.5 Hz, 1H), 3.22 (t, J=7.1 Hz, 2H), 2.94-2.88 (m, 2H), 2.85-2.68 (m, 3H), 2.09 (ddd, J=10.4, 5.4, 3.0 Hz, 1H), 1.70-1.61 (m, 4H), 1.43 (d, J=19.0 Hz, 8H). LCMS 401.36 (M+H).

3-(4-(8-Aminooctylamino)-1-oxoisoindolin-2-yl)piperidine-2,6-dione TFA salt

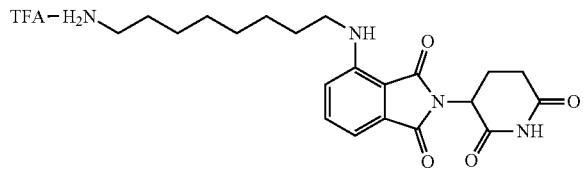

To a solution of lenalidomide (311 mg, 1.2 mmol) in MeOH (8 mL) was added tert-butyl (8-oxooctyl)carbamate (291 mg, 1.2 mmol), NaBH$_3$CN (114 mg, 1.8 mmol) and 1 drop AcOH. The mixture was stirred at 50° C. overnight. The mixture was quenched with H$_2$O, extracted with EtOAc three times. The combined organic layers was dried over Na$_2$SO$_4$, filtered and concentrated. The crude product was used in the next step without further purification.

The crude product above was dissolved in CH$_2$Cl$_2$/TFA (3 mL/3 mL). The mixture was stirred at room temperature for 1 hour. The volatile was removed under reduced pressure. The crude product was purified by prep-HPLC to afford the desired product (265 mg, 46% over 2 steps) as a light yellow solid.

$^1$H NMR (500 MHz, methanol-$d_4$) δ 7.32 (t, J=7.8 Hz, 1H), 7.07 (d, J=7.0 Hz, 1H), 6.82 (d, J=7.9 Hz, 1H), 5.16 (dd, J=13.3, 5.2 Hz, 1H), 4.38-4.19 (m, 2H), 3.23 (td, J=7.0, 2.4 Hz, 2H), 2.97-2.87 (m, 3H), 2.79 (ddd, J=17.6, 4.5, 2.4 Hz, 1H), 2.47 (qd, J=13.3, 4.6 Hz, 1H), 2.18 (dtd, J=12.9, 5.3, 2.4 Hz, 1H), 1.65 (tq, J=15.0, 7.2 Hz, 4H), 1.50-1.35 (m, 8H).

tert-Butyl (6-((2-(2,6-dioxopiperidin-3-yl)-1,3-dioxoisoindolin-5-yl)amino)hexyl)carbamate

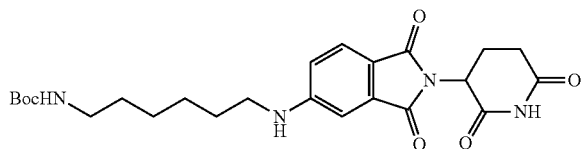 [SMILES: CC(C)(C)OC(=O)NCCCCCCNc1ccc2c(c1)C(=O)N(C1CCC(=O)NC1=O)C2=O]

To a solution of 2-(2,6-dioxopiperidin-3-yl)-5-fluoroisoindoline-1,3-dione (210 mg, 0.76 mmol, 1.0 eq) and tert-butyl (6-aminohexyl)carbamate (Alfa Aesar, 181 mg, 0.84 mmol, 1.1 eq) in NMP (3.8 mL) was added 265 µL DIPEA (1.52 mmol, 2.0 eq). After heating to 90° C. for 18 hours, the mixture was diluted to 60 mL with EtOAc, washed once with a mildly basic (Na$_2$CO$_3$) 1:1 solution of deionized water and saturated brine (20 mL), washed three times with deionized water (20 milliliters), and finally with saturated brine (20 milliliters) before drying over Na$_2$SO$_4$ and concentrating in vacuo. The residue was dissolved in DCM and purified by silica chromatography (DCM/MeOH 0 to 10% gradient) to afford the desired product as a brown oil (335 mg, 93%).

$^1$H NMR (500 MHz, chloroform-d) δ=8.31 (s, 1H), 7.49 (dd, J=7.8, 7.0, 1.4, 1H), 7.09 (d, J=7.2, 1.6, 1H), 6.87 (d, J=8.6, 1H), 6.24 (t, J=6.9, 5.6, 1H), 4.56 (s, 1H), 3.29-3.20 (m, 2H), 3.12 (q, J=6.8, 2H), 2.92-2.86 (m, 1H), 2.82-2.70 (m, 2H), 2.16-2.09 (m, 1H), 2.04-2.00 (m, 1H), 1.70-1.63 (m, 2H), 1.50 (p, J=7.2, 2H), 1.44 (s, 9H), 1.40-1.35 (m, 2H). LCMS: 473 (M).

5-((6-Aminohexyl)amino)-2-(2,6-dioxopiperidin-3-yl)isoindoline-1,3-dione TFA salt

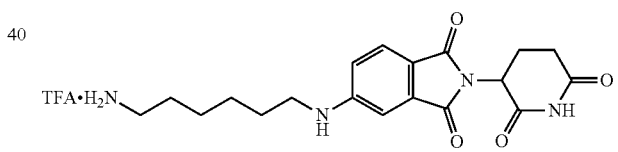

tert-Butyl (6-((2-(2,6-dioxopiperidin-3-yl)-1,3-dioxoisoindolin-5-yl)amino)hexyl)carbamate (96.0 mg 0.203 mmol) was dissolved in TFA (2.03 mL and stirred for 4 hours at room temperature. The mixture was concentrated under a stream of nitrogen, followed by vacuum to give the crude product as a brown oil (75 mg, 76%). This material was used without further purification. LCMS: 373 (M+H).

tert-Butyl (2-(2-(2-((2-(2,6-dioxopiperidin-3-yl)-1,3-dioxoisoindolin-4-yl)amino)ethoxy)ethoxy)ethyl)carbamate

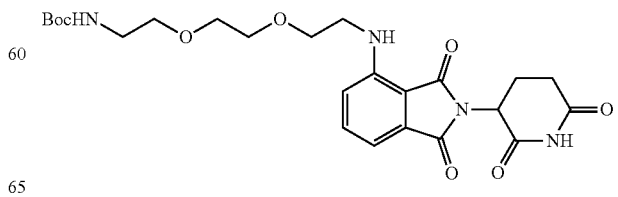

To a solution of 2-(2,6-dioxopiperidin-3-yl)-5-fluoroisoindoline-1,3-dione (210 mg, 0.76 mmol, 1.0 eq) and tert-butyl (2-(2-(2-aminoethoxy)ethoxy)ethyl)carbamate (Oakwood Chem., 170.9 mg, 0.84 mmol, 1.1 eq) in NMP (3.8 mL) was added 265 µL DIPEA (1.52 mmol, 2.0 eq). After heating to 90° C. for 18 hours, the mixture was diluted to 60 mL with EtOAc, washed once with a mildly basic (Na$_2$CO$_3$) 1:1 solution of deionized water and saturated brine (20 mL), washed three times with deionized water (20 milliliters), and once with saturated brine (20 milliliters) before drying over Na$_2$SO$_4$ and concentrating in vacuo. The resulting brown oil was dissolved in DCM and purified by silica chromatography (DCM/MeOH 0 to 10% gradient) to afford the desired product as a brown oil (330 mg, 86%).

$^1$H NMR $^1$H NMR (500 MHz. Chloroform-d) δ=8.57 (s, 1H), 7.53-7.46 (m, 1H), 7.11 (d, J=7.1, 1H), 6.92 (d, J=8.5, 1H), 6.52 (s, 1H), 4.96-4.88 (m, 1H), 3.73 (d, J=5.2, 2H), 3.66 (td, J=3.3, 1.8, 4H), 3.57 (s, 2H), 3.48 (q, J=5.3, 2H), 3.29 (d, J=32.6, 2H), 2.94-2.87 (m, 1H), 2.80-2.72 (m, 2H), 2.16-2.10 (m, 1H), 2.00 (d, J=7.7, 1H), 1.43 (d, J=3.8, 9H). LCMS: 505 (M).

4-((2-(2-(2-Aminoethoxy)ethoxy)ethyl)amino)-2-(2, 6-dioxopiperidin-3-yl)isoindoline-1,3-dione TFA salt

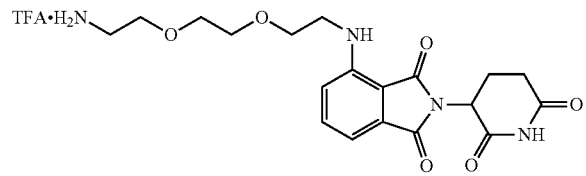

tert-Butyl (2-(2-(2-((2-(2,6-dioxopiperidin-3-yl)-1,3-dioxoisoindolin-4-yl)amino)ethoxy)ethoxy)ethyl)carbamate (330.2 mg 0.203 mmol) was dissolved in TFA (6.54 mL) and stirred for 4 hours at room temperature. The mixture was concentrated under a stream of nitrogen followed by vacuum to afford the crude product as a brown oil (264 mg, 78%). This material was used without further purification. LCMS: 405 (M+H).

Example 2. Synthesis of Bromodomain Targeting Ligand Fragments Ethyl 2-(4-bromo-2-methoxyphenoxy)acetate

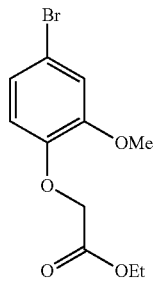 [SMILES: CCOC(=O)COc1ccc(Br)cc1OC]

To the solution of 4-bromo-2-methoxyphenol (5.0 g, 25 mmol) in acetone (100 mL) was added K$_2$CO$_3$ (10.2 g, 74 mmol) and ethyl bromoacetate (8.2 g, 49 mmol). The resulting solution was stirred at 80° C. overnight and then cooled to room temperature. The mixture solution was concentrated under reduce pressure, diluted by ice water (50 mL) and was extracted with ethyl acetate (3×30 mL). The organic layer was washed with brine (300 mL) and dried over anhydrous Na$_2$SO$_4$. The organic layer was concentrated under reduced pressure. The residue was purified by column chromatography with PE/EA (2/1), to afford ethyl 2-(4-bromo-2-methoxyphenoxy)acetate (6.3 g, 95%) as yellow oil.

Ethyl 2-(2-methoxy-4-(4,4,5,5-tetramethyl-1,3,2-dioxaborolan-2-yl)phenoxy)acetate

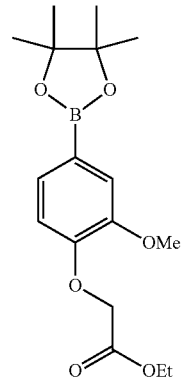 [SMILES: CCOC(=O)COc1ccc(B2OC(C)(C)C(C)(C)O2)cc1OC]

To the solution of ethyl 2-(4-bromo-2-methoxyphenoxy)acetate(2.9 g, 10 mmol) in dioxane (50 mL) was added bis(pinacolato)diboron (3.8 g, 15 mmol), Pd(dppf)C$_{12}$ (0.82 g, 1 mmol), KOAc (2.5 g, 25 mmol). The resulting solution was stirred at 80° C. overnight and then cooled to room temperature. The resulting solution was concentrated. The residue was purified by column chromatography with PE/EA (2/1), to afford ethyl 2-(2-methoxy-4-(4,4,5,5-tetramethyl-1,3,2-dioxaborolan-2-yl)phenoxy)acetate (3.0 g, 90%, 84% purity) as brown oil. LCMS: 337.2 (M+H)

Ethyl 2-(4-(2-cyano-5-methyl-4-oxo-4,5-dihydrothieno[3,2-c] pyridin-7-yl)-2-methoxyphenoxy)acetate

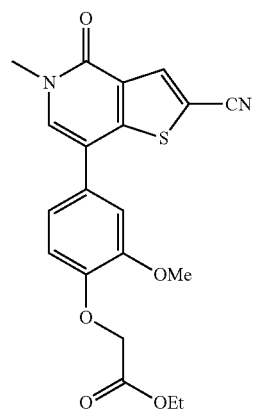 [SMILES: CCOC(=O)COc1ccc(-c2cn(C)c(=O)c3cc(C#N)sc23)cc1OC]

To the solution of 7-bromo-5-methyl-4-oxo-4,5-dihydrothieno[3,2-c]pyridine-2-carbonitrile (2.0 g, 8 mmol) in DMF/water (10/1, 44 mL) was added ethyl 2-(2-methoxy-4-(4,4,5,5-tetramethyl-1,3,2-dioxaborolan-2-yl)phenoxy) acetate (4.0 g, 12 mmol), Pd(dppf)Cl$_2$ (0.64 g, 1 mmol), and K$_3$PO$_4$ (1.8 g, 8 mmol). The resulting solution was stirred at 70° C. for 5 hours and then cooled to room temperature. The resulting solution was poured into water and extracted with ethyl acetate (3×30 mL), washed with brine (50 mL) and concentrated. The residue was purified by column chromatography (EtOAc) to afford ethyl 2-(4-(2-cyano-5-methyl-4-oxo-4,5-dihydrothieno[3,2-c]pyridin-7-yl)-2-methoxyphenoxy)acetate (1.8 g, 60%, 94% purity) as a pale-yellow solid.

$^1$H NMR (400 MHz, CDCl$_3$) δ 8.14 (s, 1H), 7.25 (s, 1H), 6.97 (s, 1H), 6.95 (d, J=8.0 Hz, 1H), 6.84 (d, J=8.0 Hz, 1H), 4.68 (s, 2H), 4.22 (q, J=7.2 Hz, 2H), 3.87 (s, 3H), 3.61 (s, 3H), 1.24 (t, J=7.2 Hz, 3H). LCMS: 399.1 (M+H)

Ethyl 2-(4-(2-(N-(1,1-dioxidotetrahydro-2H-thiopyran-4-yl)carbamimidoyl)-5-methyl-4-oxo-4,5-dihydrothieno[3,2-c]pyridin-7-yl)-2-methoxyphenoxy)acetate

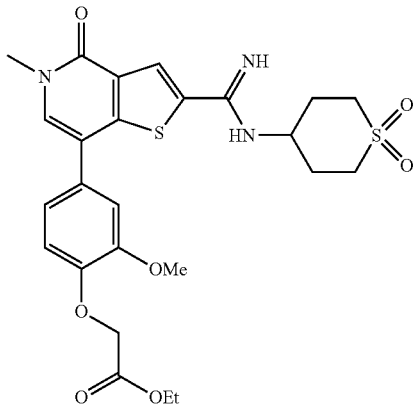

To a solution of MeONa (0.54 mg, 0.01 mmol) in (dry) MeOH (80 mL) was added ethyl 2-(4-(2-cyano-5-methyl-4-oxo-4,5-dihydrothieno[3,2-c]pyridin-7-yl)-2-methoxyphenoxy)acetate (0.2 g, 0.5 mmol). The mixture was stirred at room temperature overnight with exclusion of atmospheric moisture, 4-aminotetrahydro-2H-thiopyran 1,1-dioxide hydrochloride (0.75 g, 5.0 mmol) was added to the reaction and the reaction was stirred at 75° C. for 7 days and then cooled to room temperature. The resulting solution was concentrated and the residue was purified by column chromatography (MeOH-DCM) to afford ethyl 2-(4-(2-(N-(1,1-dioxidotetrahydro-2H-thiopyran-4-yl)carbamimidoyl)-5-methyl-4-oxo-4,5-dihydrothieno[3,2-c]pyridin-7-yl)-2-methoxyphenoxy)acetate (0.13 g, 52%, 92% purity) as a pale-yellow solid. LCMS: 534.2 (M+H)

2-(4-(2-(N-(1,1-Dioxidotetrahydro-2H-thiopyran-4-yl)carbamimidoyl)-5-methyl-4-oxo-4,5-dihydrothieno[3,2-c]pyridin-7-yl)-2-methoxyphenoxy)acetic acid

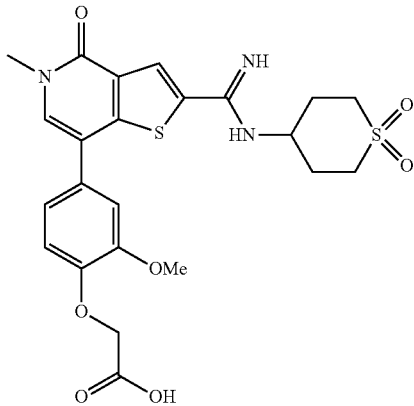 [SMILES: COc1cc(-c2cn(C)c(=O)c3cc(C(=N)NC4CCS(=O)(=O)CC4)sc23)ccc1OCC(=O)O]

To the solution of ethyl 2-(4-(2-(N-(1,1-dioxidotetrahydro-2H-thiopyran-4-yl)carbamimidoyl)-5-methyl-4-oxo-4,5-dihydrothieno[3,2-c]pyridin-7-yl)-2-methoxyphenoxy)acetate (0.2 g, 0.4 mmol) in MeOH (30 mL) was added LiOH (96.0 mg, 4.0 mmol). The result solution was stirred at room temperature for 2 hours. Then the mixture solution was concentrated under reduced pressure. The residue was added to water (5 mL) and HCl (36%) was carefully added until the pH ~3. The resulting solution was filtered and the solid was washed with water and dried to afford ethyl 2-(4-(2-(N-(1,1-dioxidotetrahydro-2H-thiopyran-4-yl)carbamimidoyl)-5-methyl-4-oxo-4,5-dihydrothieno[3,2-c]pyridin-7-yl)-2-methoxyphenoxy)acetate (104 mg, 50%, 95% purity) as a solid.

$^1$H NMR (400 MHz, DMSO-$d_6$) δ 8.18 (s, 1H), 7.75 (s, 1H), 7.16 (s, 1H), 7.11 (d, J=8.0 Hz, 1H), 6.94 (d, J=8.0 Hz, 1H), 4.57 (s, 2H), 3.84 (s, 3H), 3.73-3.71 (m, 1H), 3.56 (s, 3H), 3.18-3.08 (m, 4H), 2.03-1.96 (m, 4H). LCMS: 520.2 (M+H)

4-Bromo-2-methyl-2,7-naphthyridin-1(2H)-one

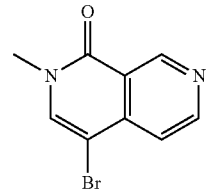

To a fine suspension of 4-bromo-2-methyl-2,7-naphthyridin-1(2H)-one (996 mg, 4.43 mmol, 1.0 eq) and cesium carbonate (4330 mg, 13.3 mmol, 3.0 eq) in THF (17.7 mL) was added iodomethane (551 μL, 8.86 mmol, 2.0 eq) and the reaction was stirred at room temperature. After 22 hours, the mixture was concentrated in vacuo, and the resulting residue dissolved in DCM. In soluble material was filtered and washed with both DCM and water before being discarded. Organic filtrate was collected (approx. 150 mL), washed three times with deionized water (30 mL), and once with saturated brine (30 milliliters) before being dried over $Na_2SO_4$ and concentrated in vacuo to afford the desired product as an off-white solid (1038 mg, 98%).

$^1$H NMR (500 MHz, DMSO-$d_6$) δ=9.36 (s, 1H), 8.88 (s, 1H), 8.25 (s, 1H), 7.61 (s, 1H), 3.54 (s, 3H). LCMS: 239 (M).

tert-Butyl 2-((4-bromo-2,6-dimethoxybenzyl)(methyl)amino)acetate

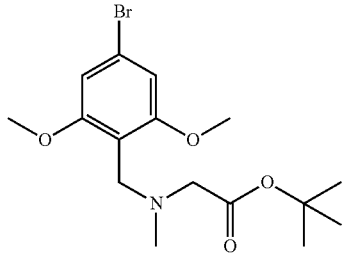 [SMILES: COc1cc(Br)cc(OC)c1CN(C)CC(=O)OC(C)(C)C]

Sarcosyl tert-butyl ester hydrochloride (556 mg, 3.06 mmol, 1.5 eq) was dissolved in a solution of NaOAc (251 mg, 3.06 mmol, 1.5 eq) in DCM (8.2 mL) and 167 μL AcOH (2.04 mmol, 1.0 eq) was added followed by 4-bromo-2,6-dimethoxybenzaldehyde (500 mg, 2.04 mmol, 1.0 eq). The mixture was stirred for 10 minutes before sodium triacetoxy borohydride was added in one portion (864.8 mg, 4.08 mmol, 2.0 eq) and the mixture was stirred for 18 hours. The reaction was basified to approximately pH 11 with 1M $K_2CO_3$ and extracted 4 times with DCM (10 mL). The combined organics were washed with deionized water (10 mL) and saturated brine (10 mL) before being dried over $Na_2SO_4$ and concentrated in vacuo to afford the desired product as an off-white solid (725 mg, 95%).

¹H NMR (500 MHz, Chloroform-d) δ=6.69 (s, 2H), 3.81 (s, 2H), 3.79 (s, 6H), 3.21 (s, 2H), 2.41 (s, 3H), 1.48 (s, 9H). LCMS: 376 (M+H).

tert-Butyl 2-((2,6-dimethoxy-4-(4,4,5,5-tetramethyl-1,3,2-dioxaborolan-2-yl)benzyl)(methyl)amino)acetate 0

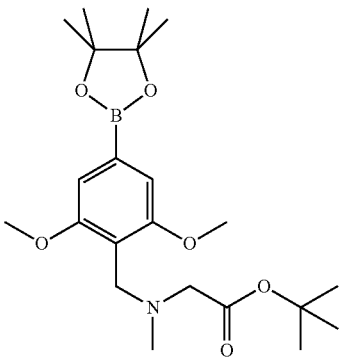 [SMILES: COc1cc(B2OC(C)(C)C(C)(C)O2)cc(OC)c1CN(C)CC(=O)OC(C)(C)C]

tert-Butyl 2-((4-bromo-2,6-dimethoxybenzyl)(methyl)amino)acetate (300 mg, 0.802 mmol, 1.0 eq) and bis(pinacolato)diboron (305 mg, 1.20 mmol, 1.5 eq), were dissolved in DMF and KOAC (394 mg, 4.01 mmol, 5.0 eq) and PdCl₂(dppf).CH₂Cl₂ (65.5 mg, 0.080 mmol, 0.1 eq) were added. The mixture was degassed and the headspace was flushed with N₂ before heating to 90° C. for 16 hours. The reaction was diluted to 80 mL with EtOAc, filtered through celite, and washed twice with a 1:1 solution of deionized water and saturated brine (20 mL), three times with deionized water (20 mL), and once with saturated brine (20 mL) before being dried over Na₂SO₄ and concentrated in vacuo. The residue was dissolved in DCM and purified by silica chromatography (EtOAc/hexanes 0 to 100% gradient) to afford the desired product as a brown solid (158 mg, 47%).

¹H NMR: (500 MHz, Chloroform-d) δ=6.98 (s, 2H), 3.90 (s, 2H), 3.85 (s, 6H), 3.20 (s, 2H), 2.41 (s, 3H), 1.48 (s, 9H), 1.35 (s, 12H). LCMS: 423 (M+H).

tert-Butyl 2-((2,6-dimethoxy-4-(2-methyl-1-oxo-1,2-dihydro-2,7-naphthyridin-4-yl)benzyl)(methyl)amino)acetate

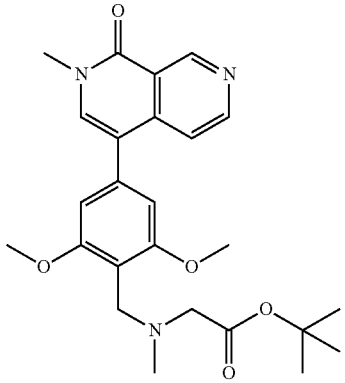 [SMILES: COc1cc(-c2cn(C)c(=O)c3cnccc23)cc(OC)c1CN(C)CC(=O)OC(C)(C)C]

4-Bromo-2-methyl-2,7-naphthyridin-1(2H)-one (45.6 mg, 0.191 mmol, 1.0 eq) and tert-butyl 2-((2,6-dimethoxy-4-(4,4,5,5-tetramethyl-1,3,2-dioxaborolan-2-yl)benzyl)(methyl)amino)acetate (96.4 mg, 0.229 mmol, 1.2 eq) were dissolved in DMF (4.6 mL) before a 2N solution of Na₂CO₃ was added (239 μL, 0.477 mmol, 2.5 eq) followed by Pd(dppf)Cl₂.DCM (15.6 mg, 0.0141 mmol, 0.1 eq). The mixture was degassed and heated to 80° C. for 13 hours. Solvent was removed by lyophilization and the residue extracted with DCM and purified by silica chromatography (DCM/MeOH 0 to 15% gradient) to afford the desired product as a brown solid (71 mg, 82%).

¹H NMR (500 MHz, Chloroform-d) δ=9.70 (s, 1H), 8.70 (d, J=5.6, 1H), 7.43 (d, J=6.2, 1H), 7.28 (s, 1H), 6.54 (s, 2H), 3.93 (s, 2H), 3.84 (s, 6H), 3.68 (s, 3H), 3.30 (s, 2H), 2.50 (s, 3H), 1.52 (s, 9H). LCMS: 454 (M+H).

2-((2,6-Dimethoxy-4-(2-methyl-1-oxo-1,2-dihydro-2,7-naphthyridin-4-yl)benzyl)(methyl)amino)acetic acid

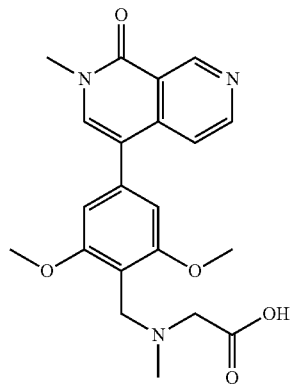 [SMILES: COc1cc(-c2cn(C)c(=O)c3cnccc23)cc(OC)c1CN(C)CC(=O)O]

tert-Butyl 2-((2,6-dimethoxy-4-(2-methyl-1-oxo-1,2-dihydro-2,7-naphthyridin-4-yl)benzyl)(methyl)amino)acetate (71.0 mg, 0.156 mmol, 1.0 eq) was dissolved in DCM (624 μL) before TFA was slowly added (624 μL). After 1 hour, deprotection was incomplete and the reaction was allowed to continue for 24 hours. The reaction was concentrated under a stream of N₂ followed by high vacuum. The resulting tar-like salt was dissolved in deionized water and lyophilized to afford a brown solid, which was triturated with Et₂O. The remaining hygroscopic solid was dried under high vacuum overnight to afford the desired product as brittle brown solid (90 mg, quantitative yield, mixture of TFA salts).

¹H NMR (500 MHz, DMSO-d₆) δ=9.76 (s, 1H), 9.48 (s, 1H), 8.75 (d, 1H), 7.94 (s, 1H), 7.64 (d, 1H), 6.87 (s, 2H), 4.42 (s, 2H), 4.02 (s, 2H), 3.87 (s, 6H), 3.63 (s, 3H), 2.76 (s, 3H). LCMS: 398 (M+H).

Example 3. Synthesis of Final Compounds

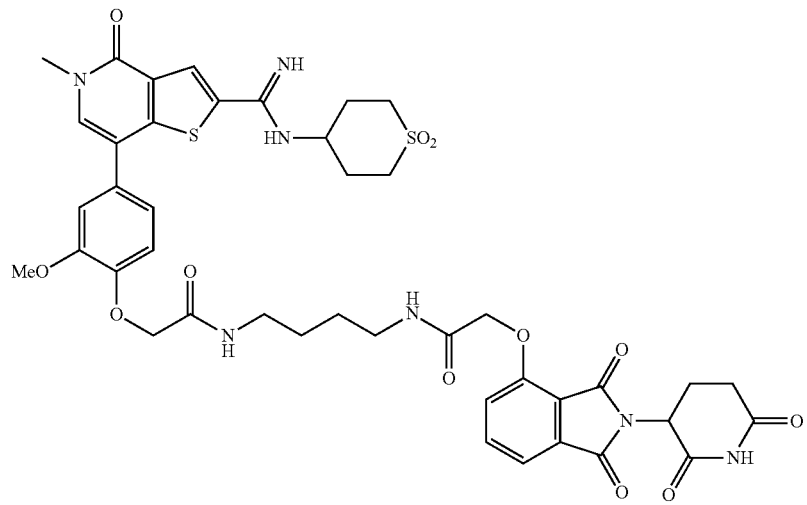

Compound I-1

N-(4-Aminobutyl)-2-((2-(2,6-dioxopiperidin-3-yl)-1,3-dioxoisoindolin-4-yl)oxy)acetamide trifluoroacetate salt (10.3 mg, 0.020 mmol, 1 eq) was added to 2-(4-(2-(N-(1,1-dioxidotetrahydro-2H-thiopyran-4-yl)carbamimidoyl)-5-methyl-4-oxo-4,5-dihydrothieno[3,2-c]pyridin-7-yl)-2-methoxyphenoxy)acetic acid (10.4 mg, 0.020 mmol, 1 eq) as a 0.1 M solution in DMF (200 microliters), DIPEA (10.5 microliters, 0.060 mmol, 3 eq) was added followed by HATU (7.6 mg, 0.020 mmol, 1 eq). After 22 hours, the mixture was diluted with DMF/MeOH and purified by preparative HPLC to afford the trifluoroacetate salt of Compound I-1 as a yellow solid (8.12 mg, 0.00798 mmol, 40%/).

$^{1}$H NMR (500 MHz, Methanol-$d_4$) δ 8.30 (d, J=4.7 Hz, 1H), 7.75 (dd, J=8.4, 7.4 Hz, 1H), 7.62 (d, J=4.9 Hz, 1H), 7.51 (d, J=7.3 Hz, 1H), 7.28 (d, J=8.4 Hz, 1H), 7.12 (d, J=8.2 Hz, 2H), 7.04 (d, J=8.1 Hz, 1H), 5.02 (dd, J=11.6, 6.2 Hz, 1H), 4.61 (dd, J=8.9, 3.7 Hz, 2H), 4.56 (s, 2H), 4.03 (dt, J=10.0, 5.0 Hz, 1H), 3.92 (s, 3H), 3.70 (s, 3H), 3.41-3.32 (m, 4H), 3.26 (d, J=4.6 Hz, 3H), 3.14 (d, J=15.1 Hz, 2H), 2.81-2.71 (m, 3H), 2.42-2.29 (m, 4H), 2.15-2.09 (m, 1H), 1.66-1.56 (m, 4H). LCMS: 904.47 (M+H).

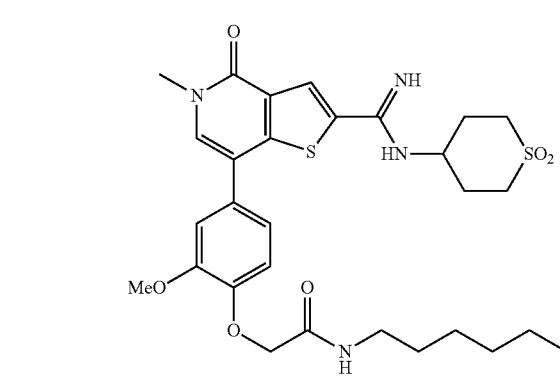

Compound I-2

N-(8-Aminooctyl)-2-((2-(2,6-dioxopiperidin-3-yl)-1,3-dioxoisoindolin-4-yl)oxy)acetamide trifluoroacetate salt (11.5 mg, 0.020 mmol, 1 eq) was added to 2-(4-(2-(N-(1,1-dioxidotetrahydro-2H-thiopyran-4-yl)carbamimidoyl)-5-methyl-4-oxo-4,5-dihydrothieno[3,2-c]pyridin-7-yl)-2-methoxyphenoxy)acetic acid (10.4 mg, 0.020 mmol, 1 eq) as a 0.1 M solution in DMF (200 microliters), DIPEA (10.5 microliters, 0.060 mmol, 3 eq) was added followed by HATU (7.6 mg, 0.020 mmol, 1 eq). After 23 hours, the mixture was diluted with DMF/MeOH and purified by preparative HPLC to afford the trifluoroacetate salt of Compound I-2 as a light brown oily residue (9.83 mg, 0.00915 mmol, 46%).

$^1$H NMR (500 MHz, Methanol-d$_4$) δ 8.35 (s, 1H), 7.84-7.76 (m, 2H), 7.52 (d, J=7.0 Hz, 1H), 7.40 (d, J=8.6 Hz, 1H), 7.27 (d, J=2.1 Hz, 1H), 7.21 (dd, J=8.2, 2.1 Hz, 1H), 7.12 (d, J=8.3 Hz, 1H), 5.14-5.10 (m, 1H), 4.72 (s, 2H), 4.58 (s, 2H), 3.97 (d, J=10.8 Hz, 4H), 3.70 (s, 3H), 3.29-3.18 (m, 6H), 2.98 (s, 1H), 2.89-2.84 (m, 1H), 2.80-2.68 (m, 3H), 2.43-2.31 (m, 4H), 1.52 (s, 4H), 1.37-1.25 (m, 8H). LCMS: 960.49 (M+H).

Compound I-3

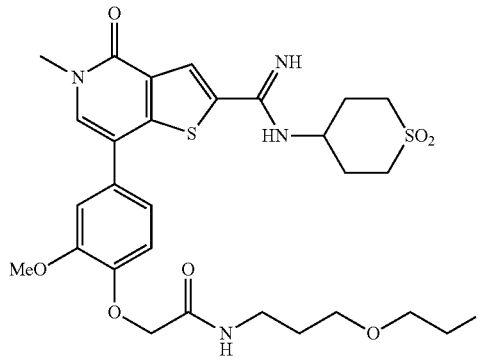
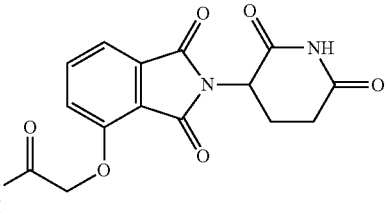

N-(3-(2-(2-(3-Aminopropoxy)ethoxy)ethoxy)propyl)-2-((2-(2,6-dioxopiperidin-3-yl)-1,3-dioxoisoindolin-4-yl)oxy)acetamide trifluoroacetate salt (13.0 mg, 0.020 mmol, 1 eq) was added to 2-(4-(2-(N-(1,1-dioxidotetrahydro-2H-thiopyran-4-yl)carbamimidoyl)-5-methyl-4-oxo-4,5-dihydrothieno[3,2-c]pyridin-7-yl)-2-methoxyphenoxy)acetic acid (10.4 mg, 0.020 mmol, 1 eq) as a 0.1 M solution in DMF (200 microliters), DIPEA (10.5 microliters, 0.060 mmol, 3 eq) was added, followed by HATU (7.6 mg, 0.020 mmol, 1 eq). After 24 hours, the mixture was diluted with DMF/MeOH and purified by preparative HPLC to give the trifluoroacetate salt of Compound I-3 as a brown oily residue (14.11 mg, 0.01227 mmol, 61%).

$^1$H NMR (500 MHz; methanol-d$_4$) δ 8.35 (s, 1H), 7.81 (s, 1H), 7.76 (dd, J=8.4, 7.4 Hz, 1H), 7.49 (d, J=7.1 Hz, 1H), 7.37 (d, J=8.3 Hz, 1H), 7.25 (d, J=2.1 Hz, 1H), 7.19 (dd, J=8.2, 2.1 Hz, 1H), 7.12 (d, J=8.3 Hz, 1H), 5.11 (dd, J=12.9, 5.5 Hz, 1H), 4.69 (s, 2H), 4.56 (s, 2H), 4.05-3.99 (m, 1H), 3.95 (s, 3H), 3.70 (s, 3H), 3.61-3.52 (m, 12H), 3.43-3.36 (m, 4H), 3.29-3.18 (m, 4H), 2.89-2.81 (m, 1H), 2.77-2.68 (m, 2H), 2.46-2.30 (m, 4H), 2.11 (ddt, J=10.2, 5.4, 2.5 Hz, 1H), 1.80 (dt, J=12.8, 6.4 Hz, 4H). LCMS: 1036.43 (M+H).

(2S,4R)-1-((S)-14-Amino-2-(tert-butyl)-4-oxo-6,9,12-trioxa-3-azatetradecan-1-oyl)-4-hydroxy-N-(4-(4-methylthiazol-5-yl)benzyl)pyrrolidine-2-carboxamide hydrochloride salt (13.1 mg, 0.020 mmol, 1 eq) was added to 2-(4-(2-(N-(1,1-dioxidotetrahydro-2H-thiopyran-4-yl)carbamimidoyl)-5-methyl-4-oxo-4,5-dihydrothieno[3,2-c]pyridin-7-yl)-2-methoxyphenoxy)acetic acid (10.4 mg, 0.020 mmol, 1 eq) as a 0.1 M solution in DMF (200 microliters), DIPEA (10.5 microliters, 0.060) mmol, 3 eq) was added followed by HATU (7.6 mg, 0.020 mmol, 1 eq), DMF (200 microliters) was added to improve solubility. After 20 hours, more HATU (7.6 mg) was added to ensure complete conversion. After an additional 2 hours, the mixture was diluted with DMF/MeOH and purified by preparative HPLC to afford the trifluoroacetate salt of Compound I-4 (5.99 mg).

$^1$H NMR (500 MHz, Methanol-d$_4$) δ 8.98 (s, 1H), 8.36 (s, 1H), 7.81 (d, J=3.2 Hz, 1H), 7.46-7.40 (m, 4H), 7.26 (dd, J=9.5, 2.1 Hz, 1H), 7.19 (dd, J=8.2, 2.1 Hz, 1H), 7.12 (d, J=8.3 Hz, 1H), 4.72-4.67 (m, 1H), 4.56 (d, J=7.6 Hz, 2H), 4.50 (d, J=8.3 Hz, 2H), 4.35 (d. J=15.5 Hz, 1H), 4.03-3.93 (m, 5H), 3.86 (d, J=11.1 Hz, 1H), 3.79 (dd, J=10.9, 3.8 Hz, 1H), 3.73-3.62 (m, 12H), 3.59 (t, J=5.5 Hz, 2H), 3.51-3.45

Compound I-4

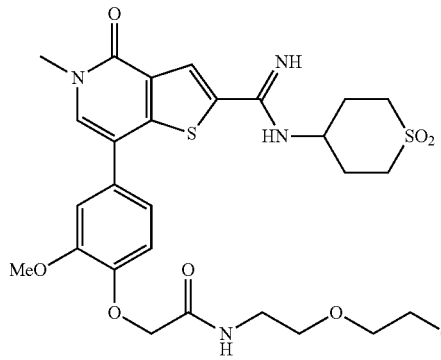
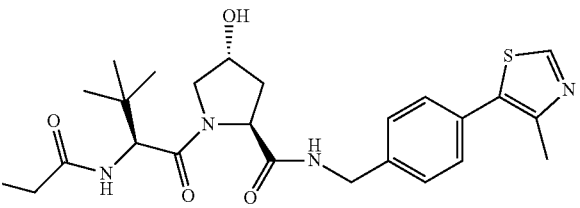

(m, 2H), 3.29-3.17 (m, 4H), 2.51-2.45 (m, 4H), 2.36 (dt, J=37.2, 12.8 Hz, 4H), 2.23 (dd. J=13.2, 7.6 Hz, 1H), 2.08 (ddd, J=13.3, 9.3, 4.4 Hz, 1H), 1.03 (d, J=12.3 Hz, 9H). LCMS: 1121.53 (M+H).

Compound I-5

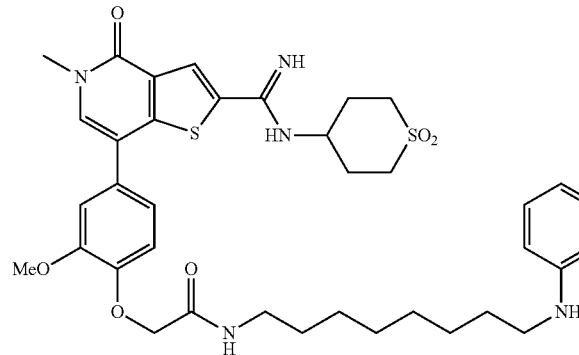

4-((8-Aminooctyl)amino)-2-(26-dioxopiperidin-3-yl)isoindoline-1,3-dione trifluoroacetate salt (10.3 mg, 0.020 mmol, 1 eq) was added to 2-(4-(2-(N-(1,1-dioxidotetrahydro-2H-thiopyran-4-yl)carbamimidoyl)-5-methyl-4-oxo-4,5-dihydrothieno[3,2-c]pyridin-7-yl)-2-methoxyphenoxy)acetic acid (10.4 mg, 0.020 mmol, 1 eq) as a 0.1 M solution in DMF (200 microliters), DIPEA (10.5 microliters, 0.060 mmol, 3 eq) was added, followed by HATU (7.6 mg, 0.020 mmol, 1 eq). After 20 hours, the mixture was diluted with DMF/MeOH and purified by preparative HPLC to afford the trifluoroacetate salt of Compound I-5 as a yellow solid (11.18 mg, 0.0110 mmol, 55%).

$^1$H NMR (500 MHz, Methanol-$d_4$) δ 8.34 (s, 1H), 7.81 (s, 1H), 7.49 (dd, J=8.5, 7.1 Hz, 1H), 7.25 (d, J=2.1 Hz, 1H), 7.20 (dd, J=8.3, 2.1 Hz, 1H), 7.12 (d, J=8.3 Hz, 1H), 6.97 (dd, J=10.8, 7.8 Hz, 2H), 5.04 (dd, J=12.6, 5.5 Hz, 1H), 4.58 (s, 2H), 4.02-3.92 (m, 4H), 3.71 (s, 3H), 3.30-3.17 (m, 6H), 2.98 (d, J=9.5 Hz, 2H), 2.85 (ddd, J=19.2, 13.9, 5.3 Hz, 1H), 2.78-2.66 (m, 2H), 2.36 (dt, J=37.4, 11.4 Hz, 4H), 2.10 (ddq, J=10.6, 5.5, 2.9 Hz, 1H), 1.64-1.53 (m, 4H), 1.37 (d, J=16.3 Hz, 8H). LCMS: 902.50 (M+H).

(2S,4R)-1-((S)-2-(2-(2-(2-Aminoethoxy)ethoxy)acetamido)-3,3-dimethylbutanoyl)-4-hydroxy-N-(4-(4-methylthiazol-5-yl)benzyl)pyrrolidine-2-carboxamide hydrochloride salt (12.2 mg, 0.020 mmol, 1 eq) was added to 2-(4-(2-(N-(1,1-dioxidotetrahydro-2H-thiopyran-4-yl)carbamimidoyl)-5-methyl-4-oxo-4,5-dihydrothieno[3,2-c]pyridin-7-yl)-2-methoxyphenoxy)acetic acid (10.4 mg, 0.020 mmol, 1 eq) as a 0.1 M solution in DMF (200 microliters), DIPEA (10.5 microliters, 0.060 mmol, 3 eq) was added followed by HATU (7.6 mg, 0.020 mmol, 1 eq). Additional DMF (200 microliters) was added to improve solubility. After 27 hours, extra HATU (7.6 mg) was added to ensure complete conversion. After 3 more hours, the mixture was diluted with DMF/MeOH and purified by preparative HPLC to afford the trifluoroacetate salt of Compound I-6 as yellow oily residue (12.35 mg, 0.0104 mmol, 52%).

$^1$H NMR (500 MHz. Methanol-$d_4$) δ 8.95 (s, 1H), 8.36 (d, J=5.0 Hz, 1H), 7.80 (d, J=6.6 Hz, 1H), 7.45-7.39 (m, 4H), 7.23 (d, J=2.0 Hz, 1H), 7.17 (dd, J=8.3, 2.0 Hz, 1H), 7.09 (d, J=8.3 Hz, 1H), 4.74-4.70 (m, 1H), 4.58-4.49 (m, 4H), 4.34 (d, J=15.4 Hz, 1H), 4.04-3.97 (m, 3H), 3.93 (s, 2H), 3.87-3.78 (m, 2H), 3.73-3.62 (m, 10H), 3.51 (dt, J=28.6, 5.1 Hz, 2H), 3.24 (dd, J=29.6, 14.3 Hz, 4H), 2.48 (d, J=15.7 Hz, 4H), 2.36 (dd, J=25.4, 12.2 Hz, 4H), 2.24-2.18 (m, 1H), 2.10 (dt, J=13.1, 6.6 Hz, 1H), 1.03 (s, 9H). LCMS: 1077.72 (M+H).

Compound I-6

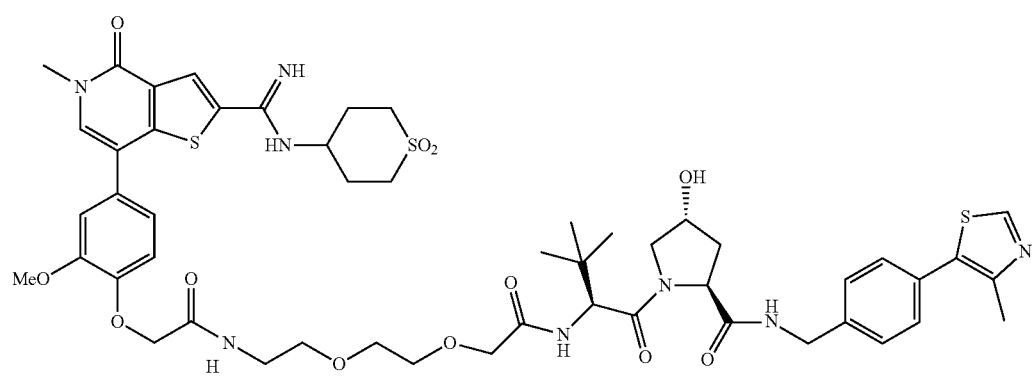

Compound I-7

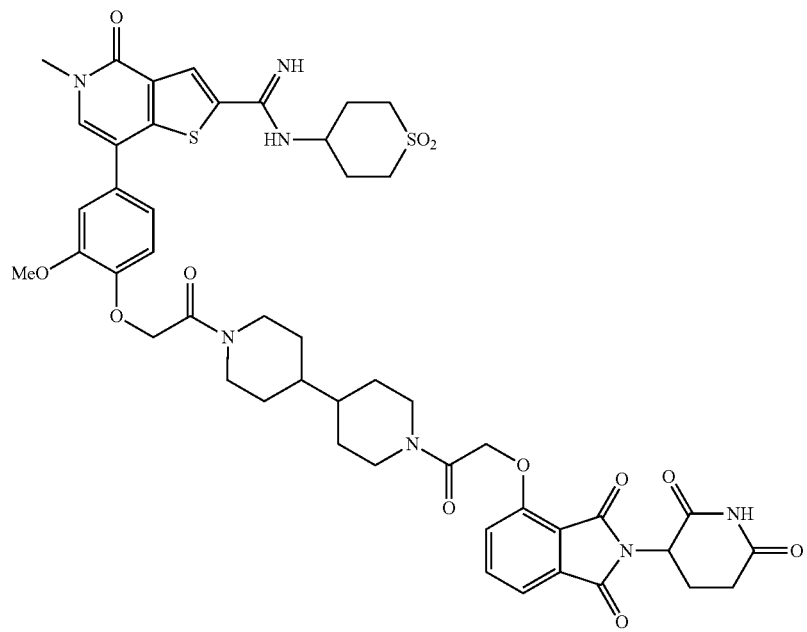

4-(2-([4,4'-Bipiperidin]-1-yl)-2-oxoethoxy)-2-(2,6-dioxopiperidin-3-yl)isoindoline-1,3-dione trifluoroacetate salt (11.9 mg, 0.020 mmol, 1 eq) was added to 2-(4-(2-(N-(1,1-dioxidotetrahydro-2H-thiopyran-4-yl)carbamimidoyl)-5-methyl-4-oxo-4,5-dihydrothieno[3,2-c]pyridin-7-yl)-2-methoxyphenoxy)acetic acid (10.4 mg, 0.020 mmol, 1 eq) as a 0.1 M solution in DMF (200 microliters), DIPEA (10.5 microliters, 0.060 mmol, 3 eq) was added followed by HATU (7.6 mg, 0.020 mmol, 1 eq). After 24 hours, the mixture was diluted with DMF/MeOH and purified by preparative HPLC to afford the trifluoroacetate salt of Compound I-7 as yellow solid (11.6 mg, 0.01016 mmol, 51%).

$^1$H NMR (500 MHz, Methanol-$d_4$) δ 8.34 (s, 1H), 7.75-7.71 (m, 2H), 7.49 (dd, J=6.7, 3.9 Hz, 1H), 7.35-7.32 (m, 1H), 7.21-7.11 (m, 2H), 7.04 (d J=8.3 Hz, 1H), 5.11-4.95 (m, 3H), 4.87 (d, J=14.1 Hz, 1H), 4.52 (s, 2H), 4.06-3.96 (m, 2H), 3.92 (d, J=2.5 Hz, 3H), 3.72 (s, 3H), 3.18 (d, J=11.9 Hz, 2H), 3.08 (d, J=11.0 Hz, 2H), 2.93 (d, J=17.9 Hz, 2H), 2.81-2.72 (m, 2H), 2.62 (s, 1H), 2.43-2.30 (m, 3H), 2.13 (s, 1H), 1.74 (d, J=27.5 Hz, 4H), 1.45 (s, 2H), 1.29 (d, J=29.7 Hz, 7H). LCMS: 984.57 (M+H).

4-((6-Aminohexyl)oxy)-2-(2,6-dioxopiperidin-3-yl)isoindoline-1,3-dione (0.03 mmol, 1.0 eq) was added to 2-(4-(2-(N-(1,1-dioxidotetrahydro-2H-thiopyran-4-yl)carbamimidoyl)-5-methyl-4-oxo-4,5-dihydrothieno[3,2-c]pyridin-7-yl)-2-methoxyphenoxy)acetic acid (15.6 mg, 0.030 mmol, 1 eq) as a 0.1 M solution in DMF (200 microliters), DIPEA (15.7 microliters, 0.090 mmol, 3 eq) was added followed by HATU (12.5 mg, 0.033 mmol, 1.1 eq). After 16 hours, the mixture was diluted with MeOH and purified by preparative HPLC to afford the trifluoroacetate salt of I-8 as a pale yellow solid (10.5 mg, 35.3%)

Compound I-8

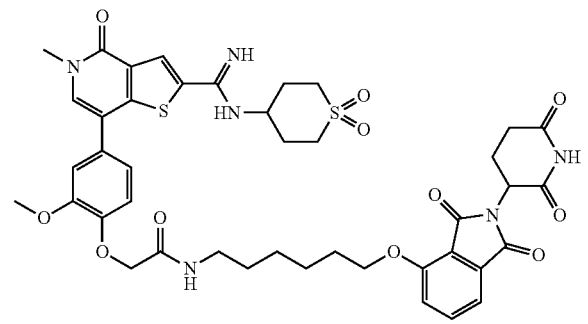

$^1$H NMR (500 MHz, methanol-$d_4$) δ=8.32 (s, 1H), 7.79 (s, 1H), 7.69-7.65 (m, 1H), 7.35 (d, J=7.1, 1H), 7.31 (d, J=8.5, 1H), 7.24 (d, J=2.1, 1H), 7.20 (dd, J=8.3, 2.1, 1H), 7.11 (d, J=8.3, 1H), 5.07 (dd, J=12.7, 5.5, 1H), 4.58 (s, 2H), 4.11 (d, J=5.4, 2H), 3.95 (s, 3H), 3.68 (s, 3H), 3.28-3.19 (m, 5H), 2.97 (s, 2H), 2.86-2.80 (m, 1H), 2.74-2.66 (m, 2H), 2.41 (d, J=12.2, 2H), 2.33 (d, J=12.6, 2H), 2.09 (d, J=10.1, 1H), 1.80-1.75 (m, 2H), 1.62-1.56 (m, 3H), 1.55-1.48 (m, 3H), 1.37 (q, J=8.0, 3H), 1.28 (s, 1H). LCMS: 875 (M+H).

Compound I-9

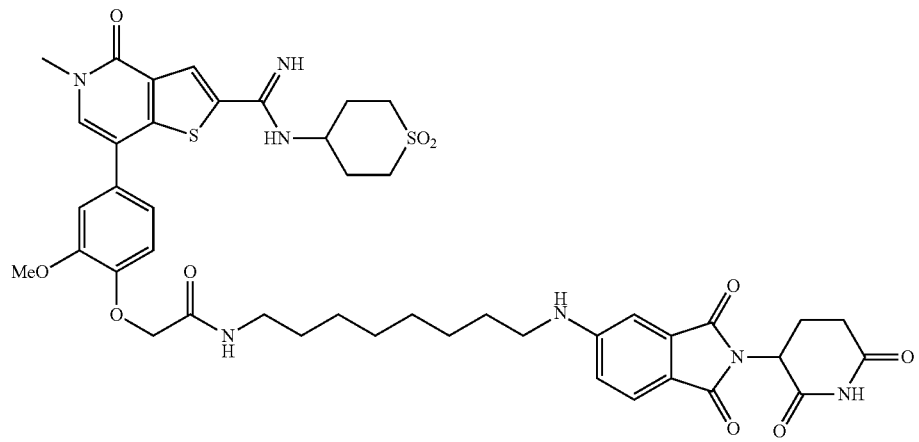

5-((8-Aminooctyl)amino)-2-(2,6-dioxopiperidin-3-yl) isoindoline-1,3-dione trifluoroacetate salt (10.3 mg, 0.020 mmol, 1 eq) was added to 2-(4-(2-(N-(1,1-dioxidotetrahydro-2H-thiopyran-4-yl)carbamimidoyl)-5-methyl-4-oxo-4,5-dihydrothieno[3,2-c]pyridin-7-yl)-2-methoxyphenoxy) acetic acid (10.4 mg, 0.020 mmol, 1 eq) as a 0.1 M solution in DMF (200 microliters), DIPEA (10.5 microliters, 0.060 mmol, 3 eq) was added followed by HATU (7.6 mg, 0.020 mmol, 1 eq). After 20 hours, the mixture was diluted with DMF/MeOH and purified by preparative HPLC to give the trifluoroacetate salt of Compound I-9 as yellow solid (6.27 mg, 0.00617 mmol, 31%).

$^1$H NMR (500 MHz, Methanol-$d_4$) δ 8.34 (s, 1H), 7.80 (s, 1H), 7.49 (d, J=8.4 Hz, 1H), 7.26 (s, 1H), 7.21 (d, J=8.4 Hz, 1H), 7.12 (d, J=8.3 Hz, 1H), 6.90 (s, 1H), 6.75 (d, J=8.0 Hz, 1H), 5.02 (dd, J=12.8, 5.4 Hz, 1H), 4.58 (s, 2H), 3.95 (s, 4H), 3.71 (s, 3H), 3.30-3.17 (m, 6H), 3.12 (t, J=7.1 Hz, 2H), 2.87-2.79 (m, 1H), 2.76-2.64 (m, 2H), 2.44-2.29 (m, 4H), 2.11-2.05 (m, 1H), 1.64-1.55 (m, 4H), 1.37 (d, J=17.9 Hz, 8H). LCMS: 902.54 (M+H).

5-((8-Aminooctyl)amino)-2-(2,6-dioxopiperidin-3-yl) isoindoline-1,3-dione trifluoroacetate salt (10.3 mg, 0.020 mmol, 1 eq) was added to 4-(2-(N-(1,1-dioxidotetrahydro-2H-thiopyran-4-yl)carbamimidoyl)-5-ethyl-4-oxo-4,5-dihydrothieno[3,2-c]pyridin-7-yl)benzoic acid (9.5 mg, 0.020 mmol, 1 eq) as a 0.1 M solution in DMF (200 microliters), DIPEA (10.5 microliters, 0.060 mmol, 3 eq) was added followed by HATU (7.6 mg, 0.020 mmol, 1 eq). After 20 hours, the mixture was diluted with MeOH and purified by preparative HPLC to give the trifluoroacetate salt of Compound I-10.

$^1$H NMR (500 MHz, methanol-$d_4$) δ 8.34 (s, 1H), 7.94 (d, J=8.1 Hz, 2H), 7.89 (s, 1H), 7.72 (d, J=8.1 Hz, 2H), 7.52-7.46 (m, 1H), 6.91 (d, J=9.6 Hz, 1H), 6.76 (d, J=8.5 Hz, 1H), 4.98 (dd, J=12.9, 5.3 Hz, 1H), 4.17 (q, J=7.1 Hz, 2H), 3.96 (t, J=10.9 Hz, 1H), 3.37 (t, J=7.0 Hz, 2H), 3.24-3.09 (m, 7H), 2.83-2.76 (m, 1H), 2.70-2.62 (m, 2H), 2.41-2.24 (m, 4H), 2.06-2.00 (m, 1H), 1.61 (d, J=6.8 Hz, 4H), 1.40-1.34 (m, 10H). LCMS: 856.53 (M+H).

Compound I-10

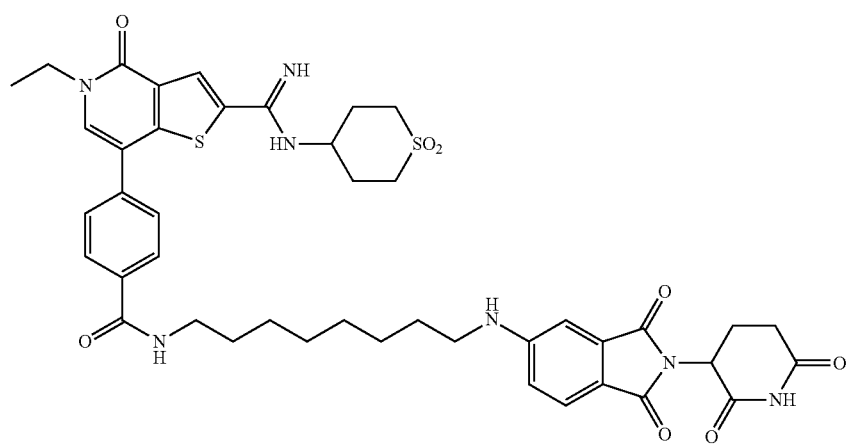

Compound I-11

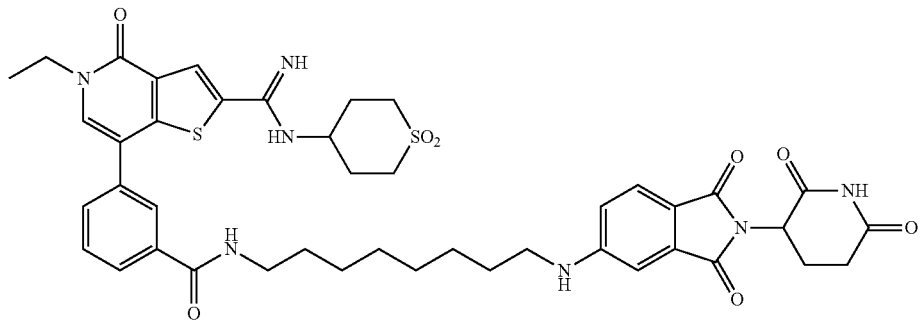

5-((8-Aminooctyl)amino)-2-(2,6-dioxopiperidin-3-yl)isoindoline-1,3-dione trifluoroacetate salt (10.3 mg, 0.020 mmol, 1 eq) was added to 3-(2-(N-(1,1-dioxidotetrahydro-2H-thiopyran-4-yl)carbamimidoyl)-5-ethyl-4-oxo-4,5-dihydrothieno[3,2-c]pyridin-7-yl)benzoic acid (9.5 mg, 0.020 mmol, 1 eq) as a 0.1 M solution in DMF (200 microliters), DIPEA (10.5 microliters, 0.060 mmol, 3 eq) was added followed by PyBop (10.4 mg, 0.020 mmol, 1 eq). After 20 hours, the mixture was diluted with MeOH and purified by preparative HPLC to afford the trifluoroacetate salt of Compound I-11.

$^1$H NMR (500 MHz, Methanol-$d_4$) δ 8.38 (s, 1H), 8.12 (d, J=1.6 Hz, 1H), 7.90 (d, J=12.2 Hz, 2H), 7.83 (d, J=8.4 Hz, 1H), 7.63 (t, J=7.8 Hz, 1H), 7.52 (d, J=8.4 Hz, 1H), 6.94 (d, J=2.1 Hz, 1H), 6.79 (dd, J=8.4, 2.1 Hz, 1H), 5.03 (dd, J=12.7, 5.5 Hz, 1H), 4.21 (q, J=7.1 Hz, 2H), 4.05-3.96 (m, 1H), 3.42 (t, J=7.1 Hz, 2H), 3.29-3.12 (m, 6H), 2.85 (ddd, J=17.7, 14.0, 5.3 Hz, 1H), 2.76-2.63 (m, 2H), 2.35 (tt, J=23.2, 12.0 Hz, 4H), 2.08 (ddd, J=13.0, 6.7, 4.2 Hz, 1H), 1.65 (s, 4H), 1.48-1.39 (m, 11H). LCMS: 856.73 (M+H).

5-((6-Aminohexyl)amino)-2-(2,6-dioxopiperidin-3-yl)isoindoline-1,3-dione trifluoroacetate salt (14.6 mg, 0.03 mmol, 1 eq) was added to 2-((2,6-dimethoxy-4-(2-methyl-1-oxo-1,2-dihydro-2,7-naphthyridin-4-yl)benzyl)methyl)amino)acetic acid ditrifluoroacetate salt (18.8 mg, 0.03 mmol, 1 eq) as a 0.1 M solution in DMF (300 microliters), DIPEA (15.7 microliters, 0.090 mmol, 3.0 eq) was added followed by HATU (12.5 mg, 0.033 mmol, 1.1 eq). After 20 hours the mixture was diluted to 10 mL with EtOAc, washed once with a mildly basic 1:1 solution of deionized water and saturated brine (2 milliliters), washed three times with deionized water (2 milliliters), and finally with saturated brine (2 milliliters) before drying over $Na_2SO_4$ and concentrating in vacuo. The residue was dissolved in 0.75 mL DCM and purified by silica chromatography (DCM/MeOH 0 to 20% gradient) to afford the freebase of I-12 as a yellow solid (12.5 mg, 56%).

$^1$H NMR (500 MHz, DMSO-$d_6$) δ 11.05 (s, 1H), 9.44 (s, 1H), 8.72 (d, J=5.7 Hz, 1H), 7.87 (s, 1H), 7.69 (s, 1H), 7.56 (d, J=6.2 Hz, 1H), 7.54 (d, J=8.4 Hz, 1H), 7.08 (t, J=5.3 Hz, 1H), 6.92 (s, 1H), 6.81 (dd, J=8.4, 1.8 Hz, 1H), 6.77 (s, 2H), 5.02 (dd, J=12.7, 5.5 Hz, 1H), 3.84 (s, 6H), 3.60 (s, 4H), 3.14 (dq, J=12.9, 6.6 Hz, 4H), 2.96 (s, 1H), 2.92-2.83 (m, 2H), 2.61-2.58 (m, 1H), 2.55 (s, 1H), 2.18 (s, 3H), 1.99 (dd, J=10.7, 5.2 Hz, 1H), 1.56 (p, J=6.9 Hz, 2H), 1.46 (p, J=7.1 Hz, 2H), 1.42-1.23 (in, 6H). LCMS: 752.6 (M+H).

Compound I-12

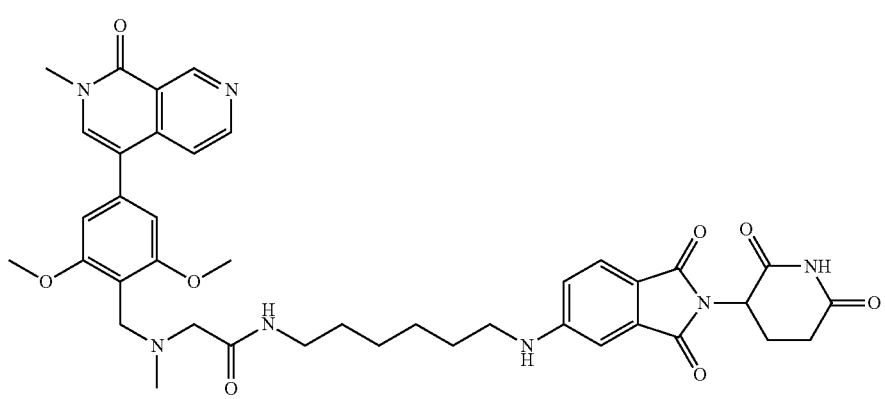

Compound I-13

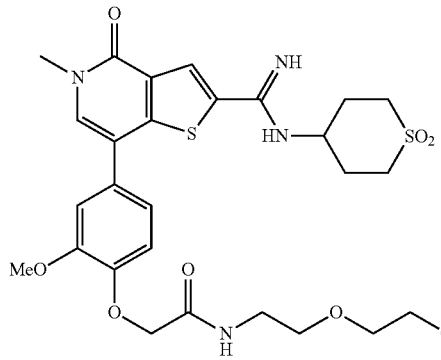

(2S,4R)-1-((S)-14-Amino-2-(tert-butyl)-4-oxo-6,9,12-tri-oxa-3-azatetradecan-1-oyl)-4-hydroxy-N-(4-(4-methylthi-azol-5-yl)benzyl)pyrrolidine-2-carboxamide hydrochloride salt (13.1 mg, 0.020 mmol, 1 eq) was added to 2-(4-(2-(N-(1,1-dioxidotetrahydro-2H-thiopyran-4-yl)carbamimidoyl)-5-methyl-4-oxo-4,5-dihydrothieno[3,2-c]pyridin-7-yl)-2-methoxyphenoxy)acetic acid (10.4 mg, 0.020 mmol, 1 eq) as a 0.1 M solution in DMF (200 microliters), DIPEA (10.5 microliters, 0.060 mmol, 3 eq) was added followed by HATU (7.6 mg, 0.020 mmol, 1 eq), DMF (200 microliters) was added to improve solubility. After 20 hours, more HATU (7.6 mg) was added to ensure complete conversion. After an additional 2 hours, the mixture was diluted with DMF/MeOH and purified by preparative HPLC to give the trifluoroacetate salt of I-13 (5.99 mg, 27%).

$^1$H NMR (500 MHz, methanol-$d_4$) δ 8.98 (s, 1H), 8.36 (s, 1H), 7.81 (d, J=3.2 Hz, 1H), 7.46-7.40 (m, 4H), 7.26 (dd, J=9.5, 2.1 Hz, 1H), 7.19 (dd, J=8.2, 2.1 Hz, 1H), 7.12 (d, J=8.3 Hz, 1H), 4.72-4.67 (m, 1H), 4.56 (d, J=7.6 Hz, 2H), 4.50 (d, J=8.3 Hz, 2H), 4.35 (d, J=15.5 Hz, 1H), 4.03-3.93 (m, 5H), 3.86 (d, J=11.1 Hz, 1H), 3.79 (dd, J=10.9, 3.8 Hz, 1H), 3.73-3.62 (m, 12H), 3.59 (t, J=5.5 Hz, 2H), 3.51-3.45 (m, 2H), 3.29-3.17 (m, 4H), 2.51-2.45 (m, 4H), 2.36 (dt, J=37.2, 12.8 Hz, 4H), 2.23 (dd, J=13.2, 7.6 Hz, 1H), 2.08 (ddd, J=13.3, 9.3, 4.4 Hz, 1H), 1.03 (d, J=12.3 Hz, 9H). LCMS: 1121.53 (M+H).

(2S,4R)-1-((S)-2-(2-(2-(2-Aminoethoxy)ethoxy)acet-amido)-3,3-dimethylbutanoyl)-4-hydroxy-N-(4-(4-methyl-thiazol-5-yl)benzyl)pyrrolidine-2-carboxamide hydrochloride salt (12.2 mg, 0.020 mmol, 1 eq) was added to 2-(4-(2-(N-(1,1-dioxidotetrahydro-2H-thiopyran-4-yl) carbamimidoyl)-5-methyl-4-oxo-4,5-dihydrothieno[3,2-c] pyridin-7-yl)-2-methoxyphenoxy)acetic acid (10.4 mg, 0.020 mmol, 1 eq) as a 0.1 M solution in DMF (200 microliters), DIPEA (10.5 microliters, 0.060 mmol, 3 eq) was added followed by HATU (7.6 mg, 0.020 mmol, 1 eq). Additional DMF (200 microliters) was added to improve solubility. After 27 hours, extra HATU (7.6 mg) was added to ensure complete conversion. After 3 more hours, the mixture was diluted with DMF/MeOH and purified by preparative HPLC to give the trifluoroacetate salt of I-14 as yellow oily residue (12.35 mg, 0.0104 mmol, 52%).

$^1$H NMR (500 MHz, methanol-$d_4$) δ 8.95 (s, 1H), 8.36 (d, J=5.0 Hz, 1H), 7.80 (d, J=6.6 Hz, 1H), 7.45-7.39 (m, 4H), 7.23 (d, J=2.0 Hz, 1H), 7.17 (dd, J=8.3, 2.0 Hz, 1H), 7.09 (d, J=8.3 Hz, 1H), 4.74-4.70 (m, 1H), 4.58-4.49 (m, 4H), 4.34 (d, J=15.4 Hz, 1H), 4.04-3.97 (m, 3H), 3.93 (s, 2H), 3.87-3.78 (m, 2H), 3.73-3.62 (m, 10H), 3.51 (dt, J=28.6, 5.1 Hz, 2H), 3.24 (dd, J=29.6, 14.3 Hz, 4H), 2.48 (d, J=15.7 Hz, 4H), 2.36 (dd, J=25.4, 12.2 Hz, 4H), 2.24-2.18 (m, 1H), 2.10 (dt, J=13.1, 6.6 Hz, 1H), 1.03 (s, 9H). LCMS: 1077.72 (M+H).

Compound I-14

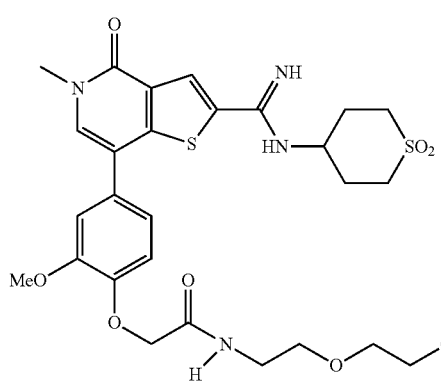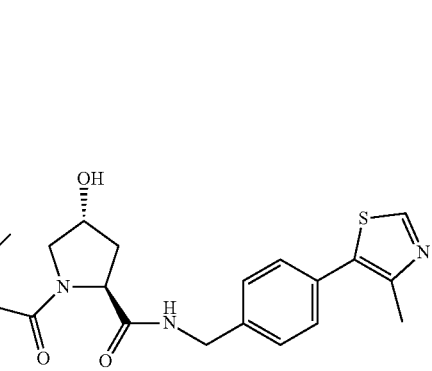

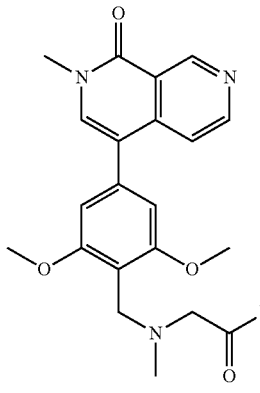

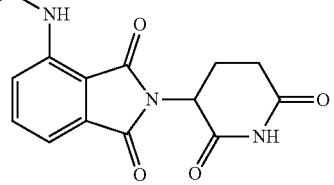

Compound I-15

5-((6-Aminohexyl)amino)-2-(2,6-dioxopiperidin-3-yl)isoindoline-1,3-dione trifluoroacetate salt (0.03 mmol, 1 eq) was added to 2-((2,6-dimethoxy-4-(2-methyl-1-oxo-1,2-dihydro-2,7-naphthyridin-4-yl)benzyl)(methyl)amino)acetic acid trifluoroacetate salt (18.8 mg, 0.037 mmol, 1 1.2 eq) as a 0.1 M solution in DMF (300 microliters), DIPEA (15.7 microliters, 0.090 mmol, 3.0 eq) was added followed by PyBOP (15.6 mg, 0.030 mmol, 1.1 eq). After 12 hours, the reaction was incomplete and an additional 3 eq DIPEA and 0.5 eq PyBOP were added. After 7.5 hours, the mixture was purified by preparative HPLC to afford 1-15 as a yellow solid (6.8 mg, 41%).

$^1$H NMR (500 MHz, methanol-$d_4$) δ 9.54 (s, 1H), 8.67 (d, J=6.1 Hz, 1H), 7.89 (s, 1H), 7.77 (d, J=6.0 Hz, 1H), 7.51 (dd, J=8.5, 7.2 Hz, 1H), 6.99 (dd, J=7.8, 2.2 Hz, 2H), 6.84 (s, 2H), 5.48 (s, 2H), 5.03 (dd, J=12.6, 5.5 Hz, 1H), 4.51 (d, J=4.9 Hz, 2H), 3.95 (s, 6H), 3.70 (s, 3H), 3.34 (s, 1H), 3.27 (t, J=6.9 Hz, 2H), 2.92 (s, 3H), 2.85 (ddd, J=17.5, 13.9, 5.2 Hz, 1H), 2.76-2.65 (m, 2H), 2.13-2.06 (m, 1H), 1.61 (p, J=6.9 Hz., 2H), 1.52-1.46 (m, 2H), 1.43-1.25 (m, 11H). LCMS: 780.9 (M+H).

3-(4-((8-Aminooctyl)amino)-1-oxoisoindolin-2-yl)piperidine-2,6-dione trifluoroacetate salt (10.0 mg, 0.020 mmol, 1 eq) was added to 2-(4-(2-(N-(1,1-dioxidotetrahydro-2H-thiopyran-4-yl)carbamimidoyl)-5-methyl-4-oxo-4,5-dihydrothieno[3,2-c]pyridin-7-yl)-2-methoxyphenoxy)acetic acid (10.4 mg, 0.020 mmol, 1 eq) as a 0.1 M solution in DMF (200 microliters), DIPEA (10.5 microliters, 0.060 mmol, 3 eq) was added followed by PyBOP (10.4 mg, 0.020 mmol, 1 eq). After 18 hours, the mixture was diluted with DMF and purified by preparative HPLC to afford the trifluoroacetate salt of I-17 as an oily, yellow solid (13.3 mg, 0.01329 mmol, 66%).

$^1$H NMR (500 MHz, methanol-$d_4$) δ 8.33 (s, 1H), 7.80 (s, 1H), 7.28-7.24 (m, 2H), 7.19 (dd, J=8.3, 2.1 Hz, 1H), 7.12 (d, J=8.3 Hz, 1H), 7.00 (d, J=7.1 Hz, 1H), 6.74 (d, J=7.9 Hz, 1H), 5.14 (dd, J=13.3, 5.2 Hz, 1H), 4.58 (s, 2H), 4.32-4.21 (m, 2H), 3.99 (ddt, J=13.6, 6.6, 3.3 Hz, 1H), 3.94 (s, 3H), 3.72 (s, 3H), 3.30-3.17 (m, 6H), 3.15 (t, J=7.2 Hz, 2H), 2.91 (ddd, J=18.7, 13.5, 5.4 Hz, 1H), 2.79 (ddd, J=17.6, 4.5, 2.4 Hz, 1H), 2.53-2.27 (m, 5H), 2.19 (dtd, J=12.9, 5.3, 2.5 Hz, 1H), 1.65-1.51 (m, 4H), 1.43-1.30 (m, 8H).

$^{13}$C NMR (126 MHz, MeOD) δ 174.67, 172.44, 170.98, 160.23, 158.42, 152.91, 151.79, 149.17, 144.94, 136.76, 132.95, 132.60, 131.25, 130.56, 128.61, 128.06, 121.32, 117.87, 117.20, 113.83, 113.03, 111.90, 70.29, 56.75, 53.61, 51.18, 50.22, 47.39, 44.45, 40.01, 37.52, 32.39, 30.39, 30.27, 30.25, 30.04, 29.86, 28.01, 27.72, 24.25.

LCMS: 888.88 (M+H).

Compound I-17

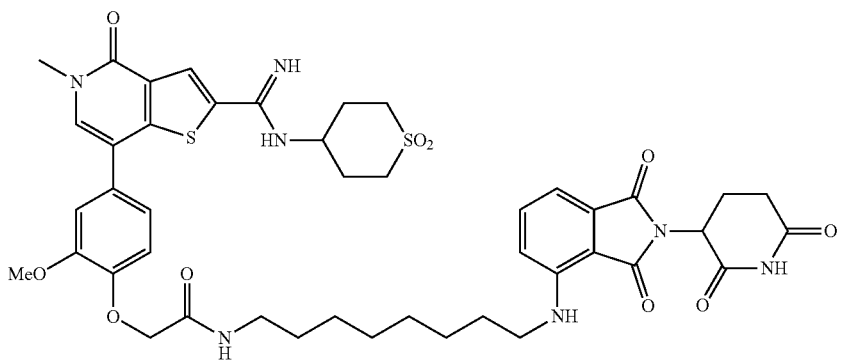

Compound I-23

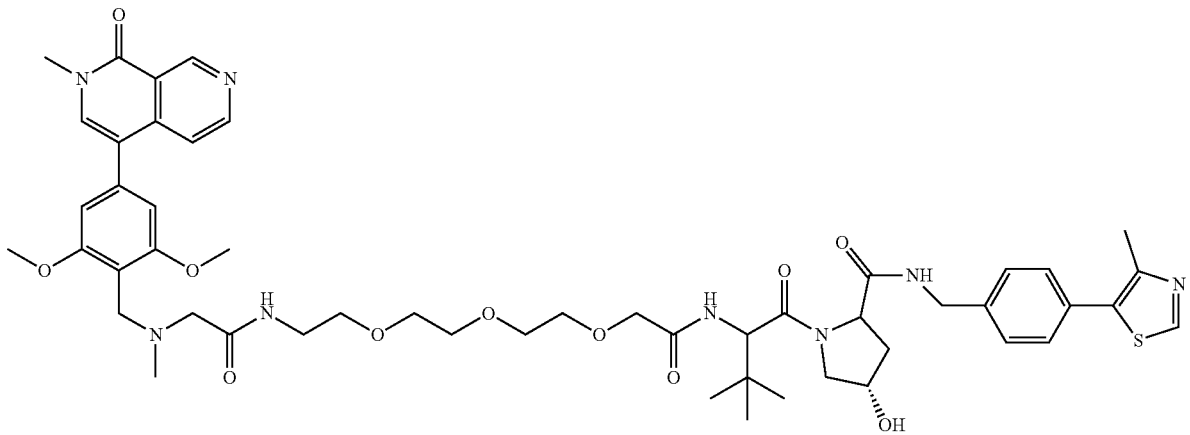

(2R,4S)-1-((R)-14-Amino-2-(tert-butyl)-4-oxo-6,9,12-trioxa-3-azatetradecan-1-oyl)-4-hydroxy-N-(4-(4-methyl-thiazol-5-yl)benzyl)pyrrolidine-2-carboxamide trifluoroacetate salt (0.02 mmol, 1 eq) was added to 2-((2,6-dimethoxy-4-(2-methyl-1-oxo-1,2-dihydro-2,7-naphthyridin-4-yl)benzyl)(methyl)amino)acetic acid trifluoroacetate salt (10.2 mg, 0.02 mmol, 1 1.0 eq) as a 0.1 M solution in DMF (200 microliters), DIPEA (10.4 microliters, 0.060 mmol, 3.0 eq) was added followed by PyBOP (11.4 mg, 0.022 mmol, 1.1 eq). After 7 hours, the reaction was incomplete and an additional 3 eq DIPEA and 0.5 eq PyBOP were added. After 14 hours, the reaction was diluted to 10 mL with EtOAc, washed once with a mildly basified ($Na_2CO_3$) 1:1 solution of deionized water and saturated brine (2 milliliters), washed three times with deionized water (2 milliliters), and once with saturated brine (2 milliliters) before drying over $Na_2SO_4$ and concentrating in vacuo. The residue was dissolved in 0.5 mL DCM and purified by silica chromatography (DCM/MeOH 0 to 10% gradient) to afford I-23 as a colorless solid (6.23, 31%).

$^1$H NMR (500 MHz, methanol-$d_4$) δ=9.50 (s, 1H), 8.86 (s, 1H), 8.66 (d, J=5.8, 1H), 7.73 (s, 1H), 7.61 (d, J=5.8, 1H), 7.45-7.42 (m, 2H), 7.39 (d, J=8.3, 2H), 6.75 (s, 2H), 4.68 (s, 1H), 4.61-4.48 (m, 4H), 4.34 (d, J=15.5, 1H), 4.00 (d, J=5.7, 2H), 3.89 (s, 6H), 3.87 (s, 2H), 3.69 (s, 3H), 3.67 (d, J=4.9, 2H), 3.62 (d, J=2.3, 3H), 3.56 (d, J=1.3, 1H), 3.53 (t, J=5.1, 2H), 3.40 (t, J=5.2, 2H), 3.25 (s, 2H), 2.45 (s, 3H), 2.41 (s, 2H), 2.23 (dd, J=11.5, 7.7, 1H), 2.11-2.05 (m, 1H), 1.96 (s, 1H), 1.94 (s, 3H), 1.02 (s, 9H). LCMS:1000 (M+H).

Compound I-24

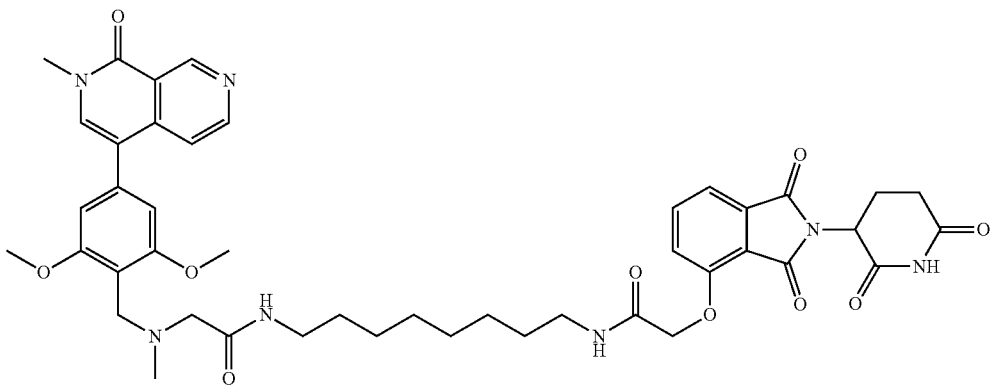

N-(8-Aminooctyl)-2-((2-(2,6-dioxopiperidin-3-yl)-1,3-dioxoisoindolin-4-yl)oxy)acetamide trifluoroacetate salt (0.02 mmol, 1 eq) was added to 2-((2,6-dimethoxy-4-(2-methyl-1-oxo-1,2-dihydro-2,7-naphthyridin-4-yl)benzyl)(methyl)amino)acetic acid trifluoroacetate salt (10.2 mg, 0.02 mmol, 1 1.0 eq) as a 0.1 M solution in DMF (200 microliters), DIPEA (10.4 microliters, 0.060 mmol, 3.0 eq) was added followed by PyBOP (11.4 mg, 0.022 mmol, 1.1 eq). After 16 hours the reaction was diluted to 10 mL with EtOAc, washed once with a mildly basified ($Na_2CO_3$) 1:1 solution of deionized water and saturated brine (2 milliliters), washed three times with deionized water (2 milliliters), and finally with saturated brine (2 milliliters) before drying over $Na_2SO_4$ and concentrating in vacuo. The residue was dissolved in 0.5 mL DCM and purified by silica chromatography (DCM/MeOH 5 to 10% gradient) to afford I-24 as a colorless solid (6.85 mg, 41%).

Figure 9A:
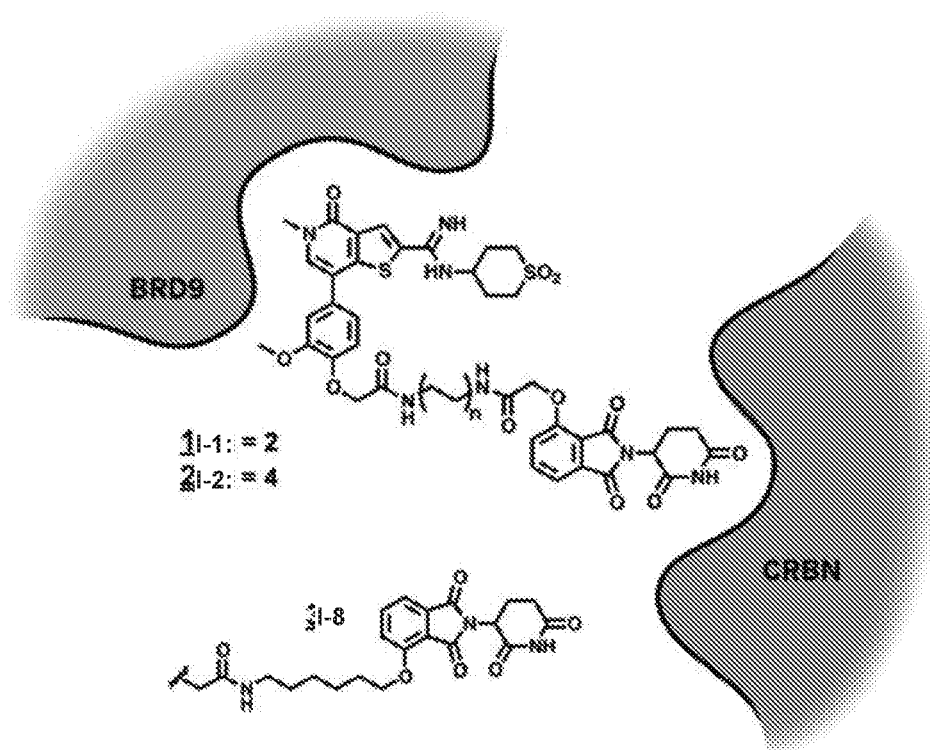
FIG. 9A is a schematic representation of the degrader design based on the compound's interaction with the CRBN protein and the BRD9 protein.
Figure 9B:
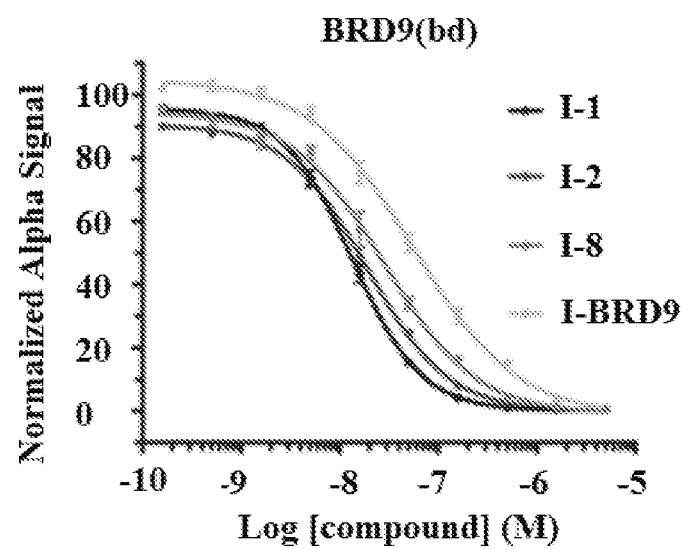
FIG. 9B is a dose-response curve comparing I-1, I-2, and I-8 in a BRD9-ligand displacement assay to determine selectivity for BRD9. The small molecule I-BRD9, a BRD9 inhibitor, was used as a control. The x-axis is the compound concentration measured in log units and the y-axis is the normalized alpha signal measured in intensity.

$^1$H NMR (500 MHz, methanol-$d_4$) δ=9.46 (s, 1H), 8.65 (d, J=5.8, 1H), 7.78 (dd, J=8.4, 7.4, 1H), 7.73 (s, 1H), 7.61 (d, J=5.7, 1H), 7.50 (d, J=7.2, 1H), 7.38 (d, J=8.4, 1H), 6.78 (s, 2H), 5.11 (dd, J=12.6, 5.5, 1H), 4.70 (s, 2H), 4.09 (s, 2H), 3.91 (s, 6H), 3.66 (s, 3H), 3.46 (s, 2H), 3.27-3.17 (m, 5H), 2.91-2.82 (m, 1H), 2.76-2.65 (m, 2H), 2.60 (s, 3H), 2.16-2.08 (m, 1H), 1.53-1.43 (m, 5H), 1.28 (s, 10H). LCMS: 838 (M+H).

over BRD4. Compound I-25 offered improved selectivity against BRD4. FIG. 9B is a graph comparing I-1, I-2, and I-8 in a BRD9-ligand displacement assay to determine activity Compound I-25

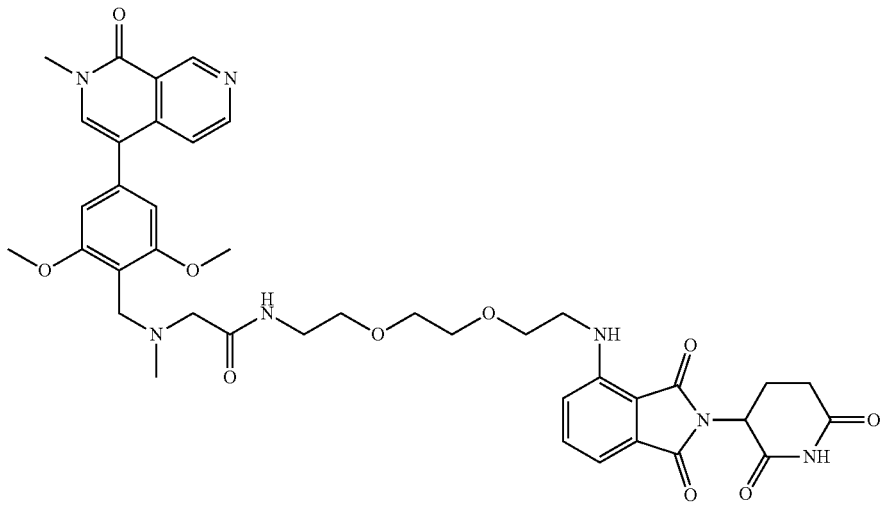

4-((2-(2-(2-Aminoethoxy)ethoxy)ethyl)amino)-2-(2,6-dioxopiperidin-3-yl)isoindoline-1,3-dione trifluoroacetate salt (0.02 mmol, 1 eq) was added to 2-((2,6-dimethoxy-4-(2-methyl-1-oxo-1,2-dihydro-2,7-naphthyridin-4-yl)benzyl)(methyl)amino)acetic acid trifluoroacetate salt (10.2 mg, 0.02 mmol, 1 1.0 eq) as a 0.1 M solution in DMF (200 microliters), DIPEA (10.4 microliters, 0.060 mmol, 3.0 eq) was added followed by PyBOP (11.4 mg, 0.022 mmol, 1.1 eq). After 16 hours the reaction was found incomplete and an additional 3.0 eq DIPEA and 0.5 eq PyBOP was added. After 24 hour the reaction was diluted to 10 mL with EtOAc, washed once with a mildly basified ($Na_2CO_3$) 1:1 solution of deionized water and saturated brine (2 milliliters), washed three times with deionized water (2 milliliters), and finally with saturated brine (2 milliliters) before drying over $Na_2SO_4$ and concentrating in vacuo. The residue was dissolved in 0.5 mL DCM and purified by silica chromatography (DCM/MeOH 5 to 20% gradient) to afford I-25 as a yellow solid (4.9 mg, 31%).

$^1$H NMR (500 MHz, methanol-$d_4$) δ=9.52 (s, 1H), 8.65 (d, J=6, 1, 1H), 8.30 (s, 1H), 7.96 (s, 1H), 7.83 (d, J=6.2, 1H), 7.52-7.41 (m, 1H), 7.00 (d, J=8.1, 2H), 6.81 (s, 2H), 4.99 (dd, J=12.5, 5.3, 1H), 4.50 (d, J=4.8, 2H), 3.96 (s, 1H), 3.94 (s, 6H), 3.87 (s, 2H), 3.70 (s, 3H), 3.70-3.60 (m, 6H), 3.56 (q, J=4.8, 2H), 3.47-3.32 (m, 4H), 2.92 (s, 3H), 2.83 (ddd, J=19.0, 13.8, 5.3, 1H), 2.71 (d, J=17.6, 2H), 2.11-2.01 (m, 1H). LCMS: 784 (M+H).

Example 4. Biological Data from Ligand Displacement Assay

Figure 8A:
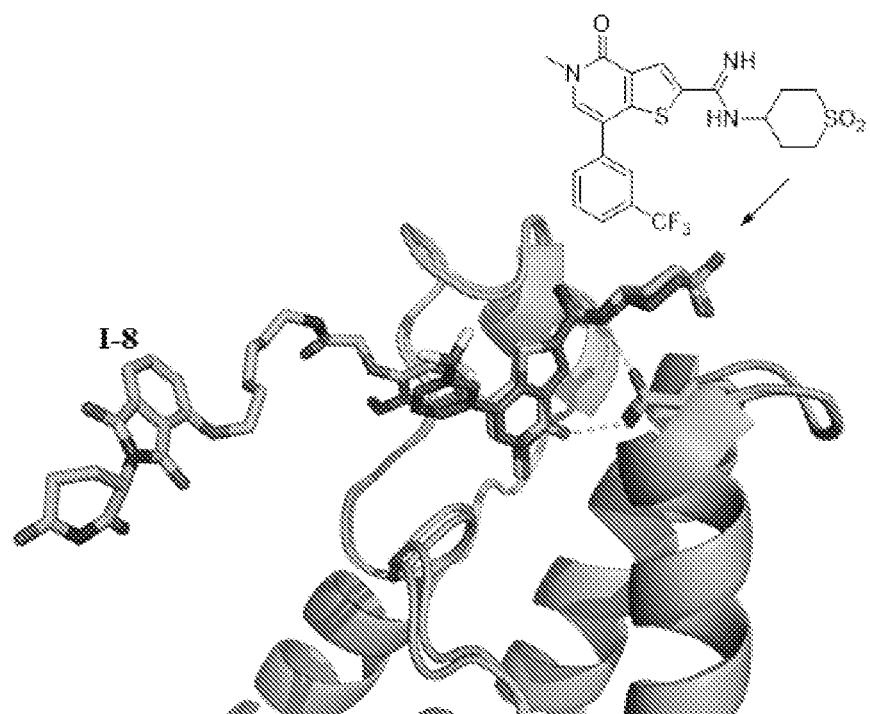
FIG. 8A is a high-resolution image showing compound I-8 overlaid with the crystal structure (PDB code 4UIV) of human BRD9 bromodomain with N-(1,1-dioxo-1-thian-4-yl)-5-methyl-4-oxo-7-3-(trifluoromethyl)phenyl-4H,5H-thieno-3,2-c-pyridine-2-carboximidamide, a small molecule with a structure similar to the bromodomain targeting ligand portion of I-8. The two compounds have significant overlap confirming that I-8 has a conserved binding mode relative to the free bromodomain targeting ligand with the derivatized methoxy position projected to solvent. Hydrogen bonding to the key Asp residue is highlighted.
Figure 8B:
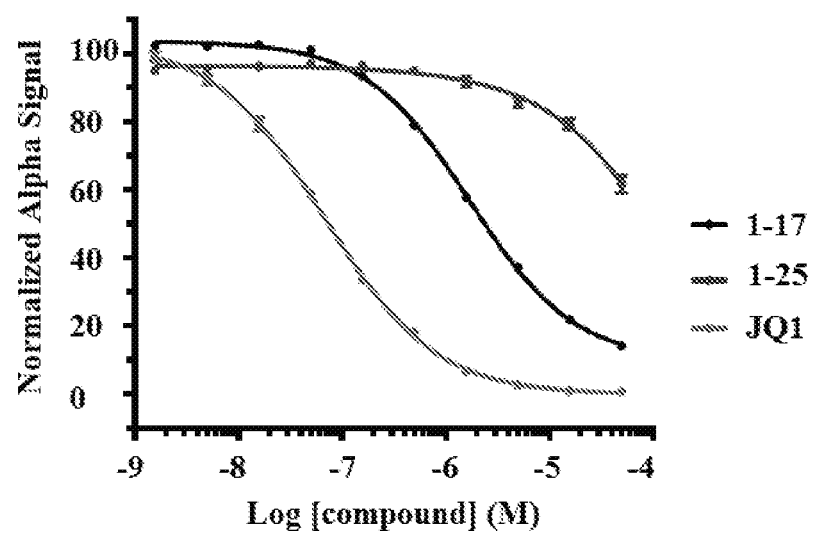
FIG. 8B is a dose-response curve comparing I-17 and I-25 in a BRD4-ligand displacement assay to determine selectivity against BRD4. The small molecule JQ1, a BRD4 inhibitor, was used as a control. Compound I-25, which exhibited less activity at BRD4 than I-17, has increased selectivity against BRD4 compared to I-17. The x-axis is the compound concentration measured in log units and the y-axis is the normalized alpha signal measured in intensity.

Selected compounds were tested in a BRD9-ligand displacement assay, a BRD9-ligand displacement assay, and a purified CRBN-DDB1-ligand displacement assay. $IC_{50}$ values at each protein are given in Table D. The experimental procedures for the BRD9- and BRD4-ligand displacement assays are given in Example 10 and the procedure for the CRBN-DDB 1 displacement assay is given in Example 11. FIG. 8B is a graph comparing I-17 and 1-25 in a BRD4-ligand displacement assay to determine selectivity for BRD9 over BRD4. Compound I-25 offered improved selectivity against BRD4. FIG. 9B is a graph comparing I-1, I-2, and I-8 in a BRD9-ligand displacement assay to determine activity of these compounds at BRD9. As shown in Table D, high BRD9 affinity was retained across all compounds of this series relative to the parental bromodomain ligand, as exemplified by $IC_{50}$ values for compounds I-1, I-2 and I-8. Moderate differences were observed in CRBN-DDB1 affinity between compounds implementing various phthalimide linkages. For example, the direct alkyl ether phthalimide linkage of I-8 showed slightly improved binding over acetamide ethers I-1 and I-2. The effect of linker rigidity was studied by installing a conformationally constrained bi-piperidine-linker in compound I-7. This molecule showed significant improvement in both dimerization (Table E) and cellular potency (Table D). To study the ability of alternate E3 ligases to degrade BRD9, the VHL-ligand conjugates I-13 and I-14 were prepared, however, these were found to be ineffective.

Figure 12A:
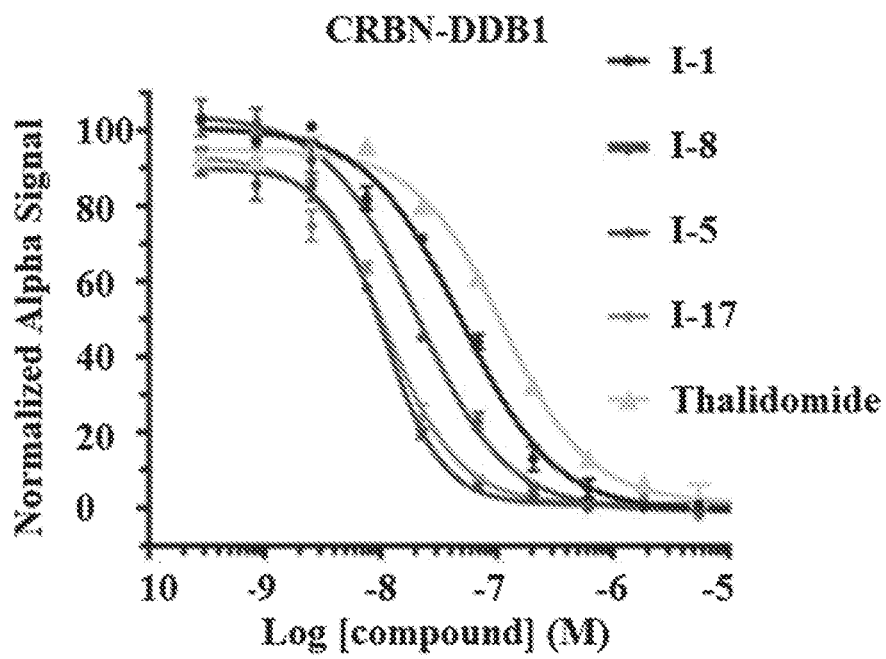
FIG. 12A is a dose-response curve measuring the formation of the BRD9:CRBN-DDB 1 complex induced by I-1, I-8, I-5, and I-17 compared to unmodified thalidomide as detected by luminescence. The x-axis is compound concentration measured in log units and the y-axis is the normalized alpha signal measured in intensity.
Figure 12B:
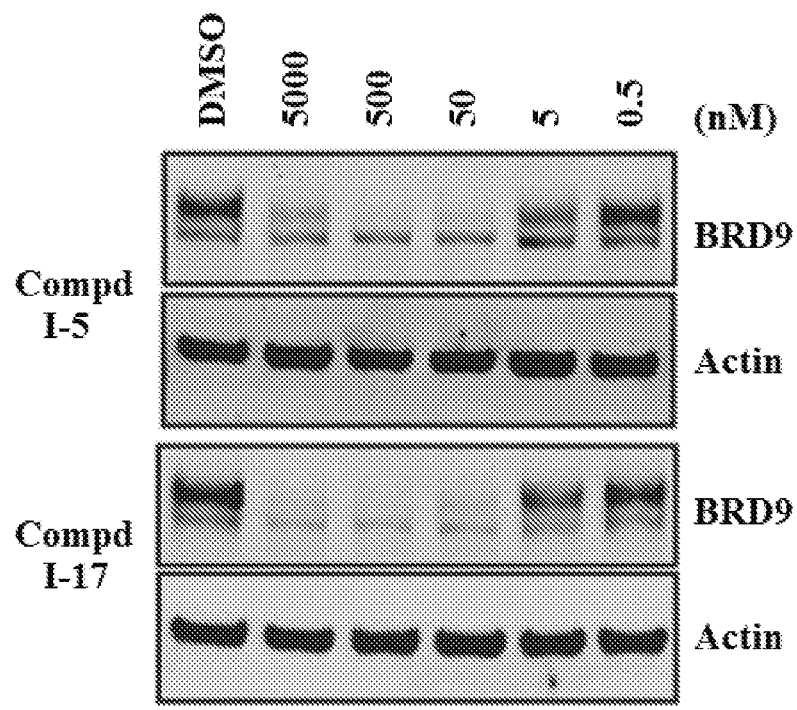
FIG. 12B are Western Blot images quantifying BRD9 and actin in a human AML-cell line (MOLM-13) by immunoblot after a 4 hour treatment with the indicated concentrations of compounds I-5 and I-17. Both compounds were able to effectively downregulate BRD9 over a broad range of concentrations.
Figure 13A:
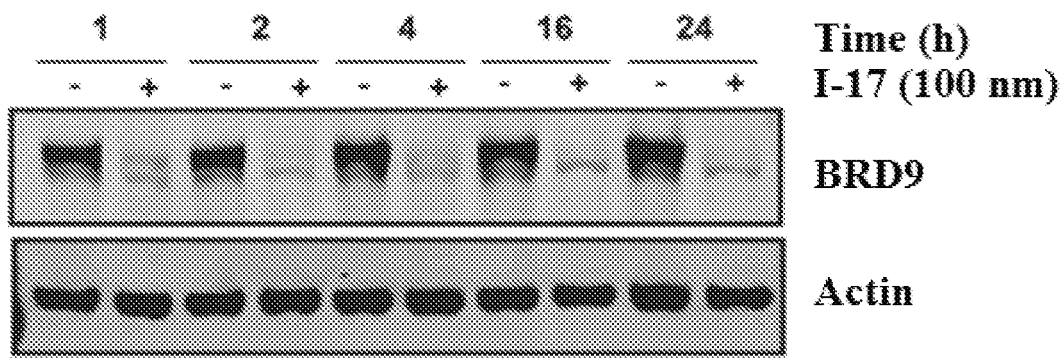
FIG. 13A is a Western Blog image quantifying BRD9 and actin in a human AML-cell line (MOLM-13) by immunoblot after 1, 2, 4, 16, and 24 hours with and without treatment of 100 nM of I-17 to assess the timecourse of degradation. Near complete BRD9 loss was observed within 1 hour of I-17 treatment, with no detectable return observed for the duration of the 24-hour treatment period. This profile is appropriate to enable study of primary consequences of acute BRD9 loss, as well as viability defects manifested over one or potentially more days.
Figure 13B:
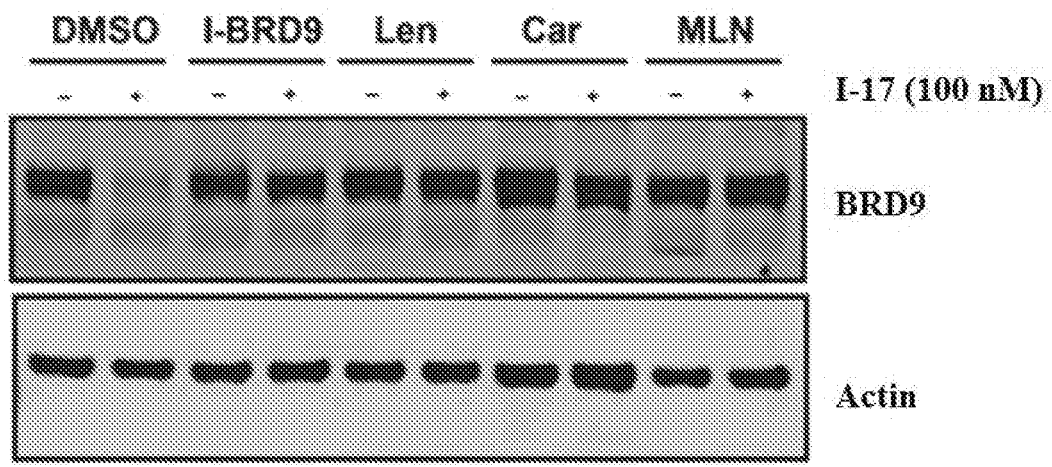
FIG. 13B is a Western Blot image quantifying BRD9 and actin in human multiple myeloma (MMIS) cells by immunoblot. The cell lines were pretreated for 4 hours with vehicle (DMSO), I-BRD9 (a BRD9 inhibitor), lenalidomide, carfilzomib (a protease inhibitor), and MLN-4924 (a neddylation inhibitor) before exposure to 100 nM of I-17 to validate the cellular mechanism of I-17. Pretreatment with excess I-BRD9 or lenalidomide competed with I-17 for binding to BRD9 or CRBN and prevented degradation, consistent with a requirement for intracellular engagement of both targets, Degradation was abolished by the co-treatment with the proteasome inhibitor carfilzomib, confirming a requirement for proteasome function. Pretreatment using a mechanism-based inhibitor of neddylation also rescued BRD9 levels, as expected given the requirement for neddylation of CRL E3 ligases for activity.
Figure 13C:
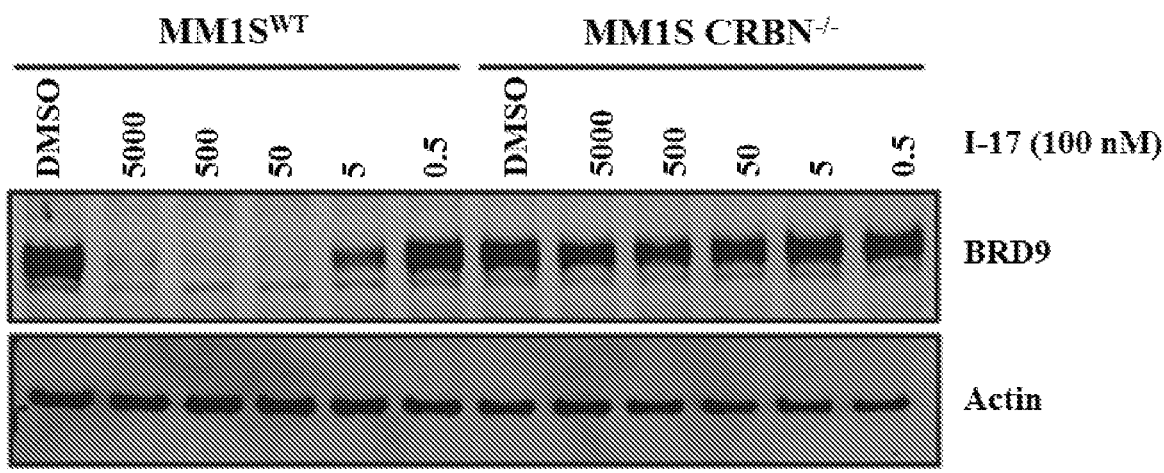
FIG. 13C is a Western Blot image quantifying BRD9 and actin in MM1S$^{WT}$ cells and isogenic MMIS CRBN knockout cells (genetically edited by CRISP/Cas9) by immunoblot after a 4 hour treatment with the indicated doses of I-17 to establish a requirement of CRBN in degrading BRD9. While treatment of wild type MM.1S cells resulted in marked dose-dependent BRD9 loss, treatment of the MM.1S CRBN knockout cell line resulted in little to no BRD9 degradation, providing support for CRBN-dependent proteasomal degradation of BRD9 by I-17.

Additional phthalimide-containing analogs explored substitution of the phenolic attachment as found in I-8 for the amine type linkages found in compounds I-9, I-5, and I-17. Compounds I-9 and I-17, substituted at the phthalimide ortho position, were superior in both biochemical dimerization (Table E) and cellular activity relative to I-9, a meta-linked derivative. These molecules showed high CRBN affinity, robust biochemical dimerization, and potent cellular activity (FIG. 12A and FIG. 12B). The lenalidomide-based analog I-17 showed the best overall performance, effectively downregulating BRD9 protein over a broad range of concentrations.

TABLE D

BRD9, BRD4, and purified CRBN-DDB1 Ligand Displacement Data

| Compd # | BRD9 $IC_{50}$ (nM) | BRD4 $IC_{50}$ (μM) | CRBN-DDB1 $IC_{50}$ (nM) |
|---|---|---|---|
| I-1 | 13.5 | 3.78 | 48.9 |
| I-2 | 18.9 | 3.39 | 43.7 |
| I-3 | 36.5 | 3.14 | 49.5 |
| I-8 | 30.0 | 7.00 | 20.1 |

TABLE D-continued

BRD9, BRD4, and purified CRBN-DDB1 Ligand Displacement Data

| Compd # | BRD9 IC$_{50}$ (nM) | BRD4 IC$_{50}$ (μM) | CRBN-DDB1 IC$_{50}$ (nM) |
|---|---|---|---|
| I-7 | 12.5 | 1.51 | 16.0 |
| I-13 | 26.9 | 1.56 | |
| I-14 | 22.7 | 1.69 | |
| I-9 | 11.5 | 1.11 | 17.6 |
| I-5 | 15.5 | 1.56 | 10.8 |
| I-17 | 12.3 | 1.71 | 11.2 |
| I-12 | 56.6 | >50 μM | 8.50 |
| I-15 | 83.1 | >50 μM | 8.35 |
| I-23 | 43.2 | >50 μM | |
| I-24 | 48.0 | >50 μM | 14.8 |
| I-25 | 104 | >50 μM | 31.3 |

Example 5. Biological Data from BRD9:CRBN-DDB1 Dimerization Assay

To elicit protein degradation, bifunctional molecules must be able to efficiently associate the E3 ligase with the target. To measure this activity, a homogenous luminescence assay was developed to report on compound-induced proximity of BRD9 and CRBN. This ternary interaction exhibited a characteristic auto-inhibitory concentration dependence consistent with bimolecular interactions dominating at saturating ligand concentrations (see Douglass et al. *JACS* 2013, 135, 6092). Across a range of concentrations, the eight-carbon linked analog I-2 demonstrated improved dimerization relative to the short four-carbon linked compound I-1. While a further extended triethyleneglycol-containing analog I-3 reduced this activity, the intermediate length alkyl ether analog I-8 showed further improved dimerization relative to compound I-2.

While I-17 was able to effectively induce biochemical association of CRBN-DDB1 with either BRD9 or BRD4, compound I-25 lost all ability to dimerize BRD4 with CRBN-DDBI above background levels, but retained robust dimerization of BRD9.

Dimerization data was collected using luminescence detection, and the AUC and C$_{max}$ values from the luminescence detection of the BRD9-DDB1 protein complex are shown in Table E. FIGS. 1A, 1B, 1C, 2A, 2B, 2C, 3A, 3B, 3C, 4A, 4B, and 4C are dose response curves of luminescence detection of the BRD9:CRBN-DDB1 protein complex exposed to decreasing concentrations of the compounds in Table E compared to unmodified thalidomide. All of the tested bifunctional compounds were able to significantly induce proximity of the BRD9 bromodomain and CRBN-DDBI relative to unmodified thalidomide: an activity subsequently referred to simply as "dimerization" (experimental details are provided in Example 12).

TABLE E

AUC and C$_{max}$ values measured from luminescence detection of dimerization assay

| Compd # | BRD9:CRB9-DDB1 AUC (nm) | BRD9:CRB9-DDB1 C$_{max}$ (nM) |
|---|---|---|
| I-1 | 44270 | 42.5 |
| I-2 | 71477 | 95.1 |
| I-3 | 50182 | 44.9 |
| I-8 | 144813 | 111 |

TABLE E-continued

AUC and C$_{max}$ values measured from luminescence detection of dimerization assay

| Compd # | BRD9:CRB9-DDB1 AUC (nm) | BRD9:CRB9-DDB1 C$_{max}$ (nM) |
|---|---|---|
| I-7 | 107794 | 54.0 |
| I-9 | 46614 | 33.7 |
| I-5 | 67227 | 37.4 |
| I-17 | 80620 | 26.2 |
| I-12 | 60256 | 8.39 |
| I-15 | 139380 | 8.22 |
| I-24 | 58563 | 27.3 |
| I-25 | 188320 | 92.9 |

Example 6. Single-Point Screening of Compound I-17 and Compound I-25 at 1 μM Using BromoScan Compound I-17 and I-25 were further characterized by obtaining their biochemical selectivity profile among 32 representative members of the human bromodomain family by conducting a BromoScan. The BromoScan is an assay that measures the engagement of compounds with bromodomain proteins by utilizing DNA-tagged bromodomain and immobilized ligand attached to solid support. In the control test, DNA-tagged bromodomain binds to the ligand and the bromodomain is captured on the solid support. Compounds that compete for the bromodomain binding location on the ligand will prevent the bromodomain from binding, resulting in less protein captured on the solid support. Table F is the percent of protein captured on the solid support during a test run with 1.0 μM of compound compared to the control where 10(0% of protein would be captured on the solid support.

Figure 14A:
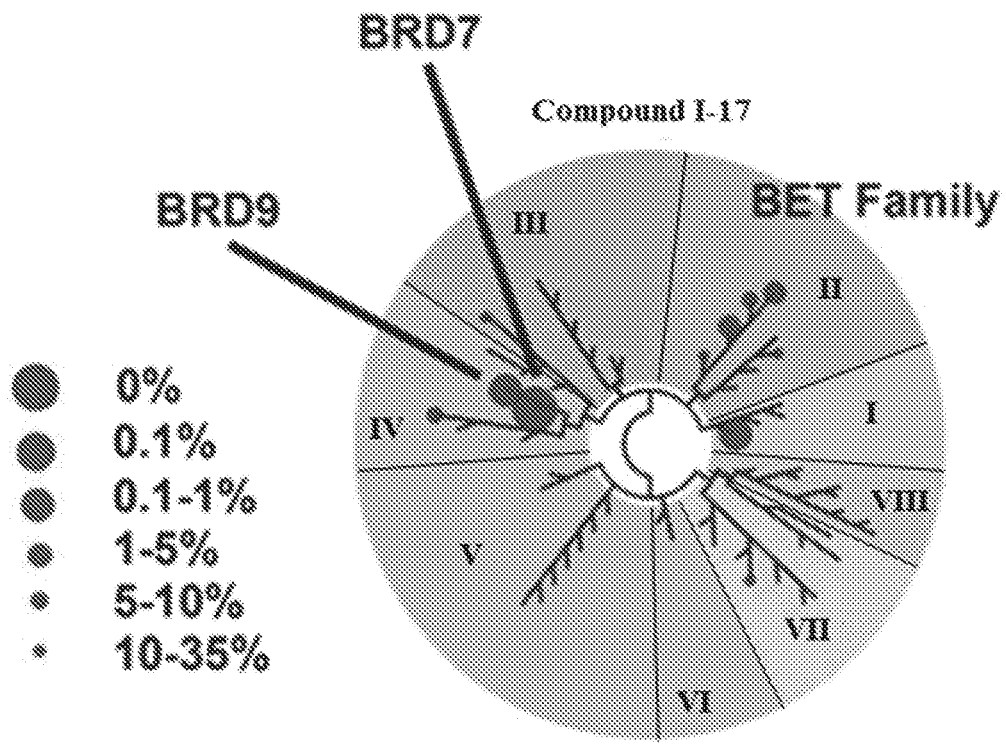
FIG. 14A is a dendrogram of the human bromodomain family organized into eight subfamilies. A single-point screen of I-17 at 32 members of the bromodomain family was conducted using BromoScan (experimental details are given in Example 6). The circles with corresponding percentages represent the percentage of bromodomain isolated on the solid support compared to control during the BromoScan. A control test without I-17 would result in 100% of broodomain on the solid support. Compound I-17 not only interacts with BRD9 as represented in the dendrogram, but also BRD7 and members of the BET family.
Figure 14B:
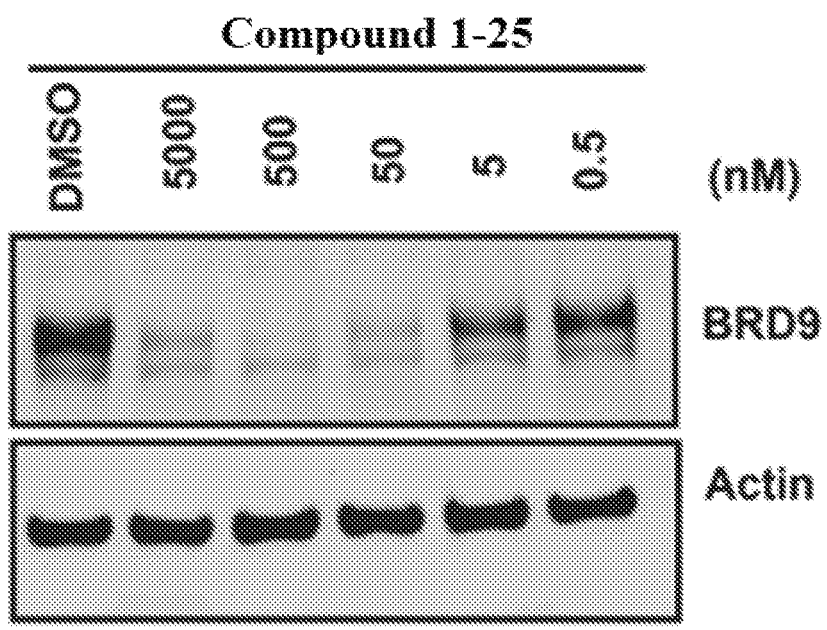
FIG. 14B are Western Blot images quantifying BRD9 and actin in a human AML-cell line (MOLM-13) by immunoblot after a 4 hour treatment with the indicated concentrations of compound I-25. Compound I-25 induced BRD9 degradation over a broad range of concentrations.
Figure 15A:
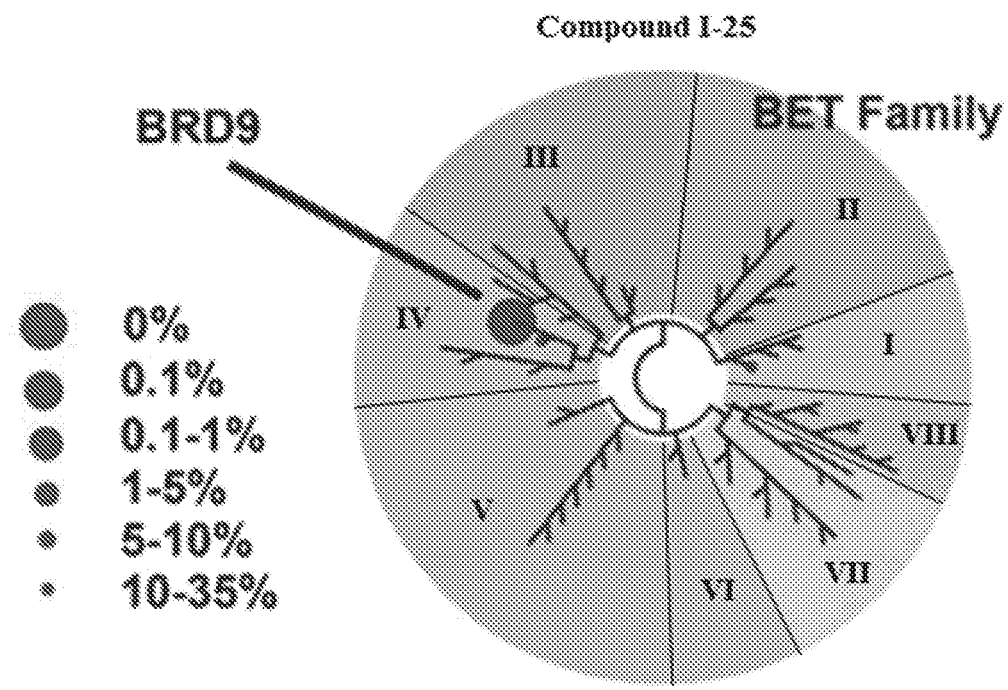
FIG. 15A is a dendrogram of the human bromodomain family organized into eight subfamilies. A single-point screen of I-25 at 32 members of the bromodomain family was conducted using BromoScan (experimental details are given in Example 6). The circles with corresponding percentages represent the percentage of bromodomain isolated on the solid support compared to control during the BromoScan. A control test without I-25 would result in 100% of broodomain on the solid support. Compound I-25 exclusively interacts with BRD9.

While the results of this analysis confirmed potent engagement of BRD9, it also revealed a number of significant off-target activities. FIG. 14A is a dendrogram of the human bromodomain family organized into eight subfamilies highlighting proteins that interacted with I-17. Compound I-17 not only interacts with BRD9 as represented in the dendrogram, but also BRD7 and members of the BET family. The novel bromodomain probe I-25 offers improved selectivity over the BET bromodomains relative to the thienopyridinone scaffold featured in I-17. FIG. 15A is a dendrogram of the human bromodomain family of I-25, showing its exclusive interaction with BRD9.

TABLE F

Effect on 1 μM of Compound I-17 and I-25 on human bromodomain family members

| Target Gene Symbol | % Ctrl @ 1 μM I-17 | % Ctrl @ 1 μM I-25 |
|---|---|---|
| ATAD2A | 100 | 94 |
| ATAD2B | 60 | 81 |
| BAZ$^2$A | 42 | 62 |
| BAZ$^2$B | 74 | 75 |
| BRD1 | 42 | 75 |
| BRD2(1) | 4 | 81 |
| BRD2(2) | 43 | 93 |
| BRD3(1) | 5 | 87 |
| BRD3(2) | 19 | 85 |
| BRD4(1) | 1.8 | 82 |
| BRD4(2) | 40 | 76 |
| BRD7 | 0 | 25 |

TABLE F-continued

Effect on 1 µM of Compound I-17 and I-25 on human bromodomain family members

| Target Gene Symbol | % Ctrl @ 1 µM I-17 | % Ctrl @ 1 µM I-25 |
|---|---|---|
| BRD9 | 0.25 | 0 |
| BRDT(1) | 18 | 90 |
| BRDT(2) | 57 | 83 |
| BRPF1 | 7.6 | 75 |
| BRPF3 | 85 | 86 |
| CECR2 | 0.15 | 14 |
| CREBBP | 10 | 88 |
| EP300 | 37 | 88 |
| FALZ | 60 | 79 |
| GCN5L2 | 62 | 77 |
| PBRM1(2) | 68 | 79 |
| PBRM1(5) | 71 | 89 |
| PCAF | 55 | 67 |
| SMARCA2 | 68 | 70 |
| SMARCA4 | 41 | 57 |
| TAF1(2) | 19 | 63 |
| TAF1L(2) | 54 | 80 |
| TRIM24 (PHD, Bromo.) | 84 | 98 |
| TRIM33 (PHD, Bromo.) | 100 | 100 |
| WDR9(2) | 83 | 86 |

Example 7. BRD9(Bd) Protein Purification

A construct of human BRD9 covering residues 134-0245 in the pET28PP vector was overexpressed in *E. coli* BL21 (DE3) in LB medium in the presence of 50 mg/ml of kanamycin. Cells were grown at 37° C. to an OD of 0.8, cooled to 17° C., induced with 500 µM isopropyl-1-thio-D-galactopyranoside, incubated overnight at 17° C., collected by centrifugation, and stored at −80° C. Cell pellets were sonicated in buffer A (50 mM hepes 7.5, 300 mM NaCl, 10% glycerol, 10 mM Imidazole, and 3 mM BME) and the resulting lysate was centrifuged at 30,000×g for 40 min. Ni-NTA beads (Qiagen) were mixed with lysate supernatant for 30 min and washed with buffer A. Beads were transferred to an FPLC-compatible column and the bound protein was washed with 15% buffer B (50 mM hepes 7.5, 300 mM NaCl, 10% glycerol, 300 mM Imidazole, and 3 mM BME) and eluted with 100% buffer B. HRV-3C was added to the eluted protein and incubated at 4° C. overnight. The eluant was concentrated and passed through a Superdex-75 10/300GL column (GE healthcare) in the following buffer: 20 mM HEPES-7.5, 200 mM NaCl, 5% glycerol, 2 mM DTT, and 1 mM TCEP. Fractions were pooled, concentrated to 15 mg/ml, and frozen at −80° C.

Example 8. BRD9 Crystallization

Figure 10A:
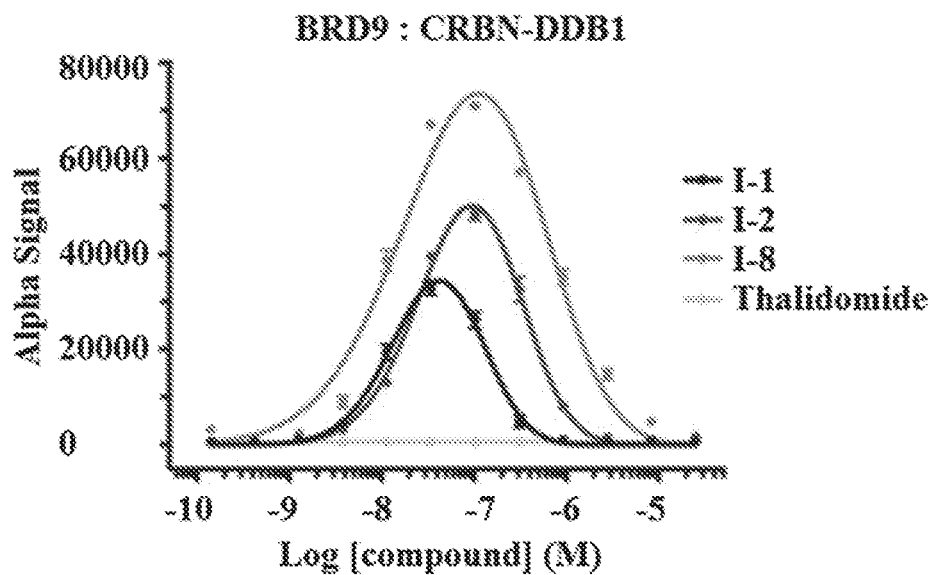
FIG. 10A is a graph measuring the formation of the BRD9:CRBN-DDBI protein complex induced by compounds I-1, I-2, I-8, and unmodified thalidomide as detected by luminescence. The luminescence signal was measured as the concentration of the compounds was decreased. All of the compounds were able to significantly induce formation of the complex relative to unmodified thalidomide. The x-axis is compound concentration measured in log units and the y-axis is the alpha signal measured in intensity.
Figure 10B:
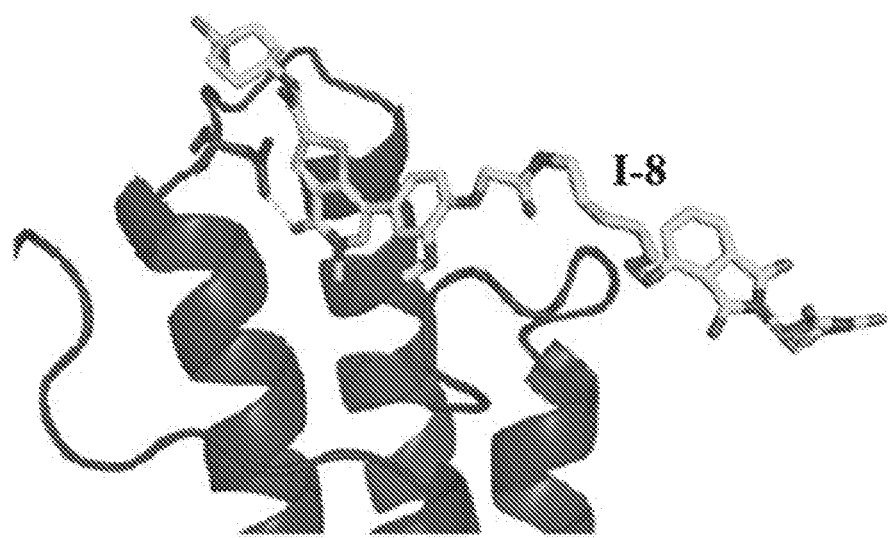
FIG. 10B is an image of compound I-8 crystallized with the BRD9 protein.
Figure 11A:
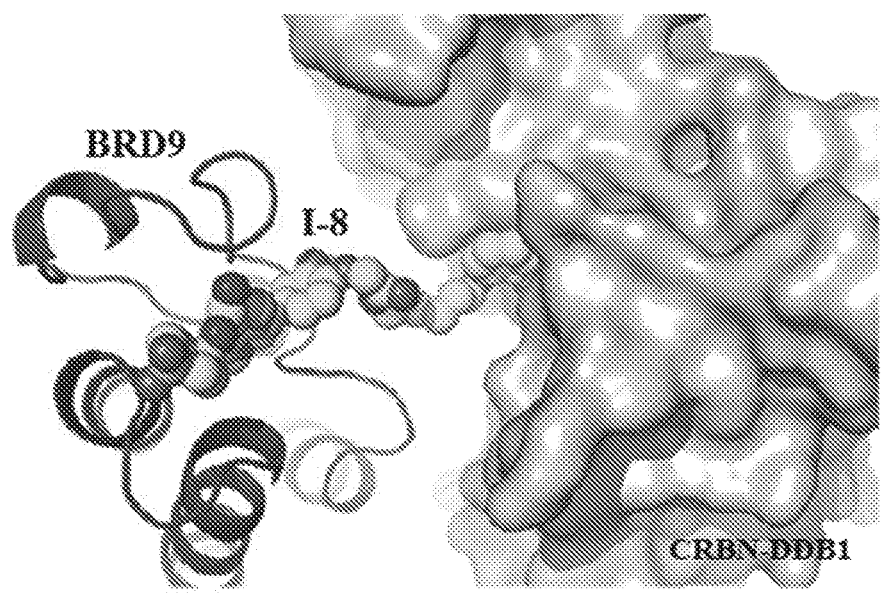
FIG. 11A is an in-silico model of the assembly of the CRBN-DDB1 and BRD9 ligand-binding domains induced by compound I-8. The ternary assembly, including CRBN-DDBI demonstrated the steric feasibility of ternary formation, with the two ligand-binding domains brought into close assembly by I-8. The crystal structure of I-8 with BRD9 (FIG. 10B) was docked into the published structure of CRBN-DDB1.
Figure 11B:
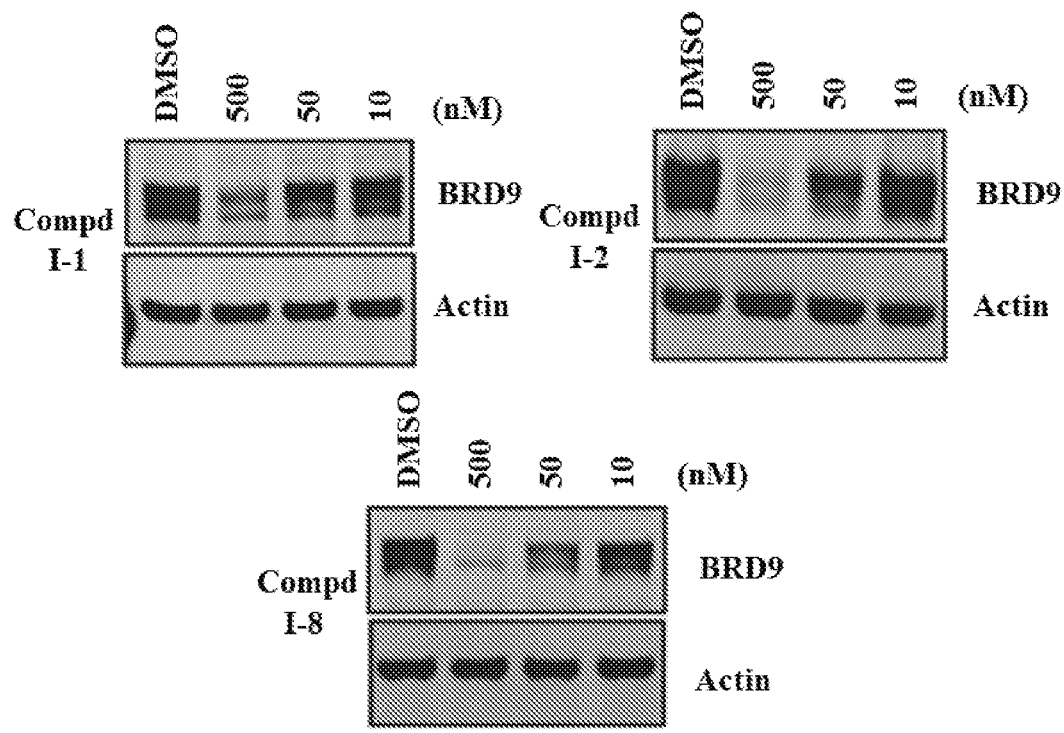
FIG. 11B are Western Blot images quantifying BRD9 and actin in a human AML-cell line (MOLM-13) by immunoblot after a 4 hour treatment with the indicated concentrations of compounds I-1, I-2, or I-8. Marked protein loss was observed at high concentrations of the potent dimerizers I-2 and I-8.

A solution containing 600 µM dBRD9-8 (from a 100 mM DMSO stock) and 500 µM protein was crystallized by sitting-drop vapor diffusion at 20° C. in the following crystallization buffer: 20% PEG3350 and 0.2 NH4F. Crystals were transferred briefly into crystallization buffer containing 25% glycerol prior to flash-freezing in liquid nitrogen. Diffraction data from complex crystals were collected at beamline 241D-E of the NE-CAT at the Advanced Photon Source (Argonne National Laboratory), Data sets were integrated and scaled using XDS (W. Kabsch, *Acta Crystallographica* 2010, 66, 1-12). Structures were solved by molecular replacement using the program Phaser (J. McCoy, R. W. Grosse-Kunstleve, P, D. Adams, M, D. Winn, L. C. Storoni, R. J. Read, *J Appl Crystallogr* 2007, 40, 658-674). and the search model PDB entry 4UIV. The ligand was positioned and preliminarily refined using Buster and Rhofit (O. S. Smart, T. O. Womack, C. Flensburg, P. Keller, W. Paciorek, A. Sharff, C. Vonrhein, G. Bricogne, *Acta Crystallogr, D Biol. Crystallogr.* 2012, 68, 368-380). Iterative manual model building and refinement using Phenix and Coot led to a model with excellent statistics (P, D. Adams, P. V. Afonine, G. Bunkóczi, V. B. Chen, I. W, Davis, N. Echols, J. J. Headd, L.-W. Hung, G. J. Kapral, R. W. Grosse-Kunstleve, et al., *Acta Crystallogr, D Biol. Crystallogr.* 2010, 66, 213-221; P. Emsley, K. Cowtan, IUCr, *Acta Crystallogr, D Biol. Crystallogr.* 2004, 60, 2126-2132). FIG. 10B is an image of compound I-8 crystallized with the BRD9 protein and FIG. 11A is the BRD9:I-8 crystal complex docked into the solved CRBN crystal structure.

Example 9. CRBN-DDB1 Expression and Purification

Expression and purification of CRBN-DDB1 were performed as described previously using Sf9 cells (Invitrogen) (E. S. Fischer, K. Böhm, J. R. Lydeard, H. Yang, M. B. Stadler, S. Cavadini, J. Nagel, F. Serluca, V. Acker, G. M. Lingaraju, et al., *Nature* 2014, 1-16).

Example 10. BRD9(Bd) & BRD4(1) Ligand-Displacement AlphaScreen

BRD9 assays were performed with minimal modifications from the manufacturer's protocol (PerkinElmer, USA). All reagents were diluted in 50 mM HEPES, 150 mM NaCl, 0.1% w/v BSA, 0.01% w/v Tween20, pH 7.5. A 2× solution of BRD9 towards a final concentration of 25 nM (see protein expression section), and 10-nM final biotin-probe (see synthetic procedures) was added at 10 ul/well to 384-well plates (Proxiplate-384 White, PerkinElmer, USA). Plates were spun down at 150×g, and 100 nL of DMSO compound stock was added from pre-diluted plates by pin transfer using a Janus Workstation (PerkinElmer, USA). Under low light, a 2× suspension of Ni-coated Acceptor Beads and Streptavidin Donor Beads, was then added at 10 ul/well to a final concentration of 5 µg/ml by EL406 automated liquid handler (Biotek, USA). The plates were spun down again at 150g, at room temperature for 1 hour and then read on an Envision 2104 (PerkinElmer, USA) using the manufacturer's protocol. (BRD4 assays were performed exactly as for BRD9 alphascreen, substituting protein and biotin-probe components for BRD4(1) protein at 20 nM final, and Biotin-JQ1 at 20 nM final. FIG. 8B is a graph of I-17 and I-25 in a BRD4-ligand displacement assay. FIG. 9B is a graph of I-1, I-2, and I-8 in a BRD9-ligand displacement assay. Control compounds for the BRD4-ligand displacement assay and the BRD9-ligand displacement assay are the BRD4 inhibitor JQ1 and the BRD9 targeting ligand 1-BRD9, respectively.

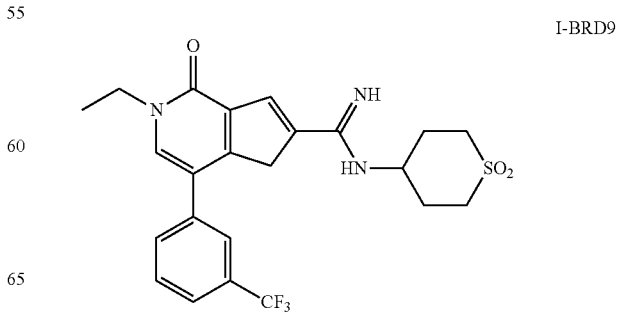

I-BRD9

-continued

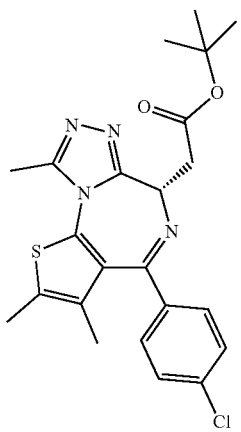

JQ1

Example 11. CRBN-DDB1 Ligand-Displacement AlphaScreen

In 384-well AlphaPlates (Perkin Elmer), 50 nM CRBN-DDB1 and 125 nM biotin-thalidomide were diluted in 20 uL assay buffer (50 mM HEPES pH 7.4, 200 mM NaCl, 1 mM TCEP, and 0.1% BSA) containing competitor compound or DMSO. Following a 30 min incubation, 20 uL detection solution containing Streptavidin Donor Beads and Nickel Chelate AlphaLISA® Acceptor Beads diluted to 20 ng/uL in assay buffer was added to each well. After 1 hr incubation at RT, luminescence was measured on the Envision 2104 plate reader, Data were analyzed using GraphPad PRISM v6.

Example 12. CRBN-DDB1/BRD4 Dimerization Assay

Figure 15B:
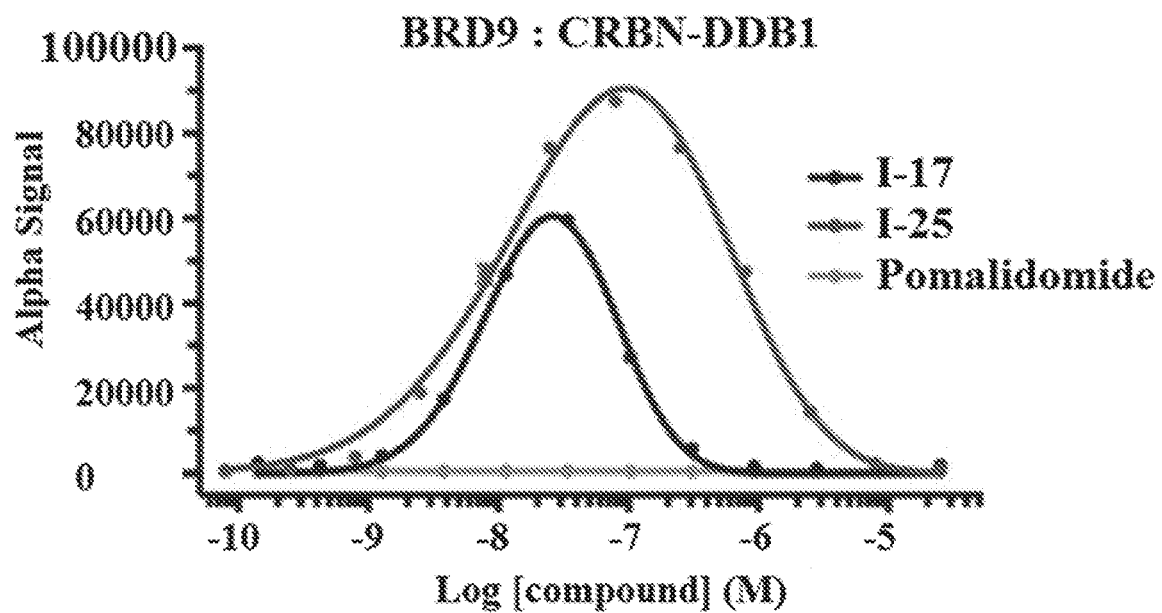
FIG. 15B is a graph measuring the formation of the BRD9:CRBN-DDBI protein complex induced by compounds I-17, I-25, and unmodified pomalidomide as detected by luminescence. The luminescence signal was measured as the concentration of the compounds was decreased. Compounds I-17 and I-25 were able to significantly induce formation of the complex relative to unmodified pomalidomide. The x-axis is compound concentration measured in log units and the y-axis is the alpha signal measured in intensity.
Figure 16A:
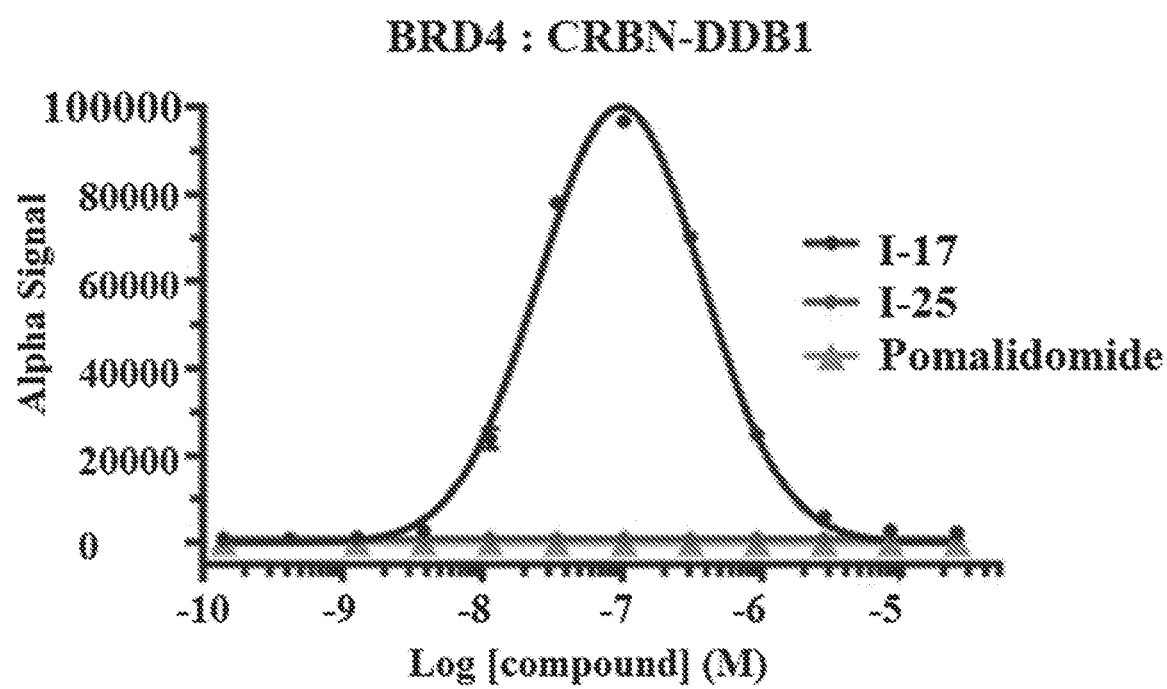
FIG. 16A is a graph measuring the formation of the BRD4:CRBN-DDBI protein complex induced by compounds I-17, I-25, and unmodified pomalidomide as detected by luminescence. The luminescence signal was measured as the concentration of the compounds was decreased. Compound I-25 exhibited selectivity for BRD9 and induced no formation of the BRD4:CRBN-DDBI protein complex. The x-axis is compound concentration measured in log units and the y-axis is the alpha signal measured in intensity.

To detect CRBN-DDBI/BRD4 dimerization, we adapted bead-based AlphaScreen technology. GST-BRD4 (2-170) was expressed and purified as previously described (M. Tanaka, J. M. Roberts, H.-S. Seo, A. Souza. J. Paulk, T. G. Scott, S. L, DeAngelo, S, Dhe-Paganon, J. E. Bradner, *Nature chemical biology* 2016, DOI 10.1038/nchembio.2209). In brief, GST-BRD4 and CRBN-DDBI were diluted to 125 nM, in assay buffer (50 mM HEPES pH 7.4, 200 mM NaCl, 0.01% Tween 20, and 0.1% BSA) and 20 μL of protein mixture was added to each well of a 384-well AlphaPlate (PerkinElmer). Compounds were then pinned at 100 nL per well from DMSO stock. After 1 incubation at room temperature. Nickel Chelate AlphaLISA Acceptor and Glutathione AlphaLISA Donor beads (PerkinElmer) were diluted in assay buffer to 20 μg/mL and added at 20 μl per well. Plates were incubated for 1 hour at room temperature prior to luminescence detection on an Envision 2104 plate reader (PerkinElmer), Data were analyzed using GraphPad PRISM v6. FIGS. 1A, 1B, 1C, 2A, 2B, 2C, 3A, 3B, 3C, 4A, 4B, and 4C are dose-response curves of formation of the BRD9:CRBN-DDBI protein following exposure to the compounds in Table E. FIG. 10A is a dose-response curve of BRD9:CRBN-DDB1 protein complex induced by I-1, I-2, and I-8. FIG. 12A is a dose-response curve of BRD9:CRBN-DDBI protein complex induced by I-1, I-8. I-5, and I-17. FIG. 15B is a dose-response curve of BRD9:CRBN-DDBI protein complex induced by I-17 and I-25, and FIG. 16A is a dose-response curve of BRD4:CRBN-DDB1 protein complex induced by I-17 and I-25

Example 13. ATPlite Viability Assay 500 cells/well were plated at a volume of 40 μL/well in white tissue culture treated 384 well assay plates (Thermo Scientific) before DMSO compound stock was added from pre-diluted plates by pin transfer using a Janus Workstation (PerkinElmer, USA). Plates were mixed for two minutes via plate shaker before 72 hour incubation. Assay plates were allowed to equilibrate to RT for 30 min before reconstituted ATPlite 1 Step reagent (Perkin Elmer) was dispensed at 1:1 volume/well by EL406 automated liquid handler (Biotek, USA). Plates were mixed for two minutes via plate shaker and incubated at room temperature an additional 10 minutes before being read on an Envision 2104 (PerkinElmer, USA) using the manufacturer's protocol. FIGS. 17B, 18A, 18B, and 19 are dose-response curves of the cell viability of human cell lines following treatment with I-17 and I-25. Additional compounds tested to compare against the activity of I-17 and I-25 are known and published BRD9 inhibitors BI-7273 and I-BRD9.

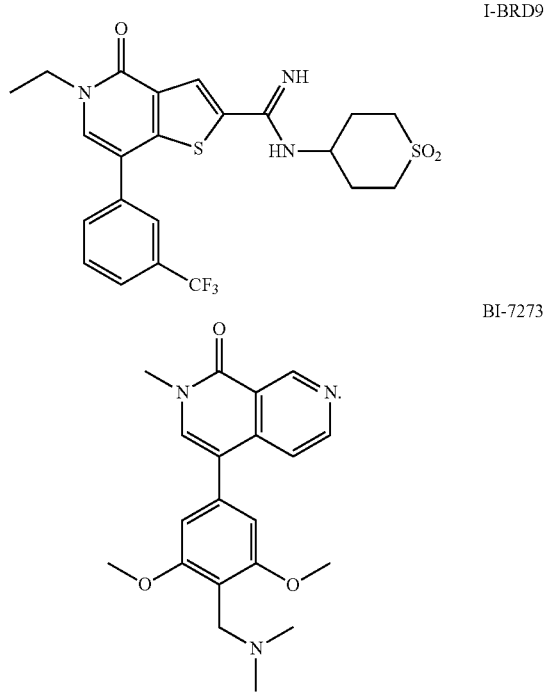

Figure 17A:
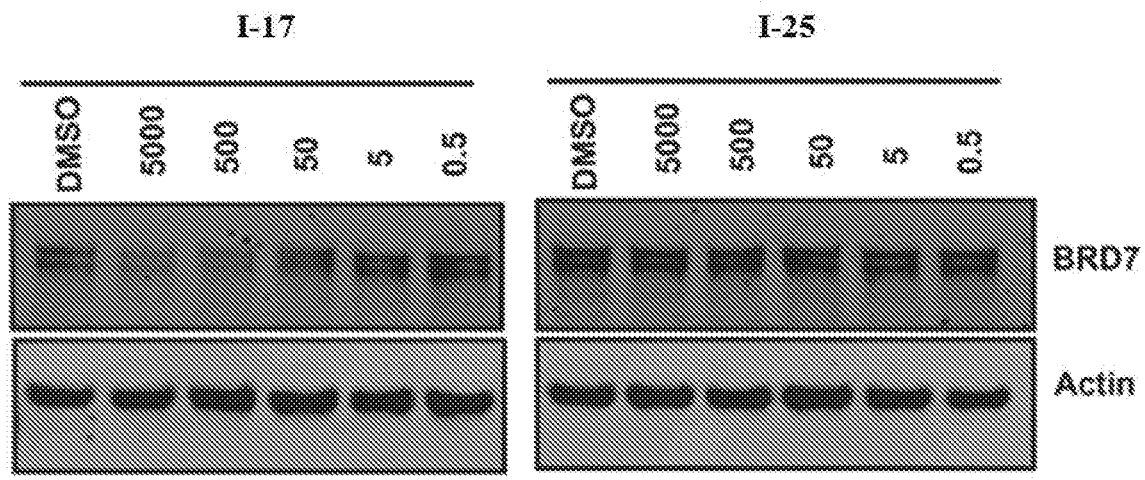
FIG. 17A are Western Blot images quantifying BRD7 and actin in a human AML-cell line (MOLM-13) by immunoblot after a 4 hour treatment with the indicated concentrations of compound I-17 and I-25. Compound I-25 was not able to induce degradation of BRD7 at any of the concentrations, but degradation was observed for I-17. Off target degradation of BRD7, observed at high concentrations of I-17, was no longer detectable for I-25, despite its potent activity on BRD9 levels.
Figure 17B:
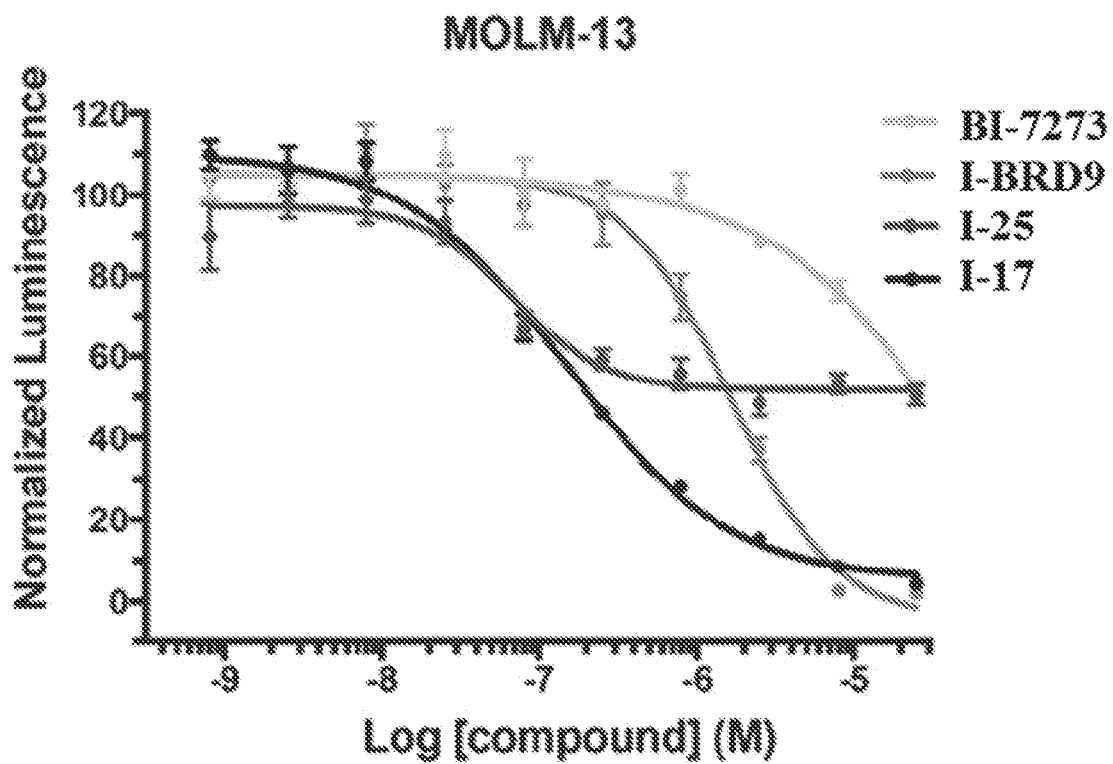
FIG. 17B is a dose-response curve of human AML (MOLM-13 cell line) cellular viability following 72 hour treatment with I-25 and I-17 compared to treatment with I-BRD9 and BI-7273, known BRD9 inhibitors. The x-axis is compound concentration measured in log units and the y-axis is normalized luminescence measured in intensity.
Figure 18A:
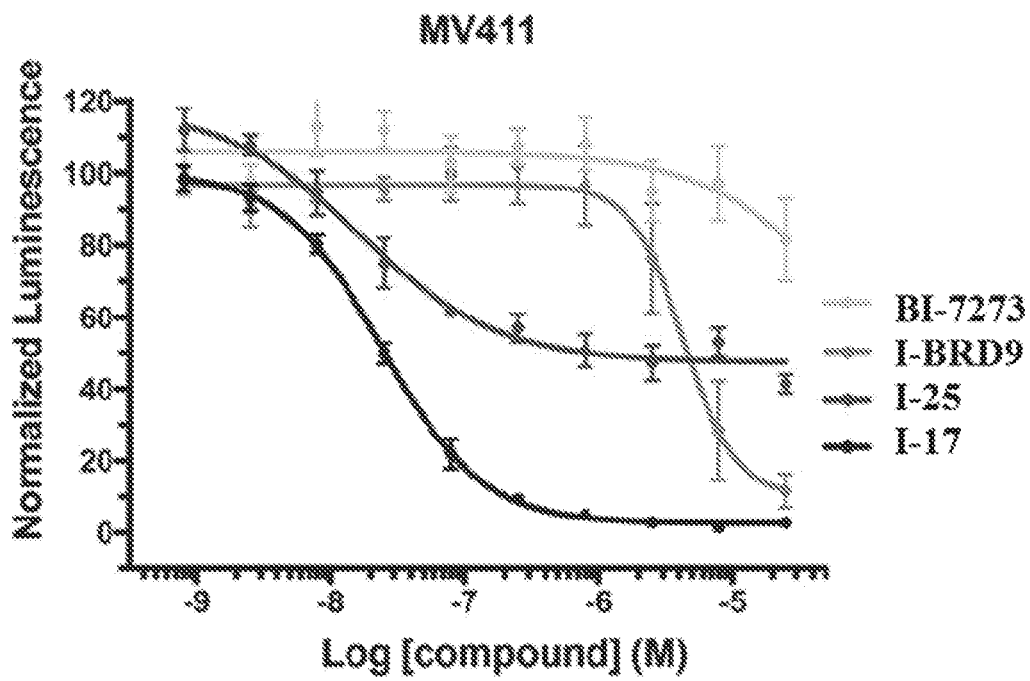
FIG. 18A is a dose-response curve of human AML (MV411 cell line) cellular viability following 72 hour treatment with I-25 and I-17 compared to treatment with I-BRD9 and BI-7273, known BRD9 inhibitors. The x-axis is compound concentration measured in log units and the y-axis is normalized luminescence measured in intensity. Experimental details are given in Example 13.

In the context of human AML lines (MOLM-13, MV4; 11), both compound I-17 and I-25 showed a potent effect on cell proliferation at 72 hours, exceeding corresponding probe potencies in excesses of 10 to 100 fold (FIG. 17B and FIG. 18A). Although the two compounds showed comparable low nanomolar half-maximal anti-proliferative concentrations, the maximal efficacy of I-17 significantly exceeded that of the more selective I-25 in both AML lines.

Figure 18B:
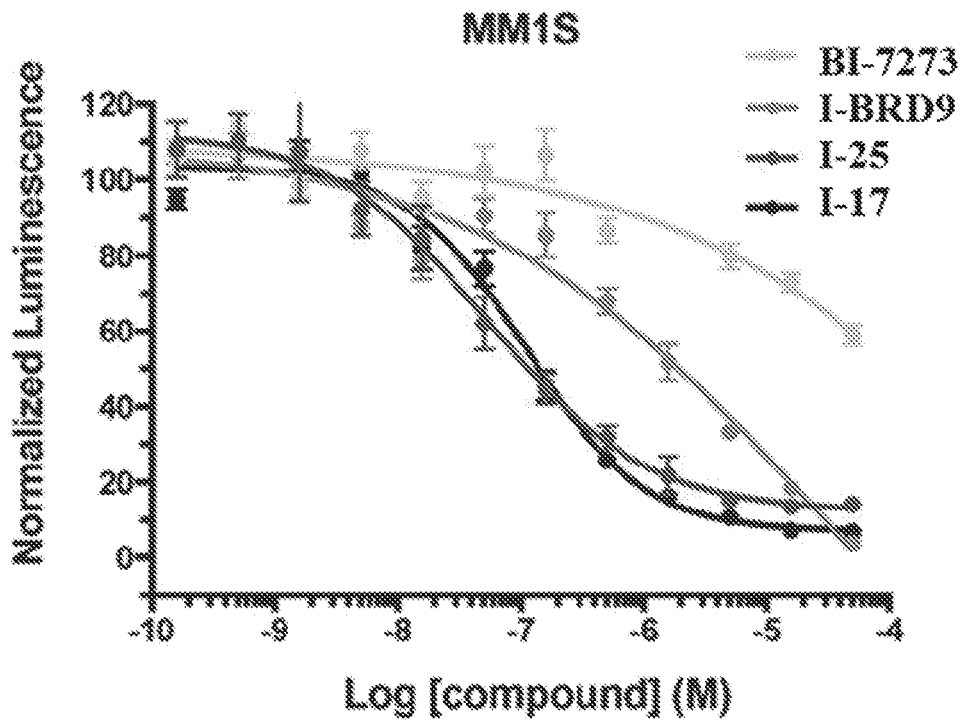
FIG. 18B is a dose-response curve of human multiple myeloma (MMIS) cellular viability following 72 hour treatment with I-25 and I-17 compared to treatment with I-BRD9 and BI-7273, known BRD9 inhibitors. The x-axis is compound concentration measured in log units and the y-axis is normalized luminescence measured in intensity. Experimental details are given in Example 13.

Sensitivity to these compounds was also observed in the MM.1S multiple myeloma line (FIG. 18B). Here, comparable efficacy was observed between I-17 and the more selective I-25. This finding suggests that selective BRD9 degradation is sufficient to effectively decrease MM1.S viability, highlighting BRD9 as a potentially attractive therapeutic target in multiple myeloma.

Figure 19:
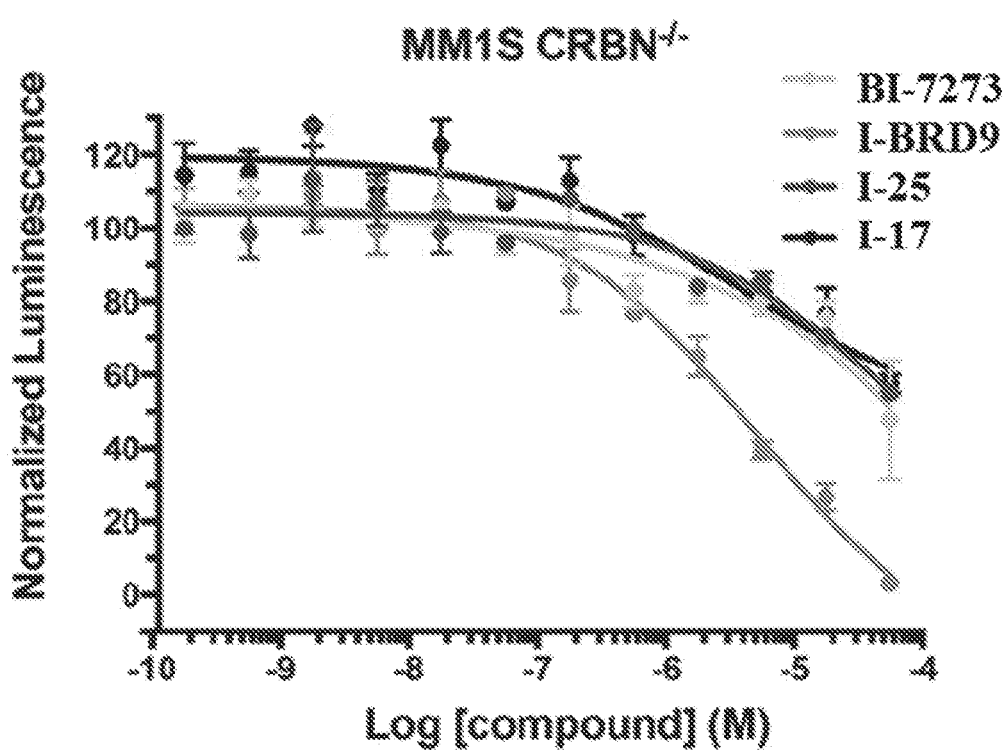
FIG. 19 is a dose-response curve of human multiple myeloma CRBN knockout (MM1S CRBN$^{-/-}$) cellular viability following 72 hour treatment with I-25 and I-17 compared to treatment with I-BRD9 and BI-7273, known BRD9 inhibitors. The x-axis is compound concentration measured in log units and the y-axis is normalized luminescence measured in intensity. Experimental details are given in Example 13.

Importantly, comparison of activity in wild-type and CRBN$^{-/-}$ MM1S lineages demonstrated that the observed pharmacologic advantage of these degraders was wholly dependent on the presence of the active CRBN CRL ligase complex (FIG. 19).

Example 14. BRD9 AlphaScreen

Assays are performed with minimal modifications from the manufacturer's protocol (PerkinElmer, USA). All reagents are diluted in 50 mM HEPES, 150 mMNaCl, 0.1% w/v BSA, 0.01% w/v Tween20, pH 7.5 and allowed to equilibrate to room temperature prior to addition to plates. After addition of Alpha beads to master solutions all subsequent steps are performed under low light conditions. A 2× solution of components with final concentrations of BRD9 at 40 nM, Ni-coated Acceptor Bead at 10 µg/mL, and 20 nM biotinylated-BRD9 targeting ligand is added in 10 µL to 384-well plates (AlphaPlate-384, PerkinElmer, USA). Plates are spun down at 150×g, 100 nL of compound in DMSO from stock plates are added by pin transfer using a Janus Workstation (PerkinElmer, USA). The streptavidin-coated donor beads (10 µg/mL final) are added as with previous the solution in a 2×, 10 µL volume. Following this addition, plates are sealed with foil to prevent light exposure and evaporation. The plates are spun down again at 150×g. Plates are incubated at room temperature for 1 hour and then read on an Envision 2104 (PerkinElmer, USA) using the manufacturer's protocol. The data are analyzed using PRISM Graphpad v6 to obtain $IC_{50}$ values.

Example 15. BRD9 Dual Luciferase Assay

A lentiviral construct containing the fusion BRD9 adjoined to nanoluciferase (Nluc) and a separate firefly luciferase (Fluc) is produced in 293 FT cells and used to transduce 293 FT cells. Transduced cells are selected with puromycin and expanded. For assays cells are dispensed into white 384-well culture plates in 20 µL at 1000 cells/well. The cells are allowed to adhere to the plate overnight, and then pinned with 100 nL of compound in DMSO using a JANUS workstation (PerkinElmer). Cells are incubated with compound for 4 hours at 37° C., 5% $CO_2$ and then allowed to cool to room temperature. To each plate is added 25 µL of Fluc buffer (200 mM Tris, 15 mM MgSO4, 100 uM EDTA, 1 mM DTT, 1 mM ATP, 200 uM Coenzyme A, 400 uM D-Luciferin, 0.1% Trition X-100). The plates are incubated for 15 min at RT, and then read on an Envision 2104 (PerkinElmer) for luminescence, 25 µL of Nluc buffer (25 mM Na4PPi, 10 mM NaOAc, 15 mM EDTA, 500 mM NaSO4, 500 mM NaCl, 16 uM coelenterazine, 50 µM 4-(6-methyl-1,3-benzothiazol-2-yl)aniline [Santa Cruz Biotechnology, sc-276812]) is then added to each well and the plate incubated for 15 min at RT and then read for luminescence. Luminescence values for each reading on each plate are normalized to DMSO controls and then the ratio of Nluc/Fluc signal is taken for each well. These data are further analyzed using PRISM Graphpad v6 to obtain $IC_{50}$ and maximum degradation values.

Example 16. Sample Preparation for Quantitative Mass Spectrometry Analysis

Sample are prepared as previously described (Weekes, M. P. et al., *Cell* 157, 1460 (2014)) with the following modification. All solutions are reported as final concentrations. Lysis buffer (8 M Urea, 1% SDS, 50 mM Tris pH 8.5, Protease and Phosphatase inhibitors from Roche) is added to the cell pellets to achieve a cell lysate with a protein concentration between 2-8 mg/mL. A micro-BCA assay (Pierce) is used to determine the final protein concentration in the cell lysate. Proteins are reduced and alkylated as previously described. Proteins are precipitated using methanol/chloroform. In brief, four volumes of methanol is added to the cell lysate, followed by one volume of chloroform, and finally three volumes of water. The mixture is vortexed and centrifuged to separate the chloroform phase from the aqueous phase. The precipitated protein is washed with one volume of ice cold methanol. The washed precipitated protein is allowed to air dry. Precipitated protein is resuspended in 4 M Urea, 50 mM Tris pH 8.5. Proteins are first digested with LysC (1:50; enzyme:protein) for 12 hours at 25° C. The LysC digestion is diluted down to 1 M Urea, 50 mM Tris pH8.5 and then digested with trypsin (1:100; enzyme:protein) for another 8 hours at 25° C. Peptides are desalted using a Cis solid phase extraction cartridges, Dried peptides are resuspended in 200 mM EPPS, pH 8.0. Peptide quantification is performed using the micro-BCA assay (Pierce). The same amount of peptide from each condition is labeled with tandem mass tag (TMT) reagent (1:4; peptide: TMT label) (Pierce). The 10-plex labeling reactions are performed for 2 hours at 25° C. Modification of tyrosine residue with TMT is reversed by the addition of 5% hydroxyl amine for 15 minutes at 25° C. The reaction is quenched with 0.5% TFA and samples are combined at a 1:1:1:1:1:1:1:1:1:1 ratio. Combined samples are desalted and offline fractionated into 24 fractions as previously described.

Example 17. Liquid Chromatography-MS3 Spectrometry (LC-MS/MS)

12 of the 24 peptide fraction from the basic reverse phase step (every other fraction) are analyzed with an LC-MS3 data collection strategy (McAlister, G. C. et al., Anal. Chem. 86, 7150 (2014)) on an Orbitrap Fusion mass spectrometer (Thermo Fisher Scientific) equipped with a Proxeon Easy nLC 11000 for online sample handling and peptide separations. Approximately 5 gig of peptide resuspended in 5% formic acid+5% acetonitrile is loaded onto a 100 µm inner diameter fused-silica micro capillary with a needle tip pulled to an internal diameter less than 5 µm. The column is packed in-house to a length of 35 cm with a $C_{18}$ reverse phase resin (GPI 18 resin 1.8 µm, 120 Å, Sepax Technologies). The peptides are separated using a 120 min linear gradient from 3% to 25% buffer B (100% ACN+0.125% formic acid) equilibrated with buffer A (3% ACN+0.125% formic acid) at a flow rate of 600 nL/min across the column. The scan sequence for the Fusion Orbitrap began with an MS 1 spectrum (Orbitrap analysis, resolution 120,000, 400-1400 m/z scan range, AGC target 2×105, maximum injection time 100 ms, dynamic exclusion of 75 seconds). "Top N" (the top precursors) is selected for MS2 analysis, which consisted of CID (quadrupole isolation set at 0.5 Da and ion trap analysis, AGC14×103, NCE 35, maximum injection time 150 ms). The top ten precursors from each MS2 scan are selected for MS3 analysis (synchronous precursor selection), in which precursors are fragmented by HCD prior to Orbitrap analysis (NCE 55, max AGC15×104, maximum injection time 150 ms, isolation window 2.5 Da, resolution 60,000.

Example 18. LC-MS3 Data Analysis

A suite of in-house software tools are used to for RAW file processing and controlling peptide and protein level false discovery rates, assembling proteins from peptides, and protein quantification from peptides as previously described. MS/MS spectra are searched against a Uniprot human database (February 2014) with both the forward and reverse sequences. Database search criteria are as follows: tryptic with two missed cleavages, a precursor mass tolerance of 50 ppm, fragment ion mass tolerance of 1.0 Da, static alkylation of cysteine (57.02146 Da), static TMT labeling of lysine residues and N-termini of peptides (229.162932 Da), and variable oxidation of methionine (15.99491 Da). TMT reporter ion intensities are measured using a 0.003 Da window around the theoretical m/z for each reporter ion in the MS3 scan. Peptide spectral matches with poor quality MS3 spectra are excluded from quantitation (<200 summed signal-to-noise across 10 channels and <0.5 precursor isolation specificity).

Example 19. Immunoblotting

Cells have been lysed using RIPA buffer supplemented with protease inhibitor cocktail (Roche) and 0.1% benzonase (Novagen) on ice for 15 minutes. The lysates are spun at 16000×g for 15 minutes on 4° C. and protein concentration is determined using BCA assay (Pierce). The following primary antibodies are used in this study: BRD9, MYC, tubulin and vinculin (all Santa Cruz). Blots are imaged using fluorescence-labeled secondary antibodies (LI-COR) on the OdysseyCLxImager (LI-COR). Quantification of band intensities has been performed using OdysseyCLx software (LI-COR).

Figure 16B:
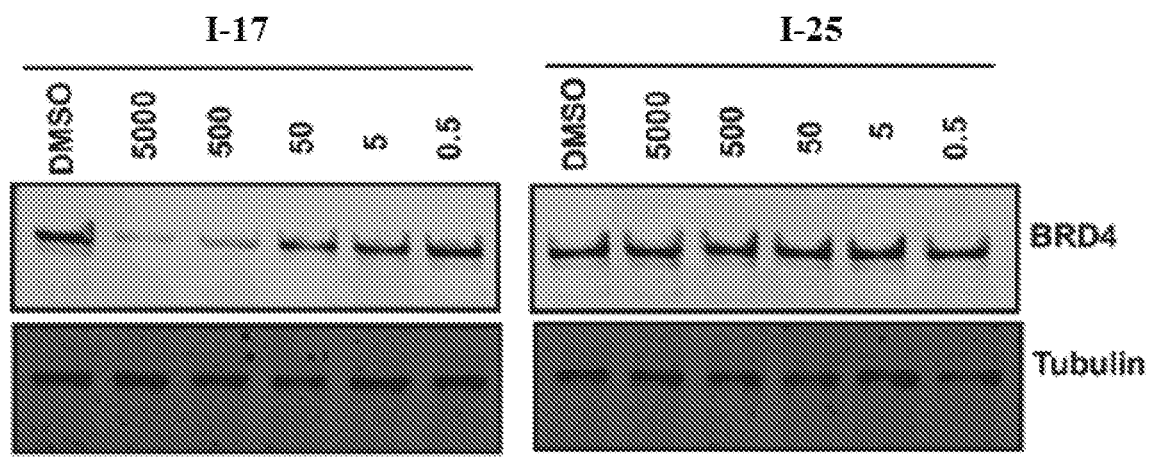
FIG. 16B are Western Blot images quantifying BRD4 and tubulin in a human AML-cell line (MOLM-13) by immunoblot after a 4 hour treatment with the indicated concentrations of compound I-17 and I-25. Compound I-25 was not able to induce degradation of BRD4 at any of the tested concentrations. Off target degradation of BRD4, observed at high concentrations of I-17, was no longer detectable for I-25, despite its potent activity on BRD9 levels.

In additional experiments, cells were washed with PBS, before being lysed in RIPA buffer supplemented with 1×HALT™ protease inhibitor cocktail (Thermo Scientific) for 10 min on ice, followed by low-amplitude sonication for 10 seconds at 4° C. (Q125, QSonica, USA). In soluble material was removed by centrifugation at 20,000×g for 20 min before protein content was quantified by BCA assay (Pierce). Electrophoretic separation was performed using the Novex Bolt or Nupage systems (Thermo Fisher Scientific) and transferred to Novex 0.45 µM Nitrocellulose membranes. The following primary antibodies were used in this study: BRD9 (Bethyl A303), Actin (Santa Cruz C-2), BRD4 (Bethyl A301), BRD7 (Cell Signaling D9K2T), α-Tubulin (abcam 7291). Blots were imaged using fluorescence-labeled secondary antibodies (LI-COR) on the OdysseyCLx-Imager (LI-COR). FIGS. 5A, 5B, 5C, 5D, 5E, 5F, 6A, 6B, 6C, 6D, 7A, 7B, 7C, 7D, 7E, 11B, 12B, 13A, 13B, 13C and 14B are Western Blot images of BRD9 degradation induced by select compounds. FIG. 16B are Western Blot images of BRD4 degradation induced by I-17 and I-25. FIG. 17A are Western Blot images of BRD7 degradation induced by I-17 and I-25.

Example 20. Immunohistochemistry

BRD9 staining is performed using the A301-985A antibody (Bethyl labs) following the recommended parameters at a concentration of 1:2000. MYC and Ki67 stainings are performed as described previously. Quantification of positively stained nuclei is conducted using the aperio software (Leica Biosystems).

Example 21. Culture of Cell Lines

293FT and 293F$^{CRBN-/-}$ are cultured in DMEM supplemented with 10% FCS and 1%0 Penicillin/Streptomycin. MV4-11, MOLM13, MM1S and MM1S$^{CRBN-/-}$ are cultured in RPMI supplemented with 10% FCS and 1% Penicillin/Streptomycin. SUM149 cells are cultured in HUMEC medium (cell application, 815-500) with DMEM F12 (coming cellgro, 10-090-CV) (1:1) and final 5/6 FCS with 1% Penicillin/Streptomycin.

Example 22. Culture of Primary Patient Material

Cells are freshly thawed and grown for 24 hours in StemSpan SFEM media (Stemcell) supplemented with (all in ng/ml final concentration): IL-3 (20), IL-6 (20), FLT3L (100), SCF (100) and GSCF (20). After that, cells are treated with a compound of the application at the indicated concentrations with renewed cytokines for 24 hours.

Subsequently, cells are either used for immunoblot analysis or for FACS analysis.

Example 23. Analysis of Apoptotic Cells by Flow Cytometry

For each sample, cells are washed with 500 µL of PBS and spun down at 400×g for 5 minutes and media aspirated off. Cells are then resuspended in Annexin V binding buffer: 140 mMNaCl, 10 mM HEPES, 2.5 mM CaCl$_2$, pH 7.4 and 500 µL L of each sample transferred to 5 mL polystyrene FACS tubes (Falcon Cat. No. 352054). Cells are spun down at 400×g for 5 minutes and buffer aspirated off. To each sample, 400 µL of Annexin V binding buffer with 250 ng/mL FITC-Annexin V and 500 ng/mL propidium iodide are added for staining. Cells are then sorted on a BD LSR-Fortessa and analyzed using FlowJo V10 software (Tree Star, Inc).

Example 24. Analysis of Apoptotic Cells by Caspase Glo Assay

Caspaseglo assay (Promega) has been conducted following the manufacturer's recommendations. Cells are seeded at a density of 5000 cells/well in a white 384 well plate (Thermo Scientific Nunc, #164610) in a total volume of 40 ul with respective compound or vehicle control treatment. After a 24 h incubation, 30 ul of the Caspaseglo substrate are added per well. Plate is incubated in the dark for 90 minutes and read on Envision plate reader (Perkin Elmer).

Example 25: Degradation of BRD9 by a Compound of the Application 10,000 cells (293T WT or 293 CRBN−/−) are seeded per well using 384-well plates. On the following day, a compound of the application is added at various concentrations. After being treated with the compound for 4 hours, cells are fixed with formaldehyde, permeabilized using 0.1% triton, blocked with LiCor blocking buffer, and incubated with the primary antibody (BRD9, 1:1000) overnight. On the following day, cells are washed (5× TBST) and stained using Odysee Cell Stain (1:500). A secondary antibody recognizing the BRD9 antibody is added simultaneously (1:800). Images are quantified using LiCOR imager.

Various cells (BAF3_K-RAS, SEMK2, Monomac1, MM1S$^{WT}$, MM1S$^{CRBN-/-}$) are treated with increasing concentrations of a compound of the application for ~16 hours. Cells are lysed and the lysates are immunoblotted to measure levels of BRD9.

Example 26: Viability of Cells Treated with a Compound of the Application

Various cell lines (T-ALL (MOLT4, DND41, CUTLL1), LOUCY, MV4-11, and RS4-11) are plated in 384 well plates at 1000 cells/well. A compound of the application was then added to the cells and incubated for 48 hours. ATP content is measured as a surrogate for cellular viability using ATPlite (Promega).

EQUIVALENTS

Those skilled in the art will recognize, or be able to ascertain using no more than routine experimentation, many equivalents to the specific embodiments and methods described herein. Such equivalents are intended to be encompassed by the scope of the present application.

All patents, patent applications, and literature references cited herein are hereby expressly incorporated by reference.

The invention claimed is:

1. A bifunctional compound which is:

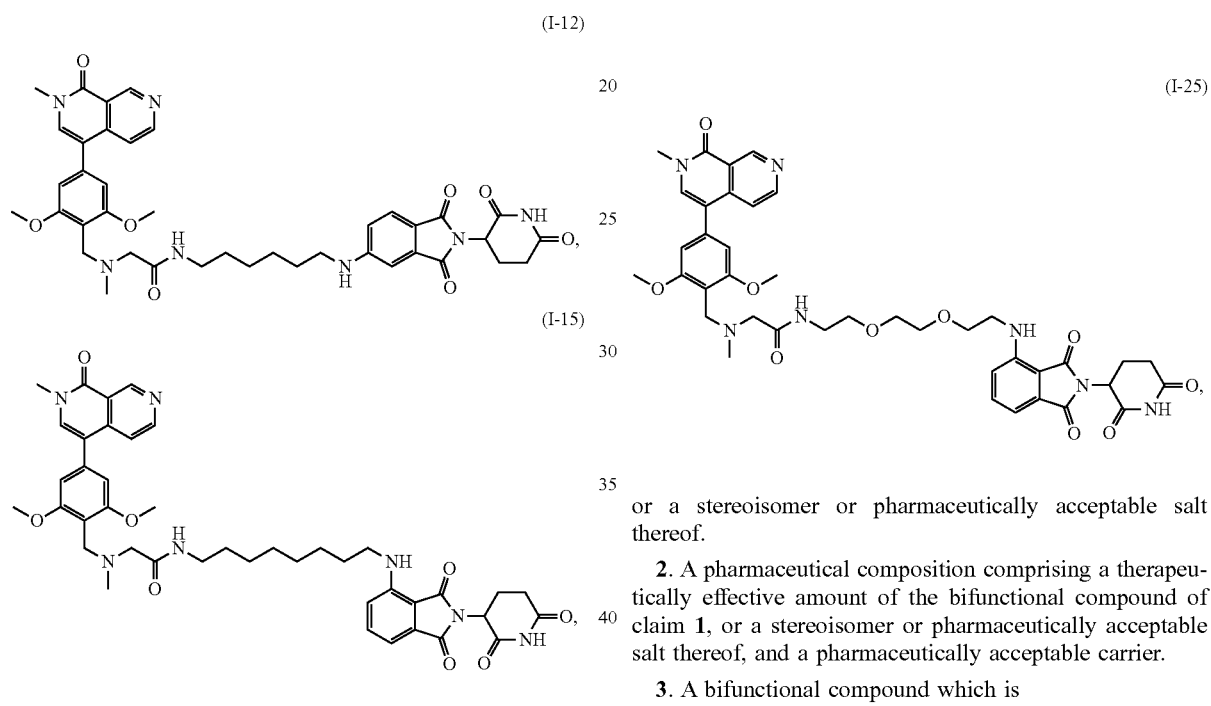

or a stereoisomer or pharmaceutically acceptable salt thereof.

2. A pharmaceutical composition comprising a therapeutically effective amount of the bifunctional compound of claim 1, or a stereoisomer or pharmaceutically acceptable salt thereof, and a pharmaceutically acceptable carrier.

3. A bifunctional compound which is

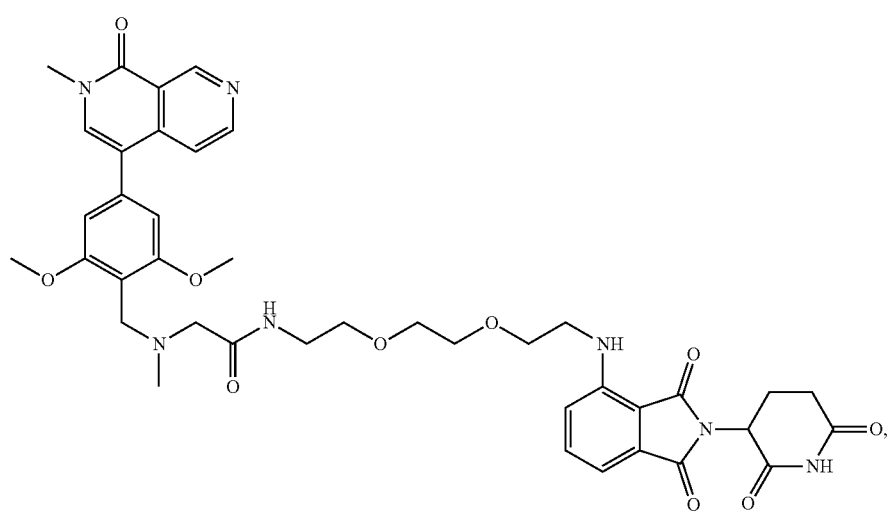

or pharmaceutically acceptable salt thereof.

4. A bifunctional compound which is
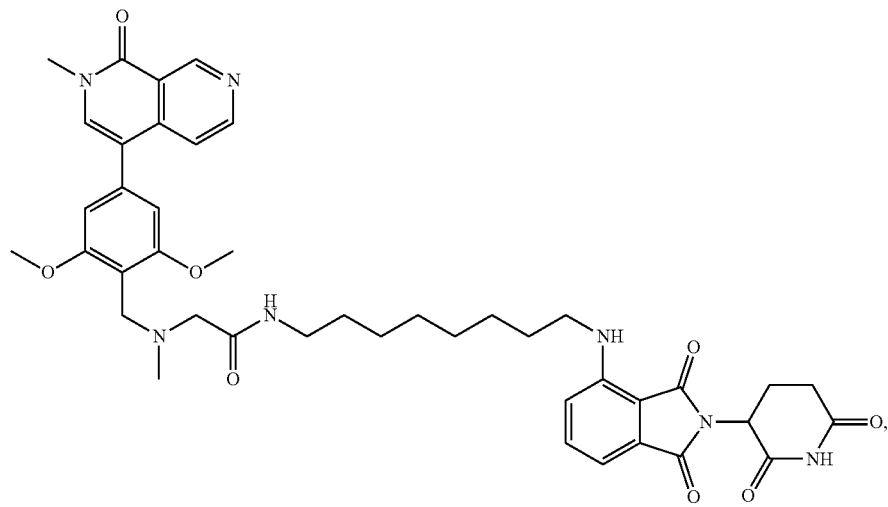
(I-15)
or pharmaceutically acceptable salt thereof.
* * * * *